United States Patent
Ngai et al.

(10) Patent No.: US 10,676,424 B2
(45) Date of Patent: Jun. 9, 2020

(54) TRIFLUOROMETHOYLATION OF ARENES VIA INTRAMOLECULAR TRIFLUOROMETHOXY GROUP MIGRATION

(71) Applicants: Ming-Yu Ngai, Stony Brook, NY (US); Katarzyna N. Hojczyk, Stony Brook, NY (US)

(72) Inventors: Ming-Yu Ngai, Stony Brook, NY (US); Katarzyna N. Hojczyk, Stony Brook, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 16/133,297

(22) Filed: Sep. 17, 2018

(65) Prior Publication Data
US 2019/0016670 A1    Jan. 17, 2019

Related U.S. Application Data

(62) Division of application No. 15/516,610, filed as application No. PCT/US2015/054958 on Oct. 9, 2015, now Pat. No. 10,118,890.

(Continued)

(51) Int. Cl.
C07C 233/25    (2006.01)
C07C 259/06    (2006.01)
(Continued)

(52) U.S. Cl.
CPC .......... *C07C 233/25* (2013.01); *C07C 231/12* (2013.01); *C07C 231/14* (2013.01); *C07C 233/33* (2013.01); *C07C 233/54* (2013.01); *C07C 233/80* (2013.01); *C07C 233/81* (2013.01); *C07C 253/30* (2013.01); *C07C 255/58* (2013.01); *C07C 255/60* (2013.01); *C07C 259/06* (2013.01); *C07C 259/10* (2013.01); *C07C 269/06* (2013.01); *C07C 271/38* (2013.01); *C07C 273/1809* (2013.01); *C07C 273/1854* (2013.01); *C07C 275/34* (2013.01); *C07D 209/08* (2013.01); *C07D 213/75* (2013.01); *C07D 213/76* (2013.01);
(Continued)

(58) Field of Classification Search
CPC .................................................. C07C 233/25
See application file for complete search history.

(56) References Cited

U.S. PATENT DOCUMENTS 10,118,890 B2    11/2018   Ngai et al.
2017/0298008 A1   10/2017   Ngai et al.

OTHER PUBLICATIONS

International Search Report in connection with PCT International Application No. PCT/US2015/054958.
(Continued)

*Primary Examiner* — Brian E McDowell
(74) *Attorney, Agent, or Firm* — Gary J. Gershik; Cooper & Dunham LLP

(57) ABSTRACT

The present invention provides a process of producing a trifluoromethoxylated aryl or trifluoromethoxylated heteroaryl having the structure:

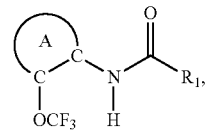

wherein
A is an aryl or heteroaryl, each with or without substitution; and
$R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl); —S-(alkyl), —S-(alkenyl), —S-(alkynyl), —S-(aryl), or —S-(heteroaryl), comprising:
(a) reacting a compound having the structure:

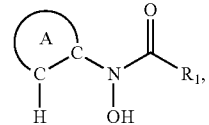

with a trifluoromethylating agent in the presence of a base in a first suitable solvent under conditions to produce a compound having the structure:

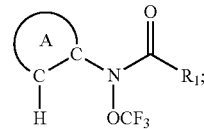

and
(b) maintaining the compound produced in step (a) in a second suitable solvent under conditions sufficient to produce the trifluoromethoxylated aryl or trifluormethoxylated heteroaryl having the structure:

(Continued)

US 10,676,424 B2

Page 2

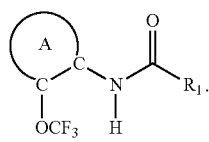

11 Claims, 5 Drawing Sheets

Related U.S. Application Data

(60) Provisional application No. 62/192,789, filed on Jul. 15, 2015, provisional application No. 62/192,462, filed on Jul. 14, 2015, provisional application No. 62/063,246, filed on Oct. 13, 2014, provisional application No. 62/062,508, filed on Oct. 10, 2014.

(51) Int. Cl.
| | |
|---|---|
| C07C 259/10 | (2006.01) |
| C07C 269/06 | (2006.01) |
| C07C 273/18 | (2006.01) |
| C07C 231/14 | (2006.01) |
| C07C 253/30 | (2006.01) |
| C07D 213/75 | (2006.01) |
| C07D 213/76 | (2006.01) |
| C07D 347/00 | (2006.01) |
| C07D 239/47 | (2006.01) |
| C07D 239/91 | (2006.01) |
| C07D 473/40 | (2006.01) |
| C07D 263/57 | (2006.01) |
| C07D 209/08 | (2006.01) |
| C07D 215/40 | (2006.01) |
| C07D 401/04 | (2006.01) |
| C07D 471/04 | (2006.01) |
| C07J 43/00 | (2006.01) |
| C07D 417/04 | (2006.01) |
| C07D 405/04 | (2006.01) |
| C07C 231/12 | (2006.01) |
| C07C 233/33 | (2006.01) |
| C07C 233/54 | (2006.01) |
| C07C 233/80 | (2006.01) |
| C07C 233/81 | (2006.01) |
| C07C 255/60 | (2006.01) |
| C07C 255/58 | (2006.01) |
| C07C 271/38 | (2006.01) |
| C07C 275/34 | (2006.01) |

(52) U.S. Cl.
CPC ......... *C07D 215/40* (2013.01); *C07D 239/47* (2013.01); *C07D 239/91* (2013.01); *C07D 263/57* (2013.01); *C07D 347/00* (2013.01); *C07D 401/04* (2013.01); *C07D 405/04* (2013.01); *C07D 417/04* (2013.01); *C07D 471/04* (2013.01); *C07D 473/40* (2013.01); *C07J 43/003* (2013.01)

(56) References Cited

OTHER PUBLICATIONS

Written Opinion of the International Searching Authority in connection with PCT International Application No. PCT/US2015/054958.

Katarzyna N. Hojczyk, et al., "Trifluoromethoxylation of Arenes: Synthesis of ortho-Trifluoromethoxylated Aniline Derivatives by $OCF_3$ Migration", Angewandte Chemie International Edition, Oct. 30, 2014, vol. 53, pp. 14559-14563.

Vaclav Matousek, et al., "O-Trifluoromethylation of N, N-Disubstituted Hydroxylamines with Hypervalent Iodine Reagents", European Journal of Organic Chemistry, Mar. 26, 2014, No. 15, pp. 3087-3092.

Jiang Xin-Yi, et al., Copper-Catalyzed Three-Component Oxytrifluoromethylation of Alkenes with Sodium Trifluoromethanesulfinate and Hydroxamic Acid.

Apr. 3, 2017 Preliminary Amendment filed in connection with U.S. Appl. No. 15/516,610.

Oct. 19, 2017 Office Action issued in connection with U.S. Appl. No. 15/516,610.

Dec. 11, 2017 Response to Oct. 19, 2017 Office Action filed in connection with U.S. Appl. No. 15/516,610.

Jan. 30, 2018 Office Action in connection with U.S. Appl. No. 15/516,610.

Apr. 30, 2018 Amendment in Response to Jan. 30, 2018 Office Action filed in connection with U.S. Appl. No. 15/516,610.

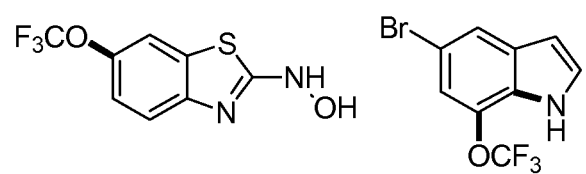
Toronto Research Chemicals
US$120,000/g
Matrix Scientifc
US$15,680/g
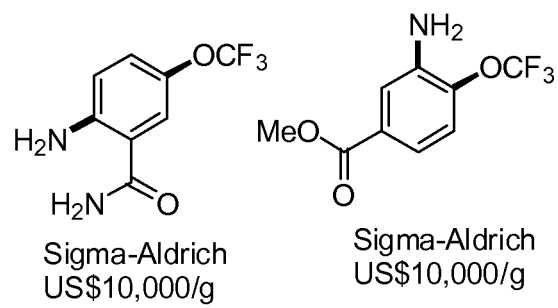
Sigma-Aldrich
US$10,000/g
Sigma-Aldrich
US$10,000/g
Fig. 1C

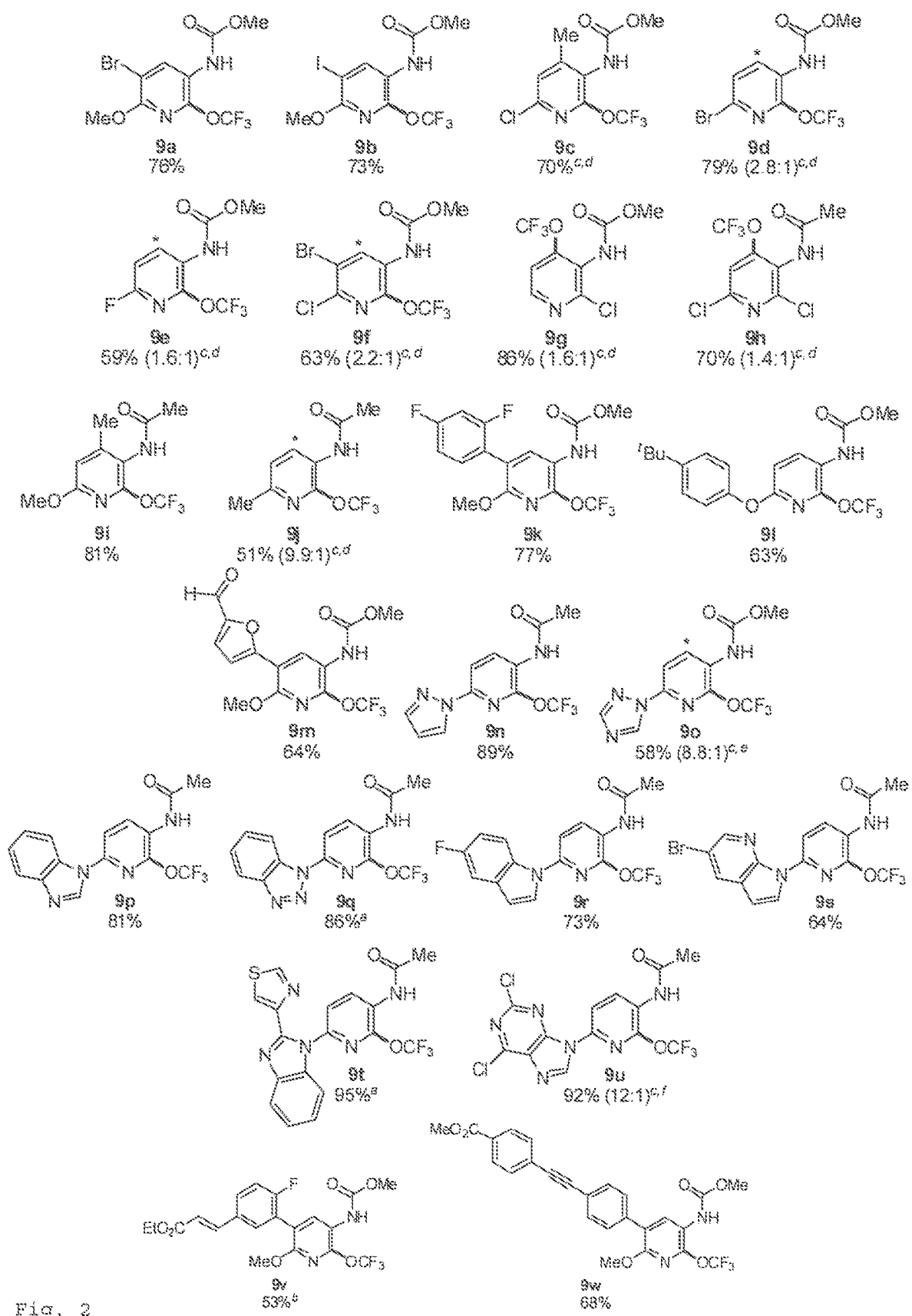

TRIFLUOROMETHOYLATION OF ARENES VIA INTRAMOLECULAR TRIFLUOROMETHOXY GROUP MIGRATION

This application is a divisional of U.S. application Ser. No. 15/516,610, filed Apr. 3, 2017, a § 371 national stage of PCT International Application No. PCT/US2015/054958, filed Oct. 9, 2015 and claims priority of U.S. Provisional Application Nos. 62/192,789, filed Jul. 15, 2015; 62/192,462, filed Jul. 14, 2015; 62/063,246, filed Oct. 13, 2014; and 62/062,508, filed Oct. 10, 2014, the contents of each of which are hereby incorporated by reference.

Throughout this application various publications are referenced. The disclosures of these documents in their entireties are hereby incorporated by reference into this application in order to more fully describe the state of the art to which this invention pertains.

BACKGROUND OF THE INVENTION

Fluorine atoms are often introduced into organic molecules to enhance their pharmacological properties such as solubility, metabolic and oxidative stability, lipophilicity, and bioavailability.[1] Among the fluorine containing functional groups, the trifluoromethoxy group ($OCF_3$) is of current interest because of its unique structural and electronic properties, which can be useful in material, agricultural, and pharmaceutical science.[2] For example, one of the distinct structural features of trifluoromethoxylated arenes (Ar—$OCF_3$) is that the $OCF_3$ bond is orthogonal to the aryl ring.[3,1b] As a result, lone pair electrons on oxygen only weakly delocalize into the ring, which renders $OCF_3$ an electron withdrawing group. In addition, the $OCF_3$ group has one of the highest lipophilicity values ($\pi_x=1.04$) compared to the $CF_3$ ($\pi_x=0.88$), $CH_3$ ($\pi_x=0.52$), F ($\pi_x=0.14$), and $OCH_3$ ($\pi_x=-0.02$) groups.[4] Compounds with higher lipophilicity show enhancement in their in vivo uptake and transport in biological systems. Indeed, many $OCF_3$ containing pharmaceuticals and agrochemicals show enhanced effectiveness often coupled with diminished side-effects (FIG. 1).[2a,2b,5]

Despite the intriguing properties of the $OCF_3$ group, introduction of this functional group into organic molecules remains a challenge. Only a handful of transformations have been developed over the last few decades and most of them either suffer from poor substrate scope or require the use of highly toxic and/or thermally unstable reagents. A pioneering study by Yagupolskii and coworkers in 1955 led to the development of a two-step chlorination/chlorine-fluorine exchange protocol for the synthesis of simple aryl trifluoromethyl ethers.[6] In 1964, Sheppard reported an alternative approach involving reactions of aromatic or aliphatic alcohols with fluorophosgene followed by deoxyfluorination with tetrafluorosulfur ($SF_4$).[7] About thirty years later, Hiyama synthesized aryl trifluoromethyl ethers via formation of dithiocarbonates followed by oxidative fluorodesulfurization.[8] Electrophilic trifluormethylations of alcohols and phenols have also been developed. Employing thermally labile O-trifluoromethyldibenzyl furanium salts, Umemoto and coworkers successfully trifluoro-methylated phenols to form aryl trifluoromethyl ethers.[9] An elegant direct trifluoromethylation of aliphatic alcohols using bench stable reagent was reported by Togni and coworkers.[10] However, poor yields were obtained for phenolic substrates due to the competing C-trifluoromethylation.[11] Most recently, a direct trifluoro-methoxylation of benzene employing toxic gaseous trifluoromethyl perfluorite[12a-b], and a transition metal-mediated trifluoro-methoxylation of aryl stannanes as well as aryl boronic acids utilizing thermally labile tris(dimethylamino)sulfonium trifluoro-methoxide have been developed.[2b] However, most of these approaches either suffer from poor substrate scope or require use of highly toxic and/or thermally labile reagents. As a result, many of $OCF_3$-containing building blocks are prohibitively expensive (FIG. 1C).

SUMMARY OF THE INVENTION

The present invention provides a process of producing a compound having the structure:

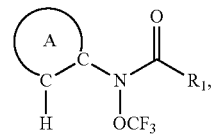

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

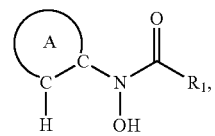

with a trifluoromethylating agent in the presence of a base in a first suitable solvent under conditions sufficient to produce the compound having the structure:

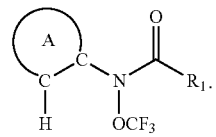

The present invention also provides a process of producing a trifluoromethoxylated aryl or trifluoromethoxylated heteroaryl having the structure:

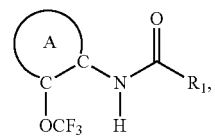

wherein

A is an aryl or heteroaryl, each with or without subsutitution; and

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(b) maintaining the compound having the structure:

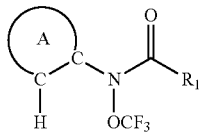

in a second suitable solvent under conditions sufficient to produce the trifluoromethoxylated aryl or trifluormethoxylated heteroaryl having the structure:

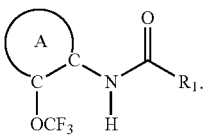

The present invention further provides a process of producing a trifluoromethoxylated aryl or trifluoromethoxylated heteroaryl having the structure:

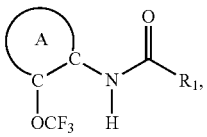

wherein

A is an aryl or heteroaryl, each with or without subsutitution; and

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

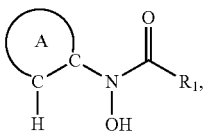

with a trifluoromethylating agent in the presence of a base in a first suitable solvent under conditions to produce a compound having the structure:

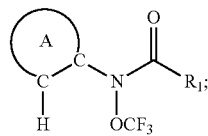

and (b) maintaining the compound produced in step (a) in a second suitable solvent under conditions sufficient to produce the trifluoromethoxylated aryl or trifluormethoxylated heteroaryl having the structure:

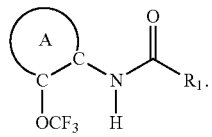

The present invention further provides a process of producing a trifluoromethoxylated aryl or trifluoromethoxylated heteroaryl having the structure:

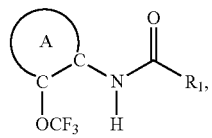

wherein

A is an aryl or heteroaryl, each with or without subsutitution; and

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

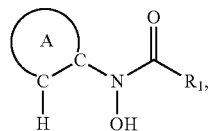

with a trifluoromethylating agent in a first suitable solvent under conditions to produce a compound having the structure:

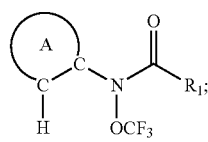

and (b) maintaining the compound produced in step (a) in the first suitable solvent under conditions sufficient to produce the trifluoromethoxylated aryl or trifluormethoxylated heteroaryl having the structure:

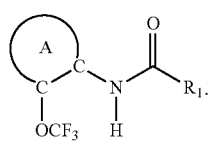

The present invention also provides a compound having the structure:

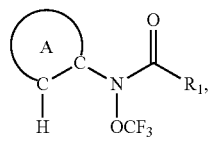

wherein
A is an aryl or heteroaryl, each with or without subsutitution; and
R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl).

BRIEF DESCRIPTION OF THE FIGURES

FIG. 1C. Examples of OCF₃-bearing building blocks.
FIG. 2. Compounds 9a-9y. Cited yields and isomeric ratios are of isolated material by column chromatography. $^{a}$RT→50° C. in CH₂Cl₂. $^{b}$4° C. in CH₂Cl₂ (0.01 M). $^{c}$Following the O-trifluoromethylation reaction in CH₂Cl₂ at RT, the reaction mixture was concentrated, the residue was dissolved in MeNO₂, and the resulting mixture was heated. $^{d}$120° C. $^{e}$80° C. $^{f}$60° C.

DETAILED DESCRIPTION OF THE INVENTION

Figure 1A:
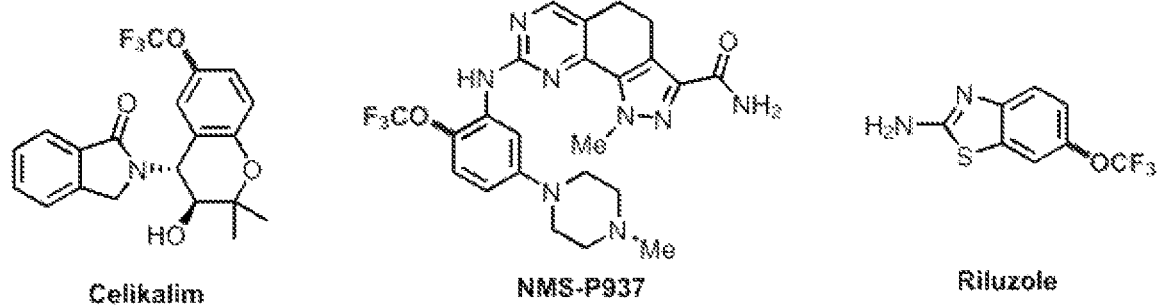
FIG. 1A. Examples of OCF₃-bearing pharmaceuticals.
Figure 1B:
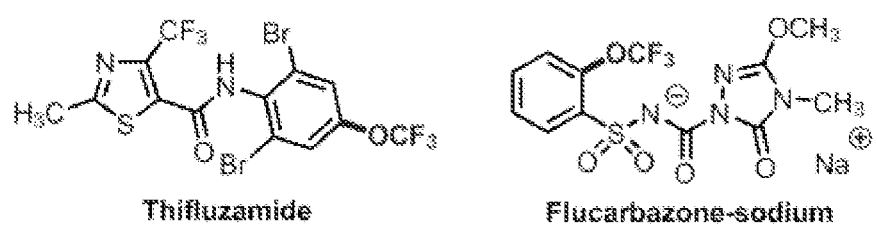
FIG. 1B. Examples of OCF₃-bearing agrochemicals.

The present invention provides a process of producing a compound having the structure:

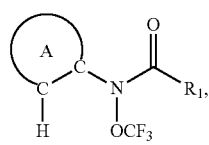

wherein
A is an aryl or heteroaryl, each with or without subsutitution; and
R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl),
comprising:
(a) reacting a compound having the structure:

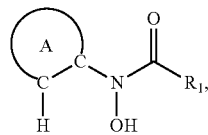

with a trifluoromethylating agent in the presence of a base in a first suitable solvent under conditions sufficient to produce the compound having the structure:

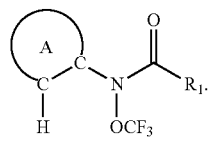

In some embodiments, the first suitable solvent is chloroform, dichloromethane, nitromethane, dimethylforamide, diethyl ether, tetrahydrofuran, dioxane, dichloroethane, or hexane.
In some embodiments, the first suitable solvent is degassed prior to use.
In some embodiments, step (a) is performed under an inert atmosphere.
In some embodiments, step (a) is carried out at room temperature.
In some embodiments, in step (a) the molar ratio of the compound to the trifluormethylation agent is 1:1 to 1:2.
In some embodiments, in step (a) the molar ratio of the compound to the trifluormethylation agent is 1:1.2.
In some embodiments, the trifluormethylating agent is Togni reagent I or Togni reagent II.
In some embodiments, the base is cesium carbonate or sodium hydride.
In some embodiments, a catalytic amount of the base is used.
In some embodiments, in step (a) the compound is reacted for 5-24 hours. In some embodiments, in step (a) the compound is reacted for about 15 hours.
In some embodiments of step (a), A is a phenyl or pyridine. In some embodiments of step (a), A is a furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.
In some embodiments, the compound produced in step (a) has the structure:

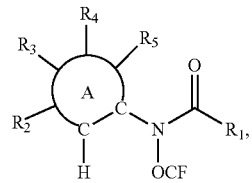

wherein

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and R₂, R₃, R₄ and R₅ is each independently —H, halogen, —CN, —CF₃, —OCF₃, -(alkyl), -(alkenyl), -(alkynyl), -(aryl), -(heteroaryl), —NH₂, —NH-(alkyl), —NH-(alkenyl), —NH-(alkynyl) —NH-(aryl), —NH-(heteroaryl), —CO₂-(alkyl), —CO₂-(alkenyl), —CO₂-(alkynyl)-CO₂-(aryl), —C(—CO₂-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)₂, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above compound R₂, R₃, R₄ and R₅ is each, independently, —H, halogen, —CN, —CF₃, —OCF₃, -(alkyl), -(alkenyl), -(alkynyl), -(aryl), -(heteroaryl), —NH₂, —NH-(alkyl), —NH-(alkenyl), —NH-(alkynyl) —NH-(aryl), —NH-(heteroaryl), —CO₂-(alkyl), —CO₂-(alkenyl), —CO₂-(alkynyl)-CO₂-(aryl), —C(—CO₂-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)₂, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

In some embodiments of the above compound R₂, R₃, R₄ and R₅ is each, independently, —H, pyrazoline, triazole, benzimidazole, benzotriazole, azaindole, or purine.

In some embodiments, the compound produced in step (a) has the structure:

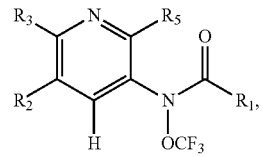

wherein

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and R₂, R₃, R₄ and R₅ is each independently —H, halogen, —CN, —CF₃, —OCF₃, -(alkyl), -(alkenyl), -(alkynyl), -(aryl), -(heteroaryl), —NH₂, —NH-(alkyl), —NH-(alkenyl), —NH-(alkynyl) —NH-(aryl), —NH-(heteroaryl), —CO₂-(alkyl), —CO₂-(alkenyl), —CO₂-(alkynyl)-CO₂-(aryl), —C(—CO₂-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)₂, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, the compound produced in step (a) has the structure:

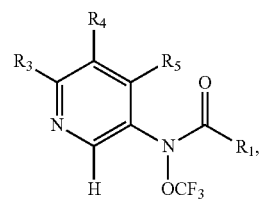

wherein

R₁ is —H, -(alkyl), -(alkenyl), -(alkynyl), -(aryl), -(heteroaryl), -(alkylaryl), -(alkylheteroaryl), —NH-(alkyl), —N(alkyl)₂, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and R₃, R₄ and R₅ is each independently —H, halogen, —CN, —CF₃, —OCF₃, -(alkyl), -(alkenyl), -(alkynyl), -(aryl), -(heteroaryl), —NH₂, —NH-(alkyl), —NH-(alkenyl), —NH-(alkynyl) —NH-(aryl), —NH-(heteroaryl), —CO₂-(alkyl), —CO₂-(alkenyl), —CO₂-(alkynyl)-CO₂-(aryl), —C(—CO₂-(heteroaryl), —C(O)NH-(alkyl), —C(O)NH-(alkenyl), —C(O)NH-(alkynyl) —C(O)NH-(aryl), —C(O)

NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

The present invention also provides a process of producing a trifluoromethoxylated aryl or trifluoromethoxylated heteroaryl having the structure:

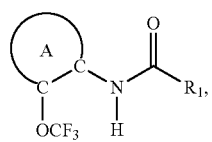

wherein
A is an aryl or heteroaryl, each with or without subsutitution; and

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(b) maintaining the compound having the structure:

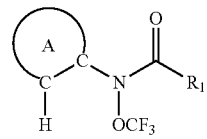

in a second suitable solvent under conditions sufficient to produce the trifluoromethoxylated aryl or trifluormethoxylated heteroaryl having the structure:

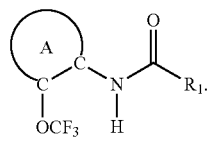

In some embodiments, the second suitable solvent is chloroform, dichloromethane, nitromethane, dimethylformamide, diethyl ether, tetrahydrofuran, dioxane, dichloroethane, or hexane.

In some embodiments, the second suitable solvent is degassed prior to use.

In some embodiments, step (b) is performed under an inert atmosphere.

In some embodiments, step (b) is carried out at room temperature.

In some embodiments, step (b) is carried out at a temperature of 50-140° C. In some embodiments, step (b) is carried out at a temperature of about 80° C.

In some embodiments, step (b) is carried out at a temperature of about 120° C.

In some embodiments, the compound is maintained in the second suitable solvent for 10-50 hours. In some embodiments, the compound is maintained in the second suitable solvent for about 24 hours.

In some embodiments of step (b), A is a phenyl or pyridine. In some embodiments of step (b), A is a furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of step (b), the compound produced has the structure:

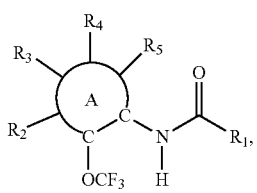

wherein
R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and R$_2$, R$_3$, R$_4$ and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above compound R$_2$, R$_3$, R$_4$ and R$_5$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

In some embodiments of the above compound R$_2$, R$_3$, R$_4$ and R$_5$ is each, independently, —H, pyrazoline, triazole, benzimidazole, benzotriazole, azaindole, or purine.

In some embodiments of step (b), the compound produced has the structure:

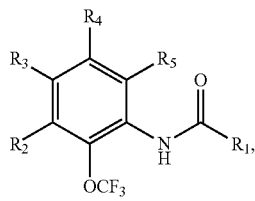

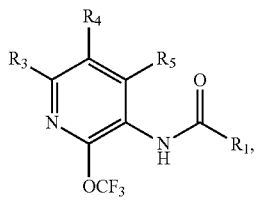

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of step (b), the compound produced has the structure:

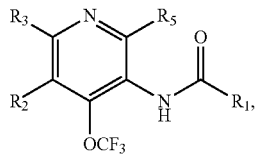

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of step (b), the compound produced has the structure:

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

The present invention further provides a process of producing a trifluoromethoxylated aryl or trifluoromethoxylated heteroaryl having the structure:

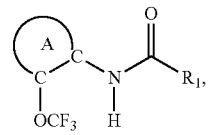

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

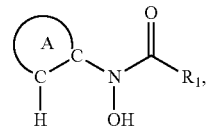

with a trifluoromethylating agent in the presence of a base in a first suitable solvent under conditions to produce a compound having the structure:

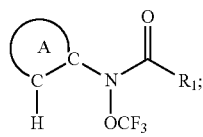

and (b) maintaining the compound produced in step (a) in a second suitable solvent under conditions sufficient to produce the trifluoromethoxylated aryl or trifluormethoxylated heteroaryl having the structure:

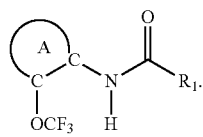

In some embodiments of the above process, the first suitable solvent is chloroform, dichloromethane, nitromethane, dimethylforamide, diethyl ether, tetrahydrofuran, dioxane, dichloroethane, or hexane.

In some embodiments of the above process, the second suitable solvent is chloroform, dichloromethane, nitromethane, dimethylforamide, diethyl ether, tetrahydrofuran, dioxane, dichloroethane, or hexane.

In some embodiments of the above process, the first suitable solvent and second suitable solvent are identical.

In some embodiments of the above process, step (a) and step (b) are performed by a sequential one-pot synthesis.

In some embodiments of the above process, step (a) and step (b) are performed by a sequential one-pot synthesis without purification or work-up in between step (a) and step (b).

In some embodiments of the above process, step (a) and step (b) are performed by a sequential two-pot synthesis.

In some embodiments of the above process, the compound produced in step (a) is subjected to a work-up prior to step (b).

In some embodiments of the above process, the compound produced in step (a) is subjected to a purification prior to step (b).

In some embodiments of the above process, the compound produced in step (a) is subjected to a work-up and purification prior to step (b).

In some embodiments of the above process, the crude compound produced in step (a) is used in step (b).

In some embodiments of the above process, the first suitable solvent is degassed prior to use.

In some embodiments of the above process, steps (a) and (b) are performed under an inert atmosphere.

In some embodiments of the above process, step (a) is carried out at room temperature.

In some embodiments of the above process, step (b) is carried out at room temperature.

In some embodiments of the above process, step (b) is carried out at a temperature of 50-140° C.

In some embodiments of the above process, step (b) is carried out at a temperature of about 80° C.

In some embodiments of the above process, step (b) is carried out at a temperature of about 120° C.

In some embodiments of the above process, in step (a) the compound is reacted for 12-24 hours.

In some embodiments of the above process, in step (a) the compound is reacted for about 15 hours.

In some embodiments of the above process, in step (b) the compound is maintained in the second suitable solvent for 10-50 hours.

In some embodiments of the above process, in step (b) the compound is maintained in the second suitable solvent for about 24 hours.

In some embodiments of the above process, in step (a) the molar ratio of the compound to the trifluormethylation agent is 1:1 to 1:2.

In some embodiments of the above process, in step (a) the molar ratio of the compound to the trifluormethylation agent is 1:1.2.

In some embodiments of the above process, the trifluormethylating agent is Togni reagent or Togni reagent II.

In some embodiments of the above process, the base is sodium hydride or cesium carbonate.

In some embodiments of the above process, A is a phenyl or pyridine.

In some embodiments of the above process, A is a furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above process, the compound produced has the structure:

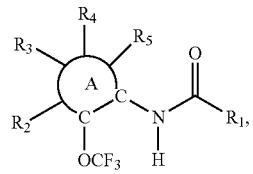

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above compound $R_2$, $R_3$, $R_4$ and $R_5$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

In some embodiments of the above compound $R_2$, $R_3$, $R_4$ and $R_5$ is each, independently, —H, pyrazoline, triazole, benzimidazole, benzotriazole, azaindole, or purine.

In some embodiments of the above process, the compound produced has the structure:

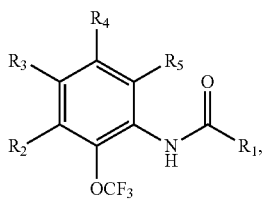

wherein
$R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above process, the compound produced has the structure:

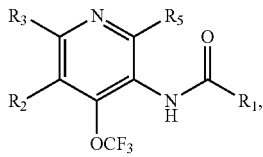

wherein
$R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above process, the compound produced has the structure:

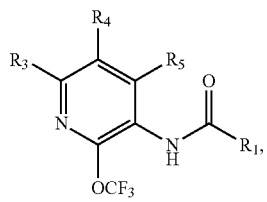

wherein
$R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

In some embodiments, the process comprising:
(a) reacting a compound having the structure:

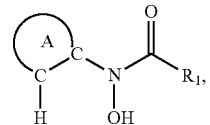

with Togni reagent II in the presence of a base in a first suitable solvent under conditions sufficient to produce a compound having the structure:

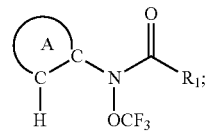

and
(b) maintaining the compound produced in step (a) in a second suitable solvent under conditions sufficient to produce the trifluoromethoxylated aryl or trifluormethoxylated heteroaryl having the structure:

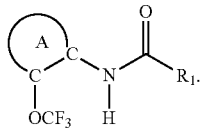

In some embodiments, the process comprising:
(a) reacting a compound having the structure:

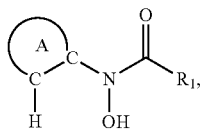

with Togni reagent II in the presence of cesium carbonate in chloroform or dichloromethane under conditions sufficient to produce a compound having the structure:

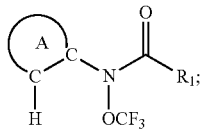

and
(b) maintaining the compound produced in step (a) in nitromethane under conditions sufficient to produce the trifluoromethoxylated aryl or trifluormethoxylated heteroaryl having the structure:

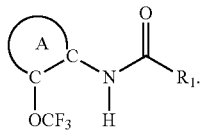

In some embodiments, the compound produced has the structure:

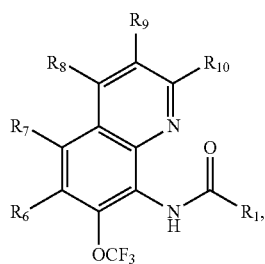

wherein
$R_1$ is —H, -(alkyl), -(alkenyl), -(alkynyl), -(aryl), -(heteroaryl), -(alkylaryl), -(alkylheteroaryl), —NH-(alkyl), —N(alkyl)2, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_6$, $R_7$, $R_8$, $R_9$, and $R_{10}$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, the compound produced has the structure:

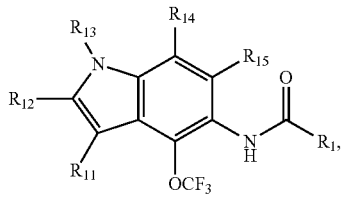

wherein
$R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_{11}$, $R_{12}$, $R_{13}$, $R_{14}$, and $R_{15}$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, the phenyl, pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone or quinazolinone is substituted with one or more of the following: halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-

(alkyl), —S-(alkenyl), —S-(alkynyl), —S-(aryl), —S-(heteroaryl), or an amino acid or protected amino acid.

In some embodiments, a process of producing a compound having the structure:

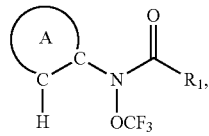

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)2, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

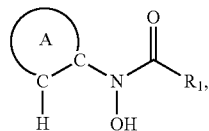

with a trifluoromethylating agent in the presence of a base in a first suitable solvent to produce the compound having the structure:

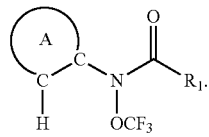

In some embodiments, a process of producing a trifluoromethoxylated aryl or trifluoromethoxylated heteroaryl having the structure:

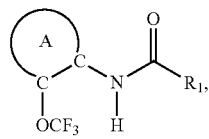

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)2, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(b) maintaining the compound having the structure:

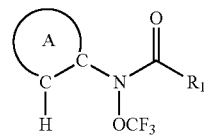

in a second suitable solvent to produce the trifluoromethoxylated aryl or trifluormethoxylated heteroaryl having the structure:

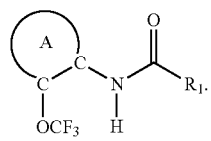

The present invention further provides a process of producing a trifluoromethoxylated aryl or trifluoromethoxylated heteroaryl having the structure:

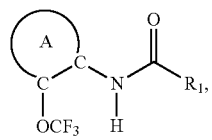

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)2, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

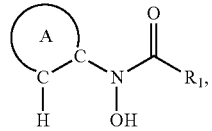

with a trifluoromethylating agent in the presence of a base in a first suitable solvent to produce a compound having the structure:

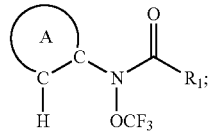

and (b) maintaining the compound produced in step (a) in a second suitable solvent to produce the trifluoromethoxylated aryl or trifluormethoxylated heteroaryl having the structure:

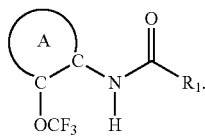

The present invention also provides a process of producing a trifluoromethoxylated aryl or trifluoromethoxylated heteroaryl having the structure:

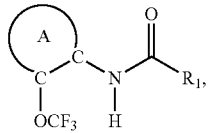

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), comprising:

(a) reacting a compound having the structure:

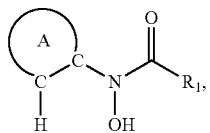

with a trifluoromethylating agent in a first suitable solvent under conditions to produce a compound having the structure:

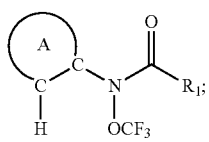

and (b) maintaining the compound produced in step (a) in the first suitable solvent under conditions sufficient to produce the trifluoromethoxylated aryl or trifluormethoxylated heteroaryl having the structure:

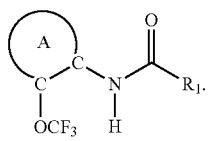

In some embodiments of the above process, A is a phenyl or pyridine.

In some embodiments of the above process, A is pyridine.

In some embodiments of the above process, the first suitable solvent is chloroform, dichloromethane, nitromethane, dimethylforamide, diethyl ether, tetrahydrofuran, dioxane, dichloroethane, or hexane.

In some embodiments of the above process, wherein trifluormethylating agent is Togni reagent I or Togni reagent II. The present invention also provides a compound having the structure:

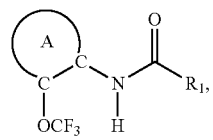

wherein

A is an aryl or heteroaryl, each with or without subsutitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl).

In some embodiments of the compound, A is a phenyl or pyridine. In some embodiments of the compound, A is a furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone, or a salt or ester thereof.

In some embodiments, a compound having the structure:

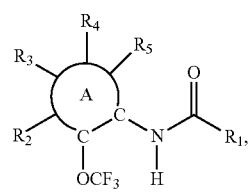

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of the above compound $R_2$, $R_3$, $R_4$ and $R_5$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine.

In some embodiments of the above compound R$_2$, R$_3$, R$_4$ and R$_5$ is each, independently, —H, pyrazoline, triazole, benzimidazole, benzotriazole, azaindole, or purine.

In some embodiments, a compound having the structure:

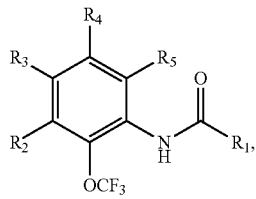

wherein

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), or —O-(heteroaryl), —S-(alkyl), —S-(alkenyl), —S-(alkynyl), —S-(aryl), or —S-(heteroaryl); and R$_2$, R$_3$, R$_4$ and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, a compound having the structure:

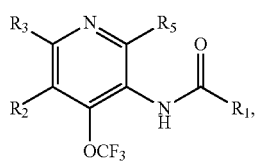

wherein

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), or —O-(heteroaryl), —S-(alkyl), —S-(alkenyl), —S-(alkynyl), —S-(aryl), or —S-(heteroaryl); and R$_2$, R$_3$, and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

The present invention also provides a compound having the structure:

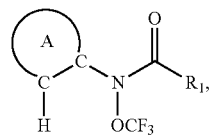

wherein

A is an aryl or heteroaryl, each with or without subsutitution; and

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl), or a salt or ester thereof.

In some embodiments of the compound, A is a phenyl or pyridine. In some embodiments of the compound, A is a furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, a compound having the structure:

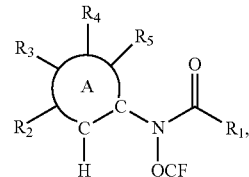

wherein

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl), —S-(alkyl), —S-(alkenyl), —S-(alkynyl), —S-(aryl), or —S-(heteroaryl); and R$_2$, R$_3$, R$_4$ and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)

NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, a compound having the structure:

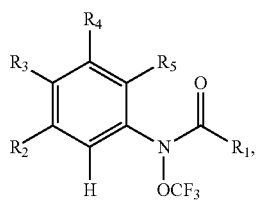

wherein

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), or —O-(heteroaryl), —S-(alkyl), —S-(alkenyl), —S-(alkynyl), —S-(aryl), or —S-(heteroaryl); and R$_2$, R$_3$, R$_4$ and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments, a compound having the structure:

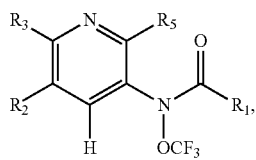

wherein

R$_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), or —O-(heteroaryl), —S-(alkyl), —S-(alkenyl), —S-(alkynyl), —S-(aryl), or —S-(heteroaryl); and R$_2$, R$_3$, and R$_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, or quinolone.

In some embodiments of any of the disclosed processes or compounds, R$_2$, R$_3$, R$_4$ and R$_5$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —C$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine, or any combination thereof.

In some embodiments of any of the disclosed processes or compounds, R$_2$, R$_3$, R$_4$ and R$_5$ is each, independently, —H, pyrazoline, triazole, benzimidazole, benzotriazole, azaindole, or purine, or any combination thereof.

In some embodiments of any of the disclosed processes or compounds, R$_6$, R$_7$, Re, R$_9$ and R$_{10}$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine, or any combination thereof.

In some embodiments of any of the disclosed processes or compounds, R$_6$, R$_7$, R$_8$, R$_9$ and R$_{10}$ is each, independently, —H, pyrazoline, triazole, benzimidazole, benzotriazole, azaindole, or purine, or any combination thereof.

In some embodiments of any of the disclosed processes or compounds, R$_{11}$, R$_{12}$, R$_{13}$, R$_{14}$ and R$_{15}$ is each, independently, —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl)-CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl), —S-(alkyl), —S-(alkenyl), —S-(alkynyl), —S-(aryl), —S-(heteroaryl), pyridine, furan, thiophene, pyrrole, thiazole, imidazole, pyrazole, isooxazole, isothiazole, naphthalene, anthracene, pyrimidine, pyrazine, pyridazine, indole, indoline, benzofuran, benzothiophene, quinolone, pyrazoline, triazole, benzimidazole, benzotriazole, azaindole, or purine, or any combination thereof.

In some embodiments of any of the disclosed processes or compounds, $R_{11}$, $R_{12}$, $R_{13}$, $R_{14}$ and $R_{15}$ is each, independently, —H, pyrazoline, triazole, benzimidazole, benzotriazole, azaindole, or purine, or any combination thereof.

In some embodiments, the compound of step (a) is purified by column chromatography prior to step (b).

In some embodiments, the trifluoromethylating reagent is 1-Trifluoromethyl-1,2-benziodoxol-3-(1H)-one (Togni reagent II), which may be purchased from Sigma Aldrich, St. Louis, Mo., USA (Catalog #771147). In some embodiments, the trifluoromethylating reagent is 3,3-Dimethyl-1-(trifluoromethyl)-1,2-benziodoxole (Togni reagent I), which may be purchased from Sigma Aldrich, St. Louis, Mo., USA (Catalog #696641).

In some embodiments, the first or second suitable solvent include, but are not limited to, inert organic solvents or mixtures thereof.

The process described herein is advantageous in that it avoids the need for highly toxic and thermally labile reagents, which is not particularly desirable for industrial implementation due to the hazards associated with such reagents.

The process described herein is also advantageous in that it may be performed in one-pot. The process described herein is further advantageous in that it avoids the need for highly toxic metal containing reagents.

The present reaction occurs under reaction conditions sufficient to produce the desired compound. Such conditions, e.g. temperature, time, molarity, etc., may be varied by one of ordinary skill in the art based on the methods and protocols described herein.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring. The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino, protected amino; ester or alkyl ester; and carboxyl. Where multiple substituent moieties are disclosed or claimed, the substituted compound can be independently substituted by one or more of the disclosed or claimed substituent moieties, singly or plurality. By independently substituted, it is meant that the (two or more) substituents can be the same or different.

The starting materials used in the method of the present invention may be prepared by techniques well known in organic synthesis and familiar to a practitioner ordinarily skilled in the art. However, these may not be the only means by which to synthesize or obtain the desired compounds.

The starting materials used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The reaction conditions used in the present invention may be varied by techniques well known in organic synthesis and familiar to a practitioner ordinarily skilled in the art to provide conditions sufficient to produce the desired product. Such techniques are described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein.

In the compounds in the process of the present invention, alkyl, alkenyl, alkynyl, aryl, heteroaryl groups can be further substituted by replacing one or more hydrogen atoms with alternative non-hydrogen groups.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect. The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect. A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidyl-cholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to methods described in PCT International Publication No. WO 2010/132815 A9. Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods

All air- and moisture-insensitive reactions were carried out under an ambient atmosphere, magnetically stirred, and monitored by thin layer chromatography (TLC) using Agela Technologies TLC plates pre-coated with 250 μm thickness silica gel 60 F254 plates and visualized by fluorescence quenching under UV light. Flash chromatography was performed on SiliaFlash® Silica Gel 40-63 μm 60 Å particle size using a forced flow of eluent at 0.3-0.5 bar pressure (Still, W. C. et al. *J. Org. Chem.* 1978, 43, 2925-2927.). All air- and moisture-sensitive manipulations were performed using oven-dried glassware, including standard Schlenk and glovebox techniques under an atmosphere of nitrogen. Diethyl etherand THF were distilled from deep purple sodium benzophenone ketyl. Methylene chloride, chloroform and acetonitrile were dried over $CaH_2$ and distilled. Nitromethane was dried over 4 Å molecular sieves. All other chemicals were used as received. All deuterated solvents were purchased from Cambridge Isotope Laboratories.

NMR spectra were recorded on either a Bruker Ascend700 spectrometer operating at 700 MHz for $^1H$ acquisitions and 175 MHz for $^{13}C$ acquisitions, a Bruker 500 Advance spectrometer operating at 500 MHz, 125 MHz, and 470 MHz for $^1H$, $^{13}C$, and $^{19}F$ acquisitions, respectively, a Bruker 400 Nanobay spectrometer operating at 400 MHz, 100 MHz, and 376 MHz for 1H, $^{13}C$, and $^{19}F$ acquisitions, respectively. Chemical shifts were referenced to the residual proton solvent peaks ($^1H$: $CDCl_3$, δ 7.26; $(CD_3)_2SO$, δ2.50; $CD_3OD$, δ3.31; $CD_3CN$, δ1.94), solvent $^{13}C$ signals ($CDCl_3$, δ77.16; $(CD_3)_2SO$, δ39.52; $CD_3OD$, δ49.00) (Fulmer, G. R. et al. *Organometallics.* 2010, 29, 2176-2179), dissolved or external neat $PhCF_3$ ($^{19}F$, δ−63.3 relative to $CFCl_3$) (Wang, X. et al. J. Am. Chem. Soc. 2013, 135, 10330-10333). Signals arelisted in ppm, and multiplicity identified as s=singlet, br=broad, d=doublet, t=triplet, q=quartet, m=multiplet; coupling constants in Hz; integration. High-resolution mass spectra were performed at Mass Spectrometry Services at the Univ. of Illinois at Urbana-Champaign and were obtained using Waters Q-TOF Ultima ESI mass spectrometer. Concentration under reduced pressure was performed by rotary evaporation at 25-30° C. at appropriate pressure. Purified compounds were further dried under high vacuum (0.01-0.05 Torr). Yields refer to purified and spectroscopically pure compounds.

Synthesis of Togni Reagent II

1-Chloro-1λ³-benzo[d] [1,2] iodaoxol-3 (1)-one

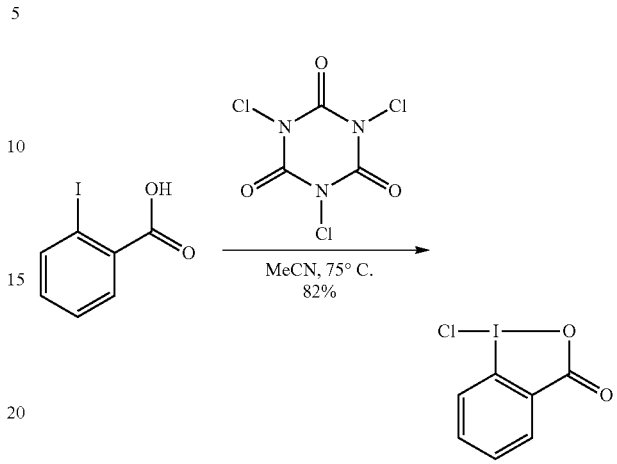

The compound was prepared according to the literature procedure (Matoušek, V. et al. *J. Org. Chem.* 2013, 78, 6763-6768). A suspension of 2-iodobenzoic acid (30.0 g, 0.121 mmol, 1.00 equiv) in MeCN (225 mL) was heated to 75° C. A solution of trichloroisocyanuric acid (9.46 g, 0.0407 mol, 1.01 $Cl^+$ equiv) in MeCN (45 mL) was added in one portion and the reaction mixture was heated at 75° C. for 10 min. The reaction mixture was diluted with MeCN (150 mL) and vacuum-filtered over an oven-preheated, sintered-glass funnel and the filter cake was rinsed with additional hot MeCN (150 mL). The filtrate was concentrated in vacuo to near dryness and the resulting yellow solid was collected by filtration and washed with cold MeCN. The mother liquor from filtration was partially concentrated in vacuo, giving a second crop of crystals. The combined crops were dried under vacuum overnight to afford the title compound as a slightly yellow crystalline solid (28.0 g, 0.0991 mol, 82%). NMR Spectroscopy: $^1H$ NMR (400 MHz, $CDCl_3$, 25° C., δ): 8.27 (dd, J=7.5, 1.5 Hz, 1H), 8.22 (dd, J=8.0, 0.5 Hz, 1H), 8.00 (ddd, J=8.5, 7.2, 1.6 Hz, 1H), 7.80 (td, J=7.4, 0.8 Hz, 1H). $^{13}C$ NMR (125 MHz, $CDCl_3$, 25° C., δ): 167.2, 136.8, 133.6, 132.0, 128.8, 127.0, 117.2. These spectroscopic data correspond to previously reported data.

(1-(trifluoromethyl)-1λ3-benzo[d][1,2]iodaoxol-3 (1H)-one)

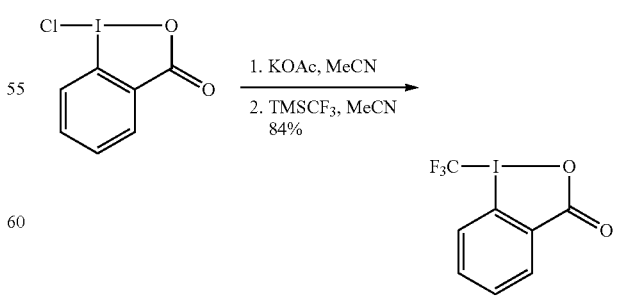

Potassium acetate (10.8 g, 0.110 mol, 2.00 equiv) was dried under vacuum at 150° C. for 30 min and then cooled to rt. 1-chloro-1λ3-benzo[d][1,2]iodaoxol-3(1H)-one (15.6 g, 0.0551 mol, 1.00 equiv) and MeCN (155 mL) were added and the reaction mixture was stirred at 75° C. for 2 h. The reaction mixture was cooled to rt. TMSCF$_3$ (8.97 mL, 0.0607 mol, 1.10 equiv) was added in one portion and the reaction mixture was stirred at rt for 15 h. MeCN (100 mL) was then added and the brown reaction mixture was heated to 75° C. and the hot reaction mixture was filtered through a pad of Celite, concentrated to about 50 mL end volume, and cooled to −20° C. The crystals were filtered off, washed with cold (−20° C.) MeCN (50 mL) and dried under vacuum. The mother liquor was again concentrated to approximately 15 mL end volume and cooled to −20° C. The crystals were filtered off and washed with a cold (−20° C.) MeCN (10 mL). Both crystalline fractions were dried under a high vacuum to afford the title compound as a white crystalline solid (14.6 g, 0.0463 mol, 84% yield). NMR Spectroscopy: $^1$H NMR (500 MHz, CDCl$_3$, 25° C., δ): 8.48 (dd, J=7.2, 1.7 Hz, 1H), 7.85-7.76 (m, 3H). $^{13}$C NMR (175 MHz, CDCl$_3$, 25° C., δ): 165.9, 135.9, 133.9, 132.1, 132.0, 127.3 (q, J=2.5 Hz), 114.9, 107.3 (q, J=378.8 Hz). $^{19}$F NMR (376 MHz, CDCl$_3$, 25° C., δ): −34.2 (s). These spectroscopic data correspond to previously reported data.

Preparation of Starting Hydroxylamines

General Procedure for the Synthesis of N-aryl-N-hydroxylamines

Under N$_2$ atmosphere, a suspension of aryl nitro compound (1.00 equiv) and Rh/C (5 mol %) in THF (0.20M) was cooled to 0° C. Hydrazine monohydrate (1.20 equiv) was added dropwise. The reaction mixture stirred at 0° C. until the TLC analysis indicated a complete consumption of the starting material. The reaction mixture was filtered through a short pad of celite and concentrated in vacuo. The residue was used directly for the next step without further purification unless otherwise stated.

General Procedure for the Synthesis of Protected N-aryl-N-hydroxylamines

To a stirred suspension of N-aryl-N-hydroxylamine (1.00 equiv) and NaHCO$_3$ (1.20 equiv) in Et$_2$O (0.20M) at 0° C. under N$_2$ was slowly added a solution of protecting group precursor (1.20 equiv) in Et$_2$O (0.24 M) via a syringe pump (at a rate of 10 mL/h). The reaction was stirred at 0° C. until the TLC analysis indicated a complete consumption of the starting material. The reaction mixture was filtered through a short pad of celite and concentrated in vacuo. The residue was purified by chromatography on silica gel.

N-Phenyl-N-hydroxylamine (S1a)

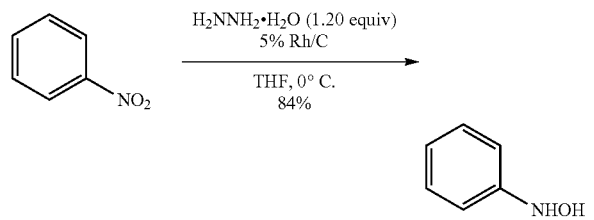

Under N$_2$ atmosphere, a suspension of nitrobenzene (1.00 g, 8.10 mmol, 1.00 equiv) and 5% Rh/C (40.5 mg, 0.30 mol % Rh) in THF (25.0 mL, 0.324 M) was cooled to 0° C. Hydrazine monohydrate (0.487 g, 9.72 mmol, 1.20 equiv) was added dropwise. The reaction mixture stirred at 0° C. for 1 h and then slowly warmed up to rt and stirred at rt for 4 h. The reaction mixture was filtered through a short pad of celite and concentrated in vacuo. Recrystallization from CH$_2$Cl$_2$/hexanes at −20° C. afforded the title compound as a white solid (0.740 g, 6.78 mmol, 84% yield). R$_f$=0.25 (hexanes/EtOAc 1:1 (v/v)). NMR Spectroscopy: $^1$H NMR (500 MHz, (CD$_3$)$_2$SO, δ): 8.25 (s, 1H), 8.21 (s, 1H), 7.14 (t, J=7.9 Hz, 2H), 6.81 (d, J=7.9 Hz, 2H), 6.72 (t, J=7.9 Hz, 1H). $_{13}$C NMR (125 MHz, (CD$_3$)$_2$SO, δ): 152.1, 128.4, 119.2, 112.9.

4-(Hydroxyamino)benzonitrile (S1b)

Under N$_2$ atmosphere, a suspension of 4-nitrobenzonitrile (2.00 g, 13.5 mmol, 1.00 equiv) and 5% Rh/C (77.6 mg, 0.30 mol % Rh) in THF (40.0 mL, 0.338 M) was cooled to 0° C. Hydrazine monohydrate (0.810 g, 16.2 mmol, 1.20 equiv) was added dropwise. The reaction mixture stirred at 0° C. for 1 h and then slowly warmed up to rt and stirred at rt for 1 h. The reaction mixture was filtered through a short pad of celite and concentrated in vacuo to afford the title compound as a yellow solid (1.80 g, 13.4 mmol, 99% yield). R$_f$=0.14 (hexanes/EtOAc 5:1 (v/v)). NMR Spectroscopy: $^1$H NMR (400 MHz, (CD$_3$)$_2$SO, δ): 9.10 (s, 1H), 8.76 (s, 1H), 7.57-7.52 (m, 2H), 7.85 (d, J=8.6 Hz, 2H). $_{13}$C NMR (100 MHz, (CD$_3$)$_2$SO, δ): 155.4, 133.1, 120.1, 111.8, 90.1.

1-(4-(Hydroxyamino)phenyl)ethan-1-one (S1c)

Under N$_2$ atmosphere, a suspension of 1-(4-nitrophenyl) ethan-1-one (3.00 g, 18.2 mmol, 1.00 equiv) and 5% Rh/C (104 mg, 0.30 mol % Rh) in THF (90.0 mL, 0.202 M) was cooled to 0° C. Hydrazine monohydrate (1.09 g, 21.8 mmol, 1.20 equiv) was added dropwise. The reaction mixture stirred at 000° C. for 3.5 h. The reaction mixture was filtered through a short pad of celite and concentrated in vacuo to afford the title compound as a yellow solid (2.80 g, 18.5 mmol, quant yield). $R_f$=0.27 (hexanes/EtOAc 5:1 (v/v)). NMR Spectroscopy: $^1$H NMR (400 MHz, (CD$_3$)$_2$SO, δ): 8.99 (s, 1H), 8.67 (s, 1H), 7.79 (d, J=8.7 Hz, 2H), 6.82 (d, J=8.7 Hz, 2H), 2.44 (s, 3H). $^{13}$C NMR (100 MHz, (CD$_3$)$_2$SO, δ): 195.6, 155.9, 129.8, 127.7, 110.9, 26.1.

4-(Hydroxyamino)-N,N-dimethylbenzamide (S1d)

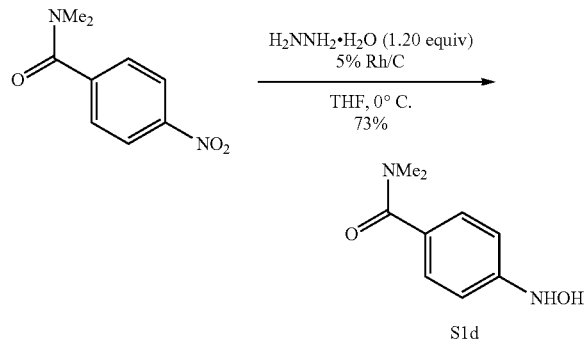

Under N$_2$ atmosphere, a suspension of N,N-dimethyl-4-nitrobenzamide (1.00 g, 6.53 mmol, 1.00 equiv) and 5% Rh/C (50.0 mg, 0.30 mol % Rh) in THF (25.0 mL, 0.261 M) was cooled to 0° C. Hydrazine monohydrate (1.09 g, 21.8 mmol, 1.20 equiv) was added dropwise. The reaction mixture stirred at 0° C. for 2 h. The reaction mixture was filtered through a short pad of celite. The celite was washed with EtOAc and the combined organic layers were concentrated in vacuo to afford the title compound as a white solid (0.860 g, 4.77 mmol, 73% yield). $R_f$=0.22 (hexanes/EtOAc 1:4 (v/v)). NMR Spectroscopy: 1H NMR (700 MHz, CD$_3$OD, 25° C., δ): 7.32 (d, J=8.5 Hz, 2H), 6.97 (d, J=8.5 Hz, 2H), 3.06 (s, 6H). $^{13}$C NMR (175 MHz, CD$_3$OD, 25° C., δ): 174.3, 154.9, 129.4, 128.2, 113.7, 40.3, 35.9. Mass Spectrometry: HRMS (ESI-TOF) (m/z): calcd for C$_9$H$_{13}$N$_2$O$_2$ ([M+H]$_+$), 181.0977, found, 181.0982.

N-(4-Fluorophenyl)hydroxylamine (S1e)

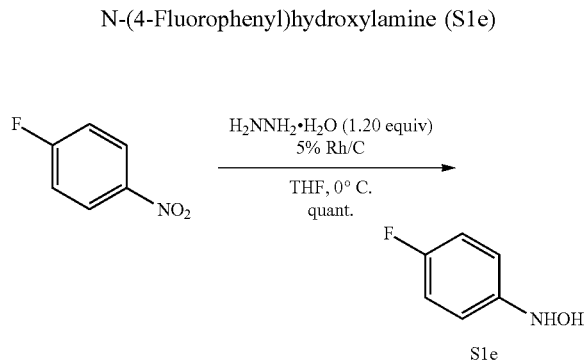

Under N$_2$ atmosphere, a suspension of 1-fluoro-4-nitrobenzene (2.00 g, 14.2 mmol, 1.00 equiv) and 5% Rh/C (81.4 mg, 0.30 mol % Rh) in THF (40.0 mL, 0.355 M) was cooled to 0° C. Hydrazine monohydrate (0.810 g, 16.2 mmol, 1.20 equiv) was added dropwise. The reaction mixture stirred at 0° C. for 2 h. The reaction mixture was filtered through a short pad of celite and concentrated in vacuo to afford the title compound as a yellow solid (1.81 g, 14.2 mmol, quant yield). $R_f$=0.29 (hexanes/EtOAc 4:1 (v/v)). NMR Spectroscopy: $^1$H NMR (500 MHz, (CD$_3$)$_2$SO, δ): 8.33 (d, J=2.4 Hz, 1H), 8.19 (s, 1H), 7.02-6.97 (m, 2H), 6.85-6.81 (m, 2H). $^{13}$C NMR (125 MHz, (CD$_3$)$_2$SO, δ): 156.2 (d, J=232.7 Hz), 148.5 (d, J=1.5 Hz), 114.8 (d, J=22.1 Hz), 114.2 (d, J=7.8 Hz). $^{19}$F NMR (376 MHz, (CD$_3$)$_2$SO, 25° C., δ): −127.6 (s). Mass Spectrometry: HRMS (ESI-TOF) (m/z): calcd for C$_6$H$_7$NOF ([M+H]$_+$), 128.0512, found, 128.0513.

N-(4-Chlorophenyl)hydroxylamine (S1f)

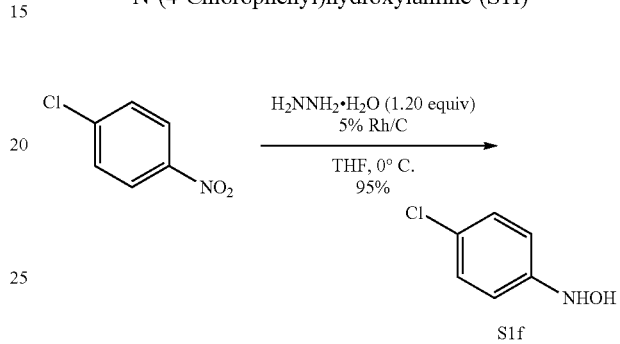

Under N$_2$ atmosphere, a suspension of 1-chloro-4-nitrobenzene (2.00 g, 12.7 mmol, 1.00 equiv) and 5% Rh/C (72.9 mg, 0.30 mol % Rh) in THF (40.0 mL, 0.318 M) was cooled to 0° C. Hydrazine monohydrate (0.762 g, 15.2 mmol, 1.20 equiv) was added dropwise. The reaction mixture stirred at 0° C. for 2.5 h. The reaction mixture was filtered through a short pad of celite and concentrated in vacuo to afford the title compound as a yellow solid (1.72 g, 12.0 mmol, 95% yield). $R_f$=0.27 (hexanes/EtOAc 5:1 (v/v)). NMR Spectroscopy: $^1$H NMR (500 MHz, (CD$_3$)$_2$SO, δ): 8.43 (d, J=2.2 Hz, 1H), 8.40 (s, 1H), 7.19 (d, J=8.8 Hz, 2H), 6.87-6.83 (m, 2H). $^{13}$C NMR (125 MHz, (CD$_3$)$_2$SO, δ): 151.0, 128.3, 122.6, 114.4.

N-(4-Bromophenyl)hydroxylamine (S1g)

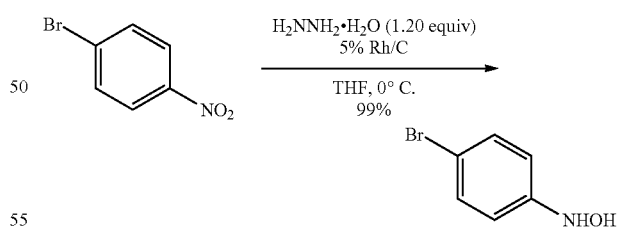

Under N$_2$ atmosphere, a suspension of 1-bromo-4-nitrobenzene (3.00 g, 14.9 mmol, 1.00 equiv) and 5% Rh/C (85.3 mg, 0.30 mol % Rh) in THF (100 mL, 0.149 M) was cooled to 0° C. Hydrazine monohydrate (0.892 g, 16.2 mmol, 1.20 equiv) was added dropwise. The reaction mixture stirred at 0° C. for 2.5 h. The reaction mixture was filtered through a short pad of celite and concentrated in vacuo to afford the title compound as a brown solid (2.78 g, 14.8 mmol, 99% yield). $R_f$=0.30 (hexanes/EtOAc 5:1 (v/v)).

NMR Spectroscopy: $^1$H NMR (500 MHz, (CD$_3$)$_2$SO, δ): 8.42 (s, 1H), 8.40 (s, 1H), 7.30 (d, J=8.8 Hz, 2H), 6.78 (d, J=8.8 Hz, 2H). $^{13}$C NMR (125 MHz, (CD$_3$)$_2$SO, δ): 151.4, 131.1, 114.8, 110.1. Mass Spectrometry: HRMS (ESI-TOF) (m/z): calcd for C$_6$H$_7$NOBr ([M+H]$_+$), 187.9711, found, 187.9714.

N-(4-Iodophenyl)hydroxylamine (S1h)

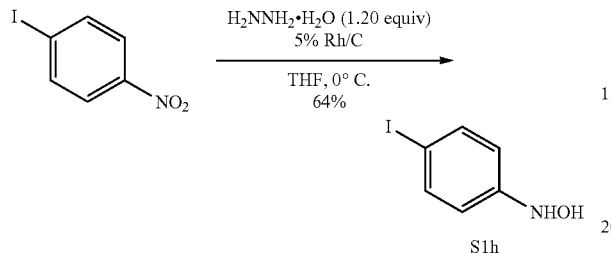

Under N$_2$ atmosphere, a suspension of 1-iodo-4-nitrobenzene (2.00 g, 8.03 mmol, 1.00 equiv) and 5% Rh/C (46.1 mg, 0.30 mol % Rh) in THF (30.0 mL, 0.268 M) was cooled to 0° C. Hydrazine monohydrate (0.482 g, 9.64 mmol, 1.20 equiv) was added dropwise. The reaction mixture stirred at 000° C. for 2 h. The reaction mixture was filtered through a short pad of celite and concentrated in vacuo. Recrystallization from CH$_2$Cl$_2$/hexanes at −20° C. afforded the title compound as a yellow solid (1.20 g, 5.11 mmol, 64% yield). R$_f$=0.26 (hexanes/EtOAc 5:1 (v/v)). NMR Spectroscopy: $^1$H NMR (500 MHz, (CD$_3$)$_2$SO, δ): 8.41 (s, 2H), 7.46 (d, J=2.7 Hz, 1H), 7.44 (d, J=2.7 Hz, 1H), 6.67 (d, J=2.6 Hz, 1H), 6.65 (d, J=2.6 Hz, 1H). $^{13}$C NMR (125 MHz, (CD$_3$)$_2$SO, δ): 152.4, 137.3, 115.8, 81.1.

N-(3-Fluorophenyl)hydroxylamine (S1i)

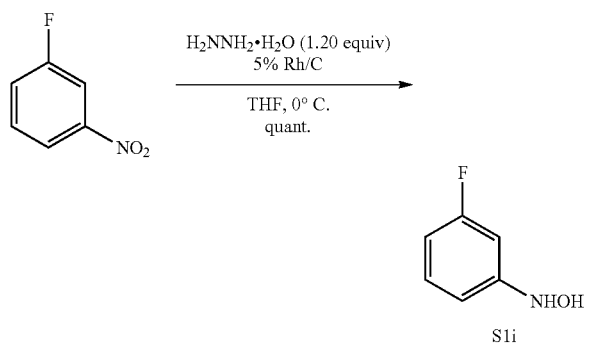

Under N$_2$ atmosphere, a suspension of 1-fluoro-3-nitrobenzene (1.00 g, 7.09 mmol, 1.00 equiv) and 5% Rh/C (50.0 mg, 0.30 mol % Rh) in THF (25.0 mL, 0.284 M) was cooled to 0° C. Hydrazine monohydrate (0.390 g, 7.80 mmol, 1.10 equiv) was added dropwise. The reaction mixture stirred at 0° C. for 1 h. The reaction mixture was filtered through a short pad of celite. The celite was washed with EtOAc and the combined organic layers were concentrated in vacuo to afford the title compound as a white solid (0.870 g, 7.12 mmol, quant yield). R$_f$=0.28 (hexanes/EtOAc 4:1 (v/v)). $^1$H NMR (400 MHz, (CD$_3$)$_2$SO, δ): 8.50 (s, 1H), 8.45 (d, J=2.1 Hz, 1H), 7.17-7.14 (m, 1H), 6.61-6.58 (m, 2H), 6.50-6.48 (m, 1H). $^{13}$C NMR (100 MHz, (CD$_3$)$_2$SO, δ): 163.0 (d, J=238.8 Hz), 154.4 (d, J=10.2 Hz), 130.0 (d, J=9.6 Hz), 108.7 (d, J=2.3 Hz), 105.1 (d, J=21.4 Hz), 99.3 (d, J=25.5 Hz). $^{19}$F NMR (376 MHz, (CD$_3$)$_2$SO, 25° C., δ): −117.3 (s). Mass Spectrometry: HRMS (ESI-TOF) (m/z): calcd for C$_6$H$_7$NOF ([M+H]$_+$), 128.0512, found, 128.0513.

N-(2-Bromophenyl)hydroxylamine (S1j)

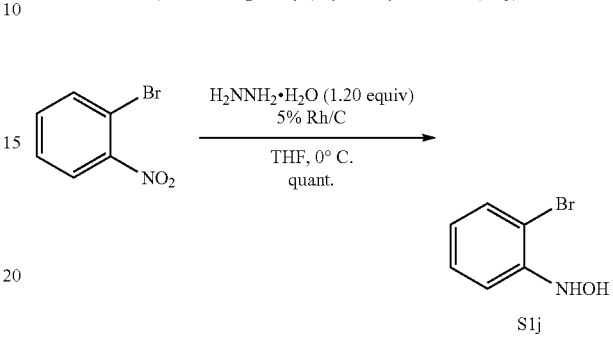

Under N$_2$ atmosphere, a suspension of 1-bromo-2-nitrobenzene (1.00 g, 4.95 mmol, 1.00 equiv) and 5% Rh/C (28.4 mg, 0.30 mol % Rh) in THF (50.0 mL, 0.0990M) was cooled to 0° C. Hydrazine monohydrate (0.297 g, 5.94 mmol, 1.20 equiv) was added dropwise. The reaction mixture stirred at 0° C. for 2.5 h. The reaction mixture was filtered through a short pad of celite, the celite was washed with EtOAc and the combined organic layers were concentrated in vacuo and solidified upon standing at −20° C. to afford the title compound as a yellow solid (0.930 g, 4.95 mmol, quant yield). R$_f$=0.21 (hexanes/EtOAc 1:1 (v/v)). NMR Spectroscopy: $^1$H NMR (500 MHz, (CD$_3$)$_2$SO, δ): 8.58 (m, 1H), 7.98 (s, 1H), 7.40 (dd, J=7.8, 0.85 Hz, 1H), 7.28-7.24 (m, 1H), 7.18-7.15 (m, 1H), 6.74-6.70 (m, 1H). $^{13}$C NMR (125 MHz, (CD$_3$)$_2$SO, δ): 148.6, 131.8, 128.2, 120.7, 114.6, 106.7. Mass Spectrometry: HRMS (ESI-TOF) (m/z): calcd for C$_6$H$_7$NOBr ([M+H]$_+$), 187.9711, found, 187.9710.

N-(3-Methoxy-5-(trifluoromethyl)phenyl)hydroxylamine (S1k)

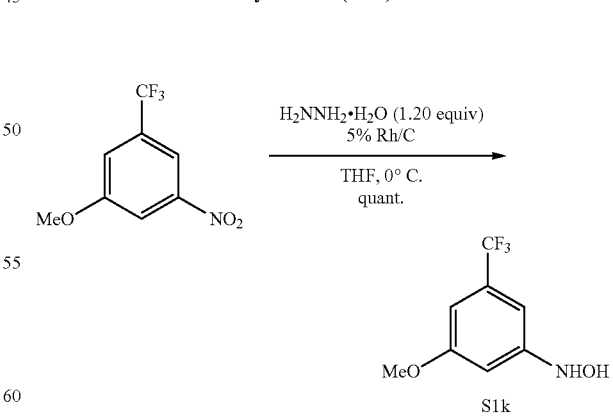

Under N$_2$ atmosphere, a suspension of 1-methoxy-3-nitro-5-(trifluoromethyl)benzene (1.00 g, 4.50 mmol, 1.00 equiv) and 5% Rh/C (25.9 mg, 0.30 mol % Rh) in THF (15.0 mL, 0.300 M) was cooled to 0° C. Hydrazine monohydrate (0.270 g, 5.40 mmol, 1.20 equiv) was added dropwise. The reaction mixture stirred at 0° C. for 1 h and then slowly warmed up to rt and stirred at rt for 1 h. The reaction mixture was filtered through a short pad of celite, the celite was washed with EtOAc and the combined organic layers were concentrated in vacuo to afford the title compound as a yellow solid (0.960 g, 4.60 mmol, quant yield). $R_f$=0.29 (hexanes/EtOAc 4:1 (v/v)). NMR Spectroscopy: $^1$H NMR (400 MHz, (CD$_3$)$_2$SO, δ): 8.65 (s, 1H), 8.58 (br. s, 1H), 6.68 (s, 1H), 6.61 (s, 1H), 6.57 (s, 1H), 3.76 (s, 3H). $^{13}$C NMR (100 MHz, (CD$_3$)$_2$SO, δ): 160.3, 154.3, 130.4 (q, J=31.0 Hz), 124.2 (q, J=271.0 Hz), 101.6 (q, J=4.1 Hz), 101.3, 101.0 (q, J=3.9 Hz), 55.3. $^{19}$F NMR (376 MHz, (CD$_3$)$_2$SO, 25° C., δ): −63.6 (s). Mass Spectrometry: HRMS (ESI-TOF) (m/z): calcd for C$_8$H$_9$NO$_2$F$_3$ ([M+H]$_+$), 208.0585, found, 208.0579.

N-(3-(Trifluoromethyl)phenyl)hydroxylamine (S1l)

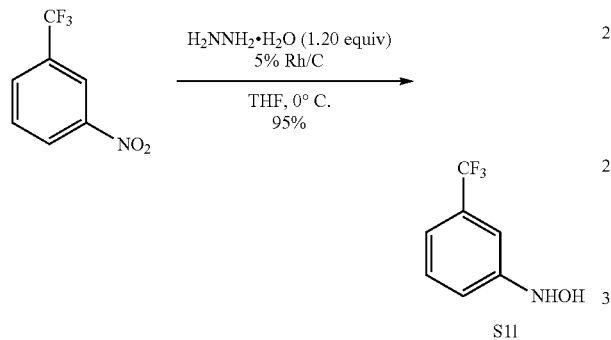

Under N$_2$ atmosphere, a suspension of 1-nitro-3-(trifluoromethyl)benzene (1.00 g, 5.21 mmol, 1.00 equiv) and 5% Rh/C (50 mg, 0.30 mol % Rh) in THF (25.0 mL, 0.208 M) was cooled to 0° C. Hydrazine monohydrate (0.314 g, 5.73 mmol, 1.10 equiv) was added dropwise. The reaction mixture stirred at 0° C. for 2 h. The reaction mixture was filtered through a short pad of celite, the celite was washed with EtOAc and the combined organic layers were concentrated in vacuo to afford the title compound as a yellow solid (0.880 g, 4.97 mmol, 95% yield). $R_f$=0.30 (hexanes/EtOAc 4:1 (v/v)). $^1$H NMR (400 MHz, (CD$_3$)$_2$SO, δ): 8.66 (s, 1H), 8.58 (s, 1H), 7.37 (t, J=7.8 Hz, 1H), 7.09 (s, 1H), 7.07-7.03 (m, 2H). $^{13}$C NMR (175 MHz, (CD$_3$)$_2$SO, δ): 152.7, 129.4 (q, J=30.6 Hz), 124.4 (q, J=270.6 Hz), 116.3, 115.2 (d, J=3.8 Hz), 111.9, 108.5 (q, J=4.0 Hz). $^{19}$F NMR (376 MHz, (CD$_3$)$_2$SO, 25° C., δ): −63.4 (s).

N-(3-Methoxyphenyl)hydroxylamine (S1m)

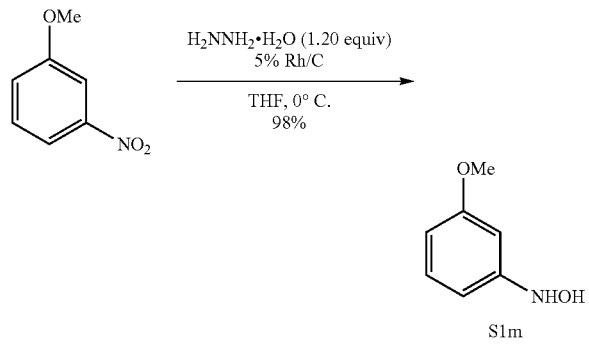

Under N$_2$ atmosphere, a suspension of 1-methoxy-3-nitrobenzene (1.00 g, 6.53 mmol, 1.00 equiv) and 5% Rh/C (50 mg, 0.30 mol % Rh) in THF (25.0 mL, 0.261 M) was cooled to 0° C. Hydrazine monohydrate (0.360 g, 7.19 mmol, 1.10 equiv) was added dropwise. The reaction mixture stirred at 0° C. for 2 h. The reaction mixture was filtered through a short pad of celite, the celite was washed with EtOAc and the combined organic layers were concentrated in vacuo to afford the title compound as a white solid (0.890 g, 6.40 mmol, 98% yield). $R_f$=0.47 (hexanes/EtOAc 3:2 (v/v)). NMR Spectroscopy: $^1$H NMR (500 MHz, (CD$_3$)$_2$SO, 25° C., δ): 8.26 (d, J=2.2 Hz, 1H), 8.23 (s, 1H), 7.04 (t, J=8.0 Hz, 1H), 6.38-6.41 (m, 2H), 6.30 (dd, J=8.0, 2.3 Hz, 1H), 3.68 (s, 3H). $_{13}$C NMR (125 MHz, (CD$_3$)$_2$SO, 25° C., δ): 159.8, 153.5, 129.1, 105.5, 104.6, 98.5, 54.6. Mass Spectrometry: HRMS (ESI-TOF) (m/z): calcd for C$_7$H$_{10}$NO$_2$ ([M+H]$_+$), 140.0712, found, 140.0714.

Methyl 3-(hydroxyamino)benzoate (S1n)

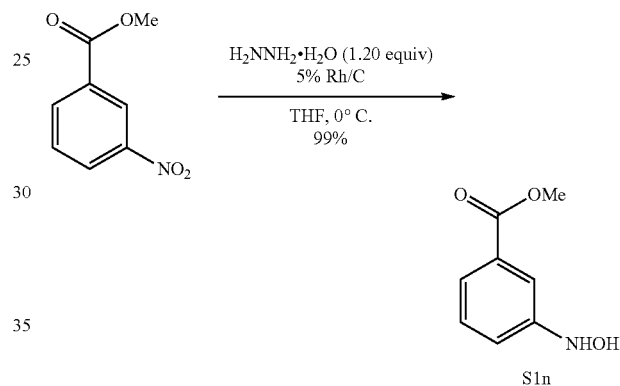

Under N$_2$ atmosphere, a suspension of methyl 3-nitrobenzoate (2.00 g, 11.0 mmol, 1.00 equiv) and 5% Rh/C (63.0 mg, 0.30 mol % Rh) in THF (40.0 mL, 0.275 M) was cooled to 0° C. Hydrazine monohydrate (0.663 g, 13.3 mmol, 1.20 equiv) was added dropwise. The reaction mixture stirred at 0° C. for 2.5 h. The reaction mixture was filtered through a short pad of celite, the celite was washed with EtOAc and the combined organic layers were concentrated in vacuo to afford the title compound as a light yellow solid (1.82 g, 10.9 mmol, 99% yield). $R_f$=0.19 (hexanes/EtOAc 4:1 (v/v)). NMR Spectroscopy: $^1$H NMR (500 MHz, (CD$_3$)$_2$SO, δ): 8.51 (s, 1H), 8.49 (d, J=2.1 Hz, 1H), 7.45 (s, 1H), 7.35-7.28 (m, 2H), 7.07-7.04 (m, 1H), 3.82 (s, 3H). $^{13}$C NMR (125 MHz, (CD$_3$)$_2$SO, δ): 166.6, 152.4, 130.0, 128.9, 119.9, 117.5, 113.2, 52.1. Mass Spectrometry: HRMS (ESI-TOF) (m/z): calcd for C$_8$H$_{10}$NO$_3$ ([M+H]$_+$), 168.0661, found, 168.0666.

N-(2-Chloro-5-(trifluoromethyl)phenyl)hydroxylamine (S1o)

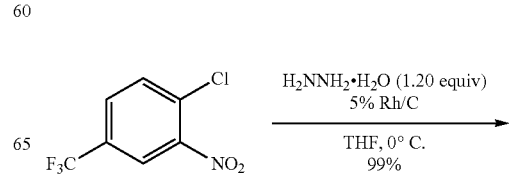

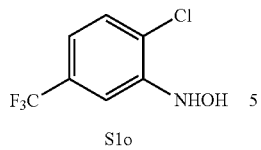

Under N₂ atmosphere, a suspension of 1-chloro-2-nitro-4-(trifluoromethyl)benzene (1.00 g, 4.43 mmol, 1.00 equiv) and 5% Rh/C (25.5 mg, 0.30 mol % Rh) in THF (45.0 mL, 0.0984 M) was cooled to 0° C. Hydrazine monohydrate (0.266 g, 5.32 mmol, 1.20 equiv) was added dropwise. The reaction mixture stirred at 0° C. for 1.5 h. The reaction mixture was filtered through a short pad of celite, the celite was washed with EtOAc and the combined organic layers were concentrated in vacuo and solidified upon standing at −20° C. to afford the title compound as a yellow solid (0.930 g, 4.40 mmol, 99% yield). $R_f$=0.31 (hexanes/EtOAc 1:1 (v/v)). NMR Spectroscopy: ¹H NMR (500 MHz, (CD₃)₂SO, δ): 8.86 (s, 1H), 8.74 (s, 1H), 7.49 (d, J=8.2 Hz, 1H), 7.36 (d, J=1.8 Hz, 1H), 7.10-7.08 (m, 1H). ¹³C NMR (125 MHz, (CD₃)₂SO, δ): 148.4, 129.8, 128.5 (q, J=31.6 Hz), 124.1 (q, J=270.6 Hz), 120.7, 115.9 (m), 109.7 (m). ¹⁹F NMR (376 MHz, (CD₃)₂SO, 25° C., δ): −63.5 (s). Mass Spectrometry: HRMS (ESI-TOF) (m/z): calcd for C₇H₆NOClF₃ ([M+H]₊), 212.0090, found, 212.0092.

3-benzyl-8-chloro-7-(hydroxyamino) quinazolin-4(3H)-one (S1p)

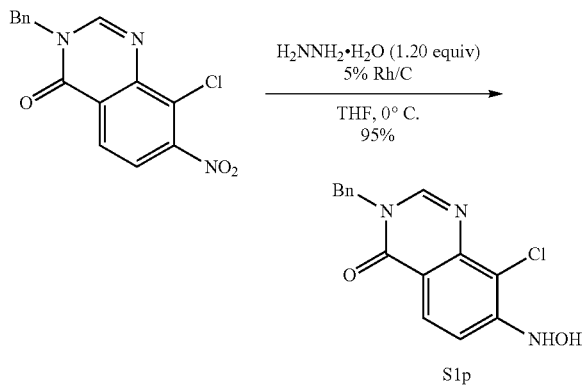

Under N₂ atmosphere, a suspension of 3-benzyl-8-chloro-7-nitroquinazolin-4(3H)-one (1.05 g, 3.33 mmol, 1.00 equiv) and 5% Rh/C (50.0 mg, 0.30 mol % Rh) in THF (20 mL, 0.167 M) was cooled to 0° C. Hydrazine monohydrate (0.183 g, 3.66 mmol, 1.20 equiv) was added dropwise. The reaction mixture stirred at 0° C. for 4 h. The reaction mixture was filtered through a short pad of celite and concentrated in vacuo to afford the title compound as a yellow solid (0.950 g, 3.15 mmol, 95% yield). $R_f$=0.22 (hexanes/EtOAc 4:1 (v/v)). NMR Spectroscopy: ¹H NMR (700 MHz, (CD₃)₂SO, δ): 8.86 (s, 1H), 8.74 (s, 1H), 8.40 (s, 1H), 7.76 (s, 1H), 7.66 (s, 1H), 7.35-7.34 (m, 4H), 7.30-7.28 (m, 1H), 5.18 (s, 21H). ¹³C NMR (175 MHz, (CD₃)₂SO, δ): 159.7, 146.9, 145.9, 141.3, 136.9, 128.6, 127.7, 127.6, 127.2, 124.8, 121.4, 108.0, 48.8. Mass Spectrometry: HRMS (ESI-TOF) (m/z): calcd for. C₁₅H₁₃N₃O₂Cl ([M+H]₊), 302.0696, found, 302.0690.

Methyl 4-(hydroxyamino)benzoate (S1q)

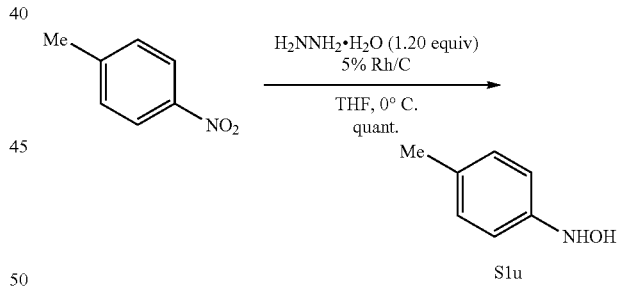

Under N₂ atmosphere, a suspension of methyl 4-nitrobenzoate (5.00 g, 27.6 mmol, 1.00 equiv) and 5% Rh/C (159 mg, 0.30 mol % Rh) in THF (300 mL, 0.0920 M) was cooled to 0° C. Hydrazine monohydrate (1.52 g, 30.4 mmol, 1.20 equiv) was added dropwise. The reaction mixture stirred at 0° C. for 5 h. The reaction mixture was filtered through a short pad of celite, the celite was washed with EtOAc and the combined organic layers were concentrated in vacuo to afford the title compound as a yellow solid (4.62 g, 27.6 mmol, quant yield). $R_f$=0.23 (hexanes/EtOAc 4:1 (v/v)). NMR Spectroscopy: ¹H NMR (500 MHz, (CD₃)₂SO, δ): 8.95 (s, 1H), 8.64 (d, J=1.5 Hz, 1H), 7.76 (d, J=8.7 Hz, 2H), 6.82 (d, J=8.7 Hz, 2H), 3.77 (s, 3H). ¹³C NMR (125 MHz, (CD₃)₂SO, δ): 166.2, 156.0, 130.4, 119.1, 111.2, 51.4. Mass Spectrometry: HRMS (ESI-TOF) (m/z): calcd for C₈H₁₀NO₃ ([M+H]₊), 168.0661, found, 168.0667.

N-(p-Tolyl)hydroxylamine (S1u)

Under N₂ atmosphere, a suspension of 1-methyl-4-nitrobenzene (2.50 g, 18.3 mmol, 1.00 equiv) and 5% Rh/C (104.8 mg, 0.30 mol % Rh) in THF (91.0 mL, 0.200 M) was cooled to 0° C. Hydrazine monohydrate (1.11 g, 21.9 mmol, 1.20 equiv) was added dropwise. The reaction mixture was stirred at 0° C. for 2.5 h, filtered through a short pad of celite and concentrated in vacuo to afford the title compound as a brown solid (2.25 g, 18.3 mmol, quant yield). $R_f$=0.20 (hexanes/EtOAc 4:1 (v/v)). NMR Spectroscopy: ¹H NMR (400 MHz, (CD₃)₂SO, δ): 8.20 (d, J=2.3 Hz, 1H), 8.06 (s, 1H), 6.96 (d, J=8.2 Hz, 2H), 6.74 (d, J=8.2 Hz, 2H), 2.19 (s, 1H). ¹³C NMR (100 MHz, (CD₃)₂SO, δ): 149.7, 128.8, 127.8, 113.3, 20.2. Mass Spectrometry: HRMS (ESI-TOF) (m/z): calcd for C₇H₁₀NO ([M+H]₊), 124.0762, found, 124.0761.

Methyl (R)-2-acetamido-3-(4-(hydroxyamino)phenyl)propanoate (S1v)

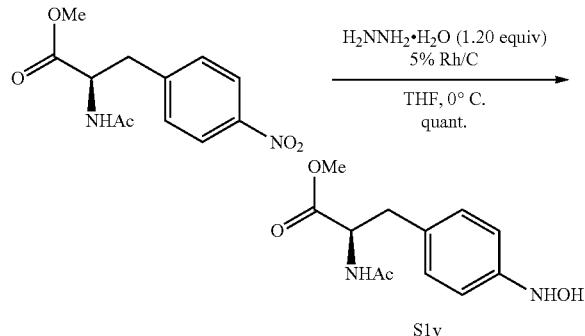

Under N₂ atmosphere, a suspension of methyl (R)-2-acetamido-3-(4-nitrophenyl)propanoate (1.00 g, 3.76 mmol, 1.00 equiv) and 5% Rh/C (21.6 mg, 0.30 mol % Rh) in THF (40 mL, 0.094 M) was cooled to 0° C. Hydrazine monohydrate (0.226 g, 4.51 mmol, 1.20 equiv) was added dropwise. The reaction mixture stirred at 0° C. for 8 h, filtered through a short pad of celite and concentrated in vacuo to afford the title compound as a yellow solid (0.950 g, 3.77 mmol, quant yield). $R_f$=0.42 (EtOAc). NMR Spectroscopy: $^1$H NMR (500 MHz, (CD₃)₂SO, δ): 8.14 (s, 1H), 8.12 (s, 1H), 8.05 (s, 1H), 7.00 (d, J=8.3 Hz, 2H), 6.76 (d, J=8.3 Hz, 2H), 4.39 (dd, J=8.3, 14.1 Hz, 1H), 3.58 (s, 3H), 2.89 (dd, J=8.8, 14.1 Hz, 1H), 2.77 (dd, J=8.8, 14.1 Hz, 1H), 1.80 (s, 3H). $^{13}$C NMR (125 MHz, (CD₃)₂SO, δ): 172.1, 169.0, 150.5, 128.8, 127.6, 112.9, 53.8, 51.4, 36.2, 22.1.

N-(Quinolin-8-yl)hydroxylamine (S1w)

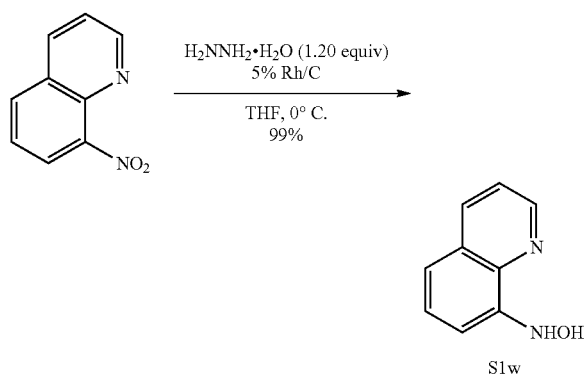

Under N₂ atmosphere, a suspension of 8-nitroquinoline (1.00 g, 5.74 mmol, 1.00 equiv) and 5% Rh/C (32.9 mg, 0.30 mol % Rh) in THF (60 mL, 0.096 M) was cooled to 0° C. Hydrazine monohydrate (0.345 g, 6.89 mmol, 1.20 equiv) was added dropwise. The reaction mixture was stirred at 0° C. for 4 h, filtered through a short pad of celite and concentrated in vacuo to afford the title compound as a brown solid (0.910 g, 5.68 mmol, 99% yield). $R_f$=0.50 (hexanes/EtOAc 5:1 (v/v)). NMR Spectroscopy: $^1$H NMR (500 MHz, (CD₃)₂SO, δ): 8.78-8.75 (m, 2H), 8.68 (s, 1H), 8.26 (d, J=8.2 Hz, 1H), 7.51 (dd, J=4.1, 8.2 Hz, 1H), 7.47 (t, J=7.9 Hz, 1H), 7.30 (d, J=8.2 Hz, 1H), 7.22 (d, J=7.9 Hz, 1H). $^{13}$C NMR (125 MHz, (CD₃)₂SO, δ): 147.7, 147.3, 137.1, 135.9, 127.7, 127.3, 121.6, 117.2, 109.3. Mass Spectrometry: HRMS (ESI-TOF) (m/z): calcd for C₉H₉N₂O ([M+H]₊), 161.0715, found, 161.0721.

N-(1-(phenylsulfonyl)-1H-indol-5-yl)hydroxylamine (S1x)

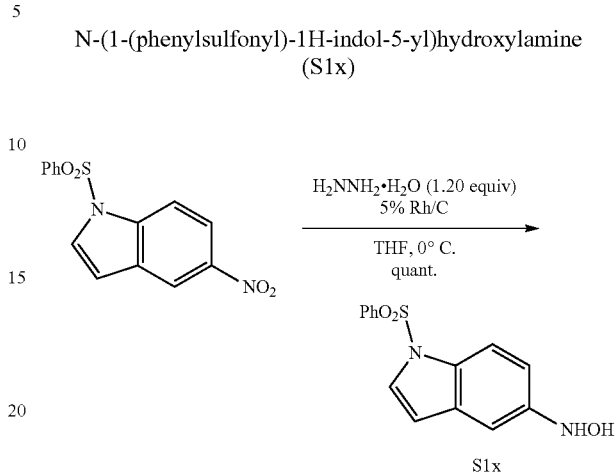

Under N₂ atmosphere, a suspension of 5-nitro-1-(phenylsulfonyl)-1H-indole (1.00 g, 3.31 mmol, 1.00 equiv) and 5% Rh/C (19.0 mg, 0.30 mol % Rh) in THF (35 mL, 0.094 M) was cooled to 0° C. Hydrazine monohydrate (0.199 g, 3.97 mmol, 1.20 equiv) was added dropwise. The reaction mixture stirred at 0° C. for 1 h, filtered through a short pad of celite and concentrated in vacuo to afford the title compound as a yellow solid (0.950 g, 3.29 mmol, quant yield). $R_f$=0.27 (hexanes/EtOAc 2:1 (v/v)). $^1$H NMR (500 MHz, (CD₃)₂SO, δ): 8.33 (d, J=2.1 Hz, 1H), 8.25 (s, 1H), 7.92 (s, 1H), 7.90 (s, 1H), 7.74 (d, J=8.9 Hz, 1H), 7.67-7.63 (m, 2H), 7.58-7.54 (m, 2H), 7.02 (d, J=1.5 Hz, 1H), 6.85 (dd, J=1.9, 8.9 Hz, 1H), 6.72 (d, J=3.6 Hz, 1H). $^{13}$C NMR (125 MHz, (CD₃)₂SO, δ): 148.8, 137.1, 134.4, 131.2, 129.8, 128.6, 127.1, 126.5, 113.2, 112.2, 110.0, 104.3. Mass Spectrometry: HRMS (ESI-TOF) (m/z): calcd for C₁₄H₁₃N₂O₃S ([M+H]₊), 289.0647, found, 289.0645.

N-Hydroxy-N-phenylacetamide (1a)

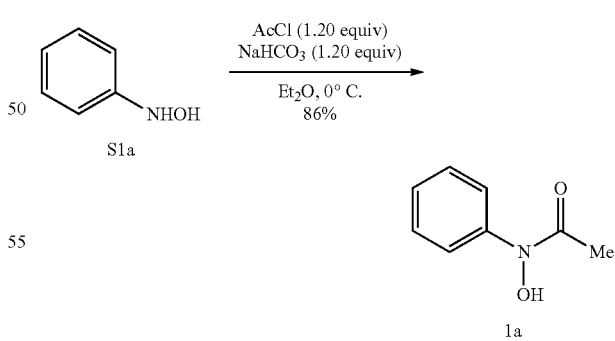

To a stirred suspension of N-phenylhydroxylamine (0.500 g, 4.58 mmol, 1.00 equiv) and NaHCO₃ (0.462 g, 5.50 mmol, 1.20 equiv) in Et₂O (15.0 mL, 0.305 M) at 0° C. under N₂ was slowly added a solution of acetyl chloride (0.432 g, 5.50 mmol, 1.20 equiv) in Et₂O (15.0 mL, 0.367 M) via a syringe pump (at a rate of 10.0 mL/h). After the addition was complete, the reaction mixture was filtered through a short pad of celite and the celite was washed with EtOAc. The combined organic layers were washed with water, dried with MgSO$_4$, filtered, and concentrated in vacuo.

The residue was purified by chromatography on silica gel, eluting with hexanes:EtOAc (4:1 to 3:2 (v/v)), to afford the title compound as a white solid (0.590 g, 3.90 mmol, 86% yield). R$_f$=0.27 (hexanes/EtOAc 3:2 (v/v)). NMR Spectroscopy: $^1$H NMR (500 MHz, (CD$_3$)$_2$SO, δ): 10.61 (s, 1H), 7.59 (d, J=6.0 Hz, 2H), 7.35 (t, J=6.0 Hz, 2H), 7.13 (t, J=6.0 Hz, 1H), 2.18 (s, 3H). $^{13}$C NMR (125 MHz, (CD$_3$)$_2$SO, δ): 169.9, 141.7, 128.4, 124.7, 120.3, 22.5.

N-(4-Cyanophenyl)-N-hydroxyacetamide (1b)

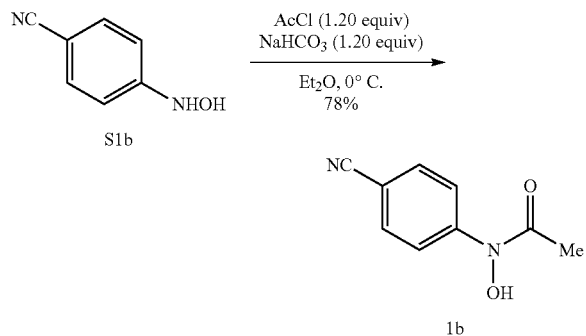

To a stirred solution of 4-(hydroxyamino)benzonitrile (0.500 g, 3.73 mmol, 1.00 equiv) and NaHCO$_3$ (0.380 g, 4.47 mmol, 1.20 equiv) in Et$_2$O (25.0 mL, 0.149 M) at 0° C. under N$_2$ was slowly added a solution of acetyl chloride (0.350 g, 4.47 mmol, 1.20 equiv) in Et$_2$O (10.0 mL, 0.447 M) via a syringe pump (at a rate of 10.0 mL/h). After the addition was complete, the reaction mixture was filtered through a short pad of celite and the celite was washed with EtOAc. The organic layers were combined, concentrated in vacuo. Recrystallization from Et$_2$O/hexanes afforded the title compound as a light pink solid (0.510 g, 2.89 mmol, 78% yield). R$_f$=0.32 (hexanes/EtOAc 1:1 (v/v)). NMR Spectroscopy: 1H NMR (400 MHz, (CD$_3$)$_2$SO, δ): 10.92 (s, 1H), 7.88 (d, J=9.0 Hz, 2H), 7.82 (d, J=9.0 Hz, 2H), 2.27 (s, 3H). $^{13}$C NMR (100 MHz, (CD$_3$)$_2$SO, δ): 171.1, 145.1, 132.9, 118.9, 118.8, 105.7, 22.9. Mass Spectrometry: HRMS (ESI-TOF) (m/z): calcd for C$_9$H$_9$N$_2$O$_2$ ([M+H]$_+$), 177.0664, found, 177.0665.

N-(4-Acetylphenyl)-N-hydroxyacetamide (1c)

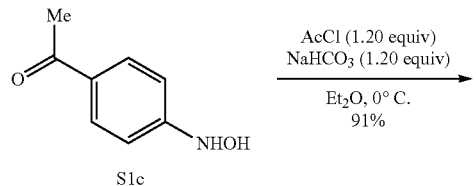

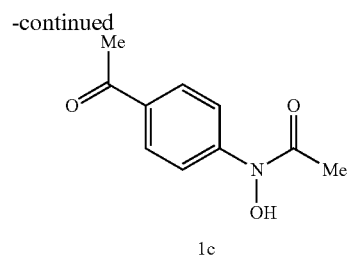

To a stirred suspension of 1-(4-(hydroxyamino)phenyl)ethan-1-one (S1c) (0.200 g, 1.32 mmol, 1.00 equiv) and NaHCO$_3$ (0.130 g, 1.59 mmol, 1.20 equiv) in Et$_2$O (10.0 mL, 0.132 M) at 0° C. under N$_2$ was slowly added a solution of acetyl chloride (0.130 g, 1.59 mmol, 1.20 equiv) in Et$_2$O (5.00 mL, 0.318 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (2:1 to 1:1 (v/v)), to afford the title compound as a white solid (0.230 g, 1.19 mmol, 91% yield). R$_f$=0.13 (hexanes/EtOAc 2:1 (v/v)). NMR Spectroscopy: $^1$H NMR (400 MHz, (CD$_3$)$_2$SO, δ): 10.84 (s, 1H), 7.96 (d, J=8.9 Hz, 2H), 7.82 (d, J=8.9 Hz, 2H), 2.54 (s, 3H), 2.27 (s, 3H). $^{13}$C NMR (100 MHz, (CD$_3$)$_2$SO, δ): 196.6, 170.8, 145.3, 132.2, 128.9, 118.3, 26.5, 22.9. Mass Spectrometry: HRMS (ESI-TOF) (m/z): calcd for C$_{10}$H$_{12}$NO$_3$ ([M+H]$_+$), 194.0817, found, 194.0820.

4-(N-Hydroxyacetamido)-N,N-dimethylbenzamide (1d)

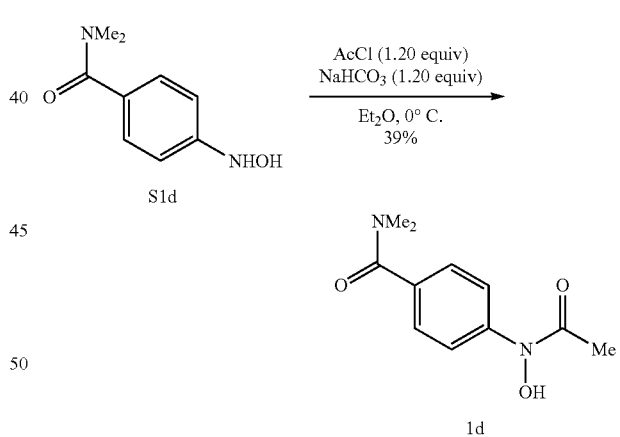

To a stirred suspension of 4-(hydroxyamino)-N,N-dimethylbenzamide (S1d) (0.800 g, 3.93 mmol, 1.00 equiv) and NaHCO$_3$ (0.400 g, 4.72 mmol, 1.20 equiv) in Et$_2$O (15.0 mL, 0.262 M) at 0° C. under N$_2$ was slowly added a solution of acetyl chloride (0.370 g, 4.72 mmol, 1.20 equiv) in Et$_2$O (20.0 mL, 0.236 M) via a syringe pump (at a rate of 10.0 mL/h). After the addition was complete, water was added, and the reaction mixture was filtered. The solid was washed with Et$_2$O, dried under vacuum at 40° C. for 2 h to afford the title compound as yellow solid (0.570 g, 2.56 mmol, 39% yield). R$_f$=0.11 (hexanes/EtOAc 2:1 (v/v)). $^1$H NMR (500 MHz, (CD$_3$)$_2$SO, δ): 10.71 (s, 1H), 7.70 (d, J=7.5 Hz, 2H), 7.41 (d, J=7.5 Hz, 2H), 2.94 (s, 6H), 2.24 (s, 3H). $^{13}$C NMR (125 MHz, (CD$_3$)$_2$SO, δ): 170.2, 169.7, 142.3, 132.0, 127.5, 118.9, 34.9, 22.6. Mass Spectrometry: HRMS (ESI-TOF) (m/z): calcd for C$_{11}$H$_{15}$N$_2$O$_3$ ([M+H]$_+$), 223.1083, found, 223.1084.

N-(4-Fluorophenyl)-N-hydroxyacetamide (1e)

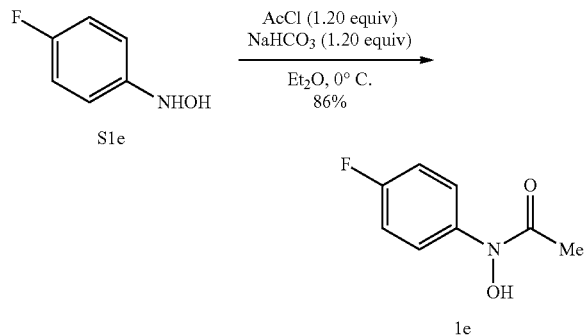

To a stirred suspension of N-(4-fluorophenyl)hydroxylamine (S1e) (0.500 g, 3.93 mmol, 1.00 equiv) and NaHCO$_3$ (0.400 g, 4.72 mmol, 1.20 equiv) in Et$_2$O (15.0 mL, 0.262 M) at 0° C. under N$_2$ was slowly added a solution of acetyl chloride (0.370 g, 4.72 mmol, 1.20 equiv) in Et$_2$O (20.0 mL, 0.236 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 to 1:1 (v/v)), to afford the title compound as a yellow solid (0.570 g, 3.37 mmol, 86% yield). R$_f$=0.10 (hexanes/EtOAc 4:1 (v/v)). NMR Spectroscopy: $^1$H NMR (400 MHz, (CD$_3$)$_2$SO, δ): 10.66 (s, 1H), 7.66-7.60 (m, 2H), 7.23-7.16 (m, 2H), 2.19 (s, 3H). $^{13}$C NMR (100 MHz, (CD$_3$)$_2$SO, δ): 169.7, 158.9 (d, J=240.2 Hz), 138.1 (d, J=2.6 Hz), 122.5, 115.0 5 (d, J=22.3 Hz), 22.2. $^{19}$F NMR (376 MHz, (CD$_3$)$_2$SO, 25° C., δ): −120.2 (s). Mass Spectrometry: HRMS (ESI-TOF) (m/z): calcd for C$_8$H$_9$NO$_2$F ([M+H]$_+$), 170.0617, found, 170.0620.

N-(4-Chlorophenyl)-N-hydroxyacetamide (1f)

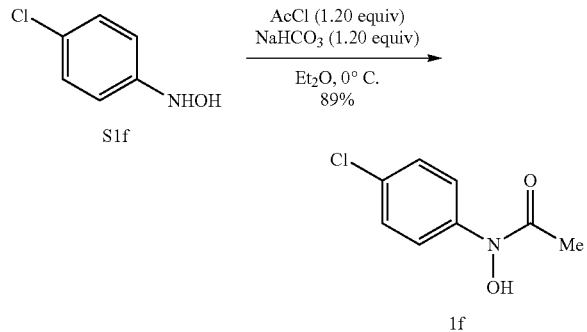

To a stirred suspension of N-(4-chlorophenyl)hydroxylamine (S1f) (1.00 g, 6.97 mmol, 1.00 equiv) and NaHCO$_3$ (0.700 g, 8.36 mmol, 1.20 equiv) in Et$_2$O (20.0 mL, 0.349 M) at 0° C. under N$_2$ was slowly added a solution of acetyl chloride (0.660 g, 8.36 mmol, 1.20 equiv) in Et$_2$O (20.0 mL, 0.418 M) via a syringe pump (at a rate of 10.0 mL/h). After the addition was complete, the reaction mixture was filtered through a short pad of celite and the celite was washed with EtOAc. The organic layers were combined and concentrated in vacuo. Recrystallization from Et$_2$O/hexanes afforded the title compound as a yellow solid (1.15 g, 6.20 mmol, 89% yield). R$_f$=0.13 (hexanes/EtOAc 4:1 (v/v)). NMR Spectroscopy: $^1$H NMR (400 MHz, (CD$_3$)$_2$SO, δ): 10.72 (s, 1H), 7.67 (d, J=8.9 Hz, 2H), 7.44-7.38 (m, 2H), 2.21 (s, 3H). $_{13}$C NMR (100 MHz, (CD$_3$)$_2$SO, δ): 170.1, 140.5, 128.3, 128.1, 121.4, 22.5. Mass Spectrometry: HRMS (ESI-TOF) (m/z): calcd for C$_8$H$_9$NO$_2$Cl ([M+H]$_+$), 186.0322, found, 186.0321.

N-(4-Bromophenyl)-N-hydroxyacetamide (1g)

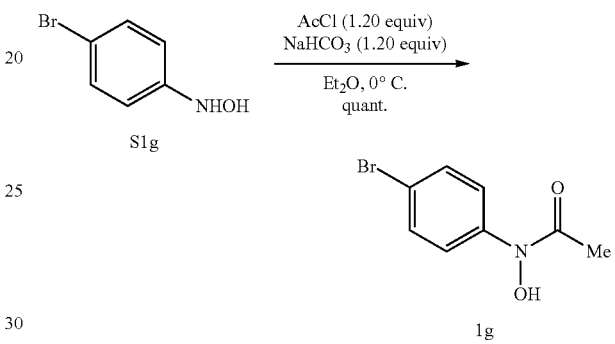

To a stirred suspension of N-(4-bromophenyl)hydroxylamine (S1g) (1.00 g, 5.32 mmol, 1.00 equiv) and NaHCO$_3$ (0.540 g, 6.38 mmol, 1.20 equiv) in Et$_2$O (25.0 mL, 0.213 M) at 0° C. under N$_2$ was slowly added a solution of acetyl chloride (0.500 g, 6.38 mmol, 1.20 equiv) in Et$_2$O (30.0 mL, 0.213 M) via a syringe pump (at a rate of 10.0 mL/h). After the addition was complete, the reaction mixture was filtered through a short pad of celite and the celite was washed with EtOAc. The organic layers were combined and concentrated in vacuo to afford the title compound as a brown solid (1.23 g, 5.34 mmol, quant yield). R$_f$=0.14 (hexanes/EtOAc 4:1 (v/v)). NMR Spectroscopy: $^1$H NMR (400 MHz, (CD$_3$)$_2$SO, δ): 10.72 (s, 1H), 7.61 (d, J=9.0 Hz, 2H), 7.54 (d, J=9.0 Hz, 2H), 2.21 (s, 3H). $^{13}$H NMR (100 MHz, (CD$_3$)$_2$SO, δ): 170.2, 140.9, 131.2, 121.6, 116.2, 22.5. Mass Spectrometry: HRMS (ESI-TOF) (m/z): calcd for C$_8$H$_9$NO$_2$Br ([M+H]$_+$), 229.9817, found, 229.9818.

N-Hydroxy-N-(4-iodophenyl)acetamide (1h)

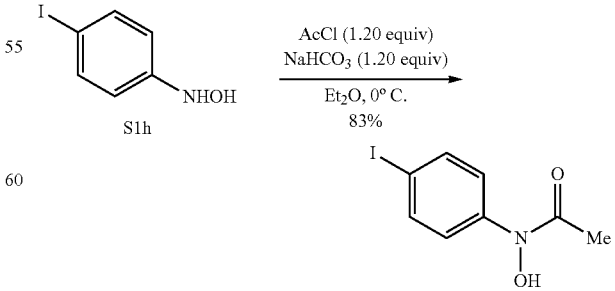

To a stirred suspension of N-(4-iodophenyl)hydroxylamine (S1h) (1.00 g, 4.25 mmol, 1.00 equiv) and NaHCO$_3$ (0.430 g, 5.11 mmol, 1.20 equiv) in Et$_2$O (30.0 mL, 0.412 M) at 0° C. under N$_2$ was slowly added a solution of acetyl chloride (0.400 g, 5.11 mmol, 1.20 equiv) in Et$_2$O (20.0 mL, 0.256 M) via a syringe pump (at a rate of 10.0 mL/h). After the addition was complete, water was added. The aqueous layer was extracted with EtOAc (4 15 mL). The combined organic layers were dried (MgSO$_4$), filtered, and concentrated in vacuo. Recrystallization from Et$_2$O/hexanes afforded the title compound as light brown solid (0.980 g, 3.54 mmol, 83% yield). R$_f$=0.18 (hexanes/EtOAc 4:1 (v/v)). NMR Spectroscopy: $^1$H NMR (400 MHz, (CD$_3$)$_2$SO, δ): 10.69 (s, 1H), 7.72-7.67 (m, 2H), 7.48 (d, J=8.5 Hz, 2H), 2.21 (s, 3H). $^{13}$C NMR (100 MHz, (CD$_3$)$_2$SO, δ): 170.1, 141.4, 137.0, 121.8, 88.4, 22.6. Mass Spectrometry: HRMS (ESI-TOF) (m/z): calcd for C$_8$H$_9$NO$_2$I ([M+H]$_+$), 277.9678, found, 277.9684.

N-(3-Fluorophenyl)-N-hydroxyacetamide (1i)

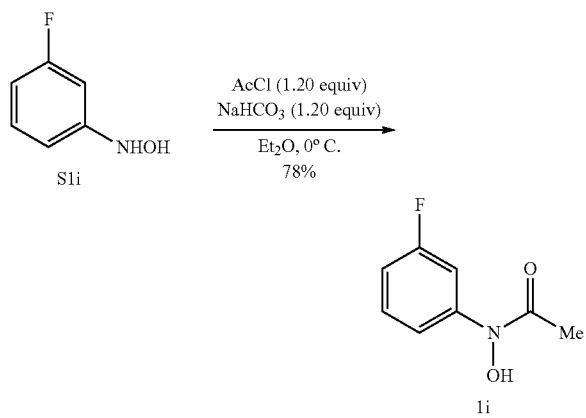

To a stirred suspension of N-(3-fluorophenyl)hydroxylamine (S1i) (0.800 g, 6.29 mmol, 1.00 equiv) and NaHCO$_3$ (0.634 g, 7.55 mmol, 1.20 equiv) in Et$_2$O (35.0 mL, 0.180 M) at 0° C. under N$_2$ was slowly added a solution of acetyl chloride (0.593 g, 7.55 mmol, 1.20 equiv) in Et$_2$O (30.0 mL, 0.252 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 to 1:1 (v/v)), to afford the title compound as a yellow liquid (0.830 g, 4.91 mmol, 78% yield). R$_f$=0.52 (hexanes/EtOAc 1:1 (v/v)). NMR Spectroscopy: $^1$H NMR (500 MHz, (CD$_3$)$_2$SO, δ): 10.77 (s, 1H), 7.54-7.50 (m, 2H), 7.50-7.37 (m, 1H), 7.00-7.6.94 (m, 1H), 2.23 (s, 3H). $^{13}$C NMR (125 MHz, (CD$_3$)$_2$SO, δ): 170.4, 161.80 (d, J=240.2 Hz), 143.1 (d, J=10.7 Hz), 130.1 (d, J=9.2 Hz), 115.0, 110.7 (d, J=20.9 Hz), 106.3 (d, J=27.7 Hz), 22.7. $^{19}$F NMR (376 MHz, (CD$_3$)$_2$SO, 25° C., δ): -114.5 (s). Mass Spectrometry: HRMS (ESI-TOF) (m/z): calcd for C$_8$H$_9$NO$_2$F ([M+H]$_+$), 170.0617, found, 170.0617.

N-(2-Bromophenyl)-N-hydroxyacetamide (1j)

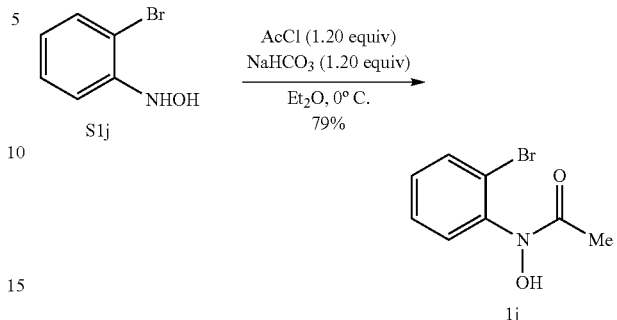

To a stirred suspension of N-(2-bromophenyl)hydroxylamine (S1j) (0.820 g, 4.36 mmol, 1.00 equiv) and NaHCO$_3$ (0.430 g, 5.23 mmol, 1.20 equiv) in Et$_2$O (20.0 mL, 0.218 M) at 0° C. under N$_2$ was slowly added a solution of acetyl chloride (0.410 g, 5.23 mmol, 1.20 equiv) in Et$_2$O (25.0 mL, 0.209 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (1:1 (v/v)), to afford the title compound as a brown solid (0.790 g, 3.43 mmol, 79% yield). R$_f$=0.21 (hexanes/EtOAc 1:1 (v/v)). NMR Spectroscopy: $^1$H NMR (500 MHz, (CD$_3$)$_2$SO, δ): 10.65 (s, 1H), 7.71-7.70 (m, 1H), 7.45-7.44 (m, 1H), 7.31-7.30 (m, 1H), 3.34 (s, 3H). $^{13}$C NMR (125 MHz, (CD$_3$)$_2$SO, δ): 170.5, 141.0, 133.0, 129.9, 128.6, 122.1, 21.0. Mass Spectrometry: HRMS (ESI-TOF) (m/z): calcd for C$_8$H$_9$NO$_2$Br ([M+H]$_+$), 229.9817, found, 229.9820.

N-Hydroxy-N-(3-methoxy-5-(trifluoromethyl)phenyl)acetamide (1k)

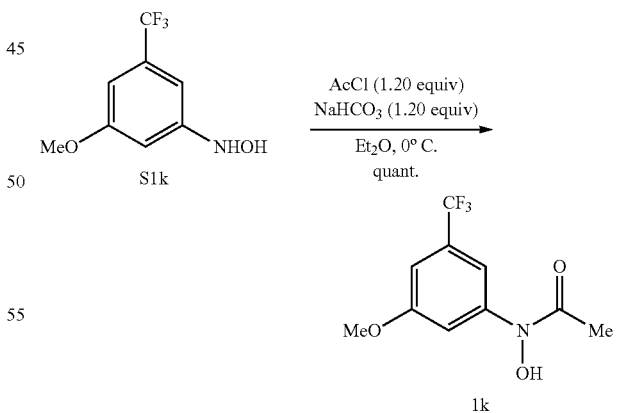

To a stirred suspension of N-(3-methoxy-5-(trifluoromethyl)phenyl) hydroxylamine (S1k) (0.720 g, 3.48 mmol, 1.00 equiv) and NaHCO$_3$ (0.350 g, 4.17 mmol, 1.20 equiv) in Et$_2$O (15.0 mL, 0.232 M) at 0° C. under N$_2$ was slowly added a solution of acetyl chloride (0.330 g, 4.17 mmol, 1.20 equiv) in Et$_2$O (20.0 mL, 0.209 M) via a syringe pump (at a rate of 10.0 mL/h). After the addition was complete, the reaction mixture was filtered through a short pad of celite and the celite was washed with EtOAc. The organic layers were combined and concentrated in vacuo to afford the title compound as a yellow solid (0.870 g, 3.49 mmol, quant yield). R$_f$=0.18 (hexanes/EtOAc 4:1 (v/v)). NMR Spectroscopy: $^1$H NMR (400 MHz, (CD$_3$)$_2$SO, δ): 10.87 (s, 1H), 7.64 (s, 1H), 7.53 (s, 1H), 7.01 (s, 1H), 3.83 (s, 3H), 2.25 (s, 3H). $^{13}$C NMR (100 MHz, (CD$_3$)$_2$SO, δ): 170.8, 159.8, 143.4, 130.2 (q, J=31.4 Hz), 123.9 (q, J=270.9 Hz), 108.6, 107.9, 105.8, 55.7, 22.8. $^{19}$F NMR (376 MHz, (CD$_3$)$_2$SO, 25° C., δ): −63.3 (s). Mass Spectrometry: HRMS (ESI-TOF) (m/z): calcd for C$_{10}$H$_{11}$NO$_3$F$_3$ ([M+H]$_+$), 250.0691, found, 250.0696.

N-Hydroxy-N-(3-(trifluoromethyl)phenyl)acetamide (1l)

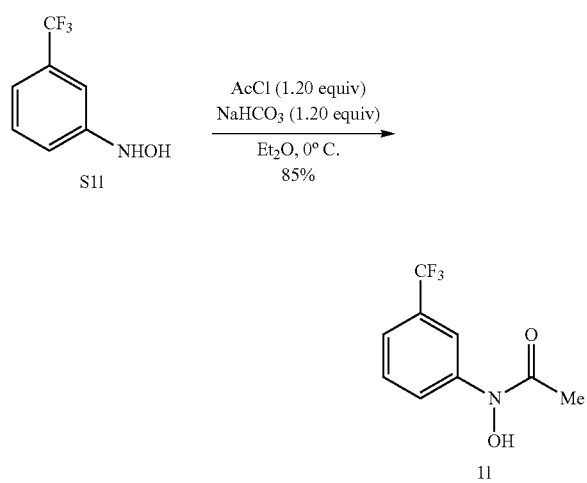

To a stirred suspension of N-(3-(trifluoromethyl)phenyl)hydroxylamine (S1l) (0.720 g, 4.06 mmol, 1.00 equiv) and NaHCO$_3$ (0.410 g, 4.88 mmol, 1.20 equiv) in Et$_2$O (20.0 mL, 0.203 M) at 0° C. under N$_2$ was slowly added a solution of acetyl chloride (0.380 g, 4.88 mmol, 1.20 equiv) in Et$_2$O (25.0 mL, 0.192 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 to 1:1 (v/v)), to afford the title compound as a yellow solid (0.760 g, 3.47 mmol, 85% yield). R$_f$=0.19 (hexanes/EtOAc 4:1 (v/v)). NMR Spectroscopy: $^1$H NMR (500 MHz, (CD$_3$)$_2$SO, δ): 10.88 (s, 1H), 8.03 (s, 1H), 7.94 (d, J=8.0 Hz, 1H), 7.61 (t, J=8.0 Hz, 1H), 7.48 (d, J=8.0 Hz, 1H), 2.08 (s, 3H). $^{13}$C NMR (125 MHz, (CD$_3$)$_2$SO, δ): 170.7, 142.2, 129.8, 129.1 (q, J=31.6 Hz), 126.2 (d, J=270.9 Hz), 122.9 (d, J=9.6 Hz), 120.6 (d, J=29.7 Hz), 115.5, 22.6. $^{19}$F NMR (376 MHz, (CD$_3$)$_2$SO, 25° C., δ): −63.1 (s). Mass Spectrometry: HRMS (ESI-TOF) (m/z): calcd for C$_9$H$_9$NO$_2$F$_3$ ([M+H]$_+$), 220.0585, found, 220.0589.

N-Hydroxy-N-(3-methoxyphenyl)acetamide (1m)

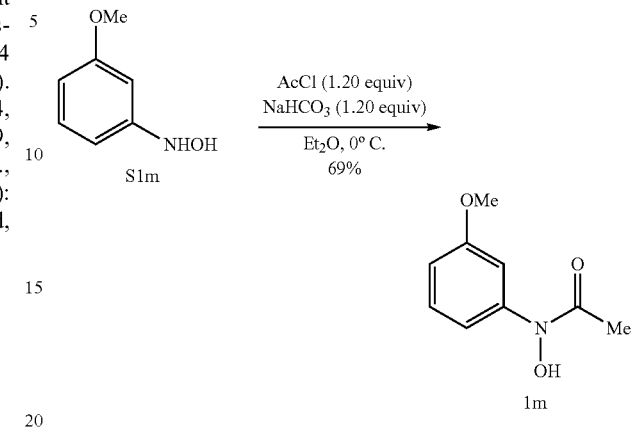

To a stirred suspension of N-(3-methoxyphenyl)hydroxylamine (S1m) (0.900 g, 6.47 mmol, 1.00 equiv) and NaHCO$_3$ (0.650 g, 7.76 mmol, 1.20 equiv) in Et$_2$O (30.0 mL, 0.216 M) at 0° C. under N$_2$ was slowly added a solution of acetyl chloride (0.610 g, 7.76 mmol, 1.20 equiv) in Et$_2$O (30.0 mL, 0.259 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (5:1 to 4:1 (v/v)), to afford the title compound as a brown liquid (0.810 g, 4.47 mmol, 69% yield). R$_f$=0.26 (hexanes/EtOAc 5:1 (v/v)). $^1$H NMR (500 MHz, (CD$_3$)$_2$SO, δ): 10.61 (s, 1H), 7.30-7.20 (m, 3H), 6.74-6.71 (m, 1H), 3.74 (s, 3H), 2.19 (s, 3H). $^{13}$C NMR (125 MHz, (CD$_3$)$_2$SO, δ): 169.9, 159.2, 142.8, 129.2, 112.3, 109.8, 106.0, 55.1, 22.6. Mass Spectrometry: HRMS (ESI-TOF) (m/z): calcd for C$_9$H$_{12}$NO$_3$ ([M+H]$_+$), 182.0817, found, 182.0816.

Methyl 3-(N-hydroxyacetamido)benzoate (1n)

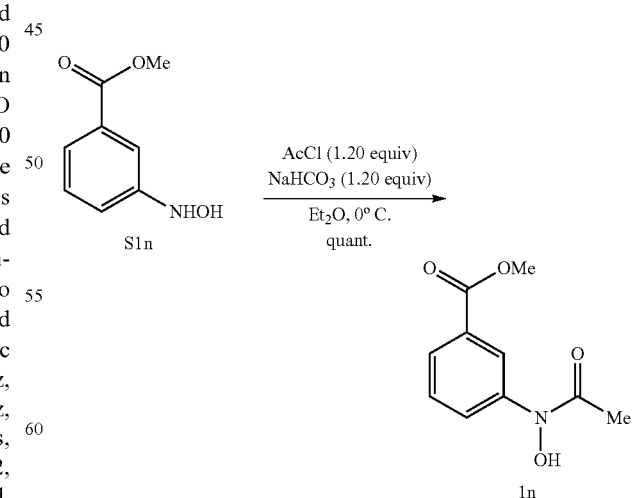

To a stirred suspension of methyl 3-(hydroxyamino)benzoate (S1n) (1.00 g, 5.98 mmol, 1.00 equiv) and NaHCO$_3$ (0.600 g, 7.18 mmol, 1.20 equiv) in Et$_2$O (30.0 mL, 0.199

M) at 0° C. under N₂ was slowly added a solution of acetyl chloride (0.560 g, 7.18 mmol, 1.20 equiv) in Et₂O (30.0 mL, 0.239 M) via a syringe pump (at a rate of 10.0 mL/h). After the addition was complete, the reaction mixture was filtered through a short pad of celite and the celite was washed with EtOAc. The organic layers were combined and concentrated in vacuo to afford the title compound as a yellow solid (1.25 g, 5.98 mmol, quant yield). $R_f$=0.10 (hexanes/EtOAc 4:1 (v/v)). NMR Spectroscopy: ¹H NMR (400 MHz, (CD₃)₂SO, δ): 10.80 (s, 1H), 8.26 (s, 1H), 7.95-7.90 (m, 1H), 7.72 (d, J=7.6 Hz, 1H), 7.51 (t, J=7.9 Hz, 1H), 3.86 (s, 3H), 2.24 (s, 3H). ¹³C NMR (100 MHz, (CD₃)₂SO, δ): 170.4, 166.0, 141.9, 129.8, 128.9, 124.9, 124.2, 120.1, 52.3, 22.5. Mass Spectrometry: HRMS (ESI-TOF) (m/z): calcd for $C_{10}H_{12}NO_4$ ([M+H]₊), 210.0766, found, 210.0764.

N-(2-Chloro-5-(trifluoromethyl)phenyl)-N-hydroxyacetamide (1o)

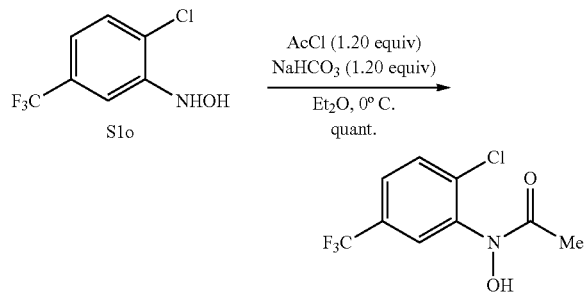

To a stirred suspension of N-(2-chloro-5-(trifluoromethyl)phenyl) hydroxylamine (S1o) (0.930 g, 4.43 mmol, 1.00 equiv) and NaHCO₃ (0.447 g, 5.32 mmol, 1.20 equiv) in Et₂O (25.0 mL, 0.177 M) at 0° C. under N₂ was slowly added a solution of acetyl chloride (0.417 g, 5.32 mmol, 1.20 equiv) in Et₂O (20.0 mL, 0.266 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 to 2:1 (v/v)), to afford title compound as a yellow liquid (1.11 g, 4.38 mmol, quant yield). $R_f$=0.39 (hexanes/EtOAc 2:1 (v/v)). ¹H NMR (500 MHz, (CD₃)₂SO, δ): 10.87 (s, 1H), 7.84-7.75 (m, 3H), 2.19 (s, 3H). ¹³C NMR (125 MHz, (CD₃)₂SO, δ): 170.7, 140.3, 135.7, 131.3, 128.6 (q, J=32.5 Hz), 126.3 (m), 125.9 (m), 123.3 (q, J=270.8 Hz), 20.8. ¹⁹F NMR (376 MHz, (CD₃)₂SO, 25° C., δ): −63.2 (s). Mass Spectrometry: HRMS (ESI-TOF) (m/z): calcd for $C_9H_8NO_2ClF_3$ ([M+H]₊), 254.0196, found, 254.0194.

N-(3-Benzyl-8-chloro-4-oxo-3,4-dihydroquinazolin-7-yl)-N-hydroxyacetamide (1p)

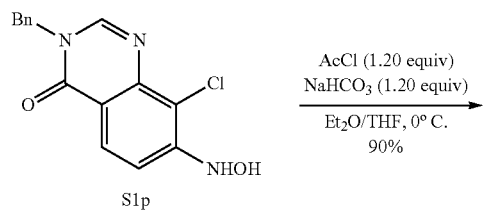

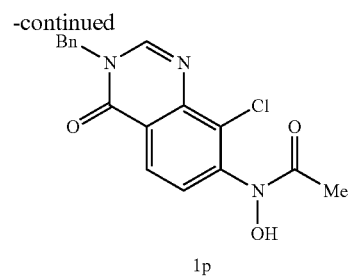

To a stirred suspension of methyl 3-benzyl-8-chloro-7-(hydroxyamino) quinazolin-4(3H)-one (S1p) (0.700 g, 2.32 mmol, 1.00 equiv) and NaHCO₃ (0.234 g, 2.78 mmol, 1.20 equiv) in Et₂O/THF 1:1 (v/v) (10 mL, 0.232 M) at 0° C. under N₂ was slowly added a solution of acetyl chloride (0.219 g, 2.78 mmol, 1.20 equiv) in Et₂O (15.0 mL, 0.185M) via a syringe pump (at a rate of 10.0 mL/h). After the addition was complete, the reaction was quenched with water, filtered and the solid was washed with Et₂O, dried at r.t. for 24 h to afford the title compound as a yellow solid (0.720 g, 2.09 mmol, 90% yield). $R_f$=0.14 (hexanes/EtOAc 4:1 (v/v)). NMR Spectroscopy: ¹H NMR (500 MHz, (CD₃)₂SO, δ): 10.83 (s, 1H), 8.65 (s, 2H), 8.15 (s, 1H), 7.91 (s, 1H), 7.25-7.40 (m, 5H), 5.20 (s, 2H), 2.19 (s, 3H). ¹³C NMR (125 MHz, (CD₃)₂SO, δ): 159.3, 150.0, 148.1, 138.1, 137.7, 136.5, 128.7, 128.2, 127.8, 127.6, 126.7, 121.3, 49.1, 20.9. Mass Spectrometry: HRMS (ESI-TOF) (m/z): calcd for $C_{17}H_{15}N_3O_3Cl$ ([M+H]₊), 344.0802, found, 344.0808.

Methyl 4-(N-hydroxyacetamido)benzoate (1q)

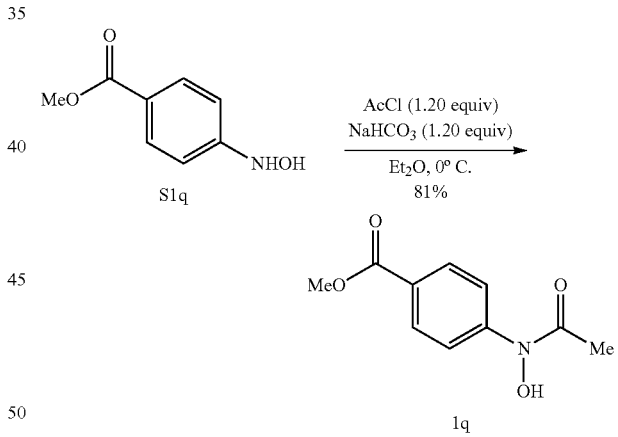

To a stirred suspension of methyl 4-(hydroxyamino)benzoate (S1q) (0.900 g, 5.38 mmol, 1.00 equiv) and NaHCO₃ (0.540 g, 6.46 mmol, 1.20 equiv) in Et₂O (30.0 mL, 0.179 M) at 0° C. under N₂ was slowly added a solution of acetyl chloride (0.510 g, 6.46 mmol, 1.20 equiv) in Et₂O (30.0 mL, 0.215 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 to 1:1 (v/v)), to afford the title compound as a light yellow solid (0.910 g, 4.35 mmol, 81% yield). $R_f$=0.13 (hexanes/EtOAc 4:1 (v/v)). NMR Spectroscopy: ¹H NMR (400 MHz, (CD₃)₂SO, δ): 10.83 (s, 1H), 7.96 (d, J=9.0 Hz, 2H), 7.83 (d, J=9.0 Hz, 2H), 3.83 (s, 3H), 2.26 (s, 3H). $^{13}$C NMR (100 MHz, (CD$_3$)$_2$SO, δ): 170.8, 165.7, 145.4, 129.8, 124.6, 118.4, 52.0, 22.9. Mass Spectrometry: HRMS (ESI-TOF) (m/z): calcd for C$_{10}$H$_{12}$NO$_4$ ([M+H]$_+$), 210.0766, found, 210.0766.

Methyl 4-(N-hydroxybenzamido)benzoate (1r)

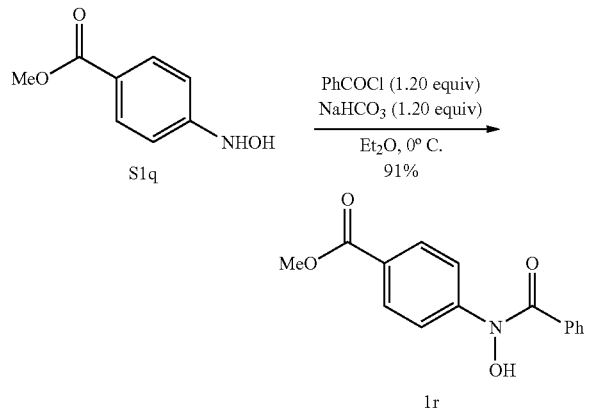

To a stirred suspension of methyl 4-(hydroxyamino)benzoate (S1q) (1.00 g, 5.98 mmol, 1.00 equiv) and NaHCO$_3$ (0.603 g, 7.18 mmol, 1.20 equiv) in Et$_2$O (30.0 mL, 0.199 M) at 0° C. under N$_2$ was slowly added a solution of acetyl chloride (1.01 g, 7.18 mmol, 1.20 equiv) in Et$_2$O (30.0 mL, 0.239 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with hexanes:EtOAc (4:1 (v/v)), to afford the title compound as a light yellow solid (1.47 g, 5.42 mmol, 91% yield). R$_f$=0.20 (hexanes/EtOAc 4:1 (v/v)). NMR Spectroscopy: $^1$H NMR (500 MHz, (CD$_3$)$_2$SO, δ): 10.93 (s, 1H), 8.00 (d, J=8.8 Hz, 2H), 7.81 (d, J=8.8 Hz, 2H), 7.69 (d, J=7.4 Hz, 2H), 7.52-7.44 (m, 3H), 3.85 (s, 3H). $^{13}$C NMR (125 MHz, (CD$_3$)$_2$SO, δ): 168.6, 165.7, 145.9, 135.2, 130.6, 129.8, 128.4, 127.9, 125.5, 120.0, 52.1. Mass Spectrometry: HRMS (ESI-TOF) (m/z): calcd for C$_{15}$H$_{14}$NO$_4$ ([M+H]$_+$), 272.0923, found, 272.0925.

Methyl 4-(hydroxy(methoxycarbonyl)amino)benzoate (1s)

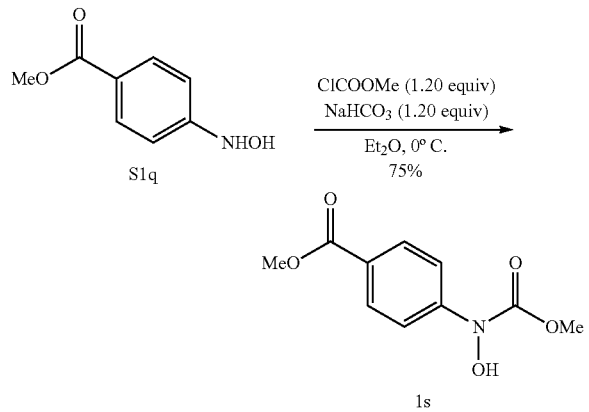

To a stirred suspension of methyl 4-(hydroxyamino)benzoate (S1q) (0.800 g, 4.84 mmol, 1.00 equiv) and NaHCO$_3$ (0.554 g, 6.55 mmol, 1.35 equiv) in Et$_2$O (15.0 mL, 0.323 M) at 0° C. under N$_2$ was slowly added a solution of methyl chloroformate (0.490 g, 5.50 mmol, 1.10 equiv) in Et$_2$O (15.0 mL, 0.367 M) via a syringe pump (at a rate of 7.50 mL/h).

After the addition was complete, the reaction mixture was filtered through a short pad of celite and the celite was washed with EtOAc.

The organic layers were combined and concentrated in vacuo. The residue was recrystallized from CH$_2$Cl$_2$/hexanes to afford the title compound as a light yellow solid (0.830 g, 3.69 mmol, 75% yield). R$_f$=0.34 (hexanes/EtOAc 3:2 (v/v)). $^1$H NMR (400 MHz, (CD$_3$)$_2$SO, δ): 10.63 (s, 1H), 7.94 (d, J=9.0 Hz, 2H), 7.70 (d, J=9.0 Hz, 2H), 3.83 (s, 3H), 3.78 (s, 3H). $^{13}$C NMR (125 MHz, (CD$_3$)$_2$SO, δ): 165.7, 154.3, 146.1, 129.8, 124.3, 118.1, 53.2, 52.0. Mass Spectrometry: HRMS (ESI-TOF) (m/z): calcd for C$_{10}$H$_{12}$NO$_5$ ([M+H]$_+$), 226.0715, found, 226.0714.

Methyl 4-(1-hydroxy-3,3-dimethylureido)benzoate (1t)

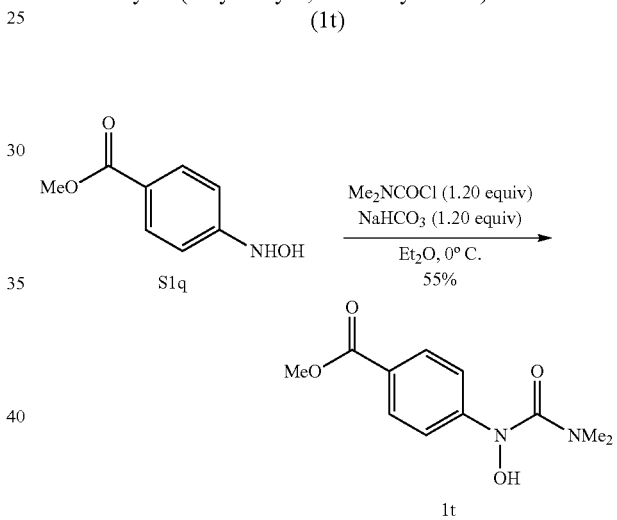

To a stirred suspension of methyl 4-(hydroxyamino)benzoate (S1q) (1.00 g, 5.98 mmol, 1.00 equiv) and NaHCO$_3$ (0.603 g, 7.18 mmol, 1.20 equiv) in Et$_2$O (30.0 mL, 0.199 M) at 0° C. under N$_2$ was slowly added a solution of dimethylcarbamic chloride (0.772 g, 7.18 mmol, 1.2 equiv) in Et$_2$O (30.0 mL, 0.239 M) via a syringe pump (at a rate of 10.0 mL/h). After the addition was complete, the reaction was quenched by water and extracted with EtOAc (20 mL×4). The combined organic layers were dried with MgSO$_4$, filtered, and concentrated in vacuo. The residue was recrystallized form Et$_2$O/hexanes to afford title compound as a yellow solid (0.780 g, 3.27 mmol, 55% yield). R$_f$=0.25 (hexanes/EtOAc 4:1 (v/v)). NMR Spectroscopy: $^1$H NMR (500 MHz, (CD$_3$)$_2$SO, δ): 10.14 (s, 1H), 7.87 (d, J=8.8 Hz, 2H), 7.23 (d, J=8.8 Hz, 2H), 3.81 (s, 3H), 2.95 (s, 6H). $^{13}$C NMR (125 MHz, (CD$_3$)$_2$SO, δ): 166.0, 159.0, 149.4, 129.6, 122.7, 117.0, 51.8, 37.3. Mass Spectrometry: HRMS (ESI-TOF) (m/z): calcd for C$_{11}$H$_{15}$N$_2$O$_4$ ([M+H]$_+$), 239.1032, found, 239.1033.

N-Hydroxy-N-(p-tolyl)acetamide (1u)

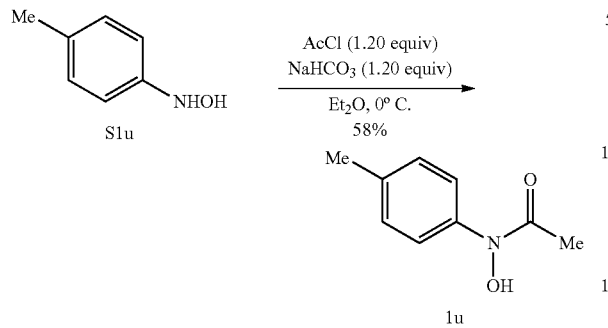

To a stirred suspension of N-(p-tolyl)hydroxylamine (S1u) (0.200 g, 1.62 mmol, 1.00 equiv) and NaHCO$_3$ (164 mg, 1.95 mmol, 1.20 equiv) in Et$_2$O (10.0 mL, 0.162 M) at 0° C. under N$_2$ was slowly added a solution of acetyl chloride (153 mg, 1.95 mmol, 1.20 equiv) in Et$_2$O (5.00 mL, 0.390 M) via a syringe pump (at a rate of 10.0 mL/h). After the addition was complete, the reaction mixture was filtered through a short pad of celite and concentrated in vacuo. The residue was purified by chromatography on silica gel, eluting with hexanes:EtOAc (4:1 to 2:1 (v/v), to afford the title compound as a yellow solid (0.156 g, 0.944 mmol, 58% yield). R$_f$=0.27 (hexanes/EtOAc 2:1 (v/v)). NMR Spectroscopy: $^1$H NMR (400 MHz, (CD$_3$)$_2$SO, δ): 10.51 (s, 1H), 7.47 (d, J=8.2 Hz, 2H), 7.15 (d, J=8.2 Hz, 2H), 2.28 (s, 3H), 2.16 (s, 3H). $^{13}$C NMR (125 MHz, (CD$_3$)$_2$SO, δ): 169.5, 139.3, 133.8, 128.8, 120.3, 22.3, 20.4. Mass Spectrometry: HRMS (ESI-TOF) (m/z): calcd for C$_9$H$_{12}$NO$_2$ ([M+H]$_+$), 166.0868, found, 166.0867.

Methyl (R)-2-acetamido-3-(4-(N-hydroxyacetamido) phenyl) propanoate (1v)

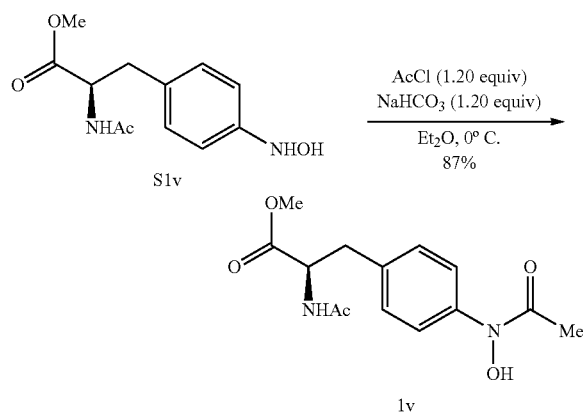

To a stirred suspension of methyl (R)-2-acetamido-3-(4-(hydroxyamino)phenyl)propanoate (S1v) (0.910 g, 3.61 mmol, 1.00 equiv) and NaHCO$_3$ (0.364 g, 4.33 mmol, 1.20 equiv) in Et$_2$O (20.0 mL, 0.185 M) at 0° C. under N$_2$ was slowly added a solution of acetyl chloride (0.340 g, 4.33 mmol, 1.20 equiv) in Et$_2$O (20.0 mL, 0.217 M) via a syringe pump (at a rate of 10.0 mL/h). After the addition was complete, the reaction mixture was slowly warmed up to rt. The reaction mixture was then quenched with water and the solid was collected by filtration and dried under vacuum overnight at 40° C. The procedure afforded the title compound as a yellow solid (0.920 g, 3.13 mmol, 87% yield). NMR Spectroscopy: $^1$H NMR (500 MHz, (CD$_3$)$_2$SO, δ): 10.57 (s, 1H), 8.32 (d, J=7.2 Hz, 1H), 7.52 (d, J=7.7 Hz, 2H), 7.19 (d, J=7.7 Hz, 2H), 4.43 (d, J=5.9 Hz, 1H), 3.60 (s, 3H), 2.98 (dd, J=5.9, 13.6 Hz, 1H), 2.85 (dd, J=5.9, 13.6 Hz, 1H), 2.18 (s, 3H), 1.79 (s, 3H). $^{13}$C NMR (125 MHz, (CD$_3$)$_2$SO, δ): 172.2, 169.7, 169.3, 140.2, 133.5, 129.0, 120.0, 53.6, 51.8, 36.2, 22.4, 22.2. Mass Spectrometry: HRMS (ESI-TOF) (m/z): calcd for C$_{14}$H$_{19}$N$_2$O$_5$ ([M+H]$_+$), 295.1294, found, 295.1296.

Methyl hydroxy(quinolin-8-yl) carbamate (1w)

To a stirred suspension of N-(quinolin-8-yl)hydroxylamine (S1w) (0.50 g, 3.12 mmol, 1.00 equiv) and NaHCO$_3$ (0.315 g, 3.75 mmol, 1.20 equiv) in Et$_2$O (15.0 mL, 0.208 M) at 0° C. under N$_2$ was slowly added a solution of methyl chloroformate (0.325 g, 3.75 mmol, 1.20 equiv) in Et$_2$O (16.0 mL, 0.234 M) via a syringe pump (at a rate of 10.0 mL/h).

After the addition was complete, the reaction mixture was warmed up to rt and stirred for another 4 h. The reaction mixture was quenched with water and the solid was collected by filtration and dried under vacuum overnight. The procedure afforded the title compound as a dark brown solid (0.550 g, 2.52 mmol, 81% yield). R$_f$=0.23 (hexanes/EtOAc 5:1 (v/v)). NMR Spectroscopy: $^1$H NMR (500 MHz, (CD$_3$)$_2$SO, δ): 10.19 (s, 1H), 8.93 (dd, J=1.7, 4.2 Hz, 1H), 8.43 (dd, J=1.7, 8.3 Hz, 1H), 8.00 (dd, J=1.3, 8.3 Hz, 1H), 7.76 (d, J=7.6 Hz, 1H), 7.64 (dd, J=7.6, 8.3 Hz, 1H), 7.59 (dd, J=4.2, 8.3 Hz, 1H), 3.57 (s, 3H). $^{13}$C NMR (125 MHz, (CD$_3$)$_2$SO, δ): 157.2, 150.5, 143.0, 139.7, 136.4, 128.8, 128.66, 128.65, 126.4, 121.9, 52.6. Mass Spectrometry: HRMS (ESI-TOF) (m/z): calcd for C$_{11}$H$_{11}$N$_2$O$_3$ ([M+H]$_+$), 219.0770, found, 219.0773.

N-hydroxy-N-(1-(phenylsulfonyl)-1H-indol-5-yl) acetamide (1x)

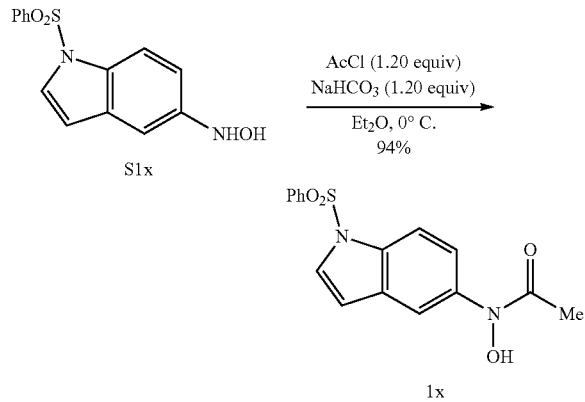

To a stirred suspension of N-(1-(phenylsulfonyl)-1H-indol-5-yl) hydroxylamine (S1x) (0.950 g, 3.31 mmol, 1.00 equiv) and NaHCO$_3$ (0.333 g, 3.97 mmol, 1.20 equiv) in Et$_2$O (25.0 mL, 0.132M) at 0° C. under N$_2$ was slowly added a solution of acetyl chloride (0.311 g, 3.97 mmol, 1.20 equiv) in EtO$_2$O (20.0 mL, 0.199M) via a syringe pump (at a rate of 10.0 mL/h). After the addition was complete, the reaction mixture was filtered through a short pad of celite and concentrated in vacuo. The residue was purified by chromatography on silica gel, eluting with hexanes:EtOAc (4:1 to 1:1 (v/v), to afford the title compound as a white solid (1.02 g, 3.09 mmol, 94% yield). R$_f$=0.19 (hexanes/EtOAc 2:1 (v/v)). NMR Spectroscopy: $^1$H NMR (500 MHz, (CD$_3$)$_2$SO, δ): 10.63 (s, 1H), 7.97 (d, J=8.1 Hz, 2H), 7.92 (d, J=9.1 Hz, 1H), 7.82 (d, J=3.6 Hz, 1H), 7.79 (s, 1H), 7.70-7.66 (m, 1H), 7.61-7.56 (m, 3H), 6.87 (d, J=3.6 Hz, 1H), 2.18 (s, 3H). $^{13}$C NMR (125 MHz, (CD$_3$)$_2$SO, δ): 169.7, 137.8, 136.9, 134.7, 131.3, 130.4, 129.8, 127.9, 126.6, 118.5, 113.7, 112.9, 109.9, 22.2. Mass Spectrometry: HRMS (ESI-TOF) (m/z): calcd for C$_{16}$H$_{15}$N$_2$O$_4$S ([M+H]$_+$), 331.0753, found, 331.0759.

Example 1. General Method for O-trifluoromethylation/OCF$_3$-Migration

Herein is described the first synthesis, isolation, and characterization of protected N-aryl-N-(trifluoromethoxy) amines and their application in the synthesis of ortho-OCF$_3$ aniline derivatives (Scheme 1).

Scheme 1. General synthetic sequence

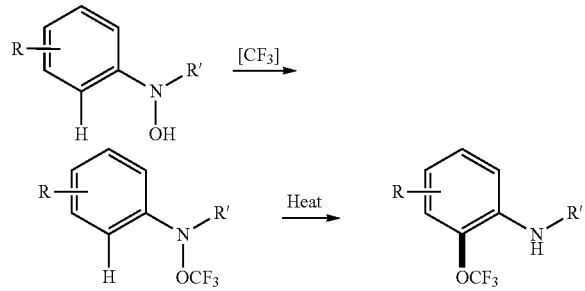

Standard Procedure for O-trifluoromethylation of Protected N-aryl-N-hydroxylamines Under N$_2$ atmosphere, to a mixture of protected N-aryl-N-hydroxylamine (1.00 equiv) and Cs$_2$CO$_3$ (10 mol %) in CHCl$_3$ (0.100 M) was added Togni reagent II (1.20 equiv) and the reaction mixture was stirred at rt for 14-23 h. The reaction mixture was then washed with sat. aq. NaHCO$_3$* and the organic layer was collected, dried (MgSO$_4$), filtered, and concentrated in vacuo. The residue was purified by chromatography on silica gel.

*The wash with sat. aq. NaHCO$_3$ was not necessary in case of compounds of low polarity, which could be easily separated from 2-iodobenzoic acid by means column chromatography.

Standard Procedure for the Synthesis of Ortho-OCF$_3$ Aniline Derivatives Via OCF$_3$-Migration A solution of protected N-aryl-N-(trifluoromethoxy) amine (0.400 mmol) in MeNO$_2$ (0.400 mL, 1.00 M) was heated at an appropriate temperature (e.g., 50° C., 80° C., 120° C. or 140° C.) under N$_2$ atmosphere for 11-48 h. The reaction mixture was concentrated in vacuo. The residue was purified by chromatography on silica gel.

Example 2. Synthesis of N—OCF$_3$ Compounds

Although synthesis and applications of N—SCF$_3$ compounds are known,[15] direct synthesis of the analogous N—OCF$_3$ compounds from protected N-aryl-N-hydroxylamines has not been reported.[14] It is known that sodium 2,6,6-tetramethylpiperidin-1-oxide (TEMPONa) reacts with 1-trifluoromethyl-1,2-benziodoxol-3(1H)-one (Togni reagent II)[16] to form TEMPO-CF$_3$.[17] Based on this reactivity, Togni and co-workers developed O-trifluoromethylation of N,N-dialkylhydroxylamines using 3,3-Dimethyl-1-(trifluoromethyl)-1,2-benziodoxole (Togni reagent I).[14b] Therefore, it was envisioned that protected N-aryl-N-hydroxylamines could react with Togni reagents to provide the desired products of O-trifluoromethylation. Indeed, treatment of N-phenyl-N-hydroxamic acid (1a) with 1.2 equiv of Togni reagent II in the presence of 10 mol % Cs$_2$CO$_3$ in CHCl$_3$ (0.1 M) at room temperature furnished the desired product 2a in 72% yield (Scheme 2). Addition of a stoichiometric amount of radical trap, 3,5-di-tert-butyl-4-hydroxytoluene (BHT), diminished the product yield. Moreover, this reaction is oxygen sensitive, so strictly degassed chloroform is required for high yield. These observations are consistent with a radical reaction mechanism.[14b,17]

Under the optimized reaction conditions, various protected N-aryl-N-hydroxylamines (1a-1t, Scheme 2) were surveyed to determine the scope and limitations of this reaction. The reaction tolerated a wide range of functional groups including nitrile (2b), ketone (2c), amide (2d), halogens (2e-2j, 2o, 2p), CF$_3$ group (2k, 2l, 2o), ether (2k, 2m), ester (2n, 2q-2t), and heterocycle substituent (2p). Examination of different nitrogen protecting groups revealed that acetyl-, benzoyl-, and methoxycarbonyl-protected N-[(4-methoxycarbonyl) phenyl] hydroxylamines showed excellent and comparable reactivities (2q-2s), while dimethylcarbamoyl-protected N-[(4-methoxycarbonyl) phenyl] hydroxylamine was found to react sluggishly (2t). Substrates bearing a dimethylcarbamoyl group (2d, 2t) afforded the corresponding products in lower yields. This is probably due to decomposition of the dimethylcarbamoyl group resulting from a hydrogen atom abstraction of N☐CH3 by a N-hydroxyl radical.[18] It is noteworthy that this class of the OCF3 compounds (2a-2t) shows the most shielded chemical shift (~−65 ppm) in 19F-NMR compared to other OCF$_3$ containing compounds such as TEMPO-CF3 (−55.7 ppm),[19] Ph-OCF3 (−58 ppm),[20] and n-C$_{10}$H$_{21}$—OCF$_3$ (−61.3 ppm).[21]
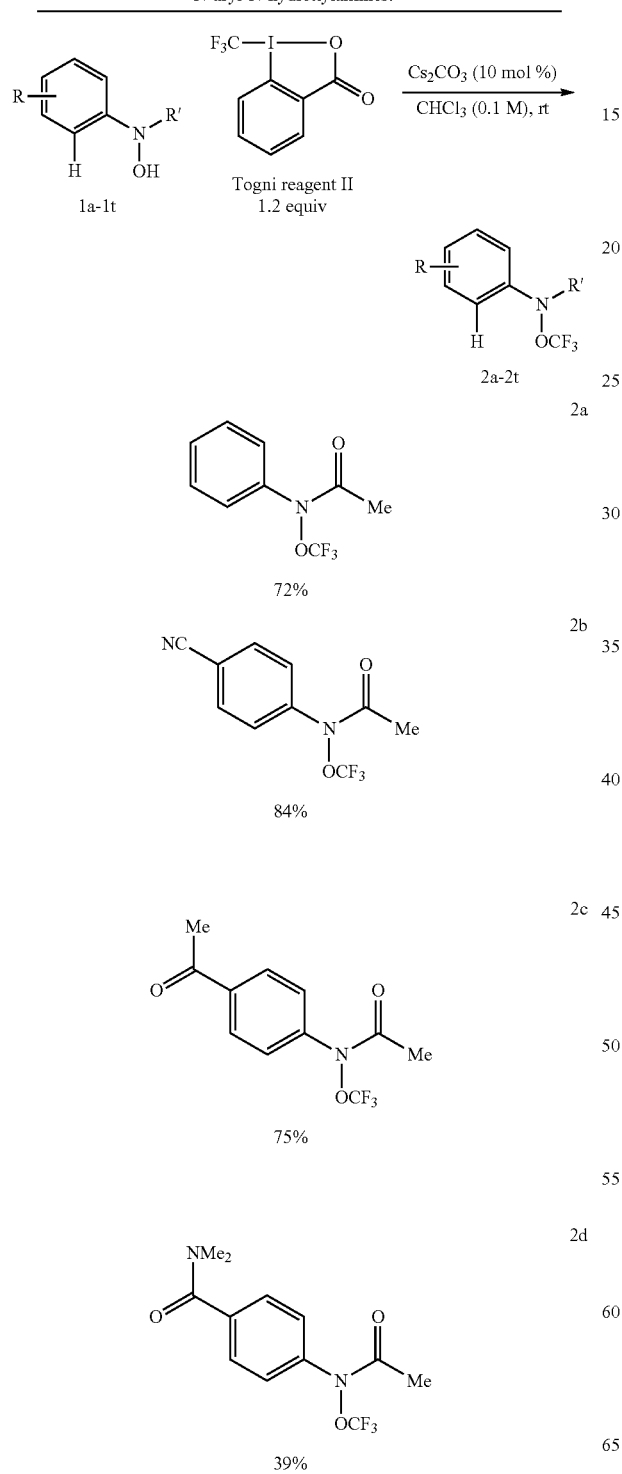
73%
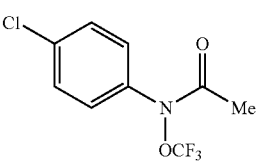
70%
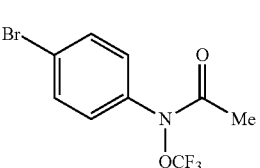
81%
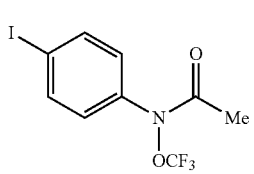
82%
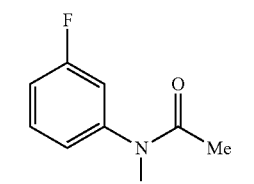
76%
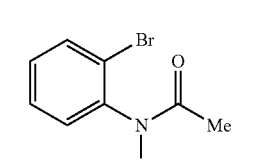
77%
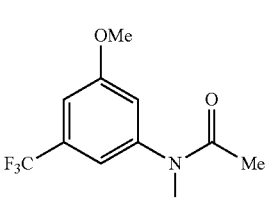
82%

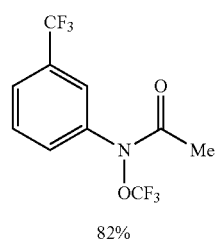

82%

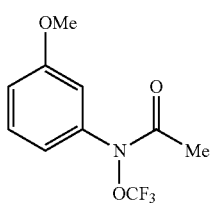

76%

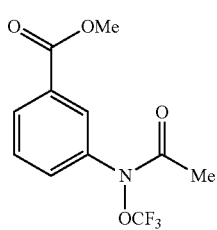

67%

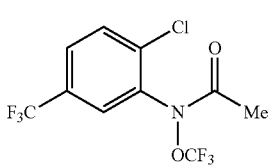

75%

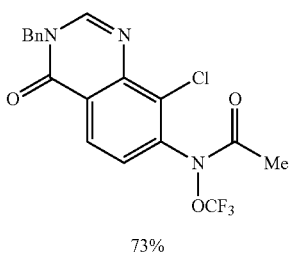

73%

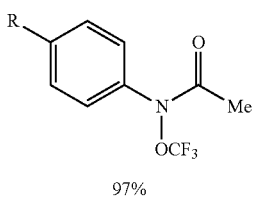

97%

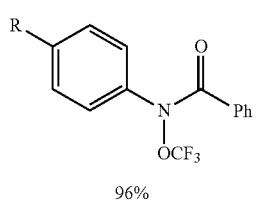

96%

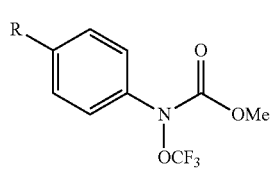

91%

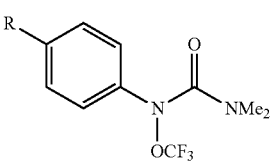

40%

R = $CO_2$Me

[a]Reaction time: 14-23 hours. Cited yields are for isolated material following chromatography.

Procedures for O-trifluoromethylation of Protected N-aryl-N-hydroxylamines N-Phenyl-N-(trifluoromethoxy)acetamide (2a)

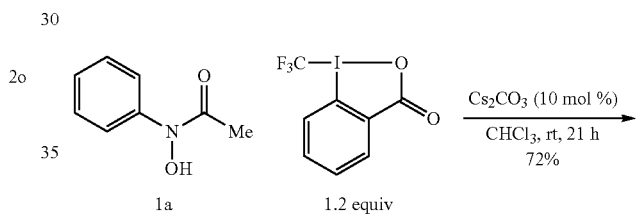

Under $N_2$ atmosphere, to a mixture of N-hydroxy-N-phenylacetamide (1a) (400 mg, 2.65 mmol, 1.00 equiv) and $Cs_2CO_3$ (86.2 mg, 0.265 mmol, 10 mol %) in $CHCl_3$ (26.5 mL, 0.100 M) was added Togni reagent II (1.00 g, 3.18 mmol, 1.20 equiv) and the reaction mixture was stirred at rt for 21 h. The reaction mixture concentrated in vacuo. The residue was purified by chromatography on silica gel, eluting with hexanes:EtOAc (19:1 to 9:1 (v/v)), to afford the title compound as a slightly yellow oil (420 mg, 1.92 mmol, 72% yield). $R_f$=0.63 (hexanes/EtOAc 9:1 (v/v)). NMR Spectroscopy: $^1$H NMR (500 MHz, $CDCl_3$, 25° C., δ): 7.49-7.41 (m, 2H), 7.41-7.31 (m, 3H), 2.22 (s, 3H). $^{13}$C NMR (125 MHz, $CDCl_3$, 25° C., δ): 172.4, 140.4, 129.5, 129.4, 126.3, 122.9 (q, J=263.0 Hz), 22.0. $^{19}$F NMR (376 MHz, $CDCl_3$, (376 MHz, $CDCl_3$, 25° C., δ): −64.8 (s). 25° C., δ): −64.8 (s). Mass Spectrometry: HRMS (ESI-TOF) (m/z): calcd for $C_9H_9NO_2F_3$ ([M+H]$^+$), 220.0585, found, 220.0580.

N-(4-Cyanophenyl)-N-(trifluoromethoxy)acetamide (2b)

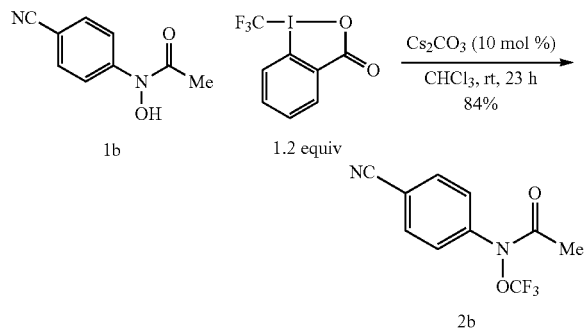

Under N$_2$ atmosphere, to a mixture of N-(4-cyanophenyl)-N-hydroxyacetamide (1b) (200 mg, 1.14 mmol, 1.00 equiv) and Cs$_2$CO$_3$ (37.0 mg, 0.114 mmol, 10 mol %) in CHCl$_3$ (11.4 mL, 0.100 M) was added Togni reagent II (432 mg, 1.37 mmol, 1.20 equiv) and the reaction mixture was stirred at rt for 23 h. The reaction mixture was filtered and the filtrate was concentrated in vacuo. The residue was purified by chromatography on silica gel, eluting with hexanes:CH$_2$Cl$_2$ (1:2 to 0:1 (v/v)), to afford the title compound as an off-white solid (234 mg, 0.958 mmol, 84% yield). R$_f$=0.66 (CH$_2$Cl$_2$). NMR Spectroscopy: 1H NMR (700 MHz, CDCl$_3$, 25° C., δ): 7.74-7.70 (m, 2H), 7.55-7.51 (m, 2H), 2.38 (s, 3H). $^{13}$C NMR (175 MHz, CDCl$_3$, 25° C., δ): 172.4, 143.6, 133.1, 123.8, 122.7 (q, J=265.2 Hz), 118.1, 111.6, 21.9. $^{19}$F NMR (376 MHz, CDCl$_3$, 25° C., δ): −65.2 (s). Mass Spectrometry: HRMS (ESI-TOF) (m/z): calcd for C$_{10}$H$_8$N$_2$O$_2$F$_3$ ([M+H]$^+$), 245.0538, found, 245.0541.

N-(4-Acetylphenyl)-N-(trifluoromethoxy)acetamide (2c)

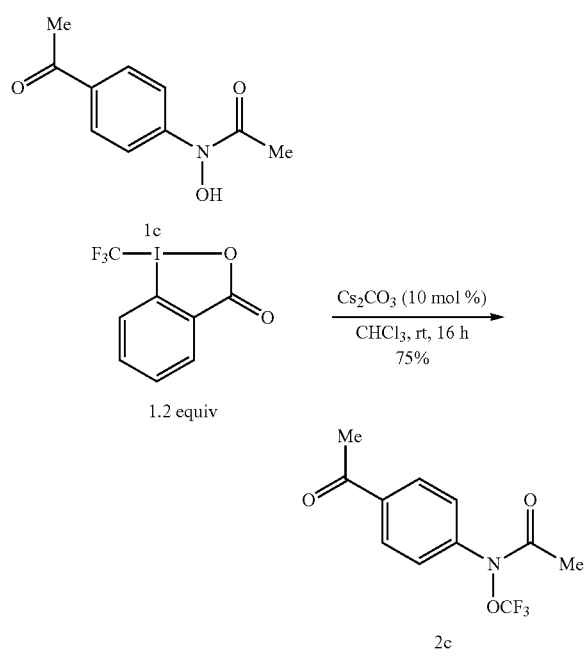

Under N$_2$ atmosphere, to a mixture of methyl N-(4-acetylphenyl)-N-hydroxyacetamide (1c) (309 mg, 1.60 mmol, 1.00 equiv) and Cs$_2$CO$_3$ (52.1 mg, 0.160 mmol, 10 mol %) in CHCl$_3$ (16.0 mL, 0.100 M) was added Togni reagent II (607 mg, 1.92 mmol, 1.20 equiv) and the reaction mixture was stirred at rt for 16 h. The reaction mixture was then washed with sat. aq. NaHCO$_3$ (30 mL) and the layers were separated. The organic layer was dried (MgSO$_4$), filtered, and concentrated in vacuo. The residue was purified by chromatography on silica gel, eluting with hexanes:EtOAc (9:1 to 7:3 (v/v)), to afford the title compound as a slightly yellow oil (314 mg, 1.20 mmol, 75% yield). R$_f$=0.62 (hexanes/EtOAc 4:1 (v/v)). NMR Spectroscopy: $^1$H NMR (700 MHz, CDCl$_3$, 25° C., δ): 8.03-8.00 (m, 2H), 7.50-7.48 (m, 2H), 2.61 (s, 3H), 2.33 (s, 3H). $^{13}$C NMR (175 MHz, CDCl$_3$, 25° C., δ): 196.9, 172.3, 143.9, 136.5, 129.3, 124.0, 122.7 (q, J=264.2 Hz), 26.8, 21.9. $^{19}$F NMR (376 MHz, CDCl$_3$, 25° C., δ): −65.00 (s). Mass Spectrometry: HRMS (ESI-TOF) (m/z): calcd for C$_{11}$H$_{11}$NO$_3$F$_3$ ([M+H]$^+$), 262.0691, found, 262.0691.

N,N-Dimethyl-4-(N-(trifluoromethoxy)acetamido)benzamide (2d)

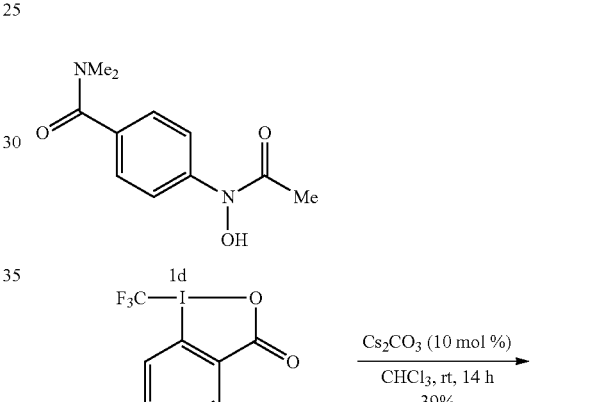

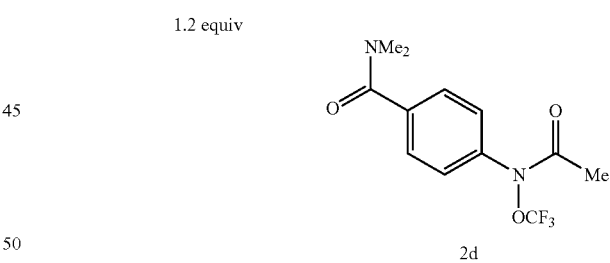

Under N$_2$ atmosphere, to a mixture of 4-(N-hydroxyacetamido)-N,N-dimethylbenzamide (1d) (192 mg, 0.864 mmol, 1.00 equiv) and Cs$_2$CO$_3$ (28.2 mg, 0.0864 mmol, 10 mol %) in CHCl$_3$ (8.64 mL, 0.100 M) was added Togni reagent II (329 mg, 1.04 mmol, 1.20 equiv) and the reaction mixture was stirred at rt for 14 h. The reaction mixture was then washed with sat. aq. NaHCO$_3$ (30 mL) and the layers were separated. The organic layer was dried (MgSO$_4$), filtered and concentrated in vacuo. The reaction mixture was purified by preparative TLC using hexanes:EtOAc (7:3 (v/v)) for development (prep TLC was developed four times). The purification afforded the title compound as a pink oil (98.4 mg, 0.339 mmol, 39% yield). R$_f$=0.30 (hexanes/EtOAc 2:3 (v/v)). NMR Spectroscopy: $^1$H NMR (700 MHz, CDCl$_3$, 25° C., δ): 7.49 (d, J=8.2 Hz, 2H), 7.42

(d, J=8.2 Hz, 2H), 3.12 (br. s, 3H), 2.99 (br. s, 3H), 2.27 (s, 3H). $^{13}$C NMR (175 MHz, CDCl$_3$, 25° C., δ): 172.4, 170.5, 141.1, 136.8, 128.2, 125.2, 122.8 (q, J=263.8 Hz), 39.7, 35.5, 21.9. $^{19}$F NMR (376 MHz, CDCl$_3$, 25° C., δ): −64.9 (s). Mass Spectrometry: HRMS (ESI-TOF) (m/z): calcd for C$_{12}$H$_{14}$N$_2$O$_3$F$_3$ ([M+H]$^+$), 291.0957, found, 291.0958.

N-(4-Fluorophenyl)-N-(trifluoromethoxy)acetamide (2e)

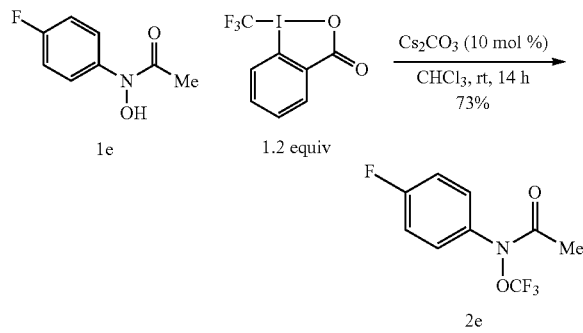

Under N$_2$ atmosphere, to a mixture of N-(4-fluorophenyl)-hydroxyacetamide (1e) (200 mg, 1.18 mmol, 1.00 equiv) and CS$_2$CO$_3$ (38.5 mg, 0.118 mmol, 10 mol %) in CHCl$_3$ (11.8 mL, 0.100 M) was added Togni reagent II (447 mg, 1.42 mmol, 1.20 equiv) and the reaction mixture was stirred at rt for 14 h. The reaction mixture was filtered and the filtrate was concentrated in vacuo. The residue was purified by chromatography on silica gel, eluting with hexanes:CH$_2$Cl$_2$ (1:1 to 0:1 (v/v)), to afford the title compound as a slightly yellow oil (206 mg, 0.868 mmol, 73% yield). R$_f$=0.42 (hexanes/CH$_2$Cl$_2$ 1:1 (v/v)). NMR Spectroscopy: $^1$H NMR (700 MHz, CDCl$_3$, 25° C., δ): 7.39-7.34 (m, 2H), 7.16-7.11 (m, 2H), 2.24 (s, 3H). $^{13}$C NMR (175 MHz, CDCl$_3$, 25° C., δ): 172.7, 162.7 (d, J=249.0 Hz), 136.4 (d, J=2.6 Hz), 128.5, 122.9 (q, J=263.1 Hz), 116.6 (d, J=22.9 Hz), 21.9. $^{19}$F NMR (376 MHz, CDCl$_3$, 25° C., δ): −64.8 (s), −111.4 (s). Mass Spectrometry: HRMS (ESI-TOF) (m/z): calcd for C$_9$H$_8$NO$_2$F$_4$ ([M+H]$^+$), 238.0491, found, 238.0493.

N-(4-Chlorophenyl)-N-(trifluoromethoxy)acetamide (2f)

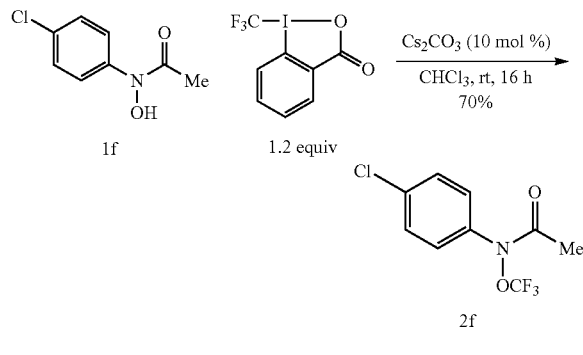

Under N$_2$ atmosphere, to a mixture of N-(4-chlorophenyl)-N-hydroxyacetamide (1f) (297 mg, 1.60 mmol, 1.00 equiv) and Cs$_2$CO$_3$ (52.1 mg, 0.160 mmol, 10 mol %) in CHCl$_3$ (16.0 mL, 0.100 M) was added Togni reagent II (607 mg, 1.92 mmol, 1.20 equiv) and the reaction mixture was stirred at rt for 16 h. The reaction mixture was filtered and the filtrate was concentrated in vacuo. The residue was purified by chromatography on silica gel, eluting with hexanes:CH$_2$Cl$_2$ (7:3 to 1:1 (v/v)), to afford the title compound a slightly yellow oil (284 mg, 1.12 mmol, 70% yield). R$_f$=0.59 (hexanes/CH$_2$Cl$_2$ 1:1 (v/v)). NMR Spectroscopy: $^1$H NMR (700 MHz, CDCl$_3$, 25° C., δ): 7.42 (d, J=8.6 Hz, 2H), 7.32 (d, J=8.6 Hz, 2H), 2.26 (s, 3H). $^{13}$C NMR (175 MHz, CDCl$_3$, 25° C., δ): 172.6, 138.8, 135.0, 129.7, 127.1, 122.8 (q, J=263.7 Hz), 21.9. $^{19}$F NMR (376 MHz, CDCl$_3$, 25° C., δ): −64.9 (s). Mass Spectrometry: HRMS (ESI-TOF) (m/z): calcd for C$_9$H$_8$NO$_2$F$_3$Cl ([M+H]$^+$), 254.0196, found, 254.0198.

N-(4-Bromophenyl)-N-(trifluoromethoxy)acetamide (2g)

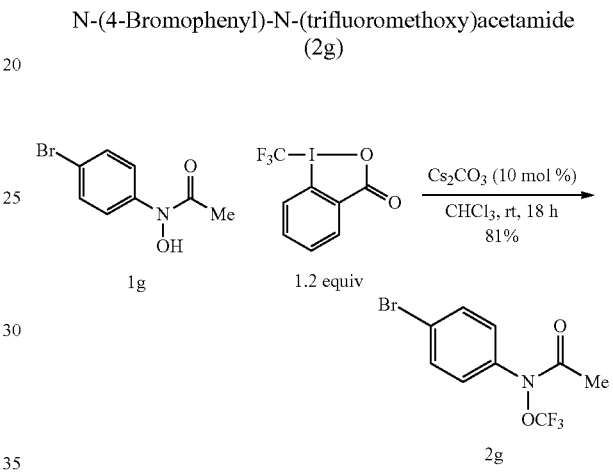

Under N$_2$ atmosphere, to a mixture of N-(4-bromophenyl)-N-hydroxyacetamide (1g) (368 mg, 1.60 mmol, 1.00 equiv) and Cs$_2$CO$_3$ (52.1 mg, 0.160 mmol, 10 mol %) in CHCl$_3$ (16.0 mL, 0.100 M) was added Togni reagent II (607 mg, 1.92 mmol, 1.20 equiv) and the reaction mixture was stirred at rt for 18 h. The reaction mixture was filtered and the filtrate was concentrated in vacuo. The residue was purified by chromatography on silica gel, eluting with hexanes:CH$_2$Cl$_2$ (1:1 to 1:3 (v/v)), to afford the title compound as a slightly yellow oil (384 mg, 1.29 mmol, 81% yield). R$_f$=0.47 (hexanes/CH$_2$Cl$_2$ 1:1 (v/v)). NMR Spectroscopy: $^1$H NMR (700 MHz, CDCl$_3$, 25° C., δ): 7.59-7.55 (m, 2H), 7.23-7.28 (m, 2H), 2.26 (s, 3H). $^{13}$C NMR (175 MHz, CDCl$_3$, 25° C., δ): 172.5, 139.3, 132.6, 127.2, 122.9, 122.8 (q, J=263.3 Hz), 21.8. $^{19}$F NMR (376 MHz, CDCl$_3$, 25° C., δ): −64.9 (s). Mass Spectrometry: HRMS (ESI-TOF) (m/z): calcd for C$_9$H$_8$NO$_2$F$_3$Br ([M+H]$^+$), 297.9690, found, 297.9694.

N-(4-Iodophenyl)-N-(trifluoromethoxy)acetamide (2h)

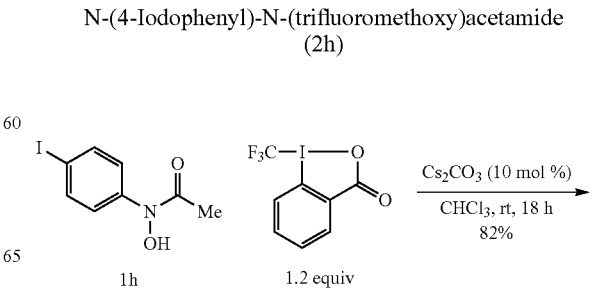

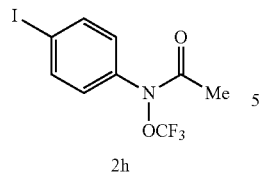

2h

Under N$_2$ atmosphere, to a mixture of N-hydroxy-N-(4-iodophenyl)acetamide (1h) (200 mg, 0.722 mmol, 1.00 equiv) and Cs$_2$CO$_3$ (23.5 mg, 0.0720 mmol, 10 mol %) in CHCl$_3$ (7.20 mL, 0.100 M) was added Togni reagent II (274 mg, 0.867 mmol, 1.20 equiv) and the reaction mixture was stirred at rt for 18 h. The reaction mixture was filtered and the filtrate was concentrated in vacuo. The residue was purified by chromatography on silica gel, eluting with hexanes:CH$_2$Cl$_2$ (1:1 (v/v)), to afford the title compound as a slightly yellow oil (205 mg, 0.594 mmol, 82% yield). R$_f$=0.48 (hexanes/CH$_2$Cl$_2$ 1:1 (v/v)). NMR Spectroscopy: $^1$H NMR (700 MHz, CDCl$_3$, 25° C., δ): 7.79-7.76 (m, 2H), 7.14-7.11 (m, 2H), 2.27 (s, 3H). $^{13}$C NMR (175 MHz, CDCl$_3$, 25° C., δ): 172.5, 140.1, 138.6, 127.2, 122.8 (q, J=263.5 Hz), 94.4, 21.9. $^{19}$F NMR (376 MHz, CDCl$_3$, 25° C., δ): −64.9 (s). Mass Spectrometry: HRMS (ESI-TOF) (m/z): calcd for C$_9$H$_8$NO$_2$F$_3$I ([M+H]$^+$), 345.9552, found, 345.9549.

N-(3-Fluorophenyl)-N-(trifluoromethoxy)acetamide (2i)

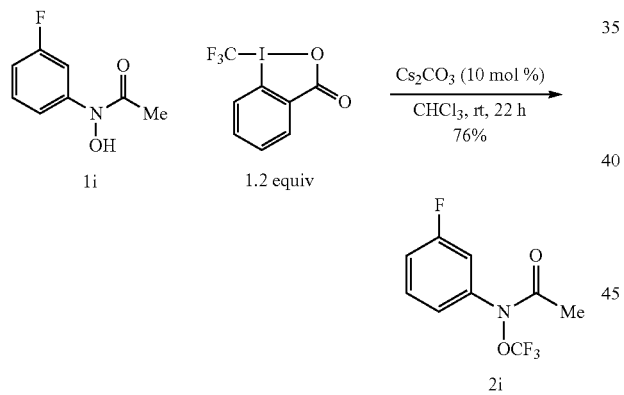

Under N$_2$ atmosphere, to a mixture of N-(3-fluorophenyl)-N-hydroxyacetamide (1i) (243 mg, 1.44 mmol, 1.00 equiv) and Cs$_2$CO$_3$ (46.9 mg, 0.144 mmol, 10 mol %) in CHCl$_3$ (14.4 mL, 0.100 M) was added Togni reagent II (546 mg, 1.73 mmol, 1.20 equiv) and the reaction mixture was stirred at rt for 22 h. The reaction mixture was concentrated in vacuo. The residue was purified by chromatography on silica gel, eluting with hexanes:CH$_2$Cl$_2$ (1:1 to 1:3 (v/v)), to afford the title compound as a slightly yellow oil (260 mg, 1.09 mmol, 76% yield). R$_f$=0.55 (hexanes/CH$_2$Cl$_2$ 1:1 (v/v)). NMR Spectroscopy: $^1$H NMR (700 MHz, CDCl$_3$, 25° C., δ): 7.41 (td, J=8.2, 6.0 Hz, 1H), 7.19 (d, J=8.2 Hz, 1H), 7.13 (dt, J=9.4, 2.2 Hz, 1H), 7.08 (td, J=8.2, 1.7 Hz, 1H), 2.28 (s, 3H). $^{13}$C NMR (175 MHz, CDCl$_3$, 25° C., δ): 172.5, 162.7 (d, J=246.8 Hz), 141.6 (d, J=9.8 Hz), 130.5 (d, J=8.8 Hz), 122.8 (q, J=263.4 Hz), 121.0, 115.9 (d, J=20.9 Hz), 112.9 (d, J=24.0 Hz), 21.9. $^{19}$F NMR (376 MHz, CDCl$_3$, 25° C., δ): −65.0 (s), −111.2 (s). Mass Spectrometry: HRMS (EI-TOF) (m/z): calcd for C$_9$H$_7$NO$_2$F$_4$ ([M]$^+$), 237.0413, found, 237.0417.

N-(2-Bromophenyl)-N-(trifluoromethoxy)acetamide (2j)

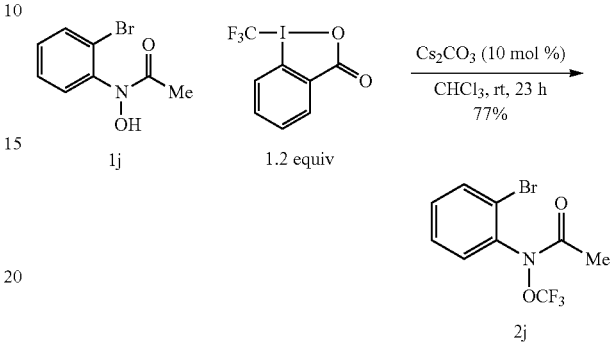

Under N$_2$ atmosphere, to a mixture of N-(2-bromophenyl)-N-hydroxyacetamide (1j) (368 mg, 1.60 mmol, 1.00 equiv) and Cs$_2$CO$_3$ (52.1 mg, 0.160 mmol, 10 mol %) in CHCl$_3$ (16.0 mL, 0.100 M) was added Togni reagent II (607 mg, 1.92 mmol, 1.20 equiv) and the reaction mixture was stirred at rt for 23 h. The reaction mixture was filtered and the filtrate was concentrated in vacuo. The residue was purified by chromatography on silica gel, eluting with hexanes:CH$_2$Cl$_2$ (1:1 to 0:1 (v/v)), to afford the title compound as a slightly yellow oil (367 mg, 1.23 mmol, 77% yield). R$_f$=0.55 (hexanes/CH$_2$Cl$_2$ 1:1 (v/v)). NMR Spectroscopy: $^1$H NMR (700 MHz, CDCl$_3$, 25° C., δ): 7.70 (d, J=7.7 Hz, 1H), 7.48 (d, J=7.7 Hz, 1H), 7.42 (t, J=7.5 Hz, 1H), 7.36-7.31 (m, 1H), 2.23 (br. s, 3H). $^{13}$C NMR (175 MHz, CDCl$_3$, 25° C., δ): 172.6, 139.6, 134.2, 132.0, 131.3, 128.7, 123.6, 123.0 (q, J=263.0 Hz), 21.6. $^{19}$F NMR (376 MHz, CDCl$_3$, 25° C., δ): −64.6 (s). Mass Spectrometry: HRMS (ESI-TOF) (m/z): calcd for C$_9$H$_8$NO$_2$F$_3$Br ([M+H]$^+$), 297.9690, found, 297.9688.

N-(3-Methoxy-5-(trifluoromethyl)phenyl)-N-(trifluoromethoxy)acetamide (2k)

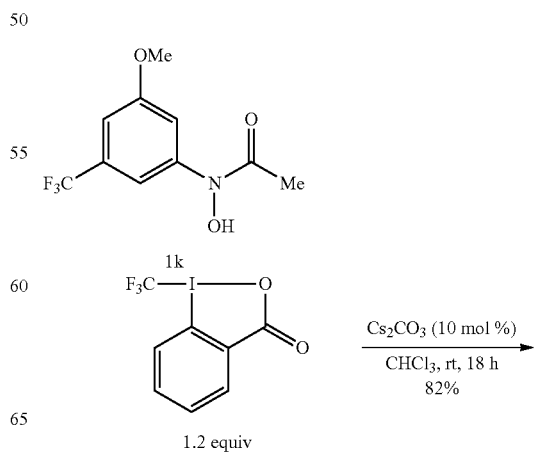

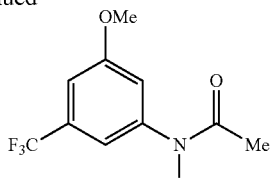

2k

Under N₂ atmosphere, to a mixture of N-hydroxy-N-(3-methoxy-5-(trifluoromethyl)phenyl)acetamide (1k) (399 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 18 h. The reaction mixture was filtered and the filtrate was concentrated in vacuo. The residue was purified by chromatography on silica gel, eluting with hexanes:CH₂Cl₂ (1:3 to 3:1 (v/v)), to afford the title compound as a slightly yellow oil (417 mg, 1.31 mmol, 82% yield). R$_f$=0.33 (hexanes/CH₂Cl₂ 3:2 (v/v)). NMR Spectroscopy: $^1$H NMR (700 MHz, CDCl₃, 25° C., δ): 7.24 (br. s, 1H), 7.12 (br. s, 1H), 7.09 (br. s, 1H), 3.87 (s, 3H), 2.32 (s, 3H). $^{13}$C NMR (175 MHz, CDCl₃, 25° C., δ): 172.7, 160.4, 141.8, 132.7 (q, J=33.0 Hz), 123.4 (q, J=271.1 Hz), 122.8 (q, J=264.0 Hz), 114.5, 113.9, 111.2, 56.0, 21.8. $^{19}$F NMR (376 MHz, CDCl₃, 25° C., δ): −63.4 (s), −65.0 (s). Mass Spectrometry: HRMS (ESI-TOF) (m/z): calcd for C₁₁H₁₀NO₃F₆ ([M+H]⁺), 318.0565, found, 318.0569.

N-(Trifluoromethoxy)-N-(3-(trifluoromethyl)phenyl)acetamide (2l)

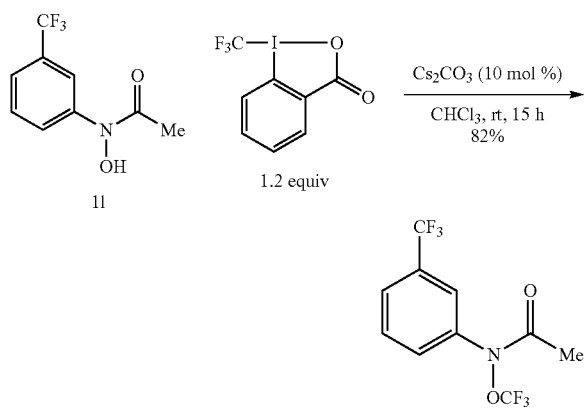

Under N₂ atmosphere, to a mixture of N-hydroxy-N-(3-(trifluoromethyl)phenyl)acetamide (1l) (351 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 15 h. The reaction mixture was filtered and the filtrate was concentrated in vacuo. The residue was purified by chromatography on silica gel, eluting with hexanes:CH₂Cl₂ (1:1 to 0:1 (v/v)), to afford the title compound as a slightly yellow oil (378 mg, 1.32 mmol, 82% yield). R$_f$=0.50 (hexanes/CH₂Cl₂ 1:1 (v/v)). NMR Spectroscopy: $^1$H NMR (500 MHz, CDCl₃, 25° C., δ): 7.66 (s, 1H), 7.64-7.60 (m, 1H), 7.60-7.56 (m, 2H), 2.33 (s, 3H). $^{13}$C NMR (125 MHz, CDCl₃, 25° C., δ): 172.8, 140.8, 132.0 (q, J=33.0 Hz), 129.9, 128.3, 125.4 (q, J=3.1 Hz), 123.5 (q, J=271.1 Hz), 122.8 (q, J=264.0 Hz), 121.7, 21.8. $^{19}$F NMR (376 MHz, CDCl₃, 25° C., δ): −63.3 (s), −65.0 (s). Mass Spectrometry: HRMS (EI-TOF) (m/z): calcd for C₁₀H₇NO₂F₆ ([M]⁺), 287.0381, found, 287.0389.

N-(3-Methoxyphenyl)-N-(trifluoromethoxy)acetamide (2m)

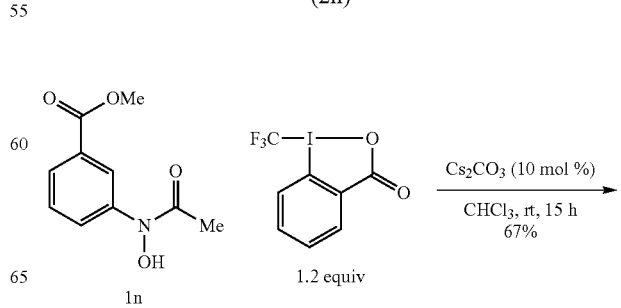

Under N₂ atmosphere, to a mixture of N-hydroxy-N-(3-methoxyphenyl)acetamide (1m) (290 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 19 h. The reaction mixture was concentrated in vacuo. The residue was purified by chromatography on silica gel, eluting with hexanes:CH₂Cl₂ (1:1 to 3:7 (v/v)), to afford the title compound as a yellow oil (303 mg, 1.21 mmol, 76% yield). R$_f$=0.34 (hexanes/CH₂Cl₂ 1:1 (v/v)). NMR Spectroscopy: $^1$H NMR (700 MHz, CDCl₃, 25° C., δ): 7.35 (t, J=8.2 Hz, 1H), 6.99-6.96 (m, 1H), 6.94 (dd, J=8.4, 1.9 Hz, 1H), 6.93-6.90 (m, 1H), 3.83 (s, 3H), 2.21 (s, 3H). $^{13}$C NMR (175 MHz, CDCl₃, 25° C., δ): 172.4, 160.4, 141.4, 130.2, 122.9 (q, J=262.7 Hz), 118.5, 115.2, 112.0, 55.6, 22.0. $^{19}$F NMR (376 MHz, CDCl₃, 25° C., δ): −64.8 (s). Mass Spectrometry: HRMS (ESI-TOF) (m/z): calcd for C₁₀H₁₁NO₃F₃ ([M+H]⁺), 250.0691, found, 250.0687.

Methyl 3-(N-(trifluoromethoxy)acetamido)benzoate (2n)

-continued

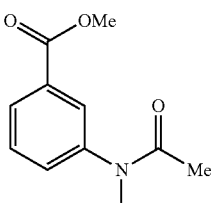

2n

Under N₂ atmosphere, to a mixture of methyl 3-(N-hydroxyacetamido)benzoate (1n) (335 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 15 h. The reaction mixture was filtered and the filtrate was concentrated in vacuo. The residue was purified by chromatography on silica gel, eluting with hexanes:CH₂Cl₂ (1:3 to 0:1 (v/v)), to afford the title compound as a slightly yellow oil (298 mg, 1.08 mmol, 67% yield). $R_f$=0.50 (CH₂Cl₂). NMR Spectroscopy: ¹H NMR (500 MHz, CDCl₃, 25° C., δ): 8.07-8.04 (m, 2H), 7.59-7.56 (m, 1H), 7.55-7.50 (m, 1H), 3.94 (s, 3H), 2.29 (s, 3H). ¹³C NMR (125 MHz, CDCl₃, 25° C., δ): 172.7, 166.0, 140.6, 131.7, 130.0, 129.9, 129.5, 126.5, 122.8 (q, J=263.7 Hz), 52.6, 21.8. ¹⁹F NMR (376 MHz, CDCl₃, 25° C., δ): −64.9 (s). Mass Spectrometry: HRMS (ESI-TOF) (m/z): calcd for C₁₁H₁₁NO₄F₃ ([M+H]⁺), 278.0640, found, 278.0640.

Methyl 2-methyl-3-(N-(trifluoromethoxy)acetamido)benzoate (2o)

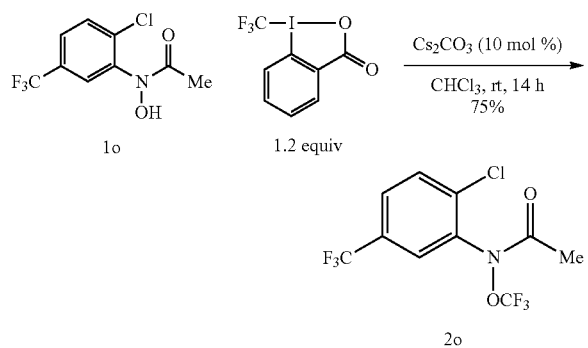

Under N₂ atmosphere, to a mixture of N-(2-chloro-5-(trifluoromethyl)phenyl)-N-hydroxyacetamide (1o) (406 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 14 h. The reaction mixture was filtered and the filtrate was concentrated in vacuo. The residue was purified by chromatography on silica gel, eluting with hexanes:CH₂Cl₂ (1:1 to 1:3 (v/v)), to afford the title compound as a slightly yellow oil (388 mg, 1.21 mmol, 75% yield). $R_f$=0.64 (hexanes/CH₂Cl₂ 1:1 (v/v)). NMR Spectroscopy: ¹H NMR (700 MHz, CDCl₃, 25° C., δ): 7.73 (s, 1H), 7.69-7.64 (m, 2H), 2.35 (br. s, 3H). ¹³C NMR (175 MHz, CDCl₃, 25° C., δ): 173.3, 138.8, 137.5, 131.6, 130.7 (q, J=33.7 Hz), 128.4 (d, J=1.8 Hz), 127.9, 123.0 (q, J=271.1 Hz), 123.0 (q, J=263.8 Hz), 21.3. ¹⁹F NMR (376 MHz, CDCl₃, 25° C., δ): −63.3 (s), −65.0 (s). Mass Spectrometry: HRMS (EI-TOF) (m/z): calcd for C₁₀H₆NO₂F₆Cl ([M]⁺), 320.9991, found, 320.9998.

N-(3-Benzyl-8-chloro-4-oxo-3,4-dihydroquinazolin-7-yl)-N-(trifluoromethoxy)acetamide (2p)

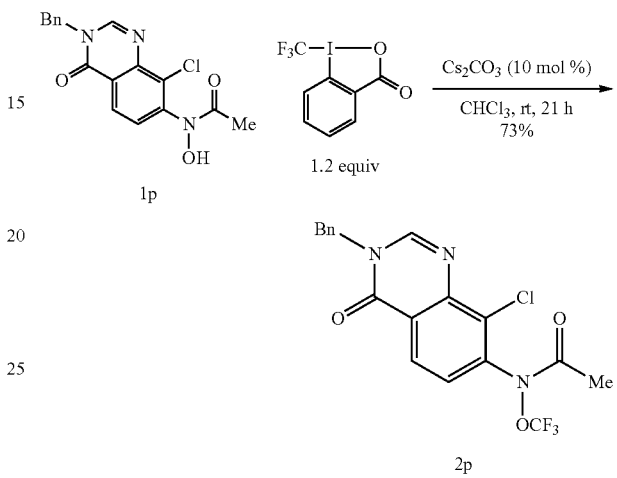

Under N₂ atmosphere, to a mixture of N-(3-benzyl-8-chloro-4-oxo-3,4-dihydroquinazolin-7-yl)-N-hydroxyacetamide (1p) (402 mg, 1.16 mmol, 1.00 equiv) and Cs₂CO₃ (37.8 mg, 0.116 mmol, 10 mol %) in CHCl₃ (11.6 mL, 0.100 M) was added Togni reagent II (439 g, 1.39 mmol, 1.20 equiv) and the reaction mixture was stirred at rt for 21 h. The reaction mixture was concentrated in vacuo. The residue was purified by chromatography on silica gel, eluting with hexanes:EtOAc (7:3 to 3:2 (v/v)), to afford the title compound as a white solid (351 mg, 0.852 mmol, 73% yield). $R_f$=0.52 (hexanes/EtOAc 3:2 (v/v)). NMR Spectroscopy: ¹H NMR (700 MHz, CDCl₃, 25° C., δ): 8.41 (s, 1H), 8.15 (s, 1H), 7.85 (s, 1H), 7.40-7.31 (m, 5H), 5.19 (s, 2H), 2.33 (br. s, 3H). ¹³C NMR (175 MHz, CDCl₃, 25° C., δ): 173.2, 159.8, 149.9, 148.9, 139.3, 136.9, 135.2, 129.8, 129.7, 129.3, 128.8, 128.2, 123.0 (q, J=263.5 Hz), 121.6, 50.0, 21.3. ¹⁹F NMR (376 MHz, CDCl₃, 25° C., δ): −64.7 (s). Mass Spectrometry: HRMS (ESI-TOF) (m/z): calcd for C₁₈H₁₄N₃O₃ClF₃ ([M+H]⁺), 412.0676, found, 412.0673.

Methyl 4-(N-(trifluoromethoxy)acetamido)benzoate (2q)

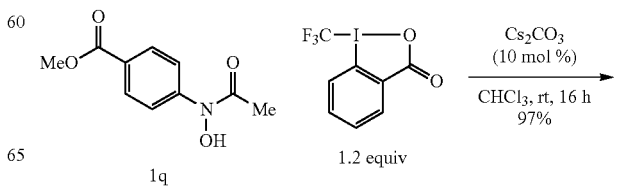

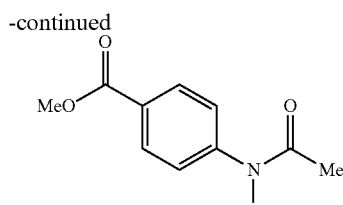

2q

Under N₂ atmosphere, to a mixture of methyl 4-(N-hydroxyacetamido)benzoate (1q) (335 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 16 h. The reaction mixture was filtered and the filtrate was concentrated in vacuo. The residue was purified by chromatography on silica gel, eluting with hexanes:CH₂Cl₂ (7:3 to 0:1 (v/v)), to afford the title compound as a slightly yellow oil (428 mg, 1.54 mmol, 97% yield). $R_f$=0.44 (CH₂Cl₂). NMR Spectroscopy: ¹H NMR (700 MHz, CDCl₃, 25° C., δ): 8.13-8.09 (m, 2H), 7.49-7.45 (m, 2H), 3.93 (s, 3H), 2.33 (s, 3H). ¹³C NMR (175 MHz, CDCl₃, 25° C., δ): 172.3, 166.2, 143.9, 130.6, 129.9, 124.0, 122.8 (q, J=264.1 Hz), 52.5, 21.9. ¹⁹F NMR (376 MHz, CDCl₃, 25° C., δ): −65.00 (s). Mass Spectrometry: HRMS (ESI-TOF) (m/z): calcd for $C_{11}H_{11}NO_4F_3$ ([M+H]⁺), 278.0640, found, 278.0637.

Methyl 4-(N-(trifluoromethoxy)benzamido)benzoate (2r)

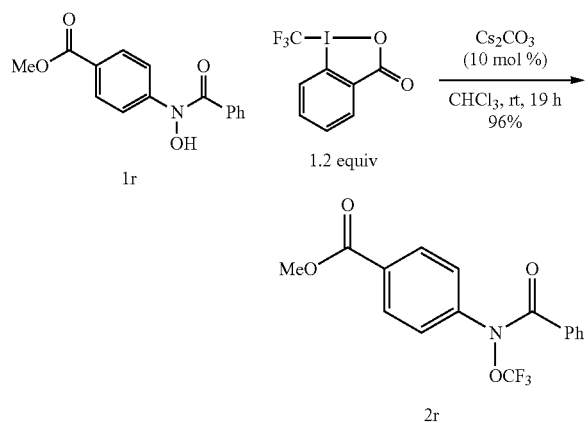

Under N₂ atmosphere, to a mixture of methyl 4-(N-hydroxybenzamido)benzoate (1r) (434 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 19 h. The reaction mixture was filtered and the filtrate was concentrated in vacuo. The residue was purified by chromatography on silica gel, eluting with hexanes:CH₂Cl₂ (1:1 to 0:1 (v/v)), to afford the title compound as a slightly yellow oil (521 mg, 1.54 mmol, 96% yield). $R_f$=0.67 (CH₂Cl₂). NMR Spectroscopy: ¹H NMR (700 MHz, CDCl₃, 25° C., δ): 8.03 (d, J=8.6 Hz, 2H), 7.65-7.61 (m, 2H), 7.47-7.41 (m, 3H), 7.32 (t, J=7.7 Hz, 2H), 3.90 (s, 3H). ¹³C NMR (175 MHz, CDCl₃, 25° C., δ): 170.7, 165.9, 145.2, 132.5, 132.1, 131.1, 131.0, 129.2, 128.6, 127.2, 122.8 (q, J=265.8 Hz), 52.6. ¹⁹F NMR (376 MHz, CDCl₃, 25° C., δ): −64.4 (s). Mass Spectrometry: HRMS (ESI-TOF) (m/z): calcd for $C_{16}H_{13}NO_4F_3$ ([M+H]⁺), 340.0797, found, 340.0801.

Methyl 4-((methoxycarbonyl)(trifluoromethoxy)amino)benzoate (2s)

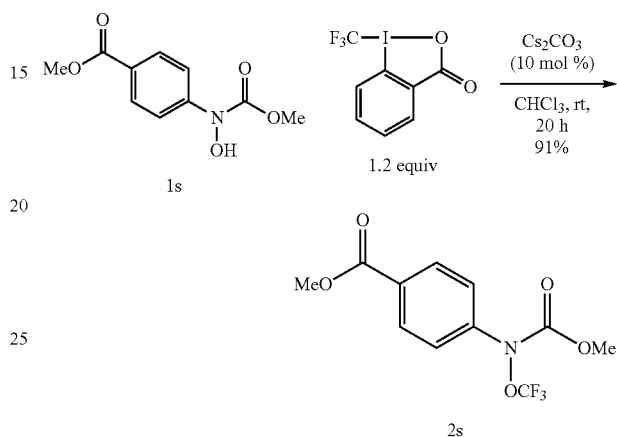

Under N₂ atmosphere, to a mixture of methyl 4-(hydroxy(methoxycarbonyl)amino)benzoate (1s) (360 mg, 1.60 mmol, 1.00 equiv) and Cs₂CO₃ (52.1 mg, 0.160 mmol, 10 mol %) in CHCl₃ (16.0 mL, 0.100 M) was added Togni reagent II (607 mg, 1.92 mmol, 1.20 equiv) and the reaction mixture was stirred at rt for 20 h. The reaction mixture was then washed with sat. aq. NaHCO₃ (30 mL) and the layers were separated. The organic layer was dried (MgSO₄), filtered and concentrated in vacuo. The residue was purified by chromatography on silica gel, eluting with hexanes:CH₂Cl₂ (1:3 to 0:1 (v/v)), to afford the title compound as a colorless oil (427 mg, 1.45 mmol, 91% yield). $R_f$=0.70 (CH₂Cl₂). NMR Spectroscopy: ¹H NMR (700 MHz, CDCl₃, 25° C., δ): 8.09 (d, J=8.6 Hz, 2H), 7.48 (d, J=8.6 Hz, 2H), 3.93 (s, 3H), 3.89 (s, 3H). ¹³C NMR (175 MHz, CDCl₃, 25° C., δ): 166.2, 155.4, 144.7, 130.6, 129.6, 123.3, 122.8 (q, J=263.1 Hz), 54.9, 52.5. ¹⁹F NMR (376 MHz, CDCl₃, 25° C., δ): −66.1 (s). Mass Spectrometry: HRMS (ESI-TOF) (m/z): calcd for $C_{11}H_{11}NO_5F_3$ ([M+H]⁺), 294.0589, found, 294.0589.

Methyl 4-(3,3-dimethyl-1-(trifluoromethoxy)ureido)benzoate (2t)

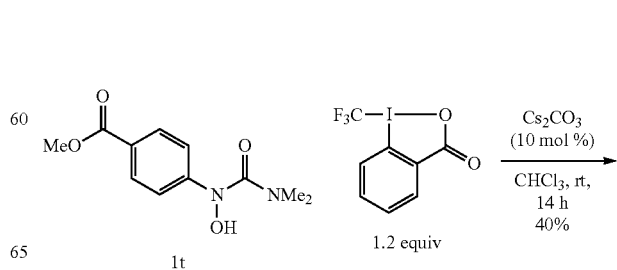

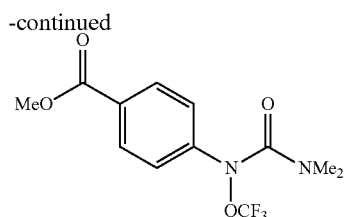

2t

Under N₂ atmosphere, to a mixture of methyl 4-(1-hydroxy-3,3-dimethylureido)benzoate (1t) (185 mg, 0.777 mmol, 1.00 equiv) and Cs₂CO₃ (25.3 mg, 0.0777 mmol, 10 mol %) in CHCl₃ (7.77 mL, 0.100 M) was added Togni reagent II (295 mg, 0.932 mmol, 1.20 equiv) and the reaction mixture was stirred at rt for 14 h. The reaction mixture was then washed with sat. aq. NaHCO₃ (30 mL) and the layers were separated. The organic layer was dried (MgSO₄), filtered and concentrated in vacuo. The residue was purified by chromatography on silica gel, eluting with CH₂Cl₂, to afford the title compound as a colorless oil (94.8 mg, 0.310 mmol, 40% yield). R$_f$=0.28 (CH₂Cl₂). NMR Spectroscopy: ¹H NMR (700 MHz, CDCl₃, 25° C., δ): 8.08 (d, J=8.6 Hz, 2H), 7.28 (d, J=8.60 Hz, 2H), 3.92 (s, 3H), 2.97 (s, 6H). ¹³C NMR (175 MHz, CDCl₃, 25° C., δ): 166.1, 158.0, 146.5, 131.4, 129.5, 122.9 (q, J=259.8 Hz), 122.2, 52.5, 37.3. ¹⁹F NMR (376 MHz, CDCl₃, 25° C., δ): −65.1 (s). Mass Spectrometry: HRMS (ESI-TOF) (m/z): calcd for C₁₂H₁₄N₂O₄F₃ ([M+H]⁺), 307.0906, found, 307.0910.

Example 3. OCF₃ Migration

With the protected N-aryl-N-(trifluoromethoxy)amines (2a-2t) in hand, attention was directed to examining the OCF₃-migration reaction. Systematic variation of different reaction parameters, including solvent, concentration, and temperature, identified optimal reaction conditions. A significant degree of structural and electronic variation on the aryl ring was tolerated (Scheme 3). Products derived from electron-rich (3m) and electron-poor (3b-3l, 3n-3t) aniline derivatives were formed in high yields, though electron-poor aniline derivatives with exception of 3p required higher reaction temperatures for full conversion. Notably, halogen functionalities, in particular Br and I, remained intact after reaction (3e-3j, 3o, 3p). These groups provide easy handles for further synthetic elaborations. Other functional groups including ester (3n, 3q-3t), nitrile (3b), ketone (3c), ether (3k, 3m), heterocycle (3p) and multiple substitution on arene (3k, 3o, 3p) were well tolerated under the reaction conditions. In general, this reaction showed high levels of ortho-selectivity (3a, 3i-3o); although, in the presence of two non-identical ortho positions, low levels of regiocontrol were obtained (3i, 3k-3n).

Scheme 3. Selected Examples of OCF₃-Migration Reaction[a]

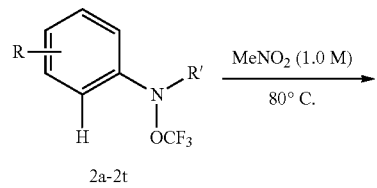

2a-2t

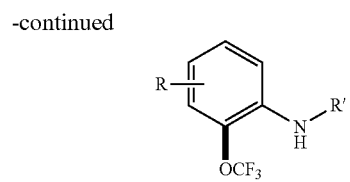

3a-3t

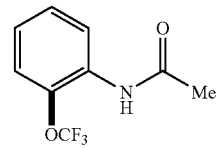

3a

91%, (o:p = 9:1)

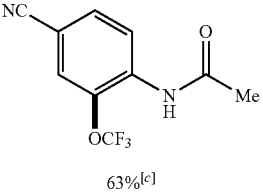

3b

63%[c]

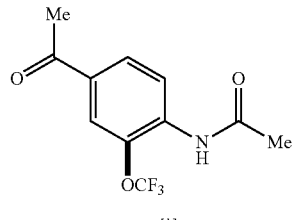

3c

90%[b]

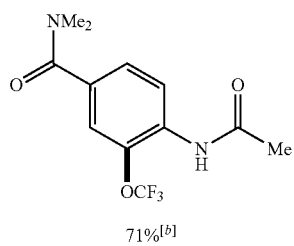

3d

71%[b]

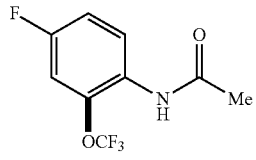

3e

88%

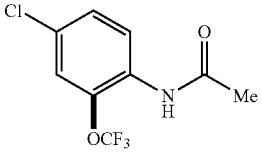

3f

85%

3g
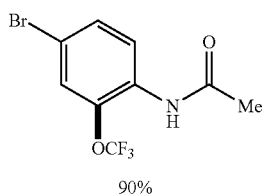
90%
3h
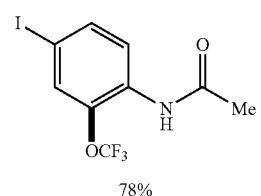
78%
3i
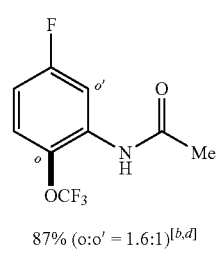
87% (o:o' = 1.6:1)[b,d]
3j
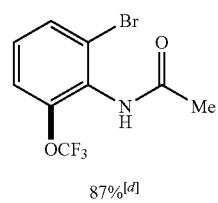
87%[d]
3k
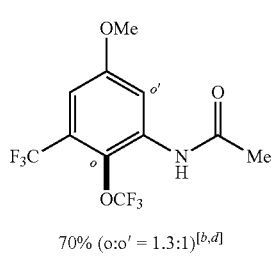
70% (o:o' = 1.3:1)[b,d]
3l
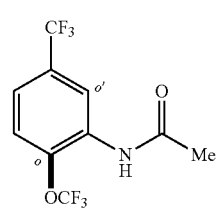
80% (o:o' = 1.6:1)[c,d]
3m
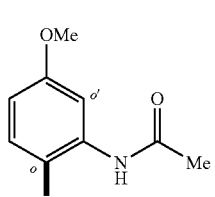
70% (o:o' = 3.7:1)[b,d]
3n
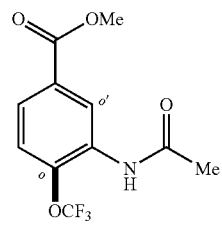
81% (o:o' = 1.1:1)[b,d]
3o
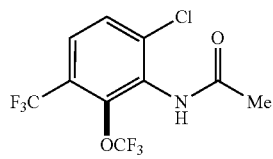
75%[c,d]
3p
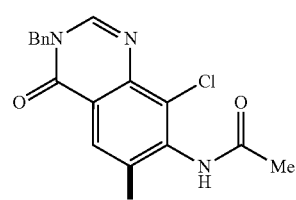
74%[a]
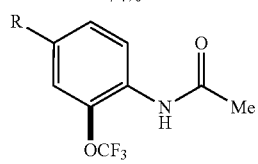
87%[b]
3r
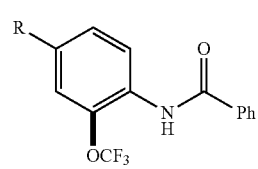
79%[b]
3s
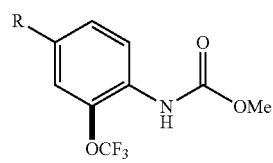
82%[b]
3t
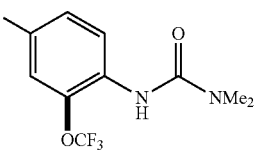
59%[b]
R = CO₂Me
[a]Reaction time: 11-48 hours. Cited yields and isomeric ratios are for isolated material following chromatography. [b]120° C. [c]140° C. [d]Less than 5% para-product was detected.

N-(2-(Trifluoromethoxy)phenyl)acetamide (3a) and N-(4-(trifluoromethoxy)phenyl)acetamide (3a-II)

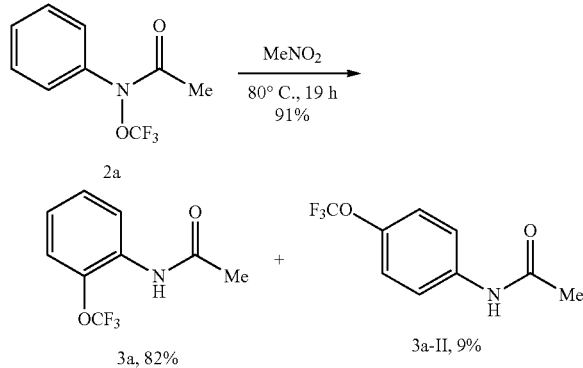

A solution of N-phenyl-N-(trifluoromethoxy)acetamide (2a) (128 mg, 100 μL, 0.584 mmol) in MeNO$_2$ (0.584 mL, 1.00 M) was heated at 80° C. under N$_2$ atmosphere for 19 h. The reaction mixture was concentrated in vacuo. The residue was purified by chromatography on silica gel, eluting with hexanes:EtOAc (9:1 to 1:1 (v/v)), to afford 3a (105 mg, 0.479 mmol, 82% yield) and 3a-II (11.2 mg, 0.0511 mmol, 9% yield). Data for 3a: white solid; R$_f$=0.36 (hexanes/EtOAc 4:1 (v/v)). NMR Spectroscopy: $^1$H NMR (700 MHz, CDCl$_3$, 25° C., δ): 8.39 (d, J=8.2 Hz, 1H), 7.39 (br. s, 1H), 7.28 (t, J=7.7 Hz, 1H), 7.25-7.24 (m, 1H), 7.12-7.08 (m, 1H), 2.23 (s, 3H). $^{13}$C NMR (175 MHz, CDCl$_3$, 25° C., δ): 168.4, 138.1, 130.7, 127.7, 124.3, 122.1, 120.7 (q, J=257.7 Hz), 120.4, 25.0. $^{19}$F NMR (376 MHz, CDCl$_3$, 25° C., δ): −58.4 (s). Mass Spectrometry: HRMS (ESI-TOF) (m/z): calcd for C$_9$H$_9$NO$_2$F$_3$ ([M+H]$^+$), 220.0585, found, 220.0583.

Data for 3a-II: white solid; R$_f$=0.33 (hexanes/EtOAc 3:2 (v/v)). NMR Spectroscopy: $^1$H NMR (500 MHz, CDCl$_3$, 25° C., δ): 7.53 (d, J=8.9 Hz, 2H), 7.18 (app d, J=8.9 Hz, 3H), 2.19 (s, 3H). $^{13}$C NMR (175 MHz, CDCl$_3$, 25° C., δ): 168.4, 145.4, 136.6, 121.9, 121.1, 120.6 (q, J=255.5 Hz), 24.7. $^{19}$F NMR (376 MHz, CDCl$_3$, 25° C., δ): −58.8 (s). Mass Spectrometry: HRMS (ESI-TOF) (m/z): calcd for C$_9$H$_9$NO$_2$F$_3$ ([M+H]$^+$), 220.0585, found, 220.0583.

N-(4-Cyano-2-(trifluoromethoxy)phenyl)acetamide (3b)

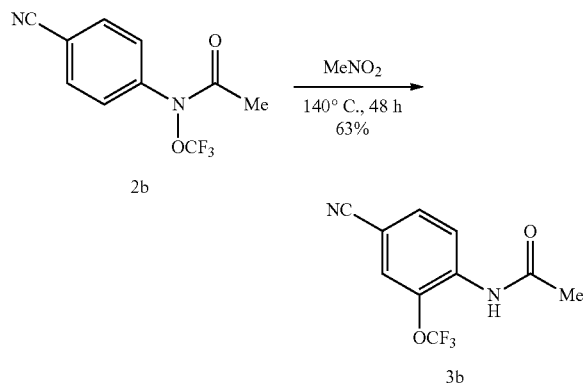

A solution of N-(4-cyanophenyl)-N-(trifluoromethoxy)acetamide (2b) (97.7 mg, 0.400 mmol) in MeNO$_2$ (0.400 mL, 1.00 M) was heated at 120° C. under N$_2$ atmosphere for 48 h. The reaction mixture was purified by preparative TLC using hexanes:EtOAc (7:3 (v/v)) for development. The purification afforded the title compound as a white crystalline solid (61.4 mg, 0.251 mmol, 63% yield). 20.0 mg (20%) of the starting material was recovered. Data for 3b: R$_f$=0.64 (hexanes/EtOAc 3:2 (v/v)). NMR Spectroscopy: $^1$H NMR (700 MHz, CDCl$_3$, 25° C., δ): 8.66 (d, J=8.6 Hz, 1H), 7.61 (br. s, 1H), 7.58 (d, J=8.6 Hz, 1H), 7.54 (s, 1H), 2.28 (s, 3H). $^{13}$C NMR (175 MHz, CDCl$_3$, 25° C., δ): 168.6, 137.1, 135.0, 132.0, 123.7, 121.8, 120.5 (q, J=260.2 Hz), 117.6, 107.2, 25.2. $^{19}$F NMR (376 MHz, CDCl$_3$, 25° C., δ): −58.4 (s). Mass Spectrometry: HRMS (ESI-TOF) (m/z): calcd for C$_{10}$H$_8$N$_2$O$_2$F$_3$ ([M+H]$^+$), 245.0538, found, 245.0539.

N-(4-Acetyl-2-(trifluoromethoxy)phenyl)acetamide (3c)

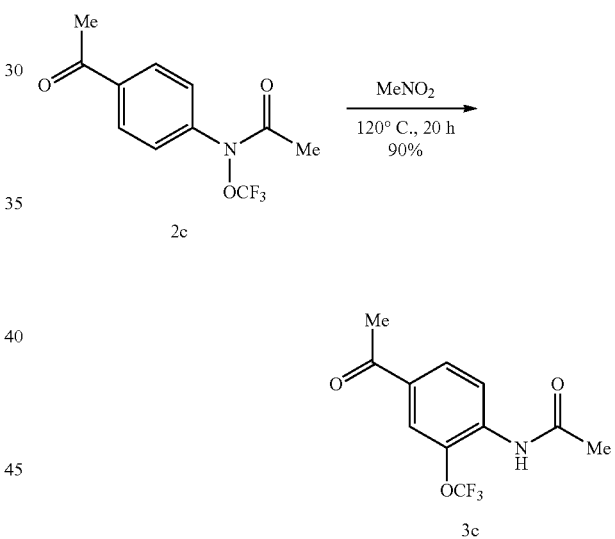

A solution of N-(4-acetylphenyl)-N-(trifluoromethoxy)acetamide (2c) (104 mg, 0.400 mmol) in MeNO$_2$ (0.400 mL, 1.00 M) was heated at 120° C. under N$_2$ atmosphere for 20 h. The reaction mixture was concentrated in vacuo. The residue was purified by chromatography on silica gel, eluting with hexanes:EtOAc (9:1 to 3:2 (v/v)), to afford the title compound as a white solid (93.6 mg, 0.358 mmol, 90% yield). R$_f$=0.46 (hexanes/EtOAc 3:2 (v/v)). NMR Spectroscopy: $^1$H NMR (700 MHz, CDCl$_3$, 25° C., δ): 8.59 (d, J=8.6 Hz, 1H), 7.89-7.86 (m, 2H), 7.58 (br. s, 1H), 2.59 (s, 3H), 2.27 (s, 3H). $^{13}$C NMR (175 MHz, CDCl$_3$, 25° C., δ): 195.7, 168.6, 137.6, 134.8, 132.9, 128.4, 120.8, 120.6 (q, J=259.1 Hz), 119.8, 26.5, 25.1. $^{19}$F NMR (376 MHz, CDCl$_3$, 25° C., δ): −58.0 (s). Mass Spectrometry: HRMS (ESI-TOF) (m/z): calcd for C$_{11}$H$_{11}$NO$_3$F$_3$ ([M+H]$^+$), 262.0691, found, 262.0692.

4-Acetamido-N,N-dimethyl-3-(trifluoromethoxy)benzamide (3d)

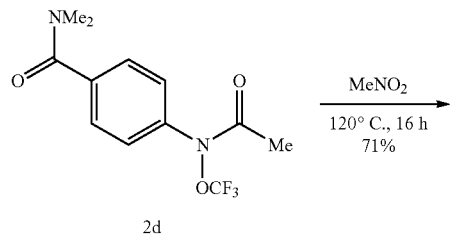

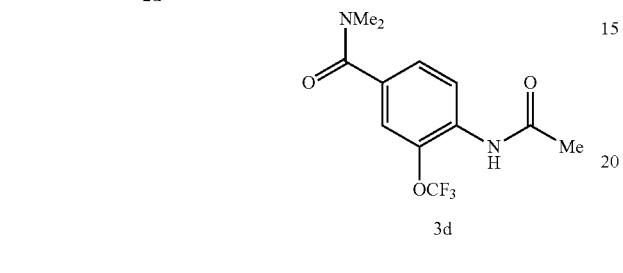

A solution of N,N-dimethyl-4-(N-(trifluoromethoxy)acetamido) benzamide (2d) (42.1 mg, 0.145 mmol) in MeNO$_2$ (0.145 mL, 1.00 M) was heated at 120° C. under N$_2$ atmosphere for 16 h. The reaction mixture was purified by preparative TLC using hexanes:EtOAc (3:7 (v/v)) for development (prep TLC was developed three times). The purification afforded the title compound as a white solid (30.0 mg, 0.103 mmol, 71% yield). R$_f$=0.36 (hexanes/EtOAc 3:7 (v/v)). NMR Spectroscopy: 1H NMR (700 MHz, CDCl$_3$, 25° C., δ): 8.38 (d, J=8.2 Hz, 1H), 7.72 (br. s, 1H), 7.35-7.30 (m, 2H), 3.08 (br. s, 3H), 2.99 (br. s, 3H), 2.23 (s, 3H). $^{13}$C NMR (175 MHz, CDCl$_3$, 25° C., δ): 169.7, 168.7, 137.8, 132.0, 131.8, 126.5, 121.8, 120.6 (q, J=258.5 Hz), 119.9, 39.7, 35.7, 24.8. $^{19}$F NMR (376 MHz, CDCl$_3$, 25° C., δ): −58.1 (s). Mass Spectrometry: HRMS (ESI-TOF) (m/z): calcd for C$_{12}$H$_{14}$N$_2$O$_3$F$_3$ ([M+H]$^+$), 291.0957, found, 291.0953.

N-(4-Fluoro-2-(trifluoromethoxy)phenyl)acetamide (3e)

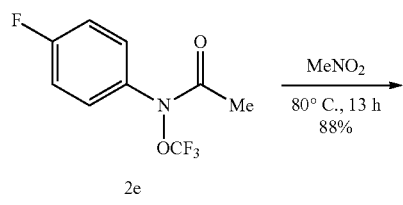

A solution of N-(4-fluorophenyl)-N-(trifluoromethoxy)acetamide (2e) (94.9 mg, 0.400 mmol) in MeNO$_2$ (0.400 mL, 1.00 M) was heated at 80° C. under N$_2$ atmosphere for 13 h. The reaction mixture was concentrated in vacuo. The residue was purified by chromatography on silica gel, eluting with hexanes:EtOAc (4:1 to 3:2 (v/v)), to afford the title compound as a beige solid (83.7 mg, 0.353 mmol, 88% yield). R$_f$=0.33 (hexanes/EtOAc 4:1 (v/v)). NMR Spectroscopy: $^1$H NMR (700 MHz, CDCl$_3$, 25° C., δ): 8.38-8.30 (m, 1H), 7.30-7.26 (m, 1H), 7.08-6.98 (m, 2H), 2.22 (s, 3H). $^{13}$C NMR (175 MHz, CDCl$_3$, 25° C., δ): 168.3, 158.4 (d, J=245.1 Hz), 138.4 (d, J=10.0 Hz), 126.9 (d, J=3.5 Hz), 123.4 (d, J=8.5 Hz), 120.5 (q, J=259.0 Hz), 114.3 (d, J=21.5 Hz), 108.4 (d, J=26.4 Hz), 24.8. $^{19}$F NMR (376 MHz, CDCl$_3$, 25° C., δ): −58.4 (s), −115.8 (m). Mass Spectrometry: HRMS (ESI-TOF) (m/z): calcd for C$_9$H$_8$NO$_2$F$_4$ ([M+H]$^+$), 238.0491, found, 238.0488.

N-(4-Chloro-2-(trifluoromethoxy)phenyl)acetamide (3f)

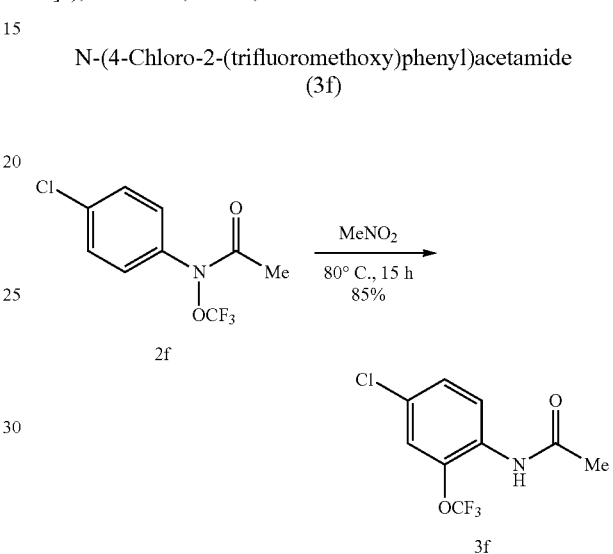

A solution of N-(4-chlorophenyl)-N-(trifluoromethoxy)acetamide (2f) (101 mg, 0.400 mmol) in MeNO$_2$ (0.400 mL, 1.00 M) was heated at 80° C. under N$_2$ atmosphere for 15 h. The reaction mixture was concentrated in vacuo. The residue was purified by chromatography on silica gel, eluting with hexanes:EtOAc (4:1 to 3:2 (v/v)), to afford the title compound as a beige solid (86.2 mg, 0.340 mmol, 85% yield). R$_f$=0.41 (hexanes/EtOAc 4:1 (v/v)). NMR Spectroscopy: $^1$H NMR (700 MHz, CDCl$_3$, 25° C., δ): 8.38 (d, J=9.0 Hz, 1H), 7.34 (br. s, 1H), 7.28-7.27 (m, 1H), 7.27-7.26 (m, 1H), 2.23 (s, 3H). $^{13}$C NMR (175 MHz, CDCl$_3$, 25° C., δ): 168.3, 138.1, 129.4, 128.9, 127.8, 122.8, 120.8, 120.6 (q, J=259.1 Hz), 24.9. $^{19}$F NMR (376 MHz, CDCl$_3$, 25° C., δ): −58.2 (s). Mass Spectrometry: HRMS (ESI-TOF) (m/z): calcd for C$_9$H$_8$NO$_2$F$_3$Cl ([M+H]$^+$), 254.0196, found, 254.0193.

N-(4-Bromo-2-(trifluoromethoxy)phenyl)acetamide (3g)

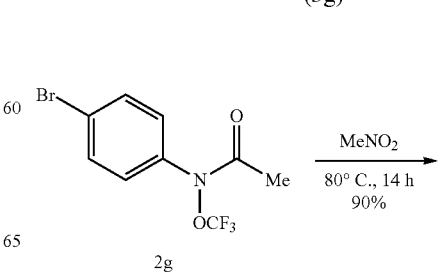

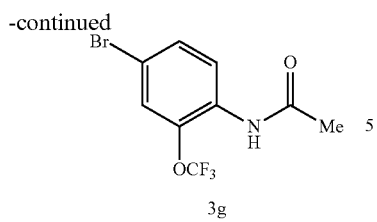

A solution of N-(4-bromophenyl)-N-(trifluoromethoxy)acetamide (2g) (119 mg, 0.400 mmol) in MeNO$_2$ (0.400 mL, 1.00 M) was heated at 80° C. under N$_2$ atmosphere for 14 h. The reaction mixture was concentrated in vacuo. The residue was purified by chromatography on silica gel, eluting with hexanes:EtOAc (17:1 to 7:3 (v/v)), to afford the title compound as a beige solid (107 mg, 0.359 mmol, 90% yield). R$_f$=0.42 (hexanes/EtOAc 4:1 (v/v)). NMR Spectroscopy: $^1$H NMR (500 MHz, CDCl$_3$, 25° C., δ): 8.32 (d, J=9.2 Hz, 1H), 7.42-7.41 (m, 1H), 7.40 (s, 1H), 7.37 (br. s, 1H), 2.22 (s, 3H). $^{13}$C NMR (125 MHz, CDCl$_3$, 25° C., δ): 168.3, 138.2, 130.8, 129.9, 123.6, 123.1, 120.6 (q, J=259.2 Hz), 115.9, 25.0. $^{19}$F NMR (376 MHz, CDCl$_3$, 25° C., δ): −58.2 (s). Mass Spectrometry: HRMS (ESI-TOF) (m/z): calcd for C$_9$H$_8$NO$_2$F$_3$Br ([M+H]$^+$), 297.9690, found, 297.9692.

N-(4-Iodo-2-(trifluoromethoxy)phenyl)acetamide (3h)

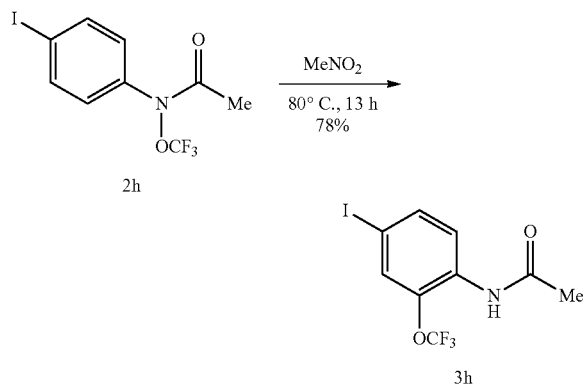

A solution of N-(4-iodophenyl)-N-(trifluoromethoxy)acetamide (2h) (138 mg, 0.400 mmol) in MeNO$_2$ (0.400 mL, 1.00 M) was heated at 80° C. under N$_2$ atmosphere for 13 h. The reaction mixture was concentrated in vacuo. The residue was purified by chromatography on silica gel, eluting with hexanes:EtOAc (4:1 to 2:3 (v/v)), to afford the title compound as a beige solid (108 mg, 0.313 mmol, 78% yield). R$_f$=0.46 (hexanes/EtOAc 4:1 (v/v)). NMR Spectroscopy: $^1$H NMR (700 MHz, CDCl$_3$, ° C., δ): 8.19 (d, J=8.6 Hz, 1H), 7.59 (dd, J=8.8, 1.5 Hz, 1H), 7.56 (s, 1H), 7.36 (br. s, 1H), 2.22 (s, 3H). $^{13}$C NMR (175 MHz, CDCl$_3$, 25° C., δ): 168.3, 138.0, 136.8, 130.7, 129.2, 123.4, 120.6 (q, J=259.1 Hz), 85.6, 25.0. $^{19}$F NMR (376 MHz, CDCl$_3$, 25° C., δ): −58.3 (s). Mass Spectrometry: HRMS (ESI-TOF) (m/z): calcd for C$_9$H$_8$NO$_2$F$_3$I ([M+H]), 345.9552, found, 345.9548.

N-(5-Fluoro-2-(trifluoromethoxy)phenyl)acetamide (3i) and N-(3-fluoro-2-(trifluoromethoxy)phenyl)acetamide (3i-II)

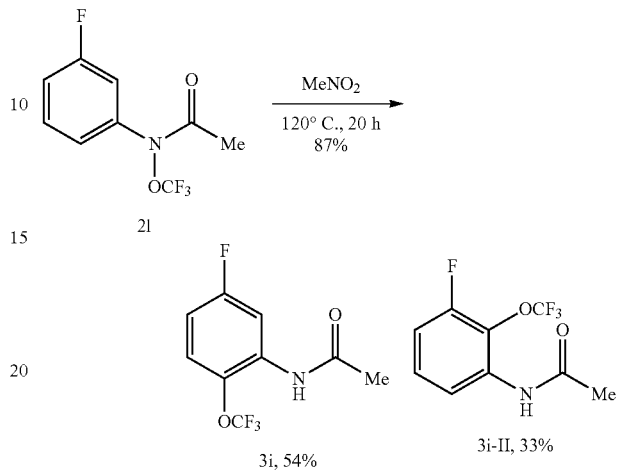

A solution of N-(3-fluorophenyl)-N-(trifluoromethoxy)acetamide (2i) (95.9 mg, 0.400 mmol) in MeNO$_2$ (0.400 mL, 1.00 M) was heated at 120° C. under N$_2$ atmosphere for 20 h. The reaction mixture was purified by preparative TLC using hexanes:EtOAc (7:3 (v/v)) for development. The purification afforded 3i (51.2 mg, 0.216 mmol, 54% yield) and 3i-II (31.5 mg, 0.132 mmol, 33% yield). Data for 3i: white solid; R$_f$=0.67 (hexanes/EtOAc 7:3 (v/v)). NMR Spectroscopy: $^1$H NMR (700 MHz, CDCl$_3$, 25° C., δ): 8.25 (d, J=9.0 Hz, 1H), 7.47 (br. s, 1H), 7.23-7.18 (m, 1H), 6.83-6.73 (m, 1H), 2.23 (s, 3H). $^{13}$C NMR (175 MHz, CDCl$_3$, 25° C., δ): 168.4, 161.0 (d, J=243.9 Hz), 133.7, 132.2 (d, J=12.1 Hz), 121.8 (d, J=9.7 Hz), 120.7 (q, J=258.0 Hz), 110.6 (d, J=24.1 Hz), 109.1 (d, J=29.6 Hz), 25.0. $^{19}$F NMR (376 MHz, CDCl$_3$, 25° C., δ): −58.5 (s), −111.9 (q). Mass Spectrometry: HRMS (ESI-TOF) (m/z): calcd for C$_9$H$_8$NO$_2$F$_4$ ([M+H]$^+$), 238.0491, found, 238.0492. Data for 3i-II: white solid; R$_f$=0.56 (hexanes/EtOAc 7:3 (v/v)). NMR Spectroscopy: $^1$H NMR (700 MHz, CDCl$_3$, 25° C., δ): 8.15 (d, J=7.7 Hz, 1H), 7.41 (br. s, 1H), 7.29-7.23 (m, 1H), 6.93 (t, J=9.0 Hz, 1H), 2.23 (s, 3H). $^{13}$C NMR (175 MHz, CDCl$_3$, 25° C., δ): 168.4, 155.2 (d, J=250.3 Hz), 133.5, 128.6 (d, J=8.5 Hz), 126.3 (d, J=13.8 Hz), 121.0 (q, J=259.9 Hz), 117.3, 111.9 (d, J=18.3 Hz), 24.9. $^{19}$F NMR (376 MHz, CDCl$_3$, 25° C., δ): −58.9 (d), −127.3 (s). Mass Spectrometry: HRMS (ESI-TOF) (m/z): calcd for C$_9$H$_8$NO$_2$F$_4$ ([M+H]$^+$), 238.0491, found, 238.0490.

N-(2-Bromo-6-(trifluoromethoxy)phenyl)acetamide (3j)

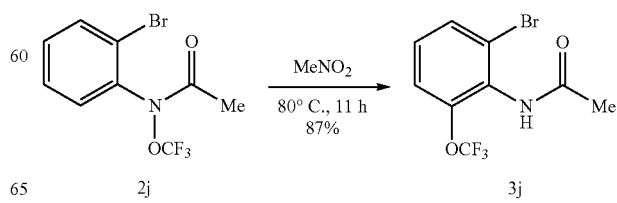

A solution of N-(2-bromophenyl)-N-(trifluoromethoxy)acetamide (2j) (119 mg, 0.400 mmol) in MeNO$_2$ (0.400 mL, 1.00 M) was heated at 80° C. under N$_2$ atmosphere for 11 h. The reaction mixture was purified by preparative TLC using hexanes:EtOAc (3:2 (v/v)) for development. The purification afforded the title compound as a white crystalline solid (103 mg, 0.346 mmol, 87% yield). R$_f$=0.62 (hexanes/EtOAc 3:2 (v/v)). NMR Spectroscopy: $^1$H NMR (700 MHz, (CD$_3$)$_2$SO, 25° C., δ): 9.80 (br. s, 1H), 7.73 (d, J=8.2 Hz, 1H), 7.46 (d, J=8.2 Hz, 1H), 7.26 (t, J=8.2 Hz, 1H), 2.04 (s, 3H). $^{13}$C NMR (175 MHz, (CD$_3$)$_2$SO, 25° C., δ): 168.2, 145.7, 131.6, 130.5, 129.4, 124.2, 120.8, 119.9 (q, J=256.5 Hz), 22.4. $^{19}$F NMR (376 MHz, (CD$_3$)$_2$SO, 25° C., δ): −58.6 (s). Mass Spectrometry: HRMS (ESI-TOF) (m/z): calcd for C$_9$H$_8$NO$_2$F$_3$Br ([M+H]$^+$), 297.9690, found, 297.9693.

N-(5-Methoxy-2-(trifluoromethoxy)-3-(trifluoromethyl) phenyl) acetamide (3k) and N-(3-methoxy-2-(trifluoromethoxy)-5-(trifluoromethyl)phenyl)acetamide (3k-II)

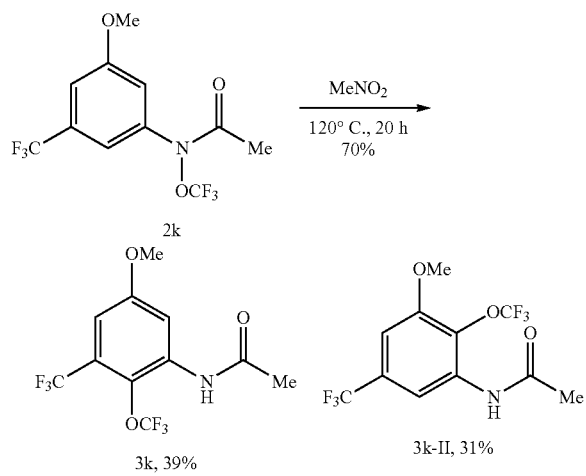

3k, 39%

3k-II, 31%

A solution of N-(3-methoxy-5-(trifluoromethyl)phenyl)-N-(trifluoro-methoxy)acetamide (2k) (127 mg, 0.400 mmol) in MeNO$_2$ (0.400 mL, 1.00 M) was heated at 120° C. under N$_2$ atmosphere for 20 h. The reaction mixture was purified by preparative TLC using hexanes:EtOAc (7:3 (v/v)) for development. The purification afforded 3k (49.2 mg, 0.155 mmol, 39% yield) and 3k-II (37.7 mg, 0.119 mmol, 31% yield). Data for 3k: beige solid; R$_f$=0.56 (hexanes/EtOAc 3:2 (v/v)). NMR Spectroscopy: $^1$H NMR (500 MHz, CDCl$_3$, 25° C., δ): 8.15 (br. s, 1H), 7.49 (br. s, 1H), 6.91 (d, J=3.1 Hz, 1H), 3.84 (s, 3H), 2.22 (s, 3H). $^{13}$C NMR (125 MHz, CDCl$_3$, 25° C., δ): 168.5, 158.5, 134.0, 128.7, 125.6 (q, J=32.4 Hz), 122.3 (q, J=271.9 Hz), 120.9 (q, J=260.0 Hz), 110.4, 108.8 (q, J=4.3 Hz), 56.1, 24.8. $^{19}$F NMR (376 MHz, CDCl$_3$, 25° C., δ): −56.2 (q), −61.3 (q). Mass Spectrometry: HRMS (ESI-TOF) (m/z): calcd for C$_{11}$H$_{10}$NO$_3$F$_6$ ([M+H]$^+$), 318.0565, found, 318.0556. Data for 2k-II: beige solid; R$_f$=0.72 (hexanes/EtOAc 3:2 (v/v)). NMR Spectroscopy: $^1$H NMR (500 MHz, CDCl$_3$, 25° C., δ): 8.35 (br. s, 1H), 7.46 (br. s, 1H), 6.95 (d, J=1.8 Hz, 1H), 3.93 (s, 3H), 2.23 (s, 3H). $^{13}$C NMR (125 MHz, CDCl$_3$, 25° C., δ): 168.5, 153.0, 133.5, 130.6 (q, J=32.9 Hz), 129.3, 123.5 (q, J=271.5 Hz), 121.0 (q, J=260.1 Hz), 110.9, 104.7, 56.6, 24.9. $^{19}$F NMR (376 MHz, CDCl$_3$, 25° C., δ): −57.7 (s), −63.4 (s). Mass Spectrometry: HRMS (ESI-TOF) (m/z): calcd for C$_{11}$H$_{10}$NO$_3$F$_6$ ([M+H]$^+$), 318.0565, found, 318.0555.

N-(2-(Trifluoromethoxy)-5-(trifluoromethyl)phenyl)acetamide (3l) and N-(2-(trifluoromethoxy)-3-(trifluoromethyl)phenyl)acetamide (3l-II)

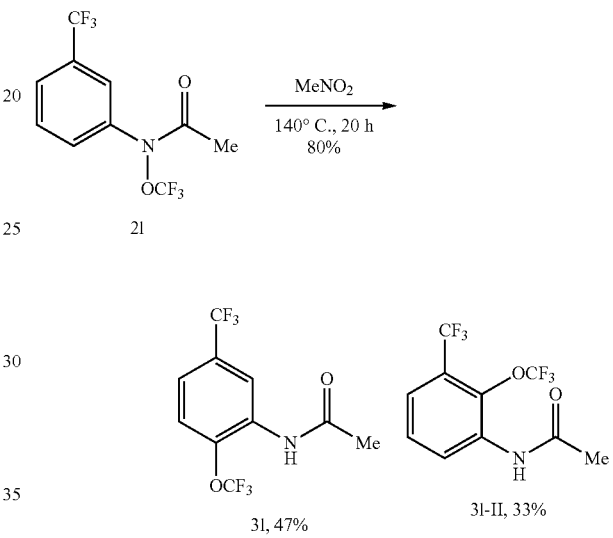

31, 47%

3l-II, 33%

A solution of N-(trifluoromethoxy)-N-(3-(trifluoromethyl)phenyl) acetamide (21) (115 mg, 0.400 mmol) in MeNO$_2$ (0.400 mL, 1.00 M) was heated at 140° C. under N$_2$ atmosphere for 20 h. The reaction mixture was purified by preparative TLC using hexanes:EtOAc (4:1 (v/v)) for development (prep TLC was developed twice). The purification afforded 3l (53.5 mg, 0.186 mmol, 47% yield) and 3l-II (37.4 mg, 0.129 mmol, 33% yield). Data for 3l: white solid; R$_f$=0.66 (hexanes/EtOAc 7:3 (v/v)). NMR Spectroscopy: $^1$H NMR (700 MHz, CDCl$_3$, 25° C., δ): 8.79 (br. s, 1H), 7.55 (br. s, 1H), 7.32-7.39 (m, 2H), 2.26 (s, 3H). $^{13}$C NMR (175 MHz, CDCl$_3$, 25° C., δ): 168.6, 139.9, 131.1, 129.9 (q, J=33.1 Hz), 123.5 (q, J=270.8 Hz), 121.1, 120.5 (q, J=259.6 Hz), 120.1, 119.2, 24.9. $^{19}$F NMR (376 MHz, CDCl$_3$, 25° C., δ): −58.0 (s), −63.2 (s). Mass Spectrometry: HRMS (ESI-TOF) (m/z): calcd for C$_{10}$H$_8$NO$_2$F$_6$ ([M+H]$^+$), 288.0459, found, 288.0457. Data for 3l-II: white solid; R$_f$=0.43 (hexanes/EtOAc 7:3 (v/v)). NMR Spectroscopy: $^1$H NMR (700 MHz, CDCl$_3$, 25° C., δ): 8.52 (br. s, 1H), 7.50 (br. s, 1H), 7.39-7.46 (m, 2H), 2.23 (s, 3H). $^{13}$C NMR (175 MHz, CDCl$_3$, 25° C., δ): 168.5, 135.7, 133.1, 128.3, 126.7, 125.2 (q, J=32.0 Hz), 122.6 (d, J=5.3 Hz), 122.5 (q, J=271.6 Hz), 120.7 (q, J=260.3 Hz), 24.7. $^{19}$F NMR (376 MHz, CDCl$_3$, 25° C., δ): −55.7 (d), −61.1 (q). Mass Spectrometry: HRMS (ESI-TOF) (m/z): calcd for C$_{10}$H$_8$NO$_2$F$_6$ ([M+H]$^+$), 288.0459, found, 288.0463.

N-(5-Methoxy-2-(trifluoromethoxy)phenyl)acetamide (3m) and N-(3-methoxy-2-(trifluoromethoxy)phenyl)acetamide (3m-II)

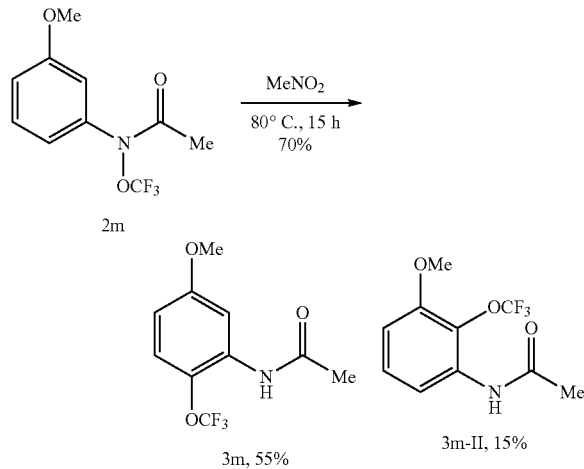

A solution of N-(3-methoxyphenyl)-N-(trifluoromethoxy)acetamide (2m) (99.7 mg, 0.400 mmol) in MeNO$_2$ (0.400 mL, 1.00 M) was heated at 80° C. under N$_2$ atmosphere for 15 h. The reaction mixture was purified by preparative TLC using hexanes:EtOAc (4:1 (v/v)) for development (prep TLC was developed four times). The purification afforded 3m (55.3 mg, 0.222 mmol, 55% yield) and 3m-II (14.9 mg, 0.0600 mmol, 15% yield). Data for 3m: white solid; R$_f$=0.77 (hexanes/EtOAc 3:2 (v/v)). NMR Spectroscopy: $^1$H NMR (400 MHz, CDCl$_3$, 25° C., δ): 8.02 (d, J=2.0 Hz, 1H), 7.48 (br. s, 1H), 7.12 (dd, J=9.2, 1.1 Hz, 1H), 6.59 (dd, J=9.0, 3.0 Hz, 1H), 3.79 (s, 3H), 2.21 (s, 3H). $^{13}$C NMR (175 MHz, CDCl$_3$, ° C., δ): 168.5, 158.5, 131.8, 131.6, 121.7, 120.8 (q, J=256.8 Hz), 109.9, 106.8, 55.8, 24.9. $^{19}$F NMR (376 MHz, CDCl$_3$, 25° C., δ): −58.7 (s). Mass Spectrometry: HRMS (ESI-TOF) (m/z): calcd for C$_{10}$H$_{11}$NO$_3$F$_3$ ([M+H]$^+$), 250.0691, found, 250.0690. Data for 3m-II: white solid; R$_f$=0.70 (hexanes/EtOAc 3:2 (v/v)). NMR Spectroscopy: $^1$H NMR (700 MHz, CDCl$_3$, 25° C., δ): 7.93 (d, J=8.2 Hz, 1H), 7.40 (br. s, 1H), 7.23 (t, J=8.4 Hz, 1H), 6.73 (d, J=8.2 Hz, 1H), 3.87 (s, 3H), 2.21 (s, 3H). $^{13}$C NMR (175 MHz, CDCl$_3$, 25° C., δ): 168.4, 152.7, 132.9, 128.2, 127.6, 121.1 (q, J=258.7 Hz), 113.8, 108.0, 56.3, 24.9. $^{19}$F NMR (376 MHz, CDCl$_3$, 25° C., δ): −57.9 (s). Mass Spectrometry: HRMS (ESI-TOF) (m/z): calcd for C$_{10}$H$_{11}$NO$_3$F$_3$ ([M+H]$^+$), 250.0691, found, 250.0692.

Methyl 3-acetamido-4-(trifluoromethoxy)benzoate (3n) and methyl 3-acetamido-2-(trifluoromethoxy)benzoate (3n-II)

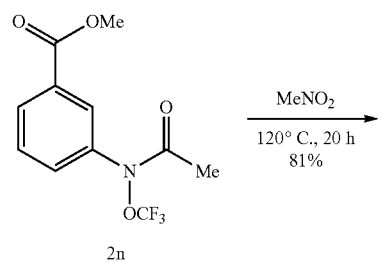

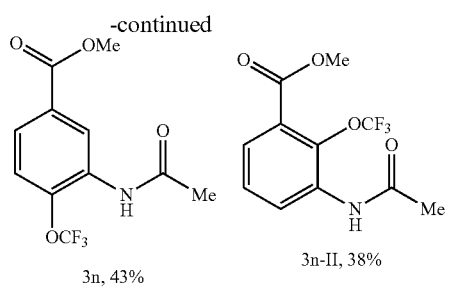

A solution of methyl 3-(N-(trifluoromethoxy)acetamido)benzoate (2n) (111 mg, 0.400 mmol) in MeNO$_2$ (0.400 mL, 1.00 M) was heated at 120° C. under N$_2$ atmosphere for 20 h. The reaction mixture was purified by preparative TLC using Et$_2$O for development. The purification afforded 90.4 mg of a 1.14:1 mixture of 3n and 3n-II (81% overall yield). Compounds 3n and 3n-II were further separated for characterization by preparative TLC (eluting twenty times with hexanes:Et$_2$O (7:3 (v/v)). Data for 3n: white solid; R$_f$=0.59 (hexanes/EtOAc 3:2 (v/v)). NMR Spectroscopy: $^1$H NMR (400 MHz, CDCl$_3$, 25° C., δ): 9.02 (br. s, 1H), 7.82 (dd, J=8.5, 2.0 Hz, 1H), 7.41 (br. s, 1H), 7.31 (dd, J=8.7, 1.6 Hz, 1H), 3.92 (s, 3H), 2.25 (s, 3H). $^{13}$C NMR (175 MHz, CDCl$_3$, 25° C., δ): 168.4, 166.0, 141.2, 130.3, 129.4, 125.9, 123.4, 120.5 (q, J=259.1 Hz), 119.5, 52.6, 24.9. $^{19}$F NMR (376 MHz, CDCl$_3$, 25° C., δ): −57.8 (s). Mass Spectrometry: HRMS (ESI-TOF) (m/z): calcd for C$_{11}$H$_{11}$NO$_4$F$_3$ ([M+H]$^+$), 278.0640, found, 278.0640.

Data for 3n-II: white solid; R$_f$=0.56 (hexanes/EtOAc 3:2 (v/v)). NMR Spectroscopy: $^1$H NMR (700 MHz, CDCl$_3$, 25° C., δ): 8.56 (d, J=8.2 Hz, 1H), 7.66 (d, J=7.7 Hz, 1H), 7.51 (br. s, 1H), 7.39 (t, J=8.0 Hz, 1H), 3.93 (s, 3H), 2.24 (s, 3H). $^{13}$C NMR (175 MHz, CDCl$_3$, 25° C., δ): 168.5, 165.0, 136.5, 132.8, 128.1, 126.6, 126.2, 126.1, 120.8 (q, J=258.6 Hz), 52.7, 24.9. $^{19}$F NMR (376 MHz, CDCl$_3$, 25° C., δ): −57.5 (s). Mass Spectrometry: HRMS (ESI-TOF) (m/z): calcd for C$_{11}$H$_{11}$NO$_4$F$_3$ ([M+H]$^+$), 278.0640, found, 278.0639.

N-(6-Chloro-2-(trifluoromethoxy)-3-(trifluoromethyl)phenyl) acetamide (3o)

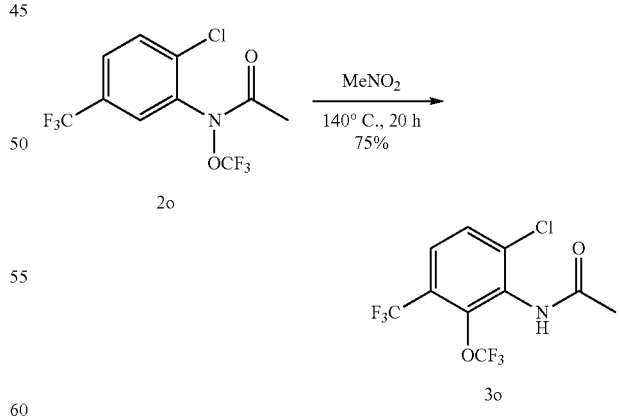

A solution of N-(2-chloro-5-(trifluoromethyl)phenyl)-N-(trifluoro-methoxy)acetamide (2o) (129 mg, 0.400 mmol) in MeNO$_2$ (0.400 mL, 1.00 M) was heated at 140° C. under N$_2$ atmosphere for 20 h. The reaction mixture was purified by preparative TLC using hexanes:EtOAc (1:19 (v/v)) for development (prep TLC was developed five times). The purification afforded the title compounds as a white solid (96.0 mg, 0.299 mmol, 75% yield). The product was obtained as a 5:3 mixture of atropisomers. The spectral data corresponds to the major atropisomer. $R_f$=0.41 (hexanes/EtOAc 19:1 (v/v)). NMR Spectroscopy: $^1$H NMR (500 MHz, CDCl$_3$, 25° C., δ): 7.70 (d, J=8.9 Hz, 1H), 7.36 (d, J=8.9 Hz, 1H), 6.89 (br. s, 1H), 2.25 (br. s, 3H). $^{13}$C NMR (125 MHz, CDCl$_3$, 25° C., δ): 168.4, 148.4, 132.3, 129.5, 127.9 (q, J=32.2 Hz), 126.8, 122.3 (q, J=271.9 Hz), 120.4 (q, J=259.5 Hz), 118.7, 23.1. $^{19}$F NMR (376 MHz, CDCl$_3$, 25° C., δ): −57.9 (s), −63.2 (s). Mass Spectrometry: HRMS (ESI-TOF) (m/z): calcd for $C_{10}H_7NO_2F_6Cl$ ([M+H]$^+$), 322.0070, found, 322.0068.

N-(3-Benzyl-8-chloro-4-oxo-6-(trifluoromethoxy)-3,4-dihydroquinazolin-7-yl)acetamide (3p)

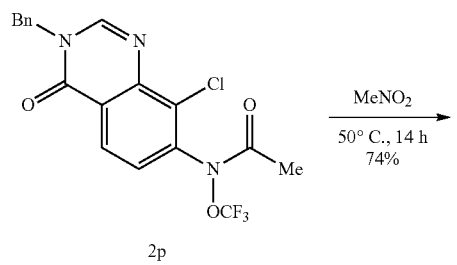

A solution of N-(3-benzyl-8-chloro-4-oxo-3,4-dihydroquinazolin-7-yl)-N-(trifluoromethoxy)acetamide (2p) (120 mg, 0.291 mmol) in MeNO$_2$ (0.582 mL, 0.500 M) was heated at 50° C. under N$_2$ atmosphere for 14 h. The reaction mixture was concentrated in vacuo. The residue was purified by chromatography on silica gel, eluting with hexanes:EtOAc (2:3 (v/v)), to afford the title compound as a white solid (89.0 mg, 0.216 mmol, 74% yield). $R_f$=0.73 (hexanes/EtOAc 3:2 (v/v)). NMR Spectroscopy: $^1$H NMR (700 MHz, CDCl$_3$, 25° C., δ): 8.07 (s, 1H), 7.81 (s, 1H), 7.39-7.30 (m, 5H), 7.03 (br. s, 1H), 5.17 (s, 2H), 2.26 (s, 3H). $^{13}$C NMR (175 MHz, CDCl$_3$, 25° C., δ): 168.6, 157.3, 148.7, 148.4, 143.9, 139.7, 135.2, 129.3, 128.7, 128.6, 128.3, 128.2, 120.6 (q, J=258.8 Hz), 116.3, 49.7, 23.2. $^{19}$F NMR (376 MHz, CDCl$_3$, 25° C., δ): −57.1 (s). Mass Spectrometry: HRMS (ESI-TOF) (m/z): calcd for $C_{18}H_{14}N_3O_3Cl\ F_3$ ([M+H]$^+$), 412.0676, found, 412.0673.

Methyl 4-acetamido-3-(trifluoromethoxy)benzoate (3q)

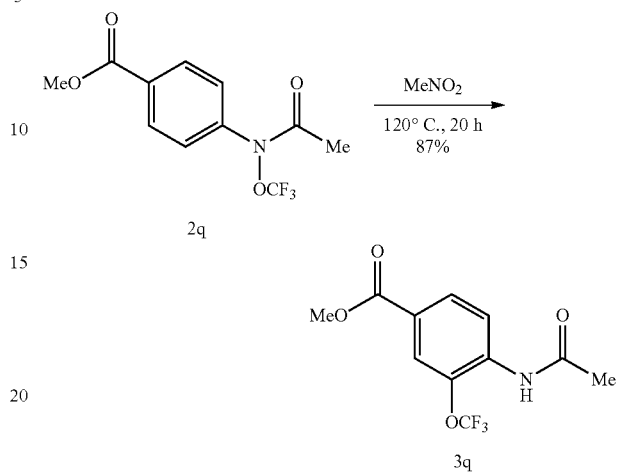

A solution of methyl 4-(N-(trifluoromethoxy)acetamido)benzoate (2q) (111 mg, 0.400 mmol) in MeNO$_2$ (0.400 mL, 1.00 M) was heated at 120° C. under N$_2$ atmosphere for 20 h. The reaction mixture was concentrated in vacuo. The residue was purified by chromatography on silica gel, eluting with hexanes:EtOAc (9:1 to 7:3 (v/v)), to afford the title compound as a white solid (97.1 mg, 0.350 mmol, 87% yield). $R_f$=0.51 (hexanes/EtOAc 4:1 (v/v)). NMR Spectroscopy: $^1$H NMR (700 MHz, CDCl$_3$, 25° C., δ): 8.56 (d, J=8.6 Hz, 1H), 7.97 (d, J=8.6 Hz, 1H), 7.93 (s, 1H), 7.56 (br. s, 1H), 3.92 (s, 3H), 2.27 (s, 3H). $^{13}$C NMR (175 MHz, CDCl$_3$, 25° C., δ): 168.5, 165.6, 137.2, 134.7, 129.3, 125.8, 121.5, 120.8, 120.6 (q, J=258.9 Hz), 52.5, 25.2. $^{19}$F NMR (376 MHz, CDCl$_3$, 25° C., δ): −58.1 (s). Mass Spectrometry: HRMS (ESI-TOF) (m/z): calcd for $C_{11}H_{11}NO_4F_3$ ([M+H]$^+$), 278.0640, found, 278.0643.

Methyl 4-benzamido-3-(trifluoromethy)benzoate (3r)

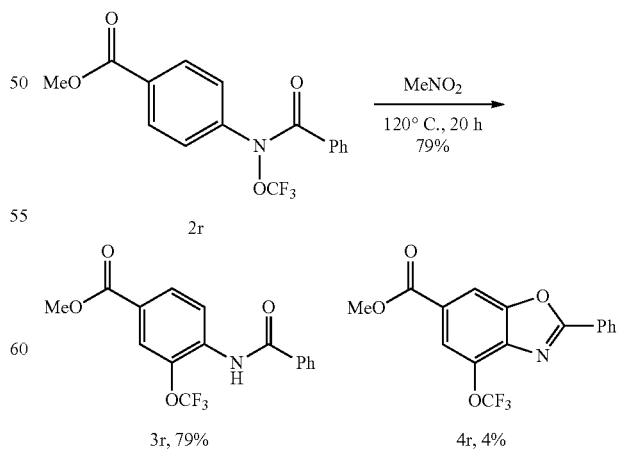

A solution of methyl 4-(N-(trifluoromethoxy)benzamido)benzoate (2r) (136 mg, 0.400 mmol) in MeNO$_2$ (0.400 mL, 1.00 M) was heated at 120° C. under N$_2$ atmosphere for 20 h. The reaction mixture was concentrated in vacuo. The residue was purified by chromatography on silica gel, eluting with hexanes:EtOAc (9:1 to 7:3 (v/v)), to afford the title compound as a white solid (107 mg, 0.315 mmol, 79% yield). The reaction also afforded methyl 2-phenyl-4-(trifluoromethoxy)benzo[d]oxazole-6-carboxylate (4r) as a white solid (5.4 mg, 0.016 mmol, 4% yield). Data for 3r: R$_f$=0.72 (hexanes/EtOAc 7:3 (v/v)). NMR Spectroscopy: $^1$H NMR (700 MHz, CDCl$_3$, 25° C., δ): 8.74 (d, J=8.6 Hz, 1H), 8.37 (br. s, 1H), 8.04 (dd, J=8.6, 1.7 Hz, 1H), 7.98 (s, 1H), 7.90-7.84 (m, 2H), 7.63-7.58 (m, 1H), 7.56-7.51 (m, 2H), 3.93 (s, 3H). $^{13}$C NMR (175 MHz, CDCl$_3$, 25° C., δ): 165.6, 165.5, 137.7, 135.0, 134.2, 132.8, 129.5, 129.3, 127.2, 126.0, 121.7, 120.8, 120.7 (q, J=259.1 Hz), 52.5. $^{19}$F NMR (376 MHz, CDCl$_3$, 25° C., δ): −58.1 (s). Mass Spectrometry: HRMS (ESI-TOF) (m/z): calcd for C$_{16}$H$_{13}$NO$_4$F$_3$ ([M+H]$^+$), 340.0797, found, 340.0793. Data for 4r: R$_f$=0.73 (hexanes/EtOAc 4:1 (v/v)). NMR Spectroscopy: $^1$H NMR (700 MHz, CDCl$_3$, 25° C., δ): 8.36-8.25 (m, 3H), 8.10 (d, J=8.2 Hz, 1H), 7.79 (d, J=8.2 Hz, 1H), 7.65-7.49 (m, 3H), 3.97 (s, 3H). $^{13}$C NMR (175 MHz, CDCl$_3$, 25° C., δ): 166.8, 165.7, 150.6, 146.2, 132.4, 129.2, 128.1, 127.3, 126.8, 126.6, 119.7, 112.4, 52.5.

Methyl 4-((methoxycarbonyl)amino)-3-(trifluoromethoxy)benzoate (3s)

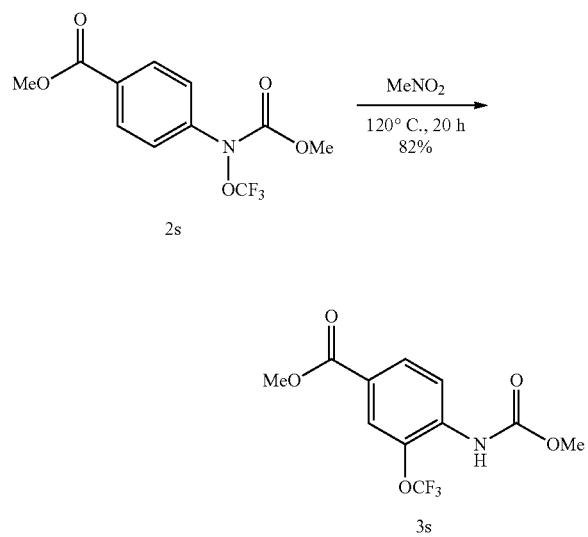

A solution of methyl 4-((methoxycarbonyl)(trifluoromethoxy) amino)benzoate (2s) (130 mg, 0.443 mmol) in MeNO$_2$ (0.443 mL, 1.00 M) was heated at 120° C. under N$_2$ atmosphere for 20 h. The reaction mixture was purified by preparative TLC using hexanes:EtOAc (19:1 (v/v)) for development (prep TLC was developed three times). The purification afforded the title compound as a white crystalline solid (106 mg, 0.362 mmol, 82% yield). R$_f$=0.63 (hexanes/EtOAc 4:1 (v/v)). NMR Spectroscopy: $^1$H NMR (700 MHz, CDCl$_3$, 25° C., δ): 8.33 (d, J=8.60 Hz, 1H), 7.97 (dd, J=8.6, 1.7 Hz, 1H), 7.92 (s, 1H), 7.13 (br. s, 1H), 3.91 (s, 3H), 3.83 (s, 3H). $^{13}$C NMR (175 MHz, CDCl$_3$, 25° C., δ): 165.7, 153.3, 136.9, 135.0, 129.4, 125.0, 121.7, 120.6 (q, J=258.9 Hz), 119.1, 53.0, 52.5. $^{19}$F NMR (376 MHz, CDCl$_3$, 25° C., δ): −58.2 (s). Mass Spectrometry: HRMS (ESI-TOF) (m/z): calcd for C$_{11}$H$_{11}$NO$_5$F$_3$ ([M+H]$^+$), 294.0589, found, 294.0587.

Methyl 4-(3,3-dimethylureido)-3-(trifluoromethoxy)benzoate (3t)

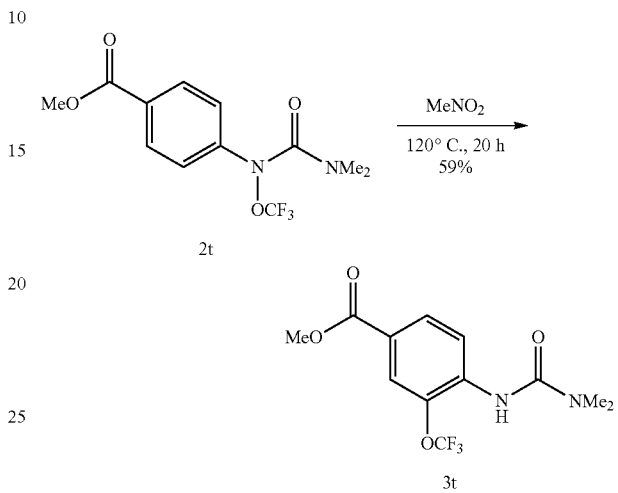

A solution of methyl 4-(3,3-dimethyl-1-(trifluoromethoxy)ureido) benzoate (2t) (43.6 mg, 0.142 mmol) in MeNO$_2$ (0.142 mL, 1.00 M) was heated at 120° C. under N$_2$ atmosphere for 20 h. The reaction mixture was purified by preparative TLC using hexanes:EtOAc (7:3 (v/v)) for development (prep TLC was developed twice). The purification afforded the title compound as a colorless oil (25.7 mg, 0.0839 mmol, 59% yield). R$_f$=0.58 (hexanes/EtOAc 1:1 (v/v)). NMR Spectroscopy: $^1$H NMR (700 MHz, CDCl$_3$, 25° C., δ): 8.42 (d, J=8.6 Hz, 1H), 7.93 (d, J=9.0 Hz, 1H), 7.88 (s, 1H), 6.98 (br. s, 1H), 3.89 (s, 3H), 3.06 (s, 6H). $^{13}$C NMR (175 MHz, CDCl$_3$, 25° C., δ): 165.9, 154.3, 136.9, 136.6, 129.4, 124.0, 121.7, 120.7 (q, J=258.4 Hz), 119.6, 52.3, 36.5. $^{19}$F NMR (376 MHz, CDCl$_3$, 25° C., δ): −58.2 (s). Mass Spectrometry: HRMS (ESI-TOF) (m/z): calcd for C$_{12}$H$_{14}$N$_2$O$_4$F$_3$ ([M+H]$^+$), 307.0906, found, 307.0902.

Example 4. One-Pot Method

Next, it was explored as to whether the two-step sequence could be converted into a one-pot transformation to further simplify the reaction protocol. Exposure of 1u to Togni reagent II and NaH in CH$_2$Cl$_2$ at room temperature provided the desired product 3u in 70% isolated yield (Scheme 4). These reaction conditions tolerate α-amino acid ester (3v), quinoline (3w), and indole (3x). Moreover, products from Scheme 3 such as 3a, 3c, 3g, and 3q can be directly obtained from the corresponding hydroxylamines via a one-pot reaction protocol without the isolation of intermediates 2. However removal of CH$_2$Cl$_2$ at the end of the trifluoromethylation reaction followed by re-dissolving the resulting residue in MeNO$_2$ is needed, because the OCF$_3$-migration for these substrates requires higher reaction temperature.

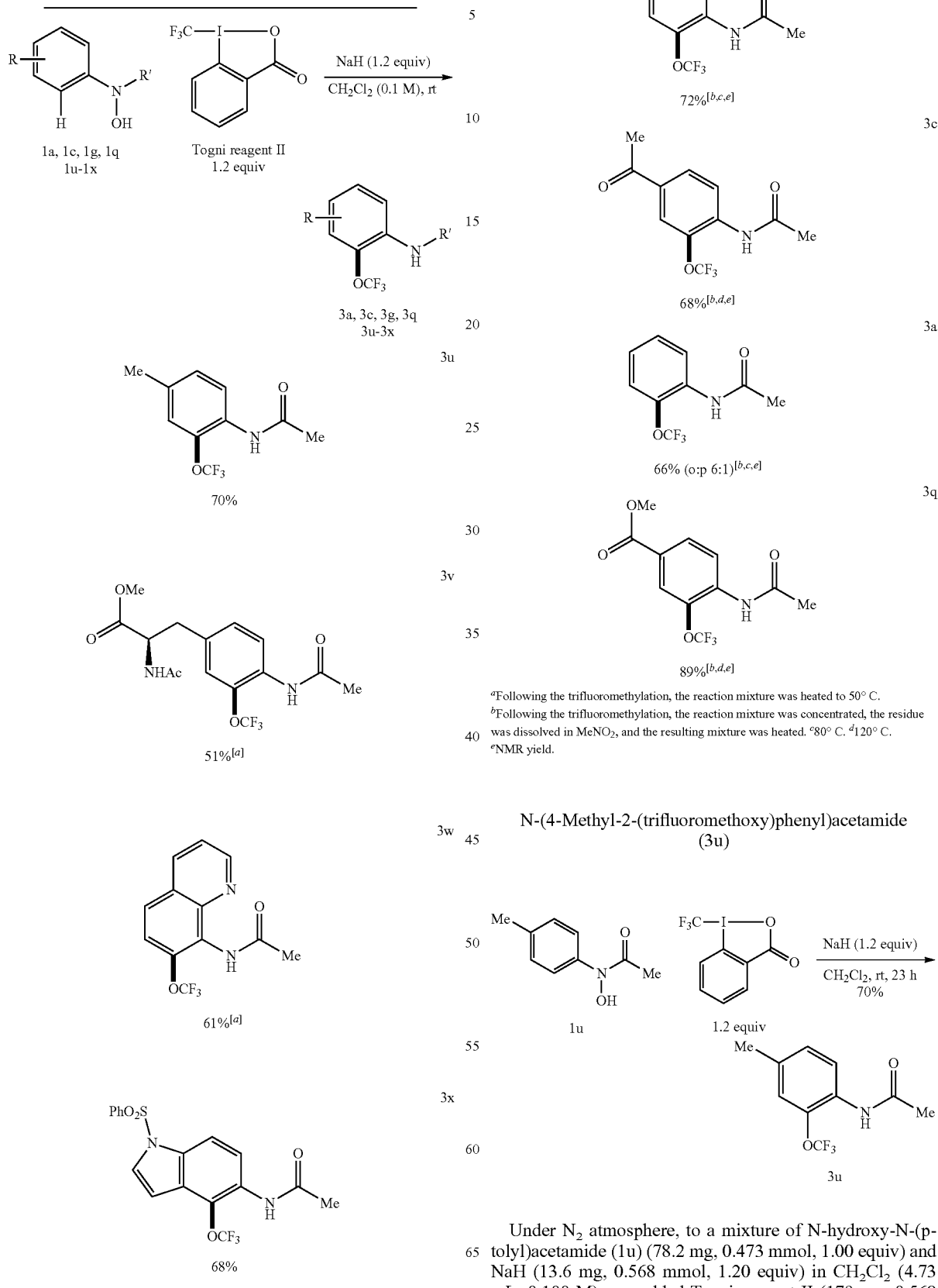
N-(4-Methyl-2-(trifluoromethoxy)phenyl)acetamide (3u)
Under $N_2$ atmosphere, to a mixture of N-hydroxy-N-(p-tolyl)acetamide (1u) (78.2 mg, 0.473 mmol, 1.00 equiv) and NaH (13.6 mg, 0.568 mmol, 1.20 equiv) in $CH_2Cl_2$ (4.73 mL, 0.100 M) was added Togni reagent II (179 mg, 0.568 mmol, 1.2 equiv) and the reaction mixture was stirred at rt for 23 h. The reaction mixture diluted with CH$_2$Cl$_2$ (30 mL) and washed with water (30 mL). The layers were separated, the organic layer was dried (MgSO$_4$), filtered and concentrated in vacuo. The residue was purified by preparative TLC using hexanes:EtOAc (4:1 (v/v)) for development (prep TLC was developed twice). The purification afforded the title compound as a white solid (76.8 mg, 0.329 mmol, 70% yield). R$_f$=0.42 (hexanes/EtOAc 4:1 (v/v)). NMR Spectroscopy: $^1$H NMR (700 MHz, CDCl$_3$, 25° C., δ): 8.21 (d, J=8.2 Hz, 1H), 7.31 (br. s, 1H), 7.08 (d, J=8.2 Hz, 1H), 7.05 (br. s, 1H), 2.33 (s, 3H), 2.21 (s, 3H). $^{13}$C NMR (175 MHz, CDCl$_3$, 25° C., δ): 168.3, 138.2, 134.7, 128.2, 128.0, 122.2, 120.9, 120.7 (q, J=257.4 Hz), 24.8, 21.0. $^{19}$F NMR (376 MHz, CDCl$_3$, 25° C., δ): −58.0 (s). Mass Spectrometry: HRMS (ESI-TOF) (m/z): calcd for C$_{10}$H$_{11}$NO$_2$F$_3$ ([M+H]$^+$), 234.0742, found, 234.0737.

Methyl (R)-2-acetamido-3-(4-acetamido-3-(trifluoromethoxy)phenyl) propanoate (3v)

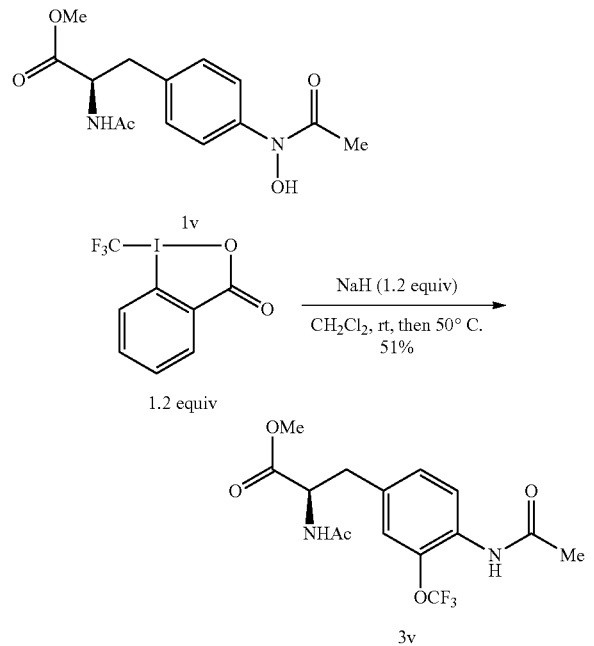

Under N$_2$ atmosphere, to a mixture of methyl (R)-2-acetamido-3-(4-(N-hydroxyacetamido)phenyl)propanoate (1v) (100 mg, 0.340 mmol, 1.00 equiv) and NaH (9.80 mg, 0.410 mmol, 1.20 equiv) in CH$_2$Cl$_2$ (3.40 mL, 0.100 M) was added Togni reagent II (128.8 mg, 0.410 mmol, 1.20 equiv) and the reaction mixture was stirred at rt for 13 h. The reaction mixture was then heated to 50° C. for 24 h. The reaction was quenched with water, extracted with CH$_2$Cl$_2$, dried (MgSO$_4$), filtered and concentrated in vacuo. The residue was purified by chromatography on silica gel, eluting with hexanes:EtOAc (1:1 to 1:3 (v/v)), and then recrystallized from hexanes/CH$_2$Cl$_2$ to afford the title compound as a slighty yellow solid (63.0 mg, 0.174 mmol, 51% yield). R$_f$=0.12 (hexanes/EtOAc 1:1 (v/v)). NMR Spectroscopy: $^1$H NMR (700 MHz, CDCl$_3$, 25° C., δ): 8.31 (d, J=8.4 Hz, 1H), 7.37 (s, 1H), 7.00 (d, J=8.4 Hz, 1H), 6.98 (s, 1H), 5.96 (d, J=7.0 Hz, 1H), 4.86 (dd, J=5.6, 12.8 Hz, 1H), 3.73 (s, 3H), 3.15 (dd, J=5.6, 14.0 Hz, 1H), 3.08 (dd, J=5.6, 14.0 Hz, 1H), 2.22 (s, 3H), 2.00 (s, 3H). $^{13}$C NMR (175 MHz, CDCl$_3$, 25° C., δ): 171.8, 169.8, 168.4, 138.0, 132.5, 129.6, 128.6, 122.1, 121.2, 120.7 (q, J=147.4 Hz), 53.2, 52.6 (d, J=14.0 Hz), 37.3, 25.0, 23.3. $^{19}$F NMR (376 MHz, CDCl$_3$, 25° C., δ): −57.7 (s). Mass Spectrometry: HRMS (ESI-TOF) (m/z): calcd for C$_{15}$H$_{18}$N$_2$O$_5$F$_3$ ([M+H]$^+$), 363.1168, found, 363.1164.

Methyl hydroxy(7-(trifluoromethoxy)quinolin-8-yl) carbamate (3w)

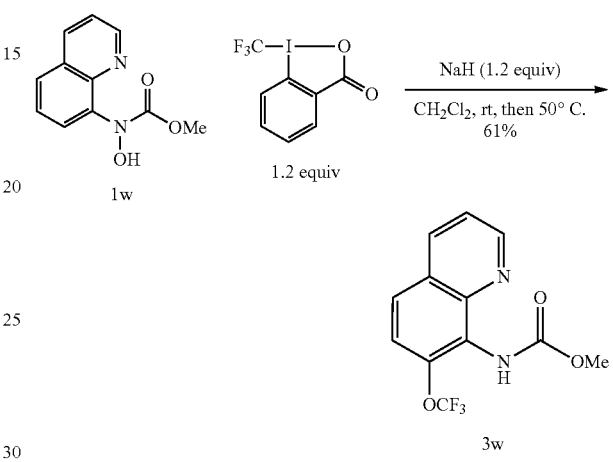

Under N$_2$ atmosphere, to a mixture of methyl hydroxy(quinolin-8-yl)carbamate (1w) (100 mg, 0.458 mmol, 1.00 equiv) and NaH (13.2 mg, 0.550 mmol, 1.20 equiv) in CH$_2$Cl$_2$ (4.58 mL, 0.100 M) was added Togni reagent II (173.6 mg, 0.550 mmol, 1.20 equiv) and the reaction mixture was stirred at rt for 13 h. The reaction was then heated to 50° C. for 24 h. The reaction was quenched with water, extracted with CH$_2$Cl$_2$, dried (MgSO$_4$), filtered and concentrated in vacuo. The residue was purified by chromatography on silica gel, eluting with hexanes:EtOAc (5:1 to 3:1 (v/v)), to afford the title compound as a brown solid (81.0 mg, 0.283 mmol, 61% yield). R$_f$=0.21 (hexanes/EtOAc 4:1 (v/v)). NMR Spectroscopy: $^1$H NMR (400 MHz, CDCl$_3$, 25° C., δ): 8.92 (dd, J=1.4, 4.1 Hz, 1H), 8.18 (dd, J=1.4, 8.3 Hz, 1H), 7.83 (s, 1H), 7.69 (d, J=9.1 Hz, 1H), 7.54 (d, J=9.1 Hz, 1H), 7.48 (dd, J=4.2, 8.3 Hz, 1H), 3.83 (s, 3H). $^{13}$C NMR (125 MHz, (CD$_3$)$_2$SO, δ): 154.6, 150.6, 143.0, 142.1, 136.3, 126.9, 126.8, 125.4, 122.1, 121.4, 120.9 (q, J=257.4 Hz), 53.2. $^{19}$F NMR (376 MHz, CDCl$_3$, (376 MHz, CDCl$_3$, 25° C., δ): −56.8 (s). Mass Spectrometry: HRMS (ESI-TOF) (m/z): calcd for C$_{12}$H$_{10}$N$_2$O$_3$F$_3$ ([M+H]$^+$), 287.0644, found, 287.0639.

N-(1-(phenylsulfonyl)-4-(trifluoromethoxy)-1H-indol-5-yl)acetamide (3x)

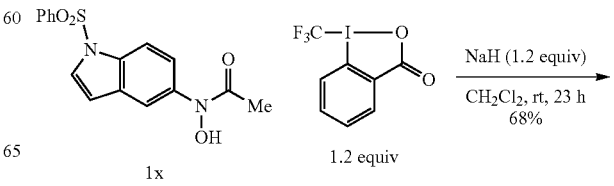

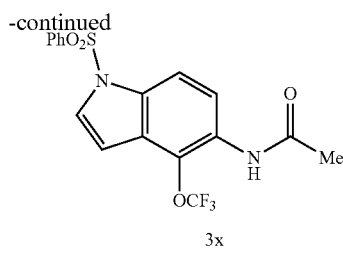

Under N₂ atmosphere, to a mixture N-hydroxy-N-(1-(phenylsulfonyl)-1H-indol-5-yl)acetamide (1x) (132 mg, 0.400 mmol, 1.00 equiv) and NaH (11.5 mg, 0.480 mmol, 1.20 equiv) in CH₂Cl₂ (4.00 mL, 0.100 M) was added Togni reagent II (152 mg, 0.480 mmol, 1.2 equiv) and the reaction mixture was stirred at rt for 23 h. The reaction mixture diluted with CH₂Cl₂ (30 mL) and washed with water (30 mL). The layers were separated, the organic layer was dried (MgSO₄), filtered and concentrated in vacuo. The residue was purified by preparative TLC using hexanes:EtOAc (3:2 (v/v)) for development (prep TLC was developed twice). The purification afforded the title compound as an off-white solid (108 mg, 0.271 mmol, 68% yield). $R_f$=0.24 (hexanes/EtOAc 7:3 (v/v)). NMR Spectroscopy: $^1$H NMR (700 MHz, CDCl₃, 25° C., δ): 8.13 (d, J=9.0 Hz, 1H), 7.93 (d, J=9.0 Hz, 1H), 7.89 (d, J=7.3 Hz, 2H), 7.63-7.54 (m, 2H), 7.52-7.43 (m, 2H), 7.33 (br. s, 1H), 6.70 (br. s, 1H), 2.22 (s, 3H). $^{13}$C NMR (175 MHz, CDCl₃, 25° C., δ): 168.6, 138.0, 134.4, 132.8, 131.2, 129.7, 127.9, 127.1, 127.0, 125.2, 121.2 (q, J=258.8 Hz), 120.4, 113.2, 105.7, 24.6. $^{19}$F NMR (376 MHz, CDCl₃, 25° C., δ): −57.9 (s). Mass Spectrometry: HRMS (ESI-TOF) (m/z): calcd for $C_{17}H_{14}N_2O_4SF_3$ ([M+H]⁺), 399.0626, found, 399.0625.

N-(4-bromo-2-(trifluoromethoxy)phenyl)acetamide (3g)

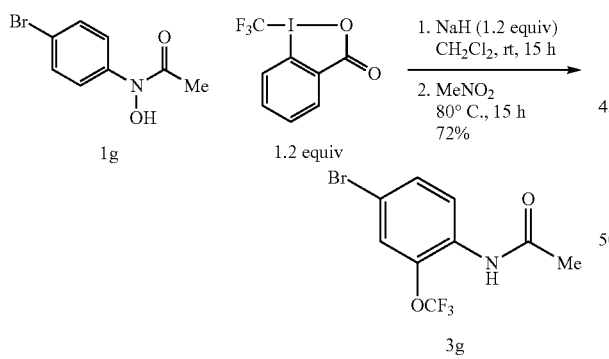

Under N₂ atmosphere, to a mixture of N-(4-bromophenyl)-N-hydroxyacetamide (1g) (11.5 mg, 0.0502 mmol, 1.00 equiv) and NaH (1.4 mg, 0.060 mmol, 1.2 equiv) in CH₂Cl₂ (0.500 mL, 0.100 M) was added Togni reagent II (19.0 mg, 0.0600 mmol, 1.2 equiv). The resulting mixture was stirred at rt for 15 h and was then concentrated in vacuo. MeNO₂ (0.500 mL) was added and the reaction mixture was stirred at 80° C. for 15 h. Trifluorotoluene (6.14 μL, 0.050 mmol, 1.00 equiv) and CDCl₃ (0.250 mL) were added and the reaction mixture was analyzed by $^{19}$F NMR. The $^{19}$F NMR analysis indicated 72% yield of the desired product.

N-(4-acetyl-2-(trifluoromethoxy)phenyl)acetamide (3c)

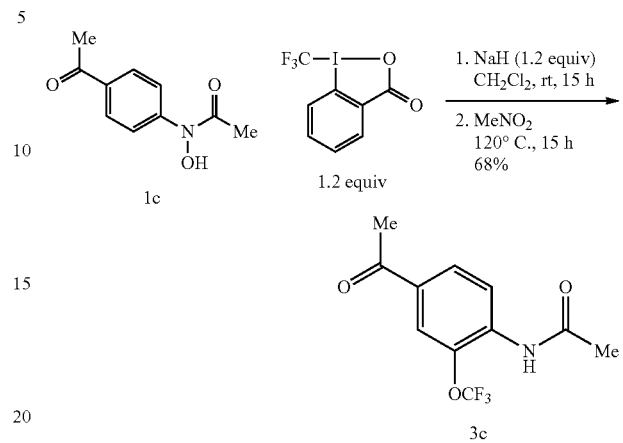

Under N₂ atmosphere, to a mixture of N-(4-acetylphenyl)-N-hydroxyacetamide (1c) (9.7 mg, 0.050 mmol, 1.0 equiv) and NaH (1.4 mg, 0.060 mmol, 1.2 equiv) in CH₂Cl₂ (0.500 mL, 0.100 M) was added Togni reagent II (19.0 mg, 0.0600 mmol, 1.2 equiv). The resulting mixture was stirred at rt for 15 h and was then concentrated in vacuo. MeNO₂ (0.500 mL) was added and the reaction mixture was stirred at 120° C. for 15 h. Trifluorotoluene (6.14 μL, 0.050 mmol, 1.00 equiv) and CDCl₃ (0.250 mL) were added and the reaction mixture was analyzed by $^{19}$F NMR. The $^{19}$F NMR analysis indicated 68% yield of the desired product.

N-(2-(Trifluoromethoxy)phenyl)acetamide (3a) and N-(4-(trifluoromethoxy)phenyl)acetamide (3a-II)

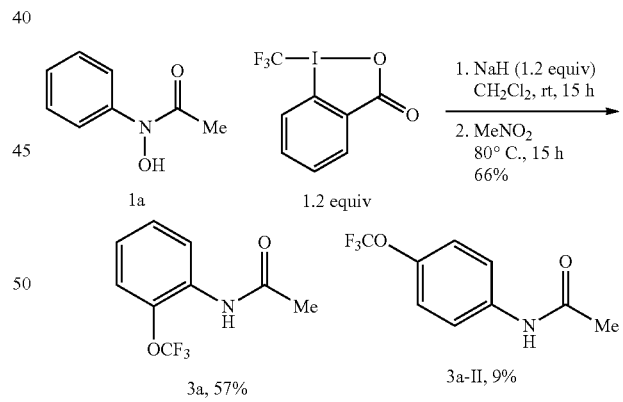

Under N₂ atmosphere, to a mixture of N-hydroxy-N-phenylacetamide (1a) (7.6 mg, 0.050 mmol, 1.0 equiv) and NaH (1.4 mg, 0.060 mmol, 1.2 equiv) in CH₂Cl₂ (0.500 mL, 0.100 M) was added Togni reagent II (19.0 mg, 0.0600 mmol, 1.2 equiv). The resulting mixture was stirred at rt for 15 h and was then concentrated in vacuo. MeNO₂ (0.500 mL) was added and the reaction mixture was stirred at 80° C. for 15 h. Trifluorotoluene (6.14 μL, 0.050 mmol, 1.00 equiv) and CDCl₃ (0.250 mL) were added and the reaction mixture was analyzed by $^{19}$F NMR. The $^{19}$F NMR analysis indicated 66% yield of the desired product.

Methyl 4-acetamido-3-(trifluoromethoxy)benzoate (3q)

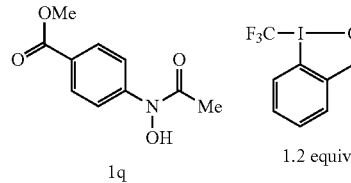 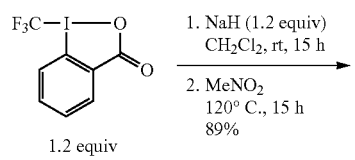

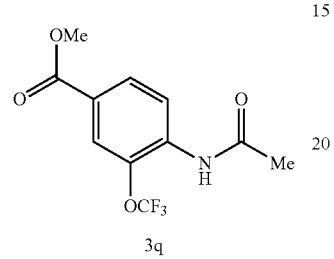

3q

Under N₂ atmosphere, to a mixture of methyl 4-(N-hydroxyacetamido)benzoate (1q) (10.5 mg, 0.0500 mmol, 1.00 equiv) and NaH (1.4 mg, 0.060 mmol, 1.2 equiv) in CH₂Cl₂ (0.500 mL, 0.100 M) was added Togni reagent II (19.0 mg, 0.0600 mmol, 1.2 equiv). The resulting mixture was stirred at rt for 15 h and was then concentrated in vacuo. MeNO₂ (0.500 mL) was added and the reaction mixture was stirred at 120° C. for 15 h. Trifluorotoluene (6.14 µL, 0.050 mmol, 1.00 equiv) and CDCl₃ (0.250 mL) were added and the reaction mixture was analyzed by ¹⁹F NMR. The ¹⁹F NMR analysis indicated 89% yield of the desired product.

Example 5. Gram Scale Synthesis

To demonstrate the practicality and effectiveness of the approach for the synthesis of o-OCF₃ aniline derivatives, the trifluoro-methoxylation reaction of 1q and OCF₃-migration of 2q on a gram scale was performed (Scheme 5). Reaction of 2.00 g (9.56 mmol) of 1q with 1.2 equiv Togni reagent II in the presence of 10 mol % Cs₂CO₃ in degassed chloroform gave 2q (2.51 g) in 95% isolated yield. Heating 2.51 g (9.49 mmol) of 2q in MeNO₂ at 120° C. afforded 3q (2.13 g) in 85% isolated yield.

Scheme 5. Gram scale synthesis.

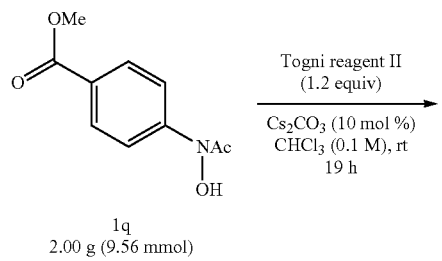

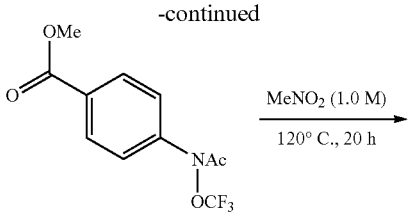

2q
95% yield
2.51 g (9.05 mmol)

3q
85% yield
2.13 g (7.68 mmol)

Methyl 4-(N-(trifluoromethoxy)acetamido)benzoate (2q)

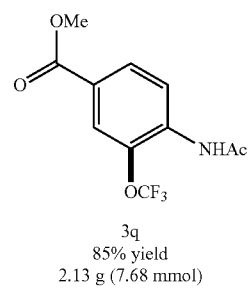

Under N₂ atmosphere, to a mixture of methyl 4-(N-hydroxyacetamido)benzoate (1q) (2.00 g, 9.56 mmol, 1.00 equiv) and Cs₂CO₃ (311 mg, 0.956 mmol, 10 mol %) in CHCl₃ (95.6 mL, 0.100 M) was added Togni reagent II (3.63 g, 11.5 mmol, 1.20 equiv) and the reaction mixture was stirred at rt for 24 h. The reaction mixture was then washed with sat. aq. NaHCO₃ (100 mL) and the layers were separated. The organic layer was dried (MgSO₄), filtered, and concentrated in vacuo. The residue was purified by chromatography on silica gel, eluting with hexanes:CH₂Cl₂ (7:3 to 0:1 (v/v)). The purification afforded the title compound (2.51 g, 9.05 mmol, 95% yield), which was spectroscopically identical to the compound prepared according to the standard procedure (vide supra).

Methyl 4-acetamido-3-(trifluoromethoxy)benzoate (3q)

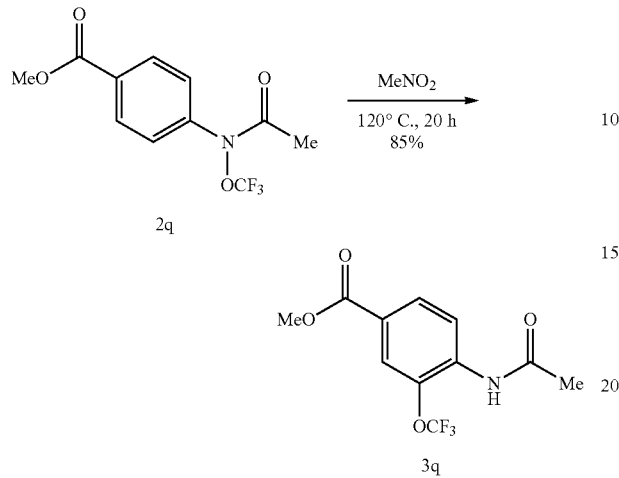

A solution of methyl 4-(N-(trifluoromethoxy)acetamido)benzoate (2q) (2.51 g, 9.05 mmol) in MeNO$_2$ (9.05 mL, 1.00 M) was heated at 120° C. under N$_2$ atmosphere for 20 h. The reaction mixture was concentrated in vacuo. The residue was purified by chromatography on silica gel, eluting with hexanes:EtOAc (9:1 to 7:3 (v/v)), to afford the title compound (2.13 g, 7.68 mmol, 85% yield), which was spectroscopically identical to the compound prepared according to the standard procedure (vide supra).

Example 6. Trifluoromethoxylation of Heteroaryl Substrates

The effectiveness of this approach was also explored using heteroaryl substrates. For the synthesis of o-OCF$_3$ pyridino derivatives, the trifluoromethoxylation reaction of 5 and OCF$_3$-migration of 6 on a gram was performed (Scheme 6). Reaction of 5 with 1.2 equiv Togni reagent II in the presence of 10 mol % Cs$_2$CO$_3$ in degassed chloroform gave 6 in 90% isolated yield. Heating of 6 in MeNO$_2$ at 120° C. for 23 hours afforded 7 (2.13 g) in 85% isolated yield.

Scheme 6. Synthesis of trifluoromethoxy pyridine derivative.

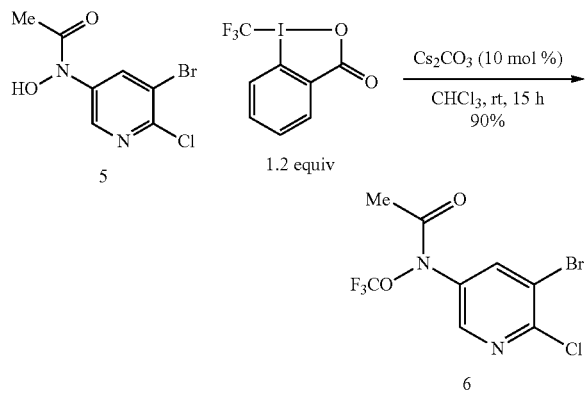

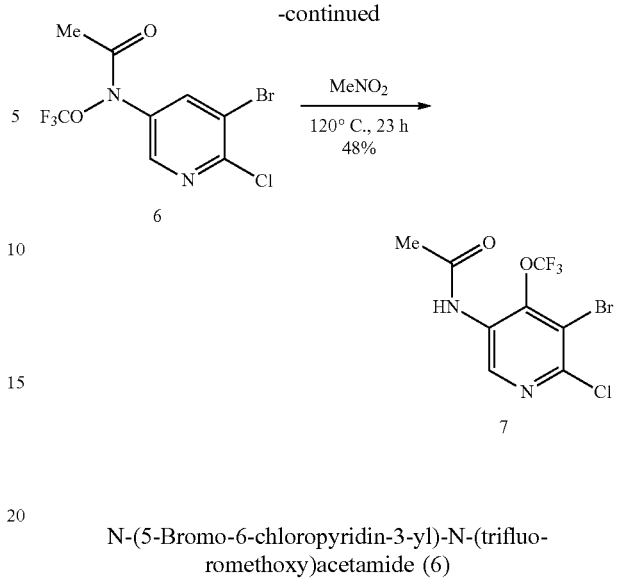

N-(5-Bromo-6-chloropyridin-3-yl)-N-(trifluoromethoxy)acetamide (6)

Under N$_2$ atmosphere, to a mixture of N-(5-bromo-6-chloropyridin-3-yl)-N-hydroxyacetamide (5) (221 mg, 0.832 mmol, 1.00 equiv) and Cs$_2$CO$_3$ (27.1 mg, 0.0832 mmol, 10 mol %) in CHCl$_3$ (8.32 mL, 0.100 M) was added Togni reagent II (316 g, 0.998 mmol, 1.20 equiv) and the reaction mixture was stirred at rt for 15 h. The reaction mixture was diluted with CH$_2$Cl$_2$, washed with sat. aq. NaHCO$_3$ (30 mL) and the layers were separated. The organic layer was dried (MgSO$_4$), filtered and concentrated in vacuo. The residue was purified by chromatography on silica gel, eluting with hexanes:CH$_2$Cl$_2$ (1:3 to 1:4 (v/v)), to afford 250 mg of the title compound as a slightly yellow oil (90% yield). R$_f$=0.55 (CH$_2$Cl$_2$:hexanes 1:1). NMR Spectroscopy: $^1$H NMR (500 MHz, CDCl$_3$, 25° C., δ): 8.41 (d, J=0.85 Hz, 1H), 7.99 (d, J=0.85 Hz, 1H), 2.38 (s, 3H). $^{13}$C NMR (125 MHz, CDCl$_3$, 25° C., δ): 172.8, 149.9, 143.0, 137.2, 136.1, 122.7 (q, J=265.2 Hz), 120.1, 21.5. $^{19}$F NMR (376 MHz, CDCl$_3$, 25° C., δ): −65.1 (s).

N-(5-bromo-6-chloro-4-(trifluoromethoxy)pyridin-3-yl)acetamide (7)

A solution of N-(5-bromo-6-chloro-2-(trifluoromethoxy)pyridin-3-yl)acetamide (6) (102 mg, 0.306 mmol) in MeNO$_2$ (0.306 mL, 1.00 M) was heated at 120° C. under N$_2$ atmosphere for 23 h. The reaction mixture was purified by preparative TLC using hexanes:EtOAc (93:7 (v/v)) for development. The purification afforded 49 mg of the title compound as a white solid (48% yield). R$_f$=0.49 (hexanes/EtOAc 4:1 (v/v)). NMR Spectroscopy: $^1$H NMR (700 MHz, CDCl$_3$, 25° C., δ): 9.12 (s, 1H), 7.30 (br. s, 1H), 2.27 (s, 3H). $^{13}$C NMR (175 MHz, CDCl$_3$, 25° C., δ): 168.7, 142.4, 140.4, 134.8, 123.7, 119.9 (q, J=263.4 Hz), 117.4, 24.9. $^{19}$F NMR (376 MHz, CDCl$_3$, 25° C., δ): −56.7 (s).

Example 7. Trifluoromethoxylation of Pyridine Substrates

Herein is disclosed the first efficient and scalable one-pot protocol for regioselective synthesis of a broad spectrum of trifluoromethoxylated pyridines and pyrimidines using commercially available, bench-stable Togni reagent I.

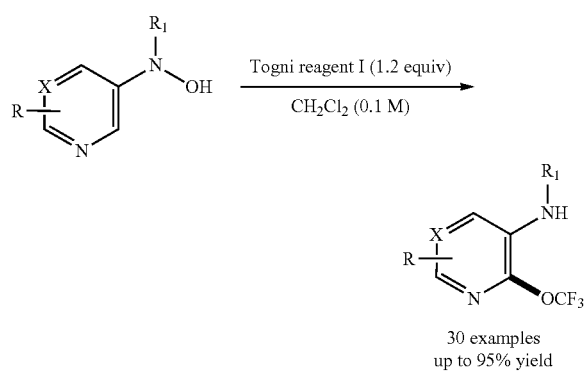

X = CH or N

Methyl (5-bromo-6-methoxypyridin-3-yl)(hydroxyl)carbamate (8a) as used as the model substrate. This compound could be readily prepared from the corresponding nitropyridine through a one-pot reduction/protection procedure. Exposure of 8a to Togni reagent II in the presence of cesium carbonate (0.1 equiv) in chloroform at room temperature for 15 hours afforded the desired product 9a in only 29% yield.[28] Examination of different trifluoromethylation reagents such as Togni reagent I, Umemoto reagent, and Shibata-Johnson reagent[23] revealed that Togni reagent I was superior to other reagents and delivered the desired product 9a in 42% yield. Higher yield was obtained in the absence of $Cs_2CO_3$. Screening of solvents showed that $CH_2Cl_2$ gave the best result, providing the desired product 9a in 87% NMR yield.

With the optimized reaction conditions in hand, the scope and generality of the trifluoromethoxylation reaction was explored. A wide range of functional groups and substitution patterns were tolerated (Scheme 7). Halogen functionalities, in particular Br and I, remain intact after the reaction, providing useful synthetic handles for further elaborations (9a-h, 9k, 9r, 9s, 9u, 9v). Other functional groups such as alkyl- and aryl-ethers (9i, 9k-m, 9v-x), aldehydes (9m), ketone (9x), alkene (9v), alkyne (9w), amide (9y), esters (9v-w), and benzo[1,3]dioxole (9y) proved compatible under the reaction conditions. In addition, this methodology was successfully applied to pyridines bearing a wide array of heteroaryl substituents such as furan (9m), pyrazole (9n), 1,2,4-triazole (9o), benzimidazole (9p), benzotriazole (9q, 9t), indole (9r, 9y), 7-azaindole (9s), thiazole (9t), and 2,6-dichloropurine (9u). More excitingly, our mild reaction conditions allow late-stage trifluoromethoxylation of complex organic molecules. For examples, estrone and Tadalafil conjugated pyridines (8x, 8y) were trifluoromethoxylated to afford the desired product 9x and 9y in 71% and 66% yield, respectively. Remarkably, no epimerization was observed under these mild reaction conditions. These results further demonstrated the synthetic utility of our strategy.

Several features of the reaction are noteworthy. First of all, the reaction is sensitive to the electronic properties of substituents on pyridine. Substrates with an electron donating substituent para to the protected N-hydroxylamine readily undergo rearrangement to yield the desired trifluoromethoxylated products at or below room temperature (9a-b, 9i, 9k-n, 9p, 9r-s, 9v-y). In the absence of such substituents, higher reaction temperatures are required for the $OCF_3$-migration step (9c-h, 9o, 9q, 9t-u). These observations are consistent with the formation of nitrenium ion through heterolytic cleavage of N—O bond (vide infra).[24]

Secondly, for the reactions that take place at or below room temperature, the $OCF_3$ group is introduced exclusively to the α'-position.[25] Since α- and α'-carbon of pyridines are metabolically labile sites, incorporation of an electron withdrawing $OCF_3$ group to the α'-position could improve the metabolic stability of the molecule.[26] If the α'-position is blocked, product of γ-$OCF_3$ pyridine is formed instead (9g and 9h). Interestingly, atropisomers are obtained in these cases. This is because the plane containing the $OCF_3$ group is orthogonal to the pyridine plane, which prevents the free rotation of amide group (see Supporting Information).[1b, 3a-3d] Thirdly, the regioselectivity erodes as the reaction temperature increases (9d-f, 9o, 9u). Finally, substrates with the protected N-hydroxylamino-group at α-, γ-, or α'-position do not give the product of trifluoromethoxylation. Presumably, the formation of nitrenium ion is energetically disfavored in these cases, because it involves placing the positive charge on the endocyclic nitrogen atom.[27] Products 9a-9y are shown in FIG. 2.

Scheme 7.

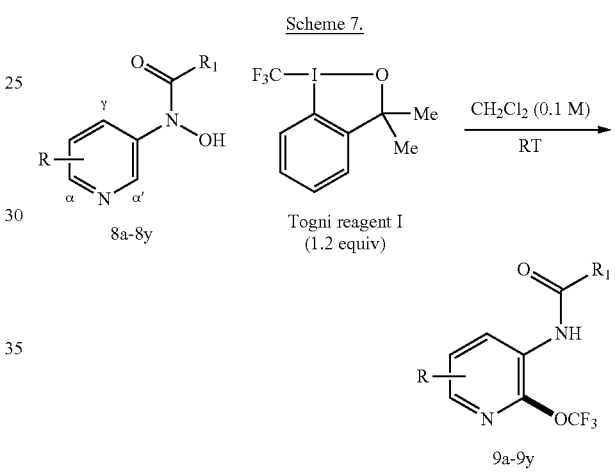

Methyl (5-bromo-6-methoxypyridin-3-yl)(hydroxy)carbamate (8a)

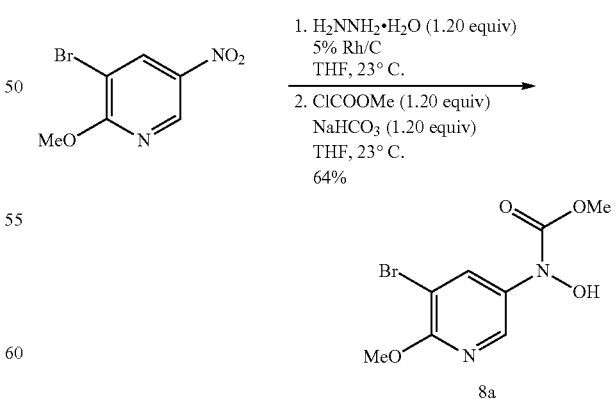

Under $N_2$ atmosphere, to a suspension of 3-bromo-2-methoxy-5-nitropyridine (5.00 g, 21.5 mmol, 1.00 equiv) and 5% Rh/C (0.123 g, 0.30 mol % Rh) in THF (107 mL, 0.200 M) hydrazine monohydrate (1.56 g, 25.8 mmol, 1.20 equiv) was added dropwise. The reaction mixture was monitored via TLC using EtOAc:hexanes 1:1 (v/v) as an eluent until the disappearance of the starting 3-bromo-2-methoxy-5-nitropyridine ($R_f$=0.90 (EtOAc:hexanes 1:1 (v/v)) and the appearance of the hydroxylamine intermediate ($R_f$=0.61 (EtOAc:hexanes 1:1 (v/v)). Subsequently, sodium bicarbonate (2.14 g, 25.8 mmol, 1.20 equiv) was added to the reaction mixture followed by a solution of methyl chloroformate (2.42 g, 25.75 mmol, 1.20 equiv) in THF (6.58 mL, 0.200 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with EtOAc:hexanes (3:7 to 1:1 (v/v)), to afford the title compound as a slightly light yellow solid (3.82 g, 13.8 mmol, 64% yield). $R_f$=0.54 (EtOAc:hexanes 1:1 (v/v)). NMR Spectroscopy: $^1$H NMR (500 MHz, (CD$_3$)$_2$SO, 25° C., δ): 10.60 (s, 1H) 8.29 (d, J=2.44 Hz, 1H) 8.13 (d, J=2.44 Hz, 1H) 3.93 (s, 3H) 3.74 (s, 3H). $^{13}$C NMR (125 MHz, (CD$_3$)$_2$SO, 25° C., δ): 156.97, 155.40, 138.89, 135.74, 134.47, 105.44, 55.01, 53.67. Mass Spectrometry: HRMS (ESI-TOF) (m/z): calcd for C$_8$H$_{10}$BrN$_2$O$_4$ ([M+H]$^+$), 276.9818, found, 276.9821.

Methyl hydroxy (5-iodo-6-methoxypyridin-3-yl) carbamate (8b)

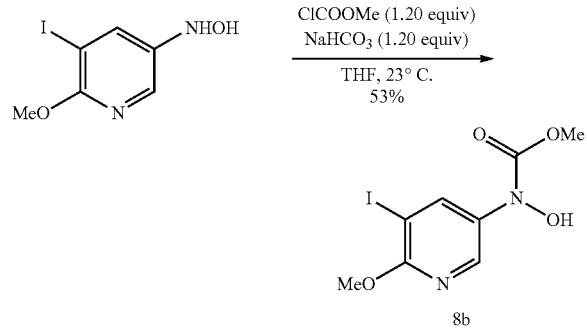

Under N$_2$ atmosphere, to a suspension of 3-iodo-2-methoxy-5-nitropyridine (0.500 g, 1.79 mmol, 1.00 equiv) and 5% Rh/C (10.3 mg, 0.30 mol % Rh) in THF (8.93 mL, 0.200 M) hydrazine monohydrate (0.130 g, 2.14 mmol, 1.20 equiv) was added dropwise. After the reaction mixture was stirred at 23° C. for 1 h, it was filtered through a short pad of celite and concentrated in vacuo to afford the title compound as a slightly brown solid (0.467 g, 1.76 mmol, 98% yield). The product was used directly without further purification. Under N$_2$ atmosphere, to a stirred suspension of N-(5-iodo-6-methoxypyridin-3-yl)hydroxylamine (0.350 g, 1.32 mmol, 1.00 equiv) and NaHCO$_3$ (0.131 g, 1.58 mmol, 1.20 equiv) in THF (6.58 mL, 0.200 M) at 23° C. was slowly added a solution of methyl chloroformate (0.148 g, 1.58 mmol, 1.20 equiv) in THF (6.58 mL, 0.200 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with EtOAc:hexanes (1:1 to 1:0 (v/v)), to afford the title compound as a slightly light brown solid (0.229 g, 0.710 mmol, 54% yield). $R_f$=0.63 (EtOAc:hexanes 1:0 (v/v)). NMR Spectroscopy: $^1$H NMR (500 MHz, (CD$_3$)$_2$SO, 25° C., δ): 10.54 (br. s, 1H) 8.26 (br. s, 2H) 3.89 (br. s, 3H) 3.73 (br. s, 3H). $^{13}$C NMR (125 MHz, (CD$_3$)$_2$SO, 25° C., δ): 158.8, 154.9, 141.5, 139.4, 134.0, 79.1, 54.8, 53.1. HRMS (ESI-TOF) (m/z): calcd for C$_8$H$_{10}$IN$_2$O$_4$ ([M+H]$^+$), 324.9680, found, 324.9682.

Methyl (6-chloro-4-methylpyridin-3-yl)(hydroxy) carbamate (8c)

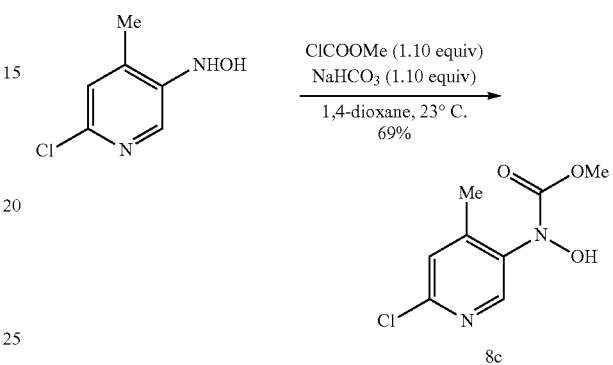

Under N$_2$ atmosphere, hydrazine monohydrate (1.04 g, 20.9 mmol, 1.20 equiv) was added dropwise to a suspension of 2-chloro-4-methyl-5-nitropyridine (3.00 g, 17.4 mmol, 1.00 equiv) and 5% Rh/C (0.300 g, 0.838 mol % Rh) in THF (85.0 mL, 0.204 M) at 23° C. The reaction mixture was stirred at 23° C. for 3 h and filtered through a short pad of celite. The celite was washed with EtOAc. The organic solutions were combined and concentrated in vacuo to afford the title compound as a white solid (2.70 g, 17.1 mmol, 98% yield). The product was used directly without further purification. Under N$_2$ atmosphere, a solution of methyl chloroformate (0.623 g, 6.59 mmol, 1.10 equiv) in 1,4-dioxane (10.0 mL, 0.660 M) was slowly added to a stirred suspension of N-(6-chloro-4-methylpyridin-3-yl)hydroxylamine (0.950 g, 5.99 mmol, 1.00 equiv) and NaHCO$_3$ (0.554 g, 6.59 mmol, 1.10 equiv) in 1,4-dioxane (40.0 mL, 0.150 M) at 23° C. After the reaction was complete (4 h), the reaction mixture was concentrated in vacuo. The residue was purified by chromatography on silica gel, eluting with hexanes:EtOAc (4:1 to 3:2 (v/v)), to afford the title compound as a red solid (0.890 g, 4.11 mmol, 69% yield). $R_f$=0.27 (hexanes/EtOAc 3:2 (v/v)). $^1$H NMR (700 MHz, (CD$_3$)$_2$SO, 25° C., δ): 10.53 (s, 1H), 8.29 (s, 1H), 7.52 (s, 1H), 3.68 (s, 3H), 2.23 (s, 3H). $^{13}$C NMR (175 MHz, (CD$_3$)$_2$SO, 25° C., δ): 155.6, 148.8, 148.4, 147.9, 137.7, 125.6, 53.2, 16.8. Mass Spectrometry: HRMS (ESI-TOF) (m/z): calcd for C$_8$H$_{10}$ClN$_2$O$_3$ ([M+H]$^+$), 217.0374, found, 217.0373.

Methyl (6-bromopyridin-3-yl)(hydroxy)carbamate (8d)

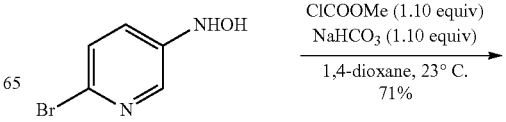

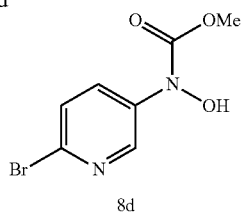

8d

Under N₂ atmosphere, hydrazine monohydrate (0.888 g, 17.7 mmol, 1.20 equiv) was added dropwise to a suspension of 2-bromo-5-nitropyridine (3.00 g, 14.8 mmol, 1.00 equiv) and 5% Rh/C (0.290 g, 0.952 mol % Rh) in THF (75.0 mL, 0.197 M) at 23° C. After the reaction was complete (2.5 h), the reaction mixture was filtered through a short pad of celite and the celite was washed with EtOAc. The organic solutions were combined and concentrated in vacuo to afford the title compound as a yellow solid (2.70 g, 14.3 mmol, 97% yield). The product was used directly without further purification. Under N₂ atmosphere, a solution of methyl chloroformate (0.520 g, 5.50 mmol, 1.10 equiv) in 1,4-dioxane (10.0 mL, 0.550 M) was added dropwise to a stirred suspension of N-(6-bromopyridin-3-yl)hydroxylamine (0.940 g, 5.00 mmol, 1.00 equiv) and NaHCO₃ (0.462 g, 5.50 mmol, 1.10 equiv) in 1,4-dioxane (40.0 mL, 0.125 M) at 23° C. After the reaction was complete (3 h), the reaction mixture was filtered through a short pad of celite and the celite was washed with EtOAc. The combined organic layers were concentrated in vacuo. The residue was purified by chromatography on silica gel, eluting with hexanes:EtOAc (4:1 to 3:2 (v/v)), to afford the title compound as a yellow solid (0.870 g, 3.52 mmol, 71% yield). R$_f$=0.27 (hexanes/EtOAc 3:2 (v/v)). $^1$H NMR (500 MHz, (CD₃)₂SO, ° C., δ): 10.74 (s, 1H), 8.58 (d, J=2.7 Hz, 1H), 7.89 (dd, J=2.7, 3.8 Hz, 1H), 7.64 (d, J=3.8 Hz, 1H), 3.78 (s, 3H). $^{13}$C NMR (125 MHz, (CD₃)₂SO, 25° C., δ): 154.4, 140.9, 138.8, 134.9, 129.6, 127.5, 53.4. Mass Spectrometry: HRMS (ESI-TOF) (m/z): calcd for C₇H₈BrN₂O₃ ([M+H]⁺), 246.9713, found, 246.9712.

Methyl (6-fluoropyridin-3-yl)(hydroxy)carbamate (8e)

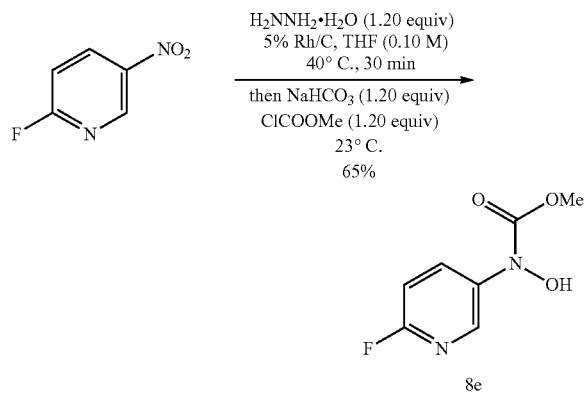

8e

Under N₂ atmosphere, a suspension of 2-fluoro-5-nitropyridine (1.00 g, 7.04 mmol, 1.00 equiv) and 5% Rh/C (80.8 mg, 0.60 mol % Rh) in THF (35.2 mL, 0.200 M) was heated to 40° C. Hydrazine monohydrate (0.422 g, 8.44 mmol, 1.20 equiv) was added all at once. The reaction mixture was stirred at 40° C. for 30 min and then cooled down to 23° C. NaHCO₃ (0.708 g, 8.44 mmol, 1.2 equiv) was added, followed by dropwise addition of methyl chloroformate (0.800 g, 8.44 mmol, 1.20 equiv) in THF (35.2 mL, 0.240 M) at 23° C. After the reaction was complete (1 h), the reaction mixture was filtered through a short pad of celite, washed with EtOAc, and concentrated in vacuo. The residue was purified by chromatography on silica gel, eluting with hexanes:EtOAc (4:1 to 2:1 (v/v)), to afford the title compound as a red solid (0.850 g, 4.57 mmol, 65% yield). R$_f$=0.22 (hexanes:EtOAc 2:1 (v/v)). $^1$H NMR (700 MHz, (CD₃)₂SO, 25° C., δ): 10.67 (s, 1H) 8.36 (d, J=1.29 Hz, 1H) 8.09-8.06 (m, 1H) 7.21 (dd, J=8.82, 3.23 Hz, 1H) 3.76 (s, 3H). $^{13}$C NMR (175 MHz, (CD₃)₂SO, 25° C., δ): 159.3 (d, J=232.8 Hz), 154.8, 138.8 (d, J=15.8 Hz), 137.3 (d, J=5.25 Hz), 133.8 (d, J=8.75 Hz), 109.2 (d, J=40.3 Hz), 53.3. $^{19}$F NMR (376 MHz, CDCl₃, 25° C., δ): −74.7 (s). Mass Spectrometry: HRMS (ESI-TOF) (m/z): calcd for C₇H₈FN₂O₃ ([M+H]⁺), 187.0513, found, 187.0513.

Methyl (5-bromo-6-chloropyridin-3-yl)(hydroxy)carbamate (8f)

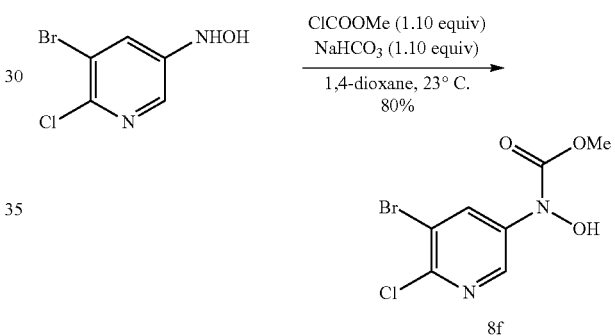

8f

Under N₂ atmosphere, hydrazine monohydrate (0.506 g, 10.1 mmol, 1.20 equiv) was added dropwise to a suspension of 3-bromo-2-chloro-5-nitropyridine (2.00 g, 8.42 mmol, 1.00 equiv) and Pt/C (0.200 g, 0.609 mol % Pt) in THF (75.0 mL, 0.112 M) at 23° C. The reaction mixture was stirred at 23° C. for 3 h, filtered through a short pad of celite, washed with EtOAc, and concentrated in vacuo. The residue was dissolved in ether and filtered off. The filtrate was kept at −20° C. overnight and filtered again to remove the solid. The filtrate was concentrated in vacuo to afford the title compound as a yellow solid (1.22 g, 5.46 mmol, 65% yield). The product was used directly without further purification. Under N₂ atmosphere, a solution of methyl chloroformate (0.256 g, 2.71 mmol, 1.10 equiv) in 1,4-dioxane (10.0 mL, 0.271 M) was added dropwise to a stirred suspension of N-(5-bromo-6-chloropyridin-3-yl)hydroxylamine (0.550 g, 2.46 mmol, 1.00 equiv) and NaHCO₃ (0.227 g, 2.71 mmol, 1.10 equiv) in 1,4-dioxane (15.0 mL, 0.164 M) at 23° C. The reaction mixture was stirred for 6 h and concentrated in vacuo. The residue was purified by chromatography on silica gel, eluting with hexanes:EtOAc (4:1 to 3:2 (v/v)), to afford the title compound as a yellow solid (0.55 g, 1.95 mmol, 80% yield). R$_f$=0.42 (hexanes/EtOAc 3:2 (v/v)). $^1$H NMR (500 MHz, (CD₃)₂SO, 25° C., δ): 10.89 (s, 1H), 8.63 (d, J=2.3 Hz, 1H), 8.33 (d, J=2.3 Hz, 1H), 3.80 (s, 3H). $^{13}$C NMR (125 MHz, (CD₃)₂SO, 25° C., δ): 154.3, 143.0, 138.9, 138.4, 131.7, 118.5, 53.6. Mass Spectrometry: HRMS (ESI-TOF) (m/z): calcd for $C_7H_7BrClN_2O_3$ ([M+H]$^+$), 282.9301, found, 282.9302.

Methyl (2-chloropyridin-3-yl)(hydroxy)carbamate (8g)

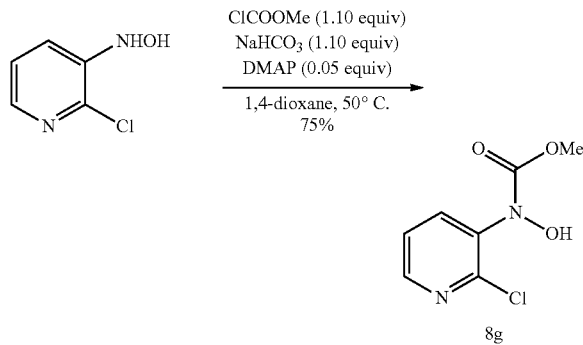

Under $N_2$ atmosphere, hydrazine monohydrate (1.89 g, 37.8 mmol, 1.20 equiv) was added dropwise to a suspension of 2-chloro-3-nitropyridine (5.00 g, 31.5 mmol, 1.00 equiv) and Rh/C (0.500 g, 0.771 mol % Rh) in THF (150 mL, 0.210 M) at 23° C. The reaction mixture was stirred at 23° C. for 3 h, filtered through a short pad of celite, washed with EtOAc, and concentrated in vacuo to afford of the title compound as a red solid (4.50 g, 31.1 mmol, 98% yield). The product was used directly without further purification. Under $N_2$ atmosphere, a solution of methyl chloroformate (0.140 g, 1.53 mmol, 1.10 equiv) in dioxane (7.00 mL, 0.220 M) was slowly added via a syringe pump (at a rate of 10.0 mL/h) to a stirred suspension of N-(2-chloropyridin-3-yl) hydroxylamine (0.200 g, 1.39 mmol, 1.00 equiv), NaHCO$_3$ (0.130 g, 1.53 mmol, 1.10 equiv) and DMAP (8.50 mg, 0.0700 mmol, 0.0500 equiv) in dioxane (7.00 mL, 0.200 M) at 50° C. After the addition was complete, the reaction mixture was stirred at 50° C. for another 12 h and then filtered through a short pad of celite and the celite was washed with EtOAc. The organic layers were combined and concentrated in vacuo. The residue was purified by chromatography on silica gel, eluting with hexanes:EtOAc (5:1 to 1:1 (v/v)), to afford the title compound as a yellow gum (0.210 g, 1.04 mmol, 75% yield). $R_f$=0.19 (hexanes/EtOAc 5:1 (v/v)). $^1$H NMR (700 MHz, (CD$_3$)$_2$SO, 25° C., δ): 10.63 (s, 1H), 8.39 (dd, J=4.73, 1.72 Hz, 1H), 7.96 (dd, J=7.74, 1.72 Hz, 1H), 7.52 (dd, J=7.74, 4.73 Hz, 1H), 3.69 (s, 3H). $^{13}$C NMR (175 MHz, (CD$_3$)$_2$SO, 25° C., δ): 155.3, 148.9, 148.1, 137.9, 136.6, 124.0, 53.2. Mass Spectrometry: HRMS (ESI-TOF) (m/z): calcd for $C_7H_8ClN_2O_3$ ([M+H]$^+$), 203.0218, found, 203.0231.

N-(2,6-Dichloropyridin-3-yl)-N-hydroxyacetamide (8h)

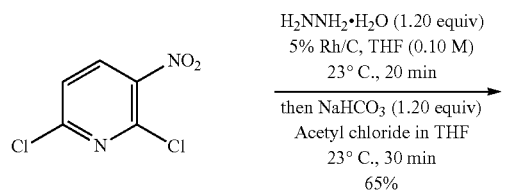

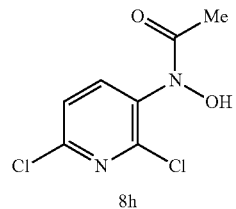

Under $N_2$ atmosphere, a suspension of 2-fluoro-5-nitropyridine (1.00 g, 7.04 mmol, 1.00 equiv) and 5% Rh/C (80.8 mg, 0.60 mol % Rh) in THF (35.2 mL, 0.200 M) was heated to 40° C. Hydrazine monohydrate (0.422 g, 8.44 mmol, 1.20 equiv) was added all at once. The reaction mixture was stirred at 40° C. for 30 min and then cooled down to 23° C. NaHCO$_3$ (0.708 g, 8.44 mmol, 1.2 equiv) was added, followed by dropwise addition of methyl chloroformate (0.800 g, 8.44 mmol, 1.20 equiv) in THF (35.2 mL, 0.240 M) at 23° C. The reaction mixture was stirred at 23° C. for 1 h and then filtered through a short pad of celite, washed with EtOAc, and concentrated in vacuo. The residue was purified by chromatography on silica gel, eluting with hexanes:EtOAc (4:1 to 2:1 (v/v)), to afford the title compound as a red solid (0.850 g, 4.57 mmol, 65% yield). $R_f$=0.22 (hexanes:EtOAc 2:1 (v/v)). $^1$H NMR (700 MHz, (CD$_3$)$_2$SO, 25° C., δ): 10.95 (br. s., 1H), 8.01 (d, J=7.74 Hz, 1H), 7.67 (d, J=8.17 Hz, 1H), 2.19 (br. s., 3H). $^{13}$C NMR (175 MHz, (CD$_3$)$_2$SO, 25° C., δ): 171.0, 147.5, 146.9, 140.9, 135.9, 124.6, 20.8. Mass Spectrometry: HRMS (ESI-TOF) (m/z): calcd for $C_7H_7Cl_2N_2O_2$ ([M+H]$^+$), 220.9879, found, 220.9878.

N-Hydroxy-N-(6-methoxy-4-methylpyridin-3-yl) acetamide (8i)

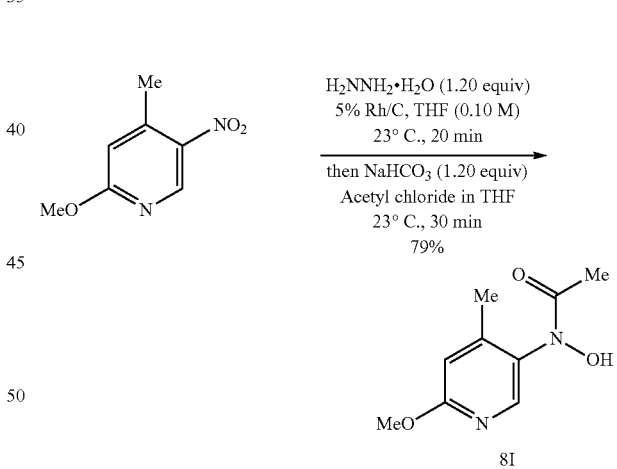

Under $N_2$ atmosphere, a suspension of 2-methoxy-4-methyl-5-nitropyridine (491 mg, 2.92 mmol, 1.00 equiv) and 5% Rh/C (33.6 mg, 0.60 mol % Rh) in dioxane (14.6 mL, 0.200 M) was stirred at 40° C. Hydrazine monohydrate (146 mg, 3.50 mmol, 1.20 equiv) in dioxane (14.6 mL, 0.240 M) was added via a syringe pump (at a rate of 15.0 mL/h). The reaction mixture was stirred at 40° C. for 1 h and then cooled down to 23° C. NaHCO$_3$ (290 mg, 3.50 mmol, 1.2 equiv) was added, followed by dropwise addition of acetyl chloride (270 mg, 3.50 mmol, 1.20 equiv) in THF (29.2 mL, 0.120 M) at 23° C. The reaction mixture was stirred at 23° C. for 1 h and then filtered through a short pad of celite, washed with EtOAc, and concentrated in vacuo. The residue was purified by chromatography on silica gel, eluting with hexanes:EtOAc (4:1 to 1:1 (v/v)), to afford the title compound as a brown solid (450 mg, 2.29 mmol, 79% yield). $R_f$=0.08 (hexanes:EtOAc 4:1 (v/v)). $^1$H NMR (700 MHz, (CD$_3$)$_2$SO, 90° C., δ): 10.21 (br. s., 1H), 8.01 (s, 1H), 6.73 (s, 1H), 3.86 (s, 3H), 2.18 (s, 3H), 2.08 (s, 3H). $^{13}$C NMR (175 MHz, (CD$_3$)$_2$SO, 25° C., δ): 170.9, 162.9, 148.1, 145.7, 132.4, 110.9, 53.4, 20.8, 17.1. Mass Spectrometry: HRMS (ESI-TOF) (m/z): calcd for C$_9$H$_{13}$N$_2$O$_3$ ([M+H]$^+$), 197.0921, found, 197.0936.

N-Hydroxy-N-(6-methylpyridin-3-yl)acetamide (8j)

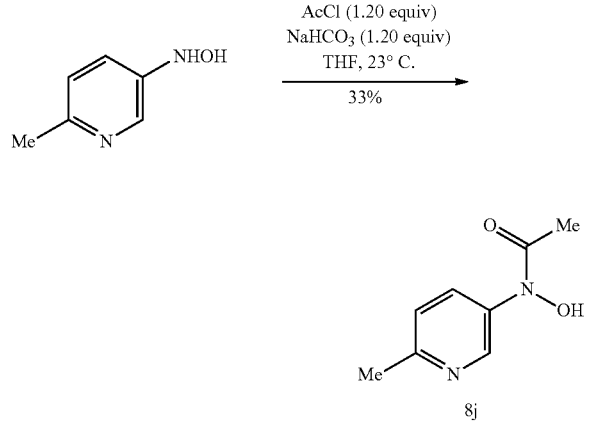

Under N$_2$ atmosphere, hydrazine monohydrate (0.870 g, 17.4 mmol, 1.20 equiv) was added dropwise to a suspension of 2-methyl-5-nitropyridine (2.00 g, 14.5 mmol, 1.00 equiv) and Rh/C (0.120 g, 0.402 mol % Rh) in THF (75.0 mL, 0.193 M) at 23° C. The reaction mixture was stirred at 23° C. for 2 h, filtered through a short pad of celite, washed with EtOAc, and concentrated in vacuo to afford the title compound as a yellow solid (1.63 g, 13.1 mmol, 91% yield). The product was used directly without further purification. Under N$_2$ atmosphere, a solution of acetyl chloride (0.300 g, 3.87 mmol, 1.20 equiv) in THF (16.00 mL, 0.240 M) was added dropwise to a stirred suspension of N-(6-methylpyridin-3-yl)hydroxylamine (S6) (0.400 g, 3.22 mmol, 1.00 equiv) and NaHCO$_3$ (0.330 g, 3.87 mmol, 1.20 equiv) in THF (16.00 mL, 0.200 M) at 23° C. The reaction mixture was stirred at 23° C. for another 30 min and then filtered through a short pad of celite and the celite was washed with EtOAc. The organic layers were combined and concentrated in vacuo. The residue was purified by chromatography on silica gel, eluting with EtOAc to afford the title compound as a light yellow solid (0.176 g, 1.06 mmol, 33% yield). $R_f$=0.17 (EtOAc). $^1$H NMR (700 MHz, (CD$_3$)$_2$SO, 25° C., δ): 10.77 (br. s, 1H), 8.72 (br. s, 1H), 7.87 (dd, J=8.17, 2.15 Hz, 1H), 7.25 (d, J=8.60 Hz, 1H), 2.43 (s, 3H), 2.21 (br. s, 3H). $^{13}$C NMR (175 MHz, (CD$_3$)$_2$SO, 25° C., δ): 170.4, 153.6, 140.5, 136.0, 127.4, 122.6, 23.4, 22.1. Mass Spectrometry: HRMS (ESI-TOF) (m/z): calcd for C$_8$H$_{11}$N$_2$O$_2$ ([M+H]$^+$), 167.0815, found, 167.0816.

Methyl (5-(2,4-difluorophenyl)-6-methoxypyridin-3-yl)(hydroxy) carbamate (8k)

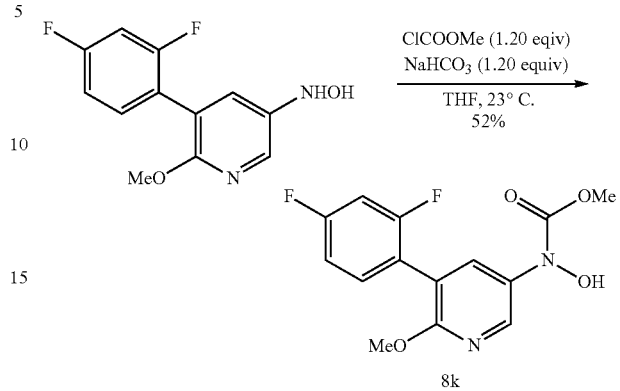

Under N$_2$ atmosphere, to a suspension of 3-(2,4-difluorophenyl)-2-methoxy-5-nitropyridine (0.300 g, 1.13 mmol, 1.00 equiv) and 5% Rh/C (6.5 mg, 0.30 mol % Rh) in THF (11.3 mL, 0.100 M) hydrazine monohydrate (0.083 g, 1.35 mmol, 1.20 equiv) was added dropwise. The reaction mixture was stirred at 23° C. for 1 h and filtered through a short pad of celite. The pad of celite was washed with EtOAc. The combined organic solution was concentrated in vacuo to afford the title compound as a slightly light yellow solid (0.245 g, 0.973 mmol, 86% yield). The product was used directly without further purification. Under N$_2$ atmosphere, to a stirred suspension of N-(5-(2,4-difluorophenyl)-6-methoxypyridin-3-yl)hydroxylamine (0.250 g, 0.99 mmol, 1.00 equiv) and NaHCO$_3$ (0.099 g, 6.46 mmol, 1.20 equiv) in THF (4.96 mL, 0.200 M) at 23° C. was slowly added a solution of methyl chloroformate (0.112 g, 1.19 mmol, 1.20 equiv) in THF (4.96 mL, 0.200 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with EtOAc:hexanes (1:2 to 1:1 (v/v)), to afford the title compound as a slightly yellow solid (0.163 g, 0.52 mmol, 52% yield). $R_f$=0.31 (EtOAc:hexanes 1:1 (v/v)). $^1$H NMR (700 MHz, (CD$_3$)$_2$SO, 25° C., δ): 10.54 (s, 1H), 8.32 (s, 1H), 7.77 (s, 1H), 7.49 (q, J=8.03 Hz, 1H), 7.35 (t, J=9.68 Hz, 1H), 7.18 (t, J=8.17 Hz, 1H), 3.85 (s, 3H), 3.73 (s, 3H). $^{13}$C NMR (175 MHz, (CD$_3$)$_2$SO, 25° C., δ): 162.2 (d, J=246.9 Hz), 159.5 (d, J=247.5 Hz), 157.7, 155.1, 139.9, 133.7, 133.4, 132.9 (m), 119.9 (d, J=15.2 Hz), 116.9, 111.7 (dd, J=22.8 Hz, J=5.3 Hz), 104.2 (t, J=26.3 Hz), 53.81, 53.1. $^{19}$F NMR (376 MHz, (CD$_3$)$_2$SO, 25° C., δ): −111.2 (m), −112.1 (m). Mass Spectrometry: HRMS (ESI-TOF) (m/z): calcd for C$_{14}$H$_{13}$F$_2$N$_2$O$_4$ ([M+H]$^+$), 311.0838, found, 311.0841.

Methyl (6-(4-(tert-butyl)phenoxy)pyridin-3-yl)(hydroxy)carbamate (8l)

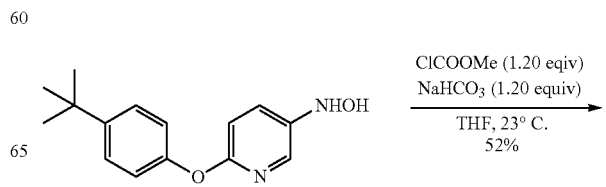

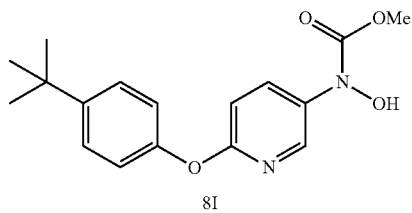

8I

Under N$_2$ atmosphere, to a suspension of 2-(4-(tert-butyl)phenoxy)-5-nitropyridine (0.600 g, 2.20 mmol, 1.00 equiv) and 5% Rh/C (12.7 mg, 0.30 mol % Rh) in THF (11.0 mL, 0.200 M) hydrazine monohydrate (0.160 g, 2.64 mmol, 1.20 equiv) was added dropwise. The reaction mixture was stirred at 23° C. for 1 h and then filtered through a short pad of celite. The celite was washed with EtOAc. The combined organic solution was concentrated in vacuo to afford the title compound as an off-white solid (0.495 g, 1.92 mmol, 86% yield). The product was used directly without further purification. Under N$_2$ atmosphere, to a stirred suspension of N-(6-(4-(tert-butyl)phenoxy)pyridin-3-yl)hydroxylamine (0.491 g, 0.990 mmol, 1.00 equiv) and NaHCO$_3$ (0.099 g, 1.19 mmol, 1.20 equiv) in THF (4.96 mL, 0.100 M) at 23° C. was slowly added a solution of methyl chloroformate (0.112 g, 1.19 mmol, 1.20 equiv) in THF (4.96 mL, 0.100 M) via a syringe pump (at a rate of 10.0 mL/h). After the addition was complete, the reaction mixture was filtered through a short pad of celite and the celite was washed with EtOAc. The organic layers were combined and concentrated in vacuo. The residue was purified by chromatography on silica gel, eluting with EtOAc:hexanes (1:2 to 1:1 (v/v)), to afford the title compound as a off-white solid (0.163 g, 0.52 mmol, 52% yield). R$_f$=0.48 (EtOAc:hexanes 1:1 (v/v)). $^1$H NMR (700 MHz, (CD$_3$)$_2$SO, 25° C., δ): 10.53 (s, 1H), 8.23 (d, J=2.58 Hz, 1H), 7.91 (dd, J=9.03, 2.58 Hz, 1H), 7.42 (d, J=8.60 Hz, 2H), 7.08-6.97 (m, 3H), 3.72 (s, 3H), 1.30 (s, 9H). $^{13}$C NMR (175 MHz, (CD$_3$)$_2$SO, 25° C., δ): 160.0, 155.0, 151.7, 146.8, 140.2, 134.8, 133.4, 126.4, 120.5, 111.0, 53.1, 34.2, 31.3. Mass Spectrometry: HRMS (ESI-TOF) (m/z): calcd for C$_{17}$H$_{21}$N$_2$O$_4$ ([M+H]$^+$), 317.1496, found, 317.1497.

Methyl (5-(5-formylfuran-2-yl)-6-methoxypyridin-3-yl)(hydroxy) carbamate (8m)

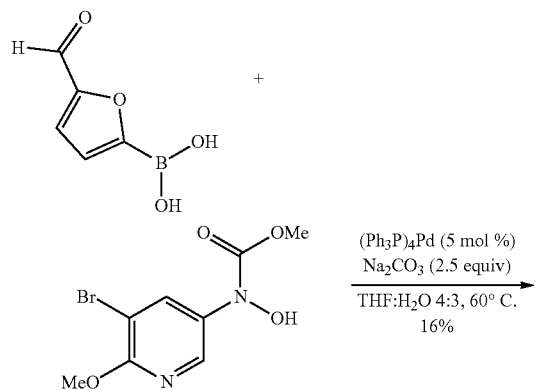

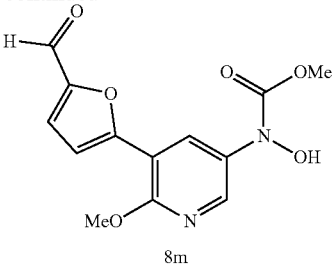

8m

Methyl (5-bromo-6-methoxypyridin-3-yl)(hydroxy)carbamate (0.400 g, 1.44 mmol, 1.00 equiv), (5-formylfuran-2-yl)boronic acid (0.283 g, 2.02 mmol, 1.40 equiv), Na$_2$CO$_3$ (0.383 g, 3.61 mmol, 2.5 equiv), THF:H$_2$O 4:3 (8.42 mL, 0.200 M), and palladium-tetrakis(triphenylphosphine) (0.0830 g, 0.0700 mmol, 0.05 equiv) were degassed via three freeze-pump-thaw cycles. The resulting mixture was heated at 60° C. overnight and then allowed to cool to room temperature after which water was added. The mixture was then extracted with dichloromethane and the organic extracts was dried with MgSO$_4$, filtered and concentrated in vacuo. The residue was purified by chromatography on silica gel, eluting with EtOAc:hexanes (3:8 to 1:1 (v/v)), to afford the pure cross-coupled product as a slightly light orange solid (0.070 g, 0.24 mmol, 16% yield). R$_f$=0.21 (EtOAc:hexanes 4:6 (v/v)). $^1$H NMR (700 MHz, (CD$_3$)$_2$SO, 25° C., δ): 10.65 (s, 1H), 9.65 (s, 1H), 8.38 (d, J=2.58 Hz, 1H), 8.32 (d, J=2.58 Hz, 1H), 7.68 (d, J=3.44 Hz, 1H), 7.28 (d, J=3.87 Hz, 1H), 4.05 (s, 3H), 3.76 (s, 3H). $^{13}$C NMR (175 MHz, (CD$_3$)$_2$SO, 25° C., δ): 178.2, 156.4, 155.0, 152.4, 151.6, 139.9, 133.8, 127.7, 125.2, 113.6, 111.4, 54.2, 53.2. Mass Spectrometry: HRMS (ESI-TOF) (m/z): calcd for C$_{13}$H$_{13}$N$_2$O$_6$ ([M+H]$^+$), 294.0799, found, 294.0801.

N-(6-(1H-Pyrazol-1-yl)pyridin-3-yl)-N-hydroxyacetamide (8n)

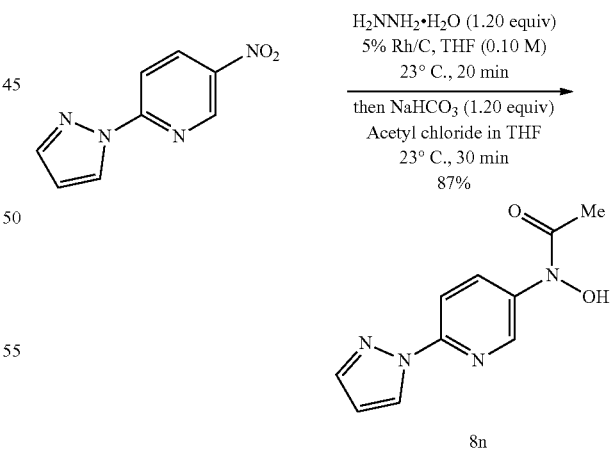

8n

Under N$_2$ atmosphere, a solution of 2-fluoro-5-nitropyridine (0.71 g, 5.00 mmol, 1.00 equiv) was added to a mixture of 1H-pyrazole (0.51 g, 7.50 mmol, 1.50 equiv) and Cs$_2$CO$_3$ (2.44 g, 7.50 mmol, 1.50 equiv) in DMF (25.0 mL, 0.300 M) and the reaction mixture was stirred at 23° C. for 20 h. The reaction mixture was poured to LiCl solution (100 mL), extracted with EtOAc. The combined organic layers was dried (MgSO$_4$), filtered and concentrated in vacuo. The residue was recrystalized from hexanes/EtOAc, to afford the title compound as a yellow solid (0.910 g, 4.78 mmol, 96% yield). R$_f$=0.77 (hexanes:EtOAc 5:1 (v/v)). $^1$H NMR (700 MHz, (CD$_3$)$_2$SO, 25° C., δ): 9.29 (br. s., 1H), 8.75 (d, J=8.17 Hz, 1H), 8.73-8.71 (m, 1H), 8.12 (d, J=9.04 Hz, 1H), 7.99-7.98 (m, 1H), 6.72-6.70 (m, 1H). $^{13}$C NMR (175 MHz, (CD$_3$)$_2$SO, 25° C., δ): 153.7, 145.0, 144.4, 142.3, 135.3, 128.5, 112.2, 110.0. Under N$_2$ atmosphere, a suspension of 5-nitro-2-(1H-pyrazol-1-yl)pyridine 200 mg, 1.05 mmol, 1.00 equiv) and 5% Rh/C (12.6 mg, 0.60 mol % Rh) in THF (10.5 mL, 0.100 M) was stirred at 23° C. Hydrazine monohydrate (63.1 mg, 1.26 mmol, 1.20 equiv) was added dropwise. The reaction mixture was stirred at 23° C. for 20 min. NaHCO$_3$ (106 mg, 1.26 mmol, 1.20 equiv) was added, followed by dropwise addition of acetyl chloride (98.9 mg, 1.26 mmol, 1.20 equiv) in THF (10.5 mL, 0.120 M) at 23° C. The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a yellow solid (200 mg, 0.917 mmol, 87% yield). R$_f$=0.26 (hexanes:EtOAc 1:1 (v/v)). $^1$H NMR (700 MHz, (CD$_3$)$_2$SO, 25° C., δ): 10.95 (br. s., 1H), 8.77 (br. s., 1H), 8.59 (d, J=2.15 Hz, 1H), 8.22 (dd, J=9.03, 2.58 Hz, 1H), 7.95 (d, J=9.03 Hz, 1H), 7.82 (s, 1H), 6.60-6.56 (m, 1H), 2.27 (s, 3H). $^{13}$C NMR (175 MHz, (CD$_3$)$_2$SO, 25° C., δ): 170.6, 146.9, 142.1, 139.1, 136.7, 130.1, 126.9, 111.7, 108.2, 22.2. Mass Spectrometry: HRMS (ESI-TOF) (m/z): calcd for C$_{10}$H$_{11}$N$_4$O$_2$ ([M+H]$^+$), 219.0877, found, 219.0877.

Methyl (6-(1H-1,2,4-triazol-1-yl)pyridin-3-yl)(hydroxy)carbamate (8o)

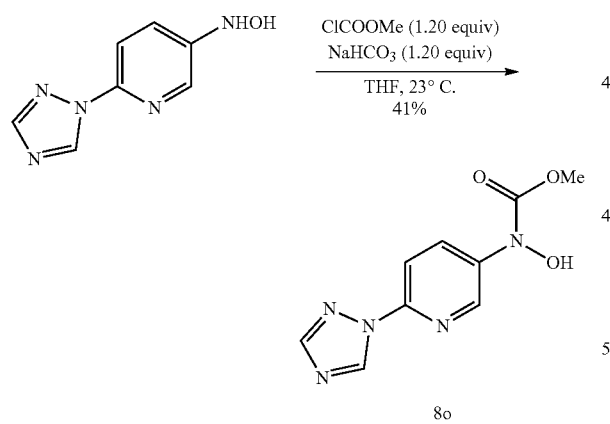

Under N$_2$ atmosphere, to a suspension of 5-nitro-2-(1H-1,2,4-triazol-1-yl)pyridine (0.500 g, 2.26 mmol, 1.00 equiv) and 5% Rh/C (15.0 mg, 0.30 mol % Rh) in THF (13.0 mL, 0.200 M) hydrazine monohydrate (0.190 g, 3.14 mmol, 1.20 equiv) was added dropwise. The reaction mixture was stirred at 23° C. for 1 h. The reaction mixture was filtered through a short pad of celite, washed with EtOAc, and concentrated in vacuo to afford the title compound as a slightly light yellow (0.691 g, 2.38 mmol, 91% yield). The product was used directly without further purification. R$_f$=0.36 (EtOAc:hexanes 1:0 (v/v)). NMR Spectroscopy: $^1$H NMR (700 MHz, (CD$_3$)$_2$SO, 25° C., δ): 9.20 (s, 1H), 8.80 (s, 1H), 8.73 (d, J=2.15 Hz, 1H), 8.22 (s, 1H), 8.05 (d, J=2.58 Hz, 1H), 7.71 (d, J=9.03 Hz, 1H), 7.45 (dd, J=8.82, 2.80 Hz, 1H). $^{13}$C NMR (175 MHz, (CD$_3$)$_2$SO, 25° C., δ): 152.3, 147.9, 141.7, 141.0, 132.8, 123.0, 113.3. Mass Spectrometry: HRMS (ESI-TOF) (m/z): calcd for C$_7$H$_8$N$_5$O ([M+H]$^+$), 178.0723, found, 178.0723. Under N$_2$ atmosphere, to a stirred suspension of N-(6-(1H-1,2,4-triazol-1-yl)pyridin-3-yl)hydroxylamine (0.150 g, 0.85 mmol, 1.00 equiv) and NaHCO$_3$ (0.084 g, 1.02 mmol, 1.20 equiv) in THF (4.23 mL, 0.100 M) at 23° C. was slowly added a solution of methyl chloroformate (0.095 g, 1.02 mmol, 1.20 equiv) in THF (4.23 mL, 0.100 M) via a syringe pump (at a rate of 10.0 mL/h). After the addition was complete, a white solid precipitated from the reaction mixture. The reaction mixture was then filtered through and the solid was washed with water to afford the title compound as a white solid (0.081 g, 0.34 mmol, 41% yield). R$_f$=0.08 (MeOH:EtOAc 1:9 (v/v)). NMR Spectroscopy: $^1$H NMR (700 MHz, (CD$_3$)$_2$SO, 25° C., δ): 10.80 (s, 1H), 9.33 (s, 1H), 8.72 (d, J=2.58 Hz, 1H), 8.29 (s, 1H), 8.19-8.17 (m, 1H), 7.89 (d, J=9.03 Hz, 1H), 3.80 (s, 3H). $^{13}$C NMR (175 MHz, (CD$_3$)$_2$SO, 25° C., δ): 154.6, 152.9, 144.6, 141.8, 139.2, 138.5, 130.2, 112.9, 53.4. Mass Spectrometry: HRMS (ESI-TOF) (m/z): calcd for C$_9$H$_9$N$_5$O$_3$Na ([M+Na]$^+$), 258.0598, found, 258.0598.

N-(6-(1H-Benzo[d]imidazol-1-yl)pyridin-3-yl)-N-hydroxyacetamide (8p)

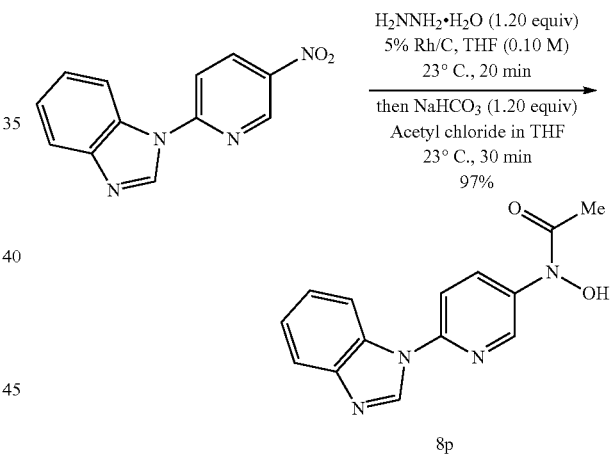

Under N$_2$ atmosphere, a solution of 2-fluoro-5-nitropyridine (1.32 g, 9.31 mmol, 1.10 equiv) in DMF (20.0 mL, 0.466 M) was added to a mixture of 1H-benzo[d]imidazole (1.00 g, 8.46 mmol, 1.00 equiv) and Cs$_2$CO$_3$ (2.76 g, 8.46 mmol, 1.50 equiv) in DMF (22.3 mL, 0.379 M) at 23° C. The resulting mixture was stirred at 23° C. for 7 h. The reaction mixture was poured to LiCl solution (100 mL), extracted with EtOAc. The combined organic layers was dried (MgSO$_4$), filtered and concentrated in vacuo. The residue was recrystalized from hexanes/EtOAc, to afford the title compound as a yellow solid (1.38 g, 5.75 mmol, 68% yield). R$_f$=0.29 (hexanes:EtOAc 1:1 (v/v)). NMR Spectroscopy: $^1$H NMR (700 MHz, CDCl$_3$, 25° C., δ): 9.46 (d, J=2.58 Hz, 1H), 8.75-8.72 (m, 1H), 8.72-8.68 (m, 1H), 8.22 (d, J=8.17 Hz, 1H), 7.90 (d, J=7.74 Hz, 1H), 7.79 (dd, J=8.82, 1.94 Hz, 1H), 7.49-7.46 (m, 1H), 7.45-7.42 (m, 1H). $^{13}$C NMR (175 MHz, CDCl$_3$, 25° C., δ): 153.6, 145.9, 144.9, 141.9, 141.1, 134.7, 131.8, 125.5, 124.7, 121.3, 113.7, 112.8. Mass Spectrometry: HRMS (ESI-TOF) (m/z): calcd for $C_{12}H_9N_4O_2$ ([M+H]$^+$), 241.0720, found, 241.0724.

Under $N_2$ atmosphere, a suspension of 1-(5-nitropyridin-2-yl)-1H-benzo[d]imidazole (600 mg, 2.50 mmol, 1.00 equiv) and 5% Rh/C (28.7 mg, 0.60 mol % Rh) in THF (25.0 mL, 0.100 M) was stirred at 23° C. Hydrazine monohydrate (150 mg, 3.00 mmol, 1.20 equiv) was added dropwise. The reaction mixture was stirred at 23° C. for 20 min. NaHCO$_3$ (252 mg, 3.00 mmol, 1.20 equiv) was added, followed by dropwise addition of a solution of acetyl chloride (236 mg, 3.00 mmol, 1.20 equiv) in THF (25.0 mL, 0.120 M). The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a yellow solid (650 mg, 2.42 mmol, 97% yield). $R_f$=0.15 (EtOAc). NMR Spectroscopy: $^1$H NMR (700 MHz, (CD$_3$)$_2$SO, 25° C., δ): 11.01 (br. s., 1H), 8.92 (s, 2H), 8.28 (dd, J=9.03, 2.58 Hz, 1H), 8.25 (d, J=7.74 Hz, 1H), 7.97 (d, J=9.03 Hz, 1H), 7.77 (d, J=7.74 Hz, 1H), 7.40-7.36 (m, 1H), 7.35-7.32 (m, 1H), 2.29 (s, 3H). $^{13}$C NMR (175 MHz, (CD$_3$)$_2$SO, 25° C., δ): 170.8, 145.5, 144.1, 142.2, 139.7, 136.6, 131.9, 130.0, 123.9, 123.0, 119.9, 114.4, 113.7, 22.2. Mass Spectrometry: HRMS (ESI-TOF) (m/z): calcd for $C_{14}H_{13}N_4O_2$ ([M+H]$^+$), 269.1033, found, 269.1037.

120.1, 114.7, 114.3. Under $N_2$ atmosphere, a suspension of 1-(5-nitropyridin-2-yl)-1H-benzo[d] [1,2,3]triazole (S15) (253 mg, 1.05 mmol, 1.00 equiv) and 5% Rh/C (12.6 mg, 0.60 mol % Rh) in THF (21.0 mL, 0.0500 M) was stirred at 23° C. Hydrazine monohydrate (63.1 mg, 1.26 mmol, 1.20 equiv) was added dropwise. The reaction mixture was stirred at 23° C. for 20 min. NaHCO$_3$ (106 mg, 1.26 mmol, 1.20 equiv) was added, followed by dropwise addition of a solution of acetyl chloride (98.9 mg, 1.26 mmol, 1.20 equiv) in THF (10.5 mL, 0.120 M). The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a yellow solid (281 mg, 1.04 mmol, 99% yield). $R_f$=0.34 (hexanes:EtOAc 1:1 (v/v)). NMR Spectroscopy: $^1$H NMR (700 MHz, (CD$_3$)$_2$SO, 25° C., δ): 11.07 (s, 1H), 9.02 (d, J=2.58 Hz, 1H), 8.56 (d, J=8.17 Hz, 1H), 8.39 (dd, J=9.03, 2.58 Hz, 1H), 8.28 (d, J=9.03 Hz, 1H), 8.22-8.19 (m, 1H), 7.72 (td, J=7.64, 1.08 Hz, 1H), 7.55 (ddd, J=8.07, 6.99, 0.86 Hz, 1H), 2.31 (s, 3H). $^{13}$C NMR (175 MHz, (CD$_3$)$_2$SO, 25° C., δ): 171.2, 146.4, 146.0, 139.0, 137.5, 130.8, 130.0, 129.2, 125.3, 119.6, 114.3, 114.2, 22.3. Mass Spectrometry: HRMS (ESI-TOF) (m/z): calcd for $C_{13}H_{12}N_5O_2$ ([M+H]$^+$), 270.0986, found, 270.0986.

N-(6-(5-Fluoro-1H-indol-1-yl)pyridin-3-yl)-N-hydroxyacetamide (8r)

N-(6-(1H-Benzo[d] [1,2,3]triazol-1-yl)pyridin-3-yl)-N-hydroxyacetamide (8q)

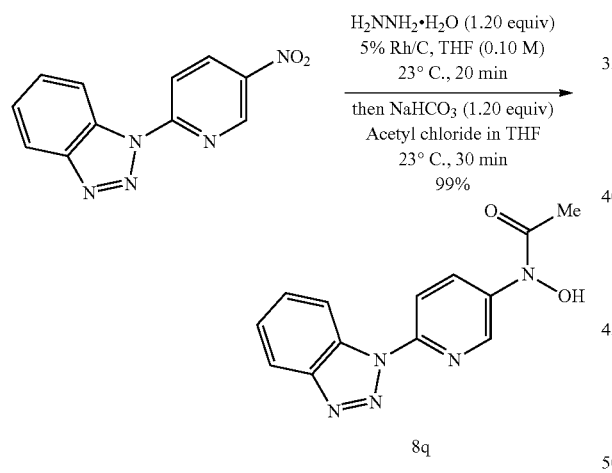

8q

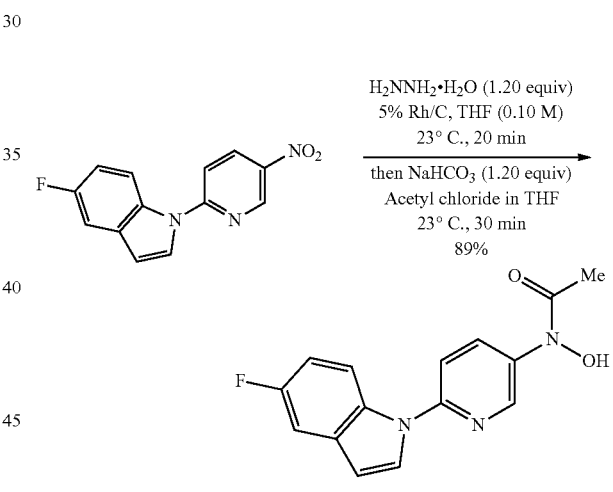

8r

Under $N_2$ atmosphere, to a mixture of 1H-benzo[d] [1,2,3]triazole (0.890 g, 7.50 mmol, 1.50 equiv) and Cs$_2$CO$_3$ (2.44 g, 7.50 mmol, 1.50 equiv) in DMF (25.0 mL, 0.300 M) was added 2-fluoro-5-nitropyridine (0.71 g, 5.00 mmol, 1.00 equiv) and the reaction mixture was stirred at 23° C. for 20 h. The reaction mixture was poured to LiCl solution (100 mL), extracted with EtOAc. The combined organic layers was dried (MgSO$_4$), filtered and concentrated in vacuo. The residue was recrystalized from hexanes/EtOAc, to afford the title compound as a yellow solid (0.870 g, 3.61 mmol, 72% yield). $R_f$=0.54 (hexanes:EtOAc 5:1 (v/v)). $^1$H NMR (700 MHz, (CD$_3$)$_2$SO, 25° C., δ): 9.52 (br. s., 1H), 8.90 (d, J=9.03 Hz, 1H), 8.65 (d, J=8.17 Hz, 1H), 8.51 (d, J=9.04 Hz, 1H), 8.28 (d, J=8.17 Hz, 1H), 7.82 (t, J=7.53 Hz, 1H), 7.63 (t, J=7.53 Hz, 1H). $^{13}$C NMR (175 MHz, (CD$_3$)$_2$SO, 25° C., δ): 153.8, 146.3, 145.1, 142.7, 135.4, 130.9, 130.2, 126.1, Under $N_2$ atmosphere, 5-fluoro-1H-indole (1.14 g, 8.45 mmol, 1.20 equiv) was dissolved in DMF (35.2 mL, 0.240 M) and stirred at 0° C. NaH (0.338 g, 8.45 mmol, 1.20 equiv, 60% dispersion in mineral oil) was added in portionwise. After 30 min, 2-fluoro-5-nitropyridine (1.00 g, 7.04 mmol. 1.00 equiv) was added and then the reaction mixture was slowly warmed up to 60° C. and stirred at 60° C. for 16 h. The reaction mixture was poured to a solution of LiCl (100 mL), extracted with EtOAc, and washed with brine. The combined organic layers was dried (MgSO$_4$), filtered and concentrated in vacuo. The residue was purified by chromatography on silica gel, eluting with hexanes:EtOAc (10:1 to 5:1 (v/v)), to afford the title compound as a yellow solid (1.63 g, 6.34 mmol, 90% yield). $R_f$=0.20 (hexanes:EtOAc 5:1 (v/v)). $^1$H NMR (700 MHz, CDCl$_3$, 25° C., δ): 9.39 (d, J=2.15 Hz, 1H), 8.58 (dd, J=9.03, 2.58 Hz, 1H), 8.51 (dd, J=9.25, 4.52 Hz, 1H), 7.76 (d, J=3.87 Hz, 1H), 7.54 (d, J=9.04 Hz, 1H), 7.30 (dd, J=9.03, 2.58 Hz, 1H), 7.11 (td, J=9.03, 2.58 Hz, 1H), 6.78 (d, J=3.01 Hz, 1H). $^{13}$C NMR (175 MHz, CDCl$_3$, 25° C., δ): 159.5 (d, J=238.8 Hz), 155.8, 145.6 (d, J=3.50 Hz), 140.4, 134.0, 132.1 (J=9.94 Hz), 126.5, 116.4 (d, J=9.00 Hz), 112.5 (d, J=24.7 Hz), 112.0, 108.9 (d, J=3.76 Hz), 106.8 (d, J=23.6 Hz). $^{19}$F NMR (376 MHz, CDCl$_3$, 25° C., δ): −121.5.0 (m). Mass Spectrometry: HRMS (ESI-TOF) (m/z): calcd for C$_{13}$H$_9$FN$_3$O$_2$ ([M+H]$^+$), 258.0673, found, 258.0675.

Under N$_2$ atmosphere, a suspension of 5-fluoro-1-(5-nitropyridin-2-yl)-1H-indole (0.500 g, 1.94 mmol, 1.00 equiv) and 5% Rh/C (21.8 mg, 0.60 mol % Rh) in THF (20.0 mL, 0.100 M) was stirred at 23° C. Hydrazine monohydrate (117 mg, 2.33 mmol, 1.20 equiv) was added dropwise. The reaction mixture was stirred at 23° C. for 20 min. NaHCO$_3$ (196 mg, 2.33 mmol, 1.20 equiv) was added, followed by dropwise addition of a solution of acetyl chloride (183 mg, 2.33 mmol, 1.20 equiv) in THF (20 mL, 0.120 M). The reaction mixture was stirred at 23° C. for 30 min and then filtered through a short pad of celite. The celite was washed with EtOAc. The combined organic solution was concentrated in vacuo. The residue was purified by chromatography on silica gel, eluting with hexanes:EtOAc (2:1 to 1:1 (v/v)), to afford the title compound as a yellow solid (0.490 g, 1.72 mmol, 89% yield). R$_f$=0.14 (hexanes:EtOAc 1:1 (v/v)). NMR Spectroscopy: $^1$H NMR (700 MHz, (CD$_3$)$_2$SO, ° C., δ): 10.95 (br. s., 1H), 8.84 (br. s., 1H), 8.39 (dd, J=8.82, 4.52 Hz, 1H), 8.23-8.17 (m, 1H), 8.09 (d, J=3.44 Hz, 1H), 7.79 (d, J=8.60 Hz, 1H), 7.43 (dd, J=9.25, 2.37 Hz, 1H), 7.10 (td, J=9.14, 2.37 Hz, 1H), 6.75 (d, J=3.01 Hz, 1H), 2.27 (br. s., 3H). $^{13}$C NMR (175 MHz, (CD$_3$)$_2$SO, 25° C., δ): 170.6, 157.8 (d, J=233.2 Hz), 148.0, 139.4, 135.4, 131.3, 130.6 (d, J=10.1 Hz), 130.2, 128.2, 115.2 (d, J=9.14 Hz), 113.6, 110.8 (d, J=25.2 Hz), 105.6 (d, J=23.3 Hz), 105.2 (d, J=3.38 Hz), 22.1. $^{19}$F NMR (376 MHz, CDCl$_3$, 25° C., δ): −123.6 (m). Mass Spectrometry: HRMS (ESI-TOF) (m/z): calcd for C$_{15}$H$_{13}$FN$_3$O$_2$ ([M+H]$^+$), 286.0986, found, 286.0989.

N-(6-(5-Bromo-1H-pyrrolo[2,3-b] pyridin-1-yl)pyridin-3-yl)-N-hydroxyacetamide (8s)

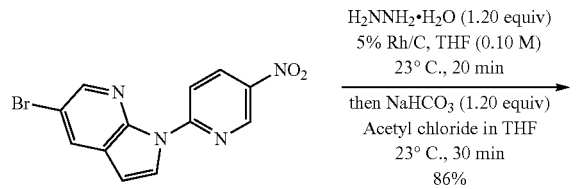

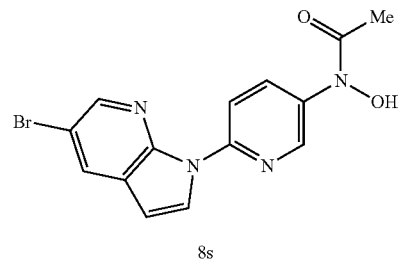

Under N$_2$ atmosphere, 5-bromo-1H-pyrrolo[2,3-b]pyridine (1.66 g, 8.45 mmol, 1.20 equiv) was dissolved in DMF (35.2 mL, 0.240 M) and stirred at 0° C. NaH (0.338 g, 8.45 mmol, 1.20 equiv, 60% dispersion in mineral oil) was added in portionwise. After 30 min, 2-fluoro-5-nitropyridine (1.00 g, 7.04 mmol. 1.00 equiv) was added and then the reaction mixture was slowly warmed up to 60° C. and stirred at 60° C. for 16 h. The reaction mixture was poured to a solution of LiCl (100 mL), extracted with EtOAc. The combined organic layers washed with brine, dried (MgSO$_4$), filtered and concentrated in vacuo. The residue was purified by chromatography on silica gel, eluting with hexanes:EtOAc (20:1 to 10:1 (v/v)), to afford the title compound as a yellow solid (1.26 g, 3.94 mmol, 56% yield). R$_f$=0.69 (hexanes:EtOAc 5:1 (v/v)). NMR Spectroscopy: $^1$H NMR (500 MHz, CDCl$_3$, 25° C., δ): 9.31 (d, J=2.58 Hz, 1H), 9.30 (d, J=9.04 Hz, 1H), 8.64 (d, J=2.58 Hz, 1H), 8.62 (d, J=2.58 Hz, 1H), 8.49 (d, J=4.30 Hz, 1H), 8.46 (d, J=2.15 Hz, 1H), 8.10 (d, J=2.15 Hz, 1H). $^{13}$C NMR (175 MHz, CDCl$_3$, 25° C., δ): 153.8, 146.4, 144.9, 144.3, 141.1, 134.0, 131.9, 127.8, 125.8, 114.6, 114.4, 104.5. Mass Spectrometry: HRMS (ESI-TOF) (m/z): calcd for C$_{12}$H$_8$BrN$_4$O$_2$ ([M+H]$^+$), 318.9825, found, 318.9826. Under N$_2$ atmosphere, a suspension of 5-bromo-1-(5-nitropyridin-2-yl)-1H-pyrrolo[2,3-b]pyridine (350 mg, 1.10 mmol, 1.00 equiv) and 5% Rh/C (12.6 mg, 0.60 mol % Rh) in THF (11.0 mL, 0.100 M) was stirred at 23° C. Hydrazine monohydrate (65.9 mg, 1.32 mmol, 1.20 equiv) was added dropwise. The reaction mixture was stirred at 23° C. for 20 min. NaHCO$_3$ (111 mg, 1.32 mmol, 1.2 equiv) was added, followed by dropwise addition of a solution of acetyl chloride (104 mg, 1.32 mmol, 1.20 equiv) in THF (11.0 mL, 0.120 M). The reaction mixture was stirred at 23° C. for 30 min and then filtered through a short pad of celite. The celite was washed with EtOAc. The combined organic solution was concentrated in vacuo. The residue was purified by chromatography on silica gel, eluting with hexanes:EtOAc (5:1 to 1:1 (v/v)), to afford the title compound as a yellow solid (330 mg, 0.950 mmol, 86% yield). R$_f$=0.17 (hexanes:EtOAc 1:1 (v/v)). $^1$H NMR (700 MHz, (CD$_3$)$_2$SO, 25° C., δ): 10.94 (br. s., 1H), 8.83 (br. s., 1H), 8.71 (d, J=8.60 Hz, 1H), 8.46 (br. s., 1H), 8.39 (d, J=3.44 Hz, 1H), 8.36 (br. s., 1H), 8.24 (d, J=9.03 Hz, 1H), 6.74 (d, J=3.44 Hz, 1H), 2.27 (br. s., 3H). $^{13}$C NMR (175 MHz, (CD$_3$)$_2$SO, 25° C., δ): 170.6, 145.5, 145.0, 143.3, 139.6, 136.0, 131.6, 129.6, 128.1, 124.4, 114.7, 112.7, 102.4, 22.2. Mass Spectrometry: HRMS (ESI-TOF) (m/z): calcd for C$_{14}$H$_{12}$BrN$_4$O$_2$ ([M+H]$^+$), 347.0138, found, 347.0142.

N-Hydroxy-N-(6-(2-(thiazol-4-yl)-1H-benzo[d] imidazol-1-yl)pyridin-3-yl)acetamide (8t)

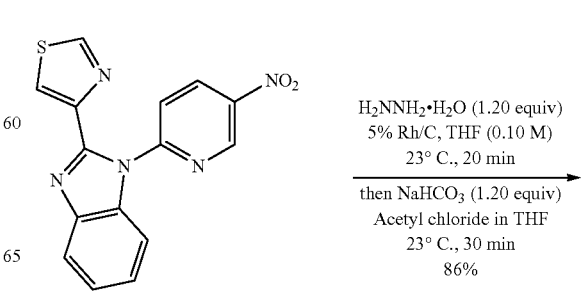

128

N-(6-(2,6-Dichloro-9H-purin-9-yl)pyridin-3-yl)-N-hydroxyacetamide (8u)

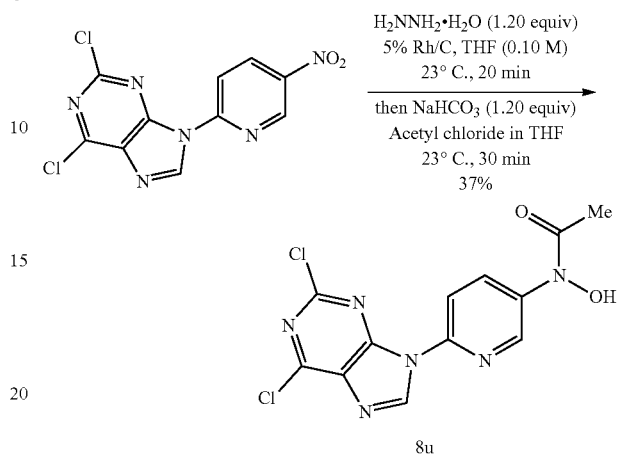

Under N₂ atmosphere, a solution of 2-fluoro-5-nitropyridine (0.78 g, 5.50 mmol, 1.10 equiv) in DMF (5 mL, 1.1 M) was added to a mixture of 2,6-dichloro-9H-purine (0.950 g, 5.00 mmol, 1.00 equiv) and Cs₂CO₃ (1.63 g, 5.00 mmol, 1.00 equiv) in DMF (20 mL, 0.25 M) at 23° C. The reaction mixture was stirred at 23° C. for 12 h, poured to LiCl solution (100 mL), extracted with EtOAc. The combined organic layers was dried (MgSO₄), filtered and concentrated in vacuo. The residue was purified by chromatography on silica gel, eluting with hexanes:EtOAc (10:1 to 4:1 (v/v)), to afford the title compound as a yellow solid (0.500 g, 1.61 mmol, 32% yield). $R_f$=0.50 (hexanes:EtOAc 4:1 (v/v)). NMR Spectroscopy: $^1$H NMR (500 MHz, CDCl₃, 25° C., δ): 9.40 (d, J=2.44 Hz, 1H), 9.30 (s, 1H), 8.95 (d, J=8.85 Hz, 1H), 8.81 (dd, J=9.00, 2.59 Hz, 1H). $^{13}$C NMR (125 MHz, CDCl₃, 25° C., δ): 154.4, 153.3, 152.0, 150.7, 145.2, 143.8, 143.3, 135.4, 132.8, 115.0. Mass Spectrometry: HRMS (ESI-TOF) (m/z): calcd for C₁₀H₅Cl₂N₆O₂ ([M+H]⁺), 310.9846, found, 310.9848. Under N₂ atmosphere, a suspension of 2,6-dichloro-9-(5-nitropyridin-2-yl)-9H-purine (270 mg, 0.870 mmol, 1.00 equiv) and 5% Rh/C (10.0 mg, 0.60 mol % Rh) in THF (8.7 mL, 0.100 M) was stirred at 23° C. Hydrazine monohydrate (52.0 mg, 1.04 mmol, 1.20 equiv) was added dropwise. The reaction mixture was stirred at 23° C. for 20 min. NaHCO₃ (87.4 g, 1.04 mmol, 1.2 equiv) was added, followed by dropwise addition of a solution of acetyl chloride (81.6 mg, 1.04 mmol, 1.20 equiv) in THF (8.7 mL, 0.120 M). The reaction mixture was stirred at 23° C. for 30 min and then filtered through a short pad of celite. The celite was washed with EtOAc. The combined organic solution was concentrated in vacuo. The residue was purified by chromatography on silica gel, eluting with hexanes:EtOAc (1:1 to EtOAc (v/v)), to afford the title compound as a yellow solid (110 mg, 0.324 mmol, 37% yield). $R_f$=0.13 (EtOAc). NMR Spectroscopy: $^1$H NMR (500 MHz, (CD₃)₂SO, 25° C., δ): 11.07 (br. s., 1H), 9.34 (s, 1H), 8.95 (d, J=2.44 Hz, 1H), 8.39 (dd, J=9.00, 2.59 Hz, 1H), 8.28 (d, J=8.85 Hz, 1H), 2.29 (s, 3H). $^{13}$C NMR (125 MHz, (CD₃)₂SO, 25° C., δ): 171.0, 152.1, 151.7, 150.3, 145.7, 142.2, 139.5, 138.1, 131.8, 129.7, 115.7, 22.3. Mass Spectrometry: HRMS (ESI-TOF) (m/z): calcd for C₁₂H₈C₁₃N₆O₂ ([M+H]⁺), 339.0159, found, 339.0172.

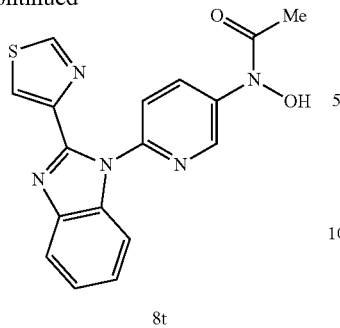

8t

Under N₂ atmosphere, a solution of 2-fluoro-5-nitropyridine (0.710 g, 5.00 mmol, 1.00 equiv) in DMF (5 mL, 1.00 M) was added to a mixture of 4-(1H-benzo[d]imidazol-2-yl)thiazole (1.51 g, 7.50 mmol, 1.50 equiv) and Cs₂CO₃ (2.44 g, 7.50 mmol, 1.50 equiv) in DMF (20.0 mL, 0.372 M) at 23° C. The resulting mixture was stirred at 23° C. for 12 h. The reaction mixture was poured to LiCl solution (100 mL), extracted with EtOAc. The combined organic layers was dried (MgSO₄), filtered and concentrated in vacuo. The residue was purified by chromatography on silica gel, eluting with hexanes:EtOAc (2:1 to 1:1 (v/v)), to afford the title compound as a yellow solid (2.30 g, 7.11 mmol, 95% yield). $R_f$=0.34 (hexanes:EtOAc 1:1 (v/v)). NMR Spectroscopy: $^1$H NMR (700 MHz, CDCl₃, 25° C., δ): 9.41 (d, J=2.15 Hz, 1H), 8.63 (d, J=2.15 Hz, 1H), 8.60-8.56 (m, 1H), 8.28 (d, J=2.15 Hz, 1H), 7.87 (d, J=7.74 Hz, 1H), 7.55 (d, J=7.74 Hz, 1H), 7.44-7.38 (m, 2H), 7.38-7.34 (m, 1H). $^{13}$C NMR (175 MHz, CDCl₃, 25° C., δ): 154.8, 153.1, 146.6, 146.4, 145.2, 143.1, 143.0, 135.3, 133.4, 125.0, 124.4, 121.9, 121.5, 120.4, 111.3. Mass Spectrometry: HRMS (ESI-TOF) (m/z): calcd for C₁₅H₁₀N₅O₂S ([M+H]⁺), 324.0550, found, 324.0555. Under N₂ atmosphere, a suspension of 4-(1-(5-nitropyridin-2-yl)-1H-benzo[d]imidazol-2-yl)thiazole (323 mg, 1.00 mmol, 1.00 equiv) and 5% Rh/C (11.5 mg, 0.60 mol % Rh) in THF (10.0 mL, 0.100 M) was stirred at 23° C. Hydrazine monohydrate (60.1 mg, 1.20 mmol, 1.20 equiv) was added dropwise. The reaction mixture was stirred at 23° C. for 20 min. NaHCO₃ (101 mg, 1.20 mmol, 1.20 equiv) was added, followed by dropwise addition of acetyl chloride (94.2 mg, 1.20 mmol, 1.20 equiv) in THF (10 mL, 0.120 M). The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a yellow solid (303 mg, 0.862 mmol, 86% yield). $R_f$=0.14 (hexanes:EtOAc 1:1 (v/v)). NMR Spectroscopy: $^1$H NMR (700 MHz, (CD₃)₂SO, 25° C., δ): 11.04 (s, 1H), 9.01 (d, J=1.72 Hz, 1H), 8.91 (br. s., 1H), 8.44 (d, J=1.72 Hz, 1H), 8.26 (dd, J=8.60, 2.58 Hz, 1H), 7.80 (d, J=8.17 Hz, 1H), 7.51 (d, J=8.60 Hz, 1H), 7.38-7.33 (m, 2H), 7.32-7.29 (m, 1H), 2.31 (s, 3H). $^{13}$C NMR (175 MHz, (CD₃)₂SO, 25° C., δ): 171.0, 154.7, 146.6, 146.1, 145.1, 142.3, 139.4, 138.0, 135.8, 128.6, 123.8, 123.2, 122.6, 121.5, 119.4, 111.1, 22.4. Mass Spectrometry: HRMS (ESI-TOF) (m/z): calcd for C₁₇H₁₄N₅O₂S ([M+H]⁺), 352.0863, found, 352.0869.

129

Ethyl (E)-3-(4-fluoro-3-(5-(hydroxy(methoxycarbonyl)amino)-2-methoxypyridin-3-yl)phenyl)acrylate (8v)

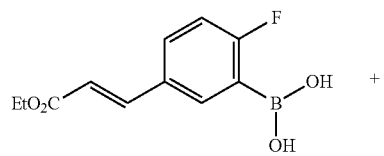
+
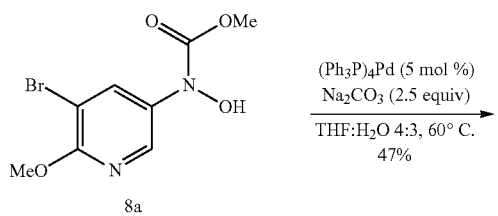
→
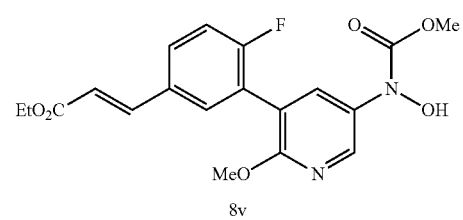

Methyl (5-bromo-6-methoxypyridin-3-yl)(hydroxy)carbamate (1a) (0.300 g, 1.08 mmol, 1.00 equiv), (E)-(5-(3-ethoxy-3-oxoprop-1-en-1-yl)-2-fluorophenyl)boronic acid (0.361 g, 1.52 mmol, 1.40 equiv), $Na_2CO_3$ (0.287 g, 2.71 mmol, 2.5 equiv), and palladium-tetrakis(triphenylphosphine) (0.062 g, 0.05 mmol, 0.05 equiv) in THF:$H_2O$ 4:3 (6.32 mL, 0.200 M), were degassed via three freeze-pump-thaw cycles. The resulting mixture was heated at 60° C. overnight and then allowed to cool to room temperature after which water was added (twice the volume of THF:$H_2O$ 4:3 used). The mixture was then extracted with dichloromethane (twice the volume of THF:$H_2O$ 4:3 used) and the organic extracts was dried with $MgSO_4$, filtered and concentrated in vacuo. The residue was purified by chromatography on silica gel, eluting with EtOAc:hexanes (3:8 to 1:1 (v/v)), to afford the pure cross-coupled product as a yellow solid (0.198 g, 0.51 mmol, 47% yield). $R_f$=0.36 (EtOAc:hexanes 1:1 (v/v)). NMR Spectroscopy: $^1$H NMR (700 MHz, $(CD_3)_2SO$, 25° C., δ): 10.55 (s, 1H), 8.33 (d, J=2.58 Hz, 1H), 7.90-7.79 (m, 3H), 7.68 (d, J=15.92 Hz, 1H), 7.35 (t, J=9.03 Hz, 1H), 6.67 (d, J=16.35 Hz, 1H), 4.18 (q, J=7.17 Hz, 2H), 3.86 (s, 3H), 3.73 (s, 3H), 1.25 (t, J=7.10 Hz, 3H). $^{13}$C NMR (175 MHz, $(CD_3)_2SO$, 25° C., δ): 166.2, 160.4 (d, J=250.2 Hz), 157.7, 155.2, 143.0, 140.1, 133.9, 133.4, 131.9 (d, J=3.5 Hz), 130.8 (d, J=3.5 Hz), 130.3 (d, J=8.6 Hz), 124.1 (d, J=16.2 Hz), 118.6, 117.3, 116.3 (d, J=22.7 Hz), 60.1, 53.8, 53.1, 14.2. $^{19}$F NMR (376 MHz, $CDCl_3$, 25° C., δ): −111.3 (m).

130

Methyl 4-((4-(5-(hydroxy(methoxycarbonyl)amino)-2-methoxypyridin-3-yl)phenyl)ethynyl)benzoate (8w)

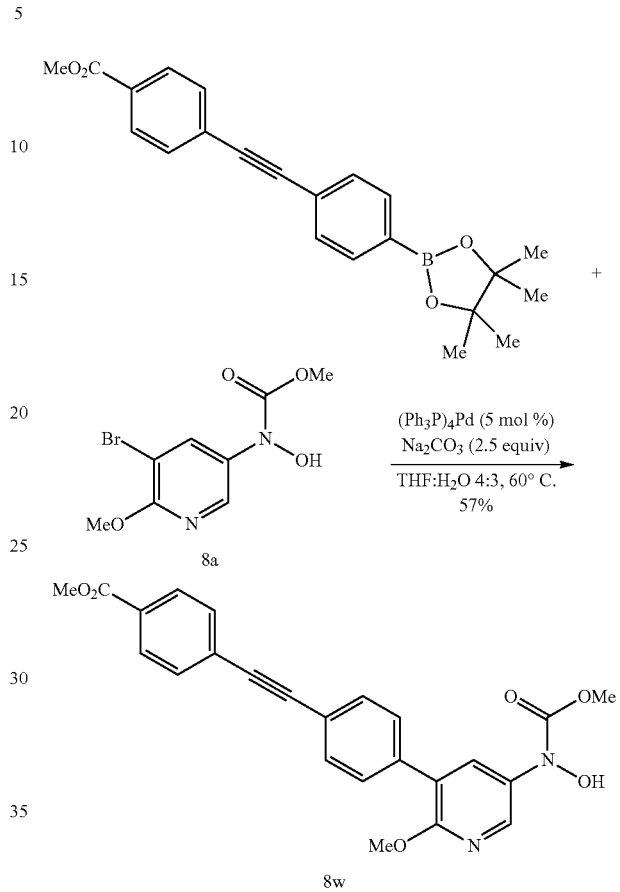

Methyl (5-bromo-6-methoxypyridin-3-yl)(hydroxy)carbamate (1a) (0.300 g, 1.08 mmol, 1.00 equiv), methyl 4-((4-(4,4,5,5-tetramethyl-1,3,2-dioxaborolan-2-yl)phenyl)ethynyl)benzoate (0.152 g, 1.52 mmol, 1.40 equiv), $Na_2CO_3$ (0.287 g, 2.71 mmol, 2.5 equiv), THF:$H_2O$ 4:3 (6.32 mL, 0.200 M), and palladium-tetrakis(triphenylphosphine) (0.062 g, 0.05 mmol, 0.05 equiv) were degassed via three freeze-pump-thaw cycles. The resulting mixture was heated at 60° C. overnight and then allowed to cool to room temperature after which water was added (twice the volume of THF:$H_2O$ 4:3 used). The mixture was then extracted with dichloromethane (twice the volume of THF:$H_2O$ 4:3 used) and the organic extracts was dried with $MgSO_4$, filtered and concentrated in vacuo. The residue was purified by chromatography on silica gel, eluting with EtOAc:hexanes (3:8 to 1:1 (v/v)), to afford the pure cross-coupled product as a white solid (0.199 g, 0.63 mmol, 57% yield). $R_f$=0.38 (EtOAc:hexanes 1:1 (v/v)). $^1$H NMR (700 MHz, $(CD_3)_2SO$, 25° C., δ): 10.40 (s, 1H), 8.29 (d, J=2.58 Hz, 1H), 8.03-7.99 (m, 2H), 7.89 (d, J=3.01 Hz, 1H), 7.73-7.70 (m, 2H), 7.68-7.63 (m, 4H), 3.93 (s, 3H), 3.89 (s, 3H), 3.75 (s, 3H). $^{13}$C NMR (175 MHz, $(CD_3)_2SO$, ° C., δ): 165.6, 157.3, 155.2, 139.3, 136.4, 133.9, 132.5, 131.7, 131.6, 129.5, 129.4, 127.0, 122.2, 121.1, 92.1, 89.2, 53.8, 53.1, 52.4.

N-Hydroxy-N-(6-(((8R,9S,13S,14S)-13-methyl-17-oxo-7,8,9,11,12,13,14,15,16,17-decahydro-6H-cyclopenta[a]phenanthren-3-yl)oxy)pyridin-3-yl)acetamide (8x)

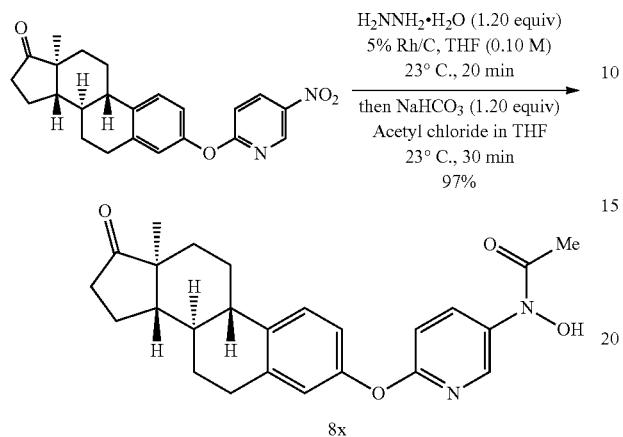

Under N₂ atmosphere, a solution of 2-fluoro-5-nitropyridine (0.320 g, 2.22 mmol, 1.20 equiv) in DMF (8.50 mL, 0.261 M) was added to a mixture of estrone (0.500 g, 1.85 mmol, 1.00 equiv) and Cs$_2$CO$_3$ (0.720 g, 2.22 mmol, 1.20 equiv) in DMF (10.0 mL, 0.185 M) at 23° C. The resulting mixture was stirred at 23° C. for 12 h. The reaction mixture was poured to LiCl solution (100 mL), extracted with EtOAc. The combined organic layers was dried (MgSO$_4$), filtered and concentrated in vacuo. The residue was recrystalized from hexanes/EtOAc, to afford the title compound as a light yellow solid (0.650 g, 1.66 mmol, 89% yield). R$_f$=0.52 (hexanes:EtOAc 2:1 (v/v)). NMR Spectroscopy: 1H NMR (700 MHz, CDCl$_3$, 25° C., δ): 9.06 (d, J=2.58 Hz, 1H), 8.46 (dd, J=9.03, 2.58 Hz, 1H), 7.36 (d, J=8.60 Hz, 1H), 7.03 (d, J=9.03 Hz, 1H), 6.93 (dd, J=8.60, 2.58 Hz, 1H), 6.89 (d, J=2.58 Hz, 1H), 2.97-2.92 (m, 2H), 2.52 (dd, J=19.36, 8.60 Hz, 1H), 2.46-2.40 (m, 1H), 2.33 (td, J=11.19, 4.30 Hz, 1H), 2.20-2.12 (m, 1H), 2.11-2.02 (m, 2H), 1.99 (dt, J=12.91, 3.01 Hz, 1H), 1.68-1.45 (m, 6H), 0.93 (s, 3H). $^{13}$C NMR (175 MHz, CDCl$_3$, 25° C., δ): 220.9, 167.2, 150.7, 145.3, 140.3, 138.8, 137.7, 135.0, 127.0, 121.5, 118.8, 111.5, 50.6, 48.1, 44.3, 38.1, 36.0, 31.7, 29.6, 26.5, 25.9, 21.7, 14.0. Mass Spectrometry: HRMS (ESI-TOF) (m/z): calcd for C$_{23}$H$_{25}$N$_2$O$_4$ ([M+H]$^+$), 393.1809, found, 393.1812.

Under N$_2$ atmosphere, a suspension of (8R,9S,13S,14S)-13-methyl-3-((5-nitropyridin-2-yl)oxy)-6,7,8,9,11,12,13,14,15,16-decahydro-17H-cyclopenta[a]phenanthren-17-one (300 mg, 0.760 mmol, 1.00 equiv) and 5% Rh/C (8.70 mg, 0.60 mol % Rh) in THF (7.60 mL, 0.100 M) was stirred at 23° C. Hydrazine monohydrate (45.9 mg, 0.910 mmol, 1.20 equiv) was added dropwise. The reaction mixture was stirred at 23° C. for 20 min. NaHCO$_3$ (76.4 mg, 0.91 mmol, 1.20 equiv) was added, followed by dropwise addition of acetyl chloride (71.4 mg, 0.91 mmol, 1.20 equiv) in THF (7.6 mL, 0.120 M). The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a yellow solid (310 mg, 0.737 mmol, 97% yield). R$_f$=0.13 (hexanes:EtOAc 1:1 (v/v)). NMR Spectroscopy: $^1$H NMR (700 MHz, (CD$_3$)$_2$SO, 25° C., δ): 10.76 (s, 1H), 8.34 (d, J=1.83 Hz, 1H), 8.00 (dd, J=8.85, 2.44 Hz, 1H), 7.31 (d, J=8.54 Hz, 1H), 7.01 (d, J=8.85 Hz, 1H), 6.86 (dd, J=8.24, 2.44 Hz, 1H), 6.81 (d, J=2.44 Hz, 1H), 2.87-2.80 (m, 2H), 2.50 (dt, J=3.66, 1.83 Hz, 3H), 2.36-2.48 (m, 2H), 2.26 (br. s., 1H), 2.20 (br. s., 3H), 2.07 (dd, J=18.92, 8.85 Hz, 1H), 2.01-1.91 (m, 2H), 1.82-1.75 (m, 1H), 1.63-1.32 (m, 6H), 0.85 (s, 3H). $^{13}$C NMR (175 MHz, (CD$_3$)$_2$SO, 25° C., δ): 219.7, 170.5, 160.0, 151.9, 139.7, 138.0, 135.9, 134.2, 133.0, 126.6, 120.8, 118.3, 110.9, 49.6, 47.3, 43.6, 37.6, 35.4, 31.4, 29.0, 25.9, 25.4, 21.9, 21.2, 13.5. Mass Spectrometry: HRMS (ESI-TOF) (m/z): calcd for C$_{25}$H$_{29}$N$_2$O$_4$ ([M+H]$^+$), 421.2122, found, 421.2125.

N-(6-((6R,12aR)-6-(Benzo[d][1,3]dioxol-5-yl)-2-methyl-1,4-dioxo-1,3,4,6,12,12a-hexahydropyrazino[1',2':1,6]pyrido[3,4-b]indol-7(2H)-yl)pyridin-3-yl)-N-hydroxyacetamide (8y)

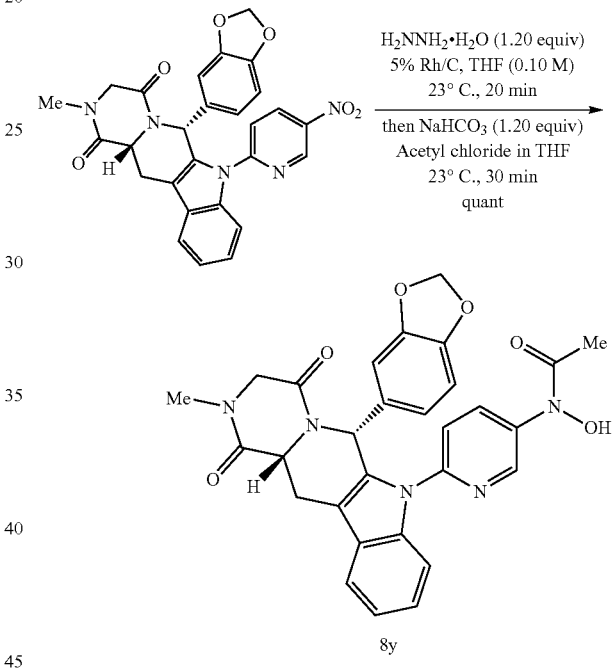

Under N$_2$ atmosphere, to a mixture of (6R,12aR)-6-(benzo[d][1,3]dioxol-5-yl)-2-methyl-2,3,6,7,12,12a-hexahydropyrazino[1',2':1,6]pyrido[3,4-b]indole-1,4-dione (1.00 g, 2.60 mmol, 1.00 equiv) and K$_2$CO$_3$ (0.36 g, 2.60 mmol, 1.00 equiv) in DMF (26.0 mL, 0.100 M) was added 2-fluoro-5-nitropyridine (0.550 g, 3.90 mmol, 1.50 equiv) and the reaction mixture was stirred at 23° C. for 40 h. The reaction mixture was poured to water (100 mL), extracted with EtOAc, washed with brine. The combined organic layers was dried (MgSO$_4$), filtered and concentrated in vacuo. The residue was purified by chromatography on silica gel, eluting with hexanes:EtOAc (1:1 to 1:3 (v/v)), to afford the title compound as a yellow solid (0.810 g, 1.58 mmol, 61% yield) R$_f$=0.51 (EtOAc). NMR Spectroscopy: $^1$H NMR (700 MHz, DMSO, 25° C., δ): 9.44 (d, J=2.58 Hz, 1H), 8.53 (dd, J=8.82, 2.80 Hz, 1H), 7.73-7.69 (m, 1H), 7.55-7.50 (m, 1H), 7.41 (d, J=9.03 Hz, 1H), 7.35-7.28 (m, 2H), 7.00 (s, 1H), 6.52-6.44 (m, 3H), 5.80 (dd, J=6.45, 1.29 Hz, 2H), 4.38 (dd, J=11.62, 4.30 Hz, 1H), 4.16-4.10 (m, 1H), 3.93 (d, J=17.21 Hz, 1H), 3.84 (dd, J=16.13, 4.52 Hz, 1H), 3.27 (ddd, J=16.35, 11.62, 1.29 Hz, 1H), 3.06-3.01 (m, 3H). $^{13}$C NMR (175 MHz, CDCl$_3$, 25° C., δ): 166.5, 166.4, 154.6, 147.6, 147.0, 145.6, 141.6, 136.6, 134.6, 134.0, 133.9, 127.6, 124.6, 122.8, 121.9, 119.6, 118.0, 113.3, 110.9, 108.2, 107.8, 101.2, 55.6, 55.4, 52.4, 33.8, 23.9. Mass Spectrometry: HRMS (ESI-TOF) (m/z): calcd for C$_{27}$H$_{22}$N$_5$O$_6$ ([M+H]$^+$), 512.1565, found, 512.1567. Under N$_2$ atmosphere, a suspension of (6R,12aR)-6-(benzo[d] [1,3]dioxol-5-yl)-2-methyl-7-(5-nitropyridin-2-yl)-2,3,6,7,12,12a-hexahydropyrazino[1',2':1,6]pyrido[3,4-b]indole-1,4-dione (300 mg, 0.590 mmol, 1.00 equiv) and 5% Rh/C (6.80 mg, 0.60 mol % Rh) in THF (5.90 mL, 0.100 M) was stirred at 23° C. Hydrazine monohydrate (35.4 mg, 0.710 mmol, 1.20 equiv) was added dropwise. The reaction mixture was stirred at 23° C. for 20 min. NaHCO$_3$ (59.6 mg, 0.710 mmol, 1.20 equiv) was added, followed by dropwise addition of a solution of acetyl chloride (55.7 mg, 0.710 mmol, 1.20 equiv) in THF (5.90 mL, 0.120 M). The reaction mixture was stirred at 23° C. for 30 min and then filtered through a short pad of celite. The celite was washed with EtOAc. The combined organic solution was concentrated in vacuo. The residue was recrystalized from hexanes/EtOAc, to afford the title compound as a white solid (320 mg, 0.59 mmol, quant yield). R$_f$=0.17 (EtOAc). NMR Spectroscopy: $^1$H NMR (700 MHz, (CD$_3$)$_2$SO, 25° C., δ): 11.03 (br. s., 1H), 8.96 (br. s., 1H), 8.22 (d, J=8.60 Hz, 1H), 7.78-7.70 (m, 1H), 7.43-7.34 (m, 2H), 7.23-7.16 (m, 2H), 6.68 (br. s., 1H), 6.54-6.47 (m, 1H), 6.28 (d, J=1.72 Hz, 1H), 6.19 (dd, J=8.17, 1.72 Hz, 1H), 5.84 (dd, J=12.91, 2.58 Hz, 2H), 4.53 (d, J=11.62 Hz, 1H), 4.19 (d, J=16.78 Hz, 1H), 3.92 (d, J=17.21 Hz, 1H), 3.66 (d, J=15.92 Hz, 1H), 2.97-2.87 (m, 3H), 2.44-2.43 (m, 1H), 2.31 (br. s., 3H). $^{13}$C NMR (175 MHz, (CD$_3$)$_2$SO, 25° C., δ): 166.9, 166.4, 146.8, 146.0, 137.0, 136.4, 135.4, 134.6, 126.0, 123.1, 120.9, 120.3, 119.5, 119.0, 110.3, 109.3, 107.5, 107.1, 100.9, 54.9, 54.2, 51.5, 32.8, 23.3, 22.3. Mass Spectrometry: HRMS (ESI-TOF) (m/z): calcd for C$_{29}$H$_{26}$N$_5$O$_6$ ([M+H]$^+$), 540.1878, found, 540.1881.

Methyl (5-bromo-6-methoxy-2-(trifluoromethoxy) pyridin-3-yl) carbamate (9a)

A solution of methyl (5-bromo-6-methoxypyridin-3-yl)(hydroxy)carbamate (8a) (50.0 mg, 0.180 mmol) and Togni reagent I (71.5 mg, 0.217 mmol, 1.20 equiv) in CH$_2$Cl$_2$ (1.80 mL, 0.100 M) was stirred at 23° C. under N$_2$ atmosphere for 16 h. The reaction mixture was purified by preparative TLC (thickness: 1 mm) using hexanes:EtOAc (19:1 (v/v)) for development (prep TLC was developed three times).

The purification afforded the title compound as a white solid (47.3 mg, 0.137 mmol, 76% yield). R$_f$=0.69 (EtOAc: hexanes 1:4 (v/v)). NMR Spectroscopy: $^1$H NMR (500 MHz, CDCl$_3$, 25° C., δ): 8.65 (br. s, 1H), 6.62 (br. s, 1H), 3.93 (s, 3H), 3.80 (s, 3H). $^{13}$C NMR (125 MHz, CDCl$_3$, ° C., δ): 153.8, 153.6, 141.9, 135.6, 120.1 (q, J=261.6 Hz), 117.3, 102.6, 55.1, 53.0. $^{19}$F NMR (376 MHz, CDCl$_3$, 25° C., δ): −56.6 (s). Mass Spectrometry: HRMS (ESI-TOF) (m/z): calcd for C$_9$H$_9$BrF$_3$N$_2$O$_4$ ([M+H]$^+$), 344.9692, found, 344.9705.

Methyl (5-iodo-6-methoxy-2-(trifluoromethoxy) pyridin-3-yl)carbamate (9b)

A solution of methyl hydroxy(5-iodo-6-methoxypyridin-3-yl)carbamate (9b) (50.0 mg, 0.154 mmol) and Togni reagent I (61.1 mg, 0.185 mmol, 1.20 equiv) in CH$_2$Cl$_2$ (1.54 mL, 0.100 M) was stirred at 23° C. under N$_2$ atmosphere for 18 h. The reaction mixture was purified by preparative TLC (thickness: 1 mm) using hexanes:EtOAc (97:3 (v/v)) for development (prep TLC was developed six times). The purification afforded the title compound as a white solid (44.2 mg, 0.113 mmol, 73% yield). R$_f$=0.53 (EtOAc: hexanes 1:9 (v/v)). NMR Spectroscopy: $^1$H NMR (500 MHz, CDCl$_3$, 25° C., δ): 8.81 (br. s, 1H), 6.58 (br. s., 1H), 3.91 (s, 3H), 3.80 (s, 3H). $^{13}$C NMR (125 MHz, CDCl$_3$, 25° C., δ): 155.8, 153.8, 143.4, 141.6, 120.1 (q, J=261.8 Hz), 117.4, 73.9, 55.4, 52.9. $^{19}$F NMR (376 MHz, CDCl$_3$, 25° C., δ): −56.5 (s). Mass Spectrometry: HRMS (ESI-TOF) (m/z): calcd for C$_9$H$_9$F$_3$IN$_2$O$_4$ ([M+H]$^+$), 392.9554, found, 392.9556.

Methyl (6-chloro-4-methyl-2-(trifluoromethoxy) pyridin-3-yl) carbamate (9c)

A solution of methyl (6-chloro-4-methylpyridin-3-yl)(hydroxy)carbamate (8c) (108 mg, 0.500 mmol) and Togni reagent I (198 mg, 0.600 mmol, 1.20 equiv) in CH$_2$Cl$_2$ (5.00 mL, 0.100 M) was stirred at 23° C. under N$_2$ atmosphere for 15 h. The reaction mixture was concentrated in vacuo. The residue was dissolved in MeNO$_2$ (5.00 mL, 0.100 M) and the reaction mixture was stirred at 120° C. for 15 h. The reaction mixture was concentrated in vacuo and purified by chromatography on silica gel, eluting with hexanes:EtOAc (8:1 to 4:1 (v/v)), to afford 2c (99.0 mg, 0.348 mmol, 70% yield). Data for 9c: white solid; R$_f$=0.45 (EtOAc:hexanes 1:4 (v/v)). NMR Spectroscopy: $^1$H NMR (700 MHz, CDCl$_3$, 25° C., δ): 8.44 (d, J=8.53 Hz, 1H), 7.38 (d, J=8.53 Hz, 1H), 6.85 (br. s, 1H), 3.83 (s, 3H). $^{13}$C NMR (175 MHz, CDCl$_3$, 25° C., δ): 154.4, 151.6, 150.6, 145.5, 124.1, 120.0 (q, J=261.9 Hz), 119.9, 53.4 (d, J=7.51 Hz), 18.4. $^{19}$F NMR (376 MHz, CDCl$_3$, 25° C., δ): −57.0 (s). Mass Spectrometry: HRMS (ESI-TOF) (m/z): calcd for C$_9$H$_9$ClF$_3$N$_2$O$_3$ ([M+H]$^+$), 285.0248, found, 285.0249.

Methyl (6-bromo-2-(trifluoromethoxy)pyridin-3-yl) carbamate (9d) and methyl (6-bromo-4-(trifluoromethoxy)pyridin-3-yl)carbamate (9d-II)

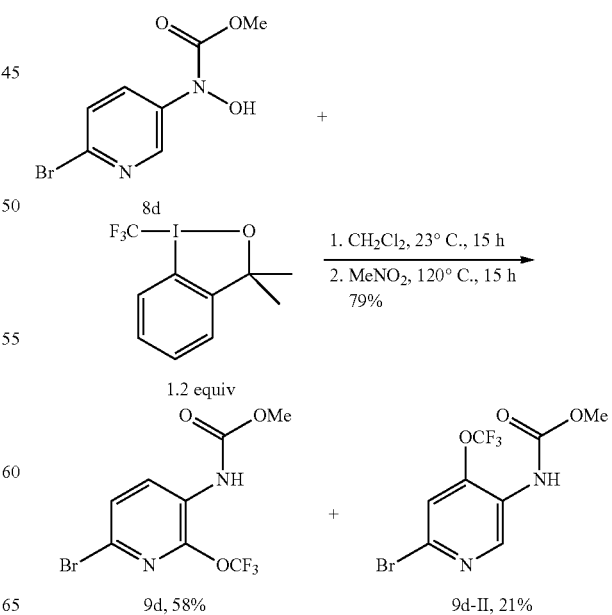

A solution of methyl (6-bromopyridin-3-yl)(hydroxy)carbamate (8d) (124 mg, 0.226 mmol) and Togni reagent I (198 mg, 0.600 mmol, 1.20 equiv) in $CH_2Cl_2$ (5.00 mL, 0.100 M) was stirred at 23° C. under $N_2$ atmosphere for 15 h. The reaction mixture was concentrated in vacuo. The residue was dissolved in $MeNO_2$ (5.00 mL, 0.100 M) and the reaction mixture was stirred at 120° C. for 15 h. The reaction mixture was concentrated in vacuo and purified by chromatography on silica gel, eluting with hexanes:EtOAc (19:1 to 9:1 (v/v)), to afford 9d (91 mg, 0.289 mmol, 58% yield) and 9d-II (33 mg, 0.105 mmol, 21% yield). Data for 9d: white solid; $R_f$=0.57 (EtOAc:hexanes 1:4 (v/v)). NMR Spectroscopy: $^1H$ NMR (400 MHz, $CDCl_3$, 25° C., δ): 8.44 (d, J=8.53 Hz, 1H), 7.38 (d, J=8.53 Hz, 1H), 6.85 (br. s, 1H), 3.83 (s, 3H). $^{13}C$ NMR (175 MHz, $CDCl_3$, 25° C., δ): 153.4, 143.8, 130.3, 129.6, 126.6, 123.5, 120.0 (q, J=265.2 Hz), 53.2. $^{19}F$ NMR (376 MHz, $CDCl_3$, 25° C., δ): −56.7 (s). Mass Spectrometry: HRMS (ESI-TOF) (m/z): calcd for $C_8H_7BrF_3N_2O_3$ ([M+H]$^+$), 314.9587, found, 314.9585. Data for 9d-II: white solid; $R_f$=0.45 (EtOAc:hexanes 1:4 (v/v)) NMR Spectroscopy: 1H NMR (400 MHz, $CDCl_3$, 25° C., δ): 9.23 (br. s, 1H), 7.35 (q, J=2.01 Hz, 1H), 6.77 (br. s, 1H), 3.84 (s, 3H). $^{13}C$ NMR (175 MHz, $CDCl_3$, 25° C., δ): 153.1, 144.8, 142.7, 134.8, 126.5, 120.2 (q, J=265.2 Hz), 116.9, 53.4. $^{19}F$ NMR (376 MHz, $CDCl_3$, 25° C., δ): −57.9 (s). Mass Spectrometry: HRMS (ESI-TOF) (m/z): calcd for $C_8H_7BrF_3N_2O_3$ ([M+H]$^+$), 314.9587, found, 314.9586.

Methyl (6-fluoro-2-(trifluoromethoxy)pyridin-3-yl) carbamate (9e) and methyl (6-fluoro-4-(trifluoromethoxy)pyridin-3-yl) carbamate (9e-II)

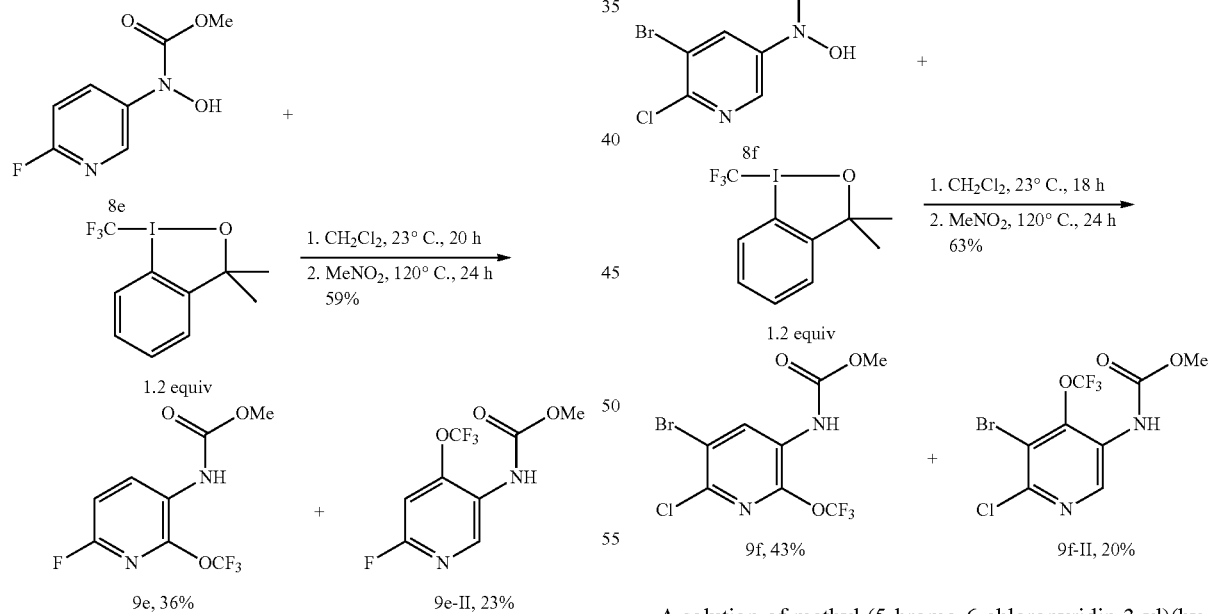

A solution of methyl (6-fluoropyridin-3-yl)(hydroxy)carbamate (8e) (93.1 mg, 0.500 mmol) and Togni reagent I (198 mg, 0.600 mmol, 1.20 equiv) in $CH_2Cl_2$ (5.00 mL, 0.100 M) was stirred at 23° C. under $N_2$ atmosphere for 20 h. The reaction mixture was concentrated in vacuo. The residue was dissolved in $MeNO_2$ (5.00 mL, 0.100 M) and the reaction mixture was stirred at 120° C. for 24 h. The crude residue was purified by flash chromatography eluting hexanes and then EtOAc:hexanes (1:4 (v/v)). The purification afforded a 1.6:1 mixture of 9e and 9e-II, which was further purified by preparative TLC (thickness: 1 mm) using hexanes:EtOAc (19:1 (v/v)) for development (prep TLC was developed five times). The purification afforded 9e (45.8 mg, 0.180 mmol, 36% yield) and 9e-II (28.7 mg, 0.113 mmol, 23% yield). Data for 9e: white solid; $R_f$=0.48 (EtOAc:hexanes 1:4 (v/v)). NMR Spectroscopy: $^1H$ NMR (400 MHz, $CDCl_3$, 25° C., δ): 8.64 (br. s, 1H), 6.87 (dd, J=8.66, 3.14 Hz, 1H), 6.79 (br. s, 1H), 3.83 (s, 3H). $^{13}C$ NMR (124 MHz, $CDCl_3$, 25° C., δ): 155.6 (d, J=242.1 Hz), 153.7, 142.2, 133.5, 121.4, 120.0 (q, J=262.7 Hz), 107.1 (d, J=35.6 Hz), 53.1. $^{19}F$ NMR (376 MHz, $CDCl_3$, 25° C., δ): −56.8 (s), −75.7 (s). Mass Spectrometry: HRMS (ESI-TOF) (m/z): calcd for $C_8H_7F_4N_2O_3$ ([M+H]$^+$), 255.0387, found, 255.0387. Data for 9e-II: off-white solid; $R_f$=0.44 (EtOAc:hexanes 1:4 (v/v)). NMR Spectroscopy: $^1H$ NMR (400 MHz, $CDCl_3$, ° C., δ): 8.98 (br. s, 1H), 6.83 (quin, J=2.13 Hz, 1H), 6.69 (br. s, 1H), 3.83 (s, 3H). $^{13}C$ NMR (125 MHz, $CDCl_3$, 25° C., δ): 159.2 (d, J=234.5 Hz), 153.5, 147.5, 140.3, 124.6, 120.2 (q, J=262.2 Hz), 99.2 (d, J=45.2 Hz), 53.3. $^{19}F$ NMR (376 MHz, $CDCl_3$, 25° C., δ): −58.2 (s), −69.6 (s). Mass Spectrometry: HRMS (ESI-TOF) (m/z): calcd for $C_8H_7F_4N_2O_3$ ([M+H]$^+$), 255.0387, found, 255.0390.

Methyl (5-bromo-6-chloro-2-(trifluoromethoxy) pyridin-3-yl)carbamate (9f) and methyl (5-Bromo-6-chloro-4-(trifluoromethoxy)pyridin-3-yl)carbamate (9f-II)

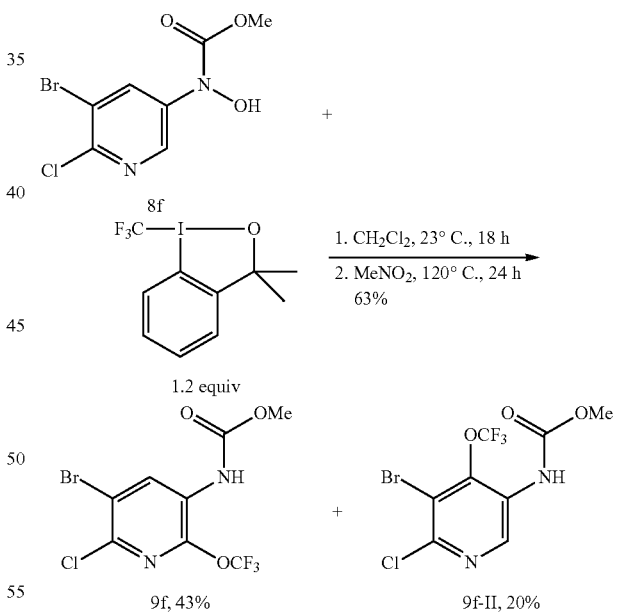

A solution of methyl (5-bromo-6-chloropyridin-3-yl)(hydroxy)carbamate (8f) (141 mg, 0.500 mmol) and Togni reagent I (198 mg, 0.600 mmol, 1.20 equiv) in $CH_2Cl_2$ (5.00 mL, 0.100 M) was stirred at 23° C. under $N_2$ atmosphere for 18 h. The reaction mixture was concentrated in vacuo. The residue was dissolved in $MeNO_2$ (5.00 mL, 0.100 M) and the reaction mixture was stirred at 120° C. for 24 h. The crude residue was purified by flash chromatography eluting with EtOAc:hexanes (1:19 to 1:4 (v/v)), to afford 9f (75.6 mg, 0.216 mmol, 43% yield) and 9f-II (34.6 mg, 0.0990 mmol, 20% yield). Data for 9f: white solid; $R_f$=0.52 (EtOAc:hexanes 1:4 (v/v)). NMR Spectroscopy: $^1$H NMR (700 MHz, CDCl$_3$, 25° C., δ): 8.86 (s, 1H), 6.85 (br. s, 1H), 3.84 (s, 3H). $^{13}$C NMR (175 MHz, CDCl$_3$, 25° C., δ): 153.2, 142.3, 139.7, 133.3, 123.7, 119.9 (q, J=263.4 Hz), 117.6, 53.4. $^{19}$F NMR (376 MHz, CDCl$_3$, 25° C., δ): −56.8 (s). Mass Spectrometry: HRMS (ESI-TOF) (m/z): calcd for C$_8$H$_6$BrClF$_3$N$_2$O$_3$ ([M+H]$^+$), 348.9197, found, 348.9196. Data for 9f-II: slightly yellow solid; $R_f$=0.43 (EtOAc:hexanes 1:4 (v/v)). NMR Spectroscopy: $^1$H NMR (500 MHz, CDCl$_3$, 25° C., δ): 9.19 (br. s, 1H), 6.78 (br. s, 1H), 3.84 (s, 3H). $^{13}$C NMR (125 MHz, CDCl$_3$, 25° C., δ): 153.1, 146.4, 143.8, 140.9, 129.5, 120.5 (q, J=263.7 Hz), 116.4, 53.6. $^{19}$F NMR (376 MHz, CDCl$_3$, 25° C., δ): −55.5 (s). Mass Spectrometry: HRMS (ESI-TOF) (m/z): calcd for C$_8$H$_6$BrClF$_3$N$_2$O$_3$ ([M+H]$^+$), 348.9197, found, 348.9198.

Methyl (2-chloro-4-(trifluoromethoxy)pyridin-3-yl) carbamate (9g)

A solution of methyl (2-chloropyridin-3-yl)(hydroxy)carbamate (8g) (101 mg, 0.500 mmol) and Togni reagent I (198 mg, 0.600 mmol, 1.20 equiv) in CH$_2$Cl$_2$ (5.00 mL, 0.100 M) was stirred at 23° C. under N$_2$ atmosphere for 15 h. The reaction mixture was concentrated in vacuo. The residue was dissolved in MeNO$_2$ (5.00 mL, 0.100 M) and the reaction mixture was stirred at 120° C. for 15 h. The reaction mixture was concentrated in vacuo and purified by chromatography on silica gel, eluting with hexanes:EtOAc (10:1 to 5:1 (v/v)), to afford 9g (73.0 mg, 0.270 mmol, 53% yield) and 9g' (45.0 mg, 0.166 mmol, 33% yield). Data for 9g: white solid; $R_f$=0.72 (EtOAc:hexanes 1:4 (v/v)). NMR Spectroscopy: $^1$H NMR (700 MHz, CDCl$_3$, 25° C., δ): 8.10 (d, J=5.59 Hz, 1H) 7.31 (d, J=5.16 Hz, 1H) 6.25 (br. s, 1H) 3.80 (s, 3H). $^{13}$C NMR (175 MHz, CDCl$_3$, 25° C., δ): 153.9, 153.1, 145.0, 143.8, 123.3, 120.8, 120.1 (q, J=261.6 Hz), 53.4. $^{19}$F NMR (376 MHz, CDCl$_3$, 25° C., δ): −57.3 (s). Mass Spectrometry: HRMS (ESI-TOF) (m/z): calcd for C$_8$HClF$_3$N$_2$O$_3$ ([M+H]$^+$), 271.0092, found, 271.0093. Data for 9g': white solid; $R_f$=0.48 (EtOAc:hexanes 1:4 (v/v)) NMR Spectroscopy: $^1$H NMR (700 MHz, CDCl$_3$, 25° C., δ): 8.32 (d, J=5.59 Hz, 1H) 7.23-7.20 (m, 1H) 6.28 (br. s, 1H) 3.80 (s, 3H). $^{13}$C NMR (175 MHz, CDCl$_3$, 25° C., δ): 153.9, 152.8, 150.6, 148.2, 123.3, 120.2 (q, J=261.5 Hz), 113.3, 53.5. $^{19}$F NMR (376 MHz, CDCl$_3$, 25° C., δ): −58.4 (s). Mass Spectrometry: HRMS (ESI-TOF) (m/z): calcd for C$_8$H$_7$ClF$_3$N$_2$O$_3$ ([M+H]$^+$), 271.0092, found, 271.0095.

Atropisomers pf 9g

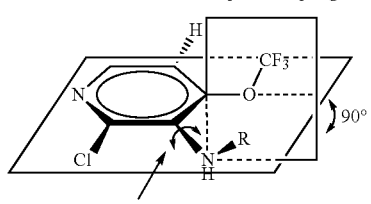

Syn-9g

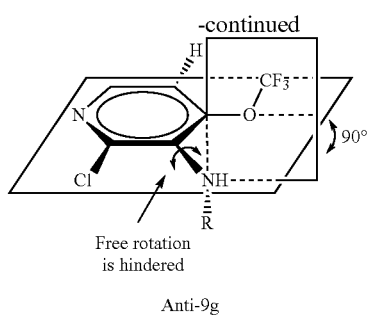

Anti-9g

R = CO$_2$Me

N-(2,6-Dichloro-4-(trifluoromethoxy)pyridin-3-yl) acetamide (9h)

A solution of N-(2,6-dichloropyridin-3-yl)-N-hydroxyacetamide (8h) (50.0 mg, 0.226 mmol) and Togni reagent I (89.5 mg, 0.271 mmol, 1.20 equiv) in CH$_2$Cl$_2$ (2.26 mL, 0.100 M) was stirred at 23° C. under N$_2$ atmosphere for 16 h. The reaction mixture was concentrated in vacuo. The residue was dissolved in MeNO$_2$ (2.26 mL, 0.100 M) and the reaction mixture was stirred at 120° C. for 22 h. The reaction mixture was purified by preparative TLC (thickness: 1 mm) using hexanes:EtOAc (17:3 (v/v)) for development (prep TLC was developed five times) followed by recrystallization from Et$_2$O:hexanes. The purification afforded the title compound as a 1.4:1 mixture of atropisomers (45.8 mg, 0.158 mmol, 70% yield). The products could not readily be separated by silica gel chromatography or preparative TLC, so they were characterized as a mixture. Data for the mixture of 9h: white solid; $R_f$=0.48 and 0.59 (EtOAc:hexanes 2:3 (v/v)). $^1$H NMR (500 MHz, CDCl$_3$, 25° C., δ): 7.36 (s, 1H), 7.24 (q, J=1.8 Hz, 1H), 6.91 (br. s, 1H), 6.89 (br. s, 1H), 2.23 (s, 3H), 2.22 (s, 3H). $^{13}$C NMR (125 MHz, CDCl$_3$, 25° C., δ): 168.3, 153.9, 151.8, 149.4, 149.1, 146.8, 145.9, 123.1, 122.4, 120.0 (q, J=262.1 Hz), 119.9 (q, J=263.1 Hz), 119.5, 113.7, 23.1. $^{19}$F NMR (376 MHz, CDCl$_3$, 25° C., δ): −56.8 (s), −57.9 (s). Mass Spectrometry: HRMS (ESI-TOF) (m/z): calcd for C$_8$H$_6$Cl$_2$F$_3$N$_2$O$_2$ ([M+H]$^+$), 288.9753, found, 288.9756.

N-(6-Methoxy-4-methyl-2-(trifluoromethoxy)pyridin-3-yl)acetamide (9i)

A solution of N-hydroxy-N-(6-methoxy-4-methylpyridin-3-yl)acetamide (8i) (50.0 mg, 0.255 mmol) and Togni reagent I (101 mg, 0.306 mmol, 1.20 equiv) in CH$_2$Cl$_2$ (2.55 mL, 0.100 M) was stirred at 23° C. under N$_2$ atmosphere for 18 h. The reaction mixture was purified by preparative TLC (thickness: 1 mm) using hexanes:EtOAc (3:2 (v/v)) for development (prep TLC was developed five times). The purification afforded the title compound as a white solid (54.5 mg, 0.206 mmol, 81% yield). $R_f$=0.63 (EtOAc:hexanes 3:2 (v/v)). NMR Spectroscopy (at rt, a mixture of rotamers was observed: $^1$H NMR (400 MHz, CDCl$_3$, 60° C., δ): 6.89 (br. s, 1H), 6.49 (br. s, 1H), 3.86 (s, 3H), 2.20 (br. s, 3H), 2.14 (br. s, 3H). $^{13}$C NMR (100 MHz, CDCl$_3$, 60° C., δ): 169.3, 161.0, 152.1, 150.1, 120.4 (q, J=260.2 Hz), 113.9, 109.6, 54.0, 23.0, 18.3. $^{19}$F NMR (376 MHz, CDCl$_3$, 60° C., δ): −56.4 (s). Mass Spectrometry: HRMS (ESI-TOF) (m/z): calcd for C$_{10}$H$_{12}$F$_3$N$_2$O$_3$ ([M+H]$^+$), 265.0795, found, 265.0801.

N-(6-Methyl-2-(trifluoromethoxy)pyridin-3-yl)acetamide (9j)

A solution of N-hydroxy-N-(6-methylpyridin-3-yl)acetamide (8j) (50.0 mg, 0.301 mmol) and Togni reagent I (119.2 mg, 0.361 mmol, 1.20 equiv) in CH$_2$Cl$_2$ (3.01 mL, 0.100 M) was stirred at 23° C. under N$_2$ atmosphere for 21 h. The reaction mixture was concentrated in vacuo. The residue was dissolved in MeNO$_2$ (3.01 mL, 0.100 M) and the reaction mixture was stirred at 120° C. for 15 h. The reaction mixture was purified by preparative TLC (thickness: 1 mm) using hexanes:EtOAc (4:1 (v/v)) for development (prep TLC was developed four times). The purification afforded the title compound as a white solid (35.8 mg, 0.153 mmol, 51% yield). R$_f$=0.24 (EtOAc:hexanes 4:1 (v/v)). $^1$H NMR (400 MHz, CDCl$_3$, 25° C., δ): 8.57 (d, J=8.28 Hz, 1H), 7.39 (br. s, 1H), 7.02 (d, J=8.28 Hz, 1H), 2.44 (s, 3H), 2.22 (s, 3H). $^{13}$C NMR (125 MHz, CDCl$_3$, 60° C., δ): 168.8, 151.1, 144.7, 130.5, 121.6, 121.1, 120.2 (q, J=261.0 Hz), 24.8, 23.4. $^{19}$F NMR (376 MHz, CDCl$_3$, 25° C., δ): −56.1 (s). Mass Spectrometry: HRMS (ESI-TOF) (m/z): calcd for C$_9$H$_{10}$F$_3$N$_2$O$_2$ ([M+H]$^+$), 235.0689, found, 235.0690.

Methyl (5-(2,4-difluorophenyl)-6-methoxy-2-(trifluoromethoxy) pyridin-3-yl)carbamate (9k)

A solution of methyl (5-(2,4-difluorophenyl)-6-methoxypyridin-3-yl)(hydroxy)carbamate (8k) (50.0 mg, 0.161 mmol) and Togni reagent I (63.8 mg, 0.193 mmol, 1.20 equiv) in CH$_2$Cl$_2$ (1.58 mL, 0.100 M) was stirred at 23° C. under N$_2$ atmosphere for 15 h. The reaction mixture was purified by preparative TLC (thickness: 1 mm) using hexanes:EtOAc (19:1 (v/v)) for development (prep TLC was developed 3x). The purification afforded the title compound as a white solid (46.6 mg, 0.123 mmol, 77% yield). R$_f$=0.60 (EtOAc:hexanes 1:4 (v/v)). $^1$H NMR (700 MHz, CDCl$_3$, 25° C., δ): 8.38 (br. s., 1H), 7.35 (td, J=8.41, 6.53 Hz, 1H), 6.97-6.85 (m, 2H), 6.65 (br. s, 1H), 3.88 (s, 3H), 3.79 (s, 3H). $^{13}$C NMR (175 MHz, CDCl$_3$, 25° C., δ): 163.0 (dd, J=248.1 Hz, J=11.6 Hz), 160.2 (dd, J=249.4 Hz, J=11.5 Hz), 154.7, 154.0, 142.8, 134.3, 132.6 (m), 120.3 (q, J=261.0 Hz), 119.4 (dd, J=15.3 Hz, J=3.8 Hz), 116.2, 115.6, 111.4 (dd, J=21.2 Hz, J=3.1 Hz), 104.3 (t, J=25.5 Hz), 54.5, 52.9. $^{19}$F NMR (376 MHz, CDCl$_3$, 25° C., δ): −56.4 (s), −110.3 (s), −110.5 (s). Mass Spectrometry: HRMS (ESI-TOF) (m/z): calcd for C$_{15}$H$_{12}$F$_5$N$_2$O$_4$ ([M+H]$^+$), 379.0712, found, 379.0719.

Methyl (6-(4-(tert-butyl)phenoxy)-2-(trifluoromethoxy)pyridin-3-yl)carbamate (9l)

A solution of methyl (6-(4-(tert-butyl)phenoxy)pyridin-3-yl)(hydroxy)carbamate (8l) (50.0 mg, 0.158 mmol) and Togni reagent I (62.9 mg, 0.190 mmol, 1.20 equiv) in CH$_2$Cl$_2$ (1.58 mL, 0.100 M) was stirred at 23° C. under N$_2$ atmosphere for 16 h. The reaction mixture was purified by preparative TLC (thickness: 1 mm) using hexanes:EtOAc (19:1 (v/v)) for development (prep TLC was developed four times). The purification afforded the title compound as a colorless oil (38.1 mg, 0.0991 mmol, 63% yield). R$_f$=0.57 (EtOAc:hexanes 1:4 (v/v)). $^1$H NMR (400 MHz, CDCl$_3$, 25° C., δ): 8.43 (br. s, 1H), 7.45-7.33 (m, 2H), 7.12-7.00 (m, 2H), 6.71 (app. d, J=8.8 Hz, 2H), 3.80 (s, 3H), 1.33 (s, 9H). $^{13}$C NMR (175 MHz, CDCl$_3$, 25° C., δ): 156.7, 153.9, 151.6, 147.9, 143.1, 132.9, 126.6, 120.2, 120.1 (q, J=261.6 Hz), 118.4, 108.3, 52.9, 34.6, 31.6. $^{19}$F NMR (376 MHz, CDCl$_3$, 25° C., δ): −56.6 (s). Mass Spectrometry: HRMS (ESI-TOF) (m/z): calcd for C$_{18}$H$_{20}$F$_3$N$_2$O$_4$ ([M+H]$^+$), 385.1370, found, 385.1375.

Methyl (5-(5-formylfuran-2-yl)-6-methoxy-2-(trifluoromethoxy) pyridin-3-yl)carbamate (9m)

A solution of methyl (5-(5-formylfuran-2-yl)-6-methoxypyridin-3-yl)(hydroxy)carbamate (8m) (31.6 mg, 0.108 mmol) and Togni reagent I (42.9 mg, 0.130 mmol, 1.20 equiv) in CH$_2$Cl$_2$ (1.08 mL, 0.100 M) was stirred at 23° C. under N$_2$ atmosphere for 16 h. The reaction mixture was purified by preparative TLC (thickness: 1 mm) using hexanes:EtOAc (3:2 (v/v)) for development (prep TLC was developed twice). The purification afforded the title compound as an off-white solid (24.8 mg, 0.0688 mmol, 64% yield). R$_f$=0.50 (EtOAc:hexanes 3:7 (v/v)). NMR Spectroscopy: $^1$H NMR (700 MHz, CDCl$_3$, 25° C., δ): 9.70 (s, 1H), 8.94 (br. s, 1H), 7.32 (d, J=3.44 Hz, 1H), 7.13 (d, J=3.44 Hz, 1H), 6.68 (br. s, 1H), 4.03 (s, 3H), 3.83 (s, 3H). $^{13}$C NMR (175 MHz, CDCl$_3$, 25° C., δ): 177.9, 154.0, 153.9, 153.2, 152.0, 143.2, 130.2, 122.4, 120.1 (q, J=261.8 Hz), 116.7, 113.1, 110.6, 54.7, 53.0. $^{19}$F NMR (376 MHz, CDCl$_3$, 25° C., δ): −56.4 (s). Mass Spectrometry: HRMS (ESI-TOF) (m/z): calcd for C$_{14}$H$_{12}$F$_3$N$_2$O$_6$ ([M+H]$^+$), 361.0642, found, 361.0643.

N-(6-(1H-Pyrazol-1-yl)-2-(trifluoromethoxy)pyridin-3-yl)acetamide (9n)

A solution of N-(6-(1H-pyrazol-1-yl)pyridin-3-yl)-N-hydroxyacetamide (8n) (50.0 mg, 0.229 mmol) and Togni reagent I (90.8 mg, 0.275 mmol, 1.20 equiv) in CH$_2$Cl$_2$ (2.29 mL, 0.100 M) was stirred at 23° C. under N$_2$ atmosphere for 18 h. The reaction mixture was purified by preparative TLC (thickness: 1 mm) using hexanes:EtOAc (9:1 (v/v)) for development (prep TLC was developed three times). The purification afforded the title compound as a white solid (58.0 mg, 0.203 mmol, 89% yield). R$_f$=0.30 (EtOAc:hexanes 3:7 (v/v)). NMR Spectroscopy: $^1$H NMR (400 MHz, CDCl$_3$, 25° C., δ): 8.85 (d, J=8.60 Hz, 1H), 8.34 (d, J=2.58 Hz, 1H), 7.83 (d, J=9.03 Hz, 1H), 7.70 (s, 1H), 7.43 (br. s, 1H), 6.43 (m, 1H), 2.25 (s, 3H). $^{13}$C NMR (175 MHz, CDCl$_3$, 25° C., δ): 168.6, 143.9, 143.5, 142.5, 133.2, 127.2, 120.9, 120.2 (q, J=262.1 Hz), 109.8, 108.2, 24.8. $^{19}$F NMR (376 MHz, CDCl$_3$, 25° C., δ): −56.5 (s). Mass Spectrometry: HRMS (ESI-TOF) (m/z): calcd for C$_{11}$H$_{10}$F$_3$N$_4$O$_2$ ([M+H]$^+$), 287.0750, found, 275.0754.

Methyl (6-(1H-1,2,4-triazol-1-yl)-2-(trifluoromethoxy)pyridin-3-yl)carbamate (9o) and methyl (6-(1H-1,2,4-triazol-1-yl)-4-(trifluoromethoxy)pyridin-3-yl)carbamate (9o-II)

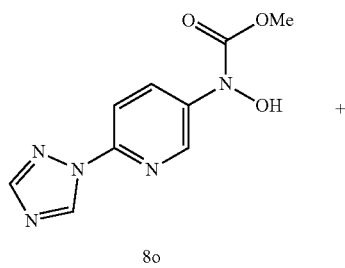

8o

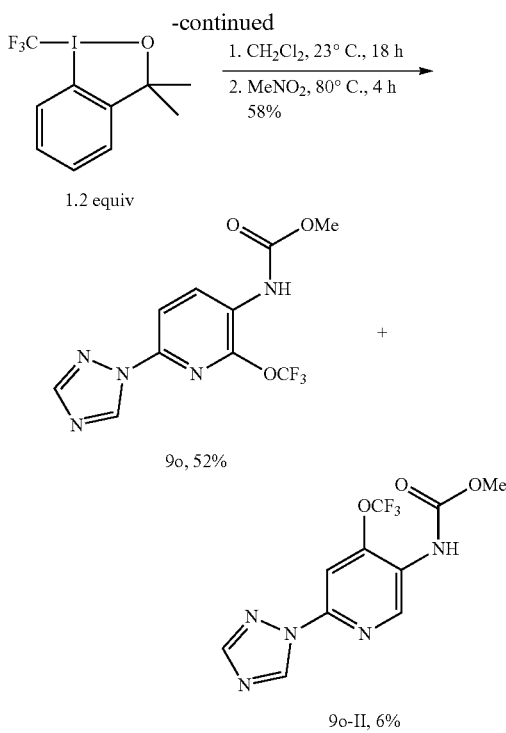

9o, 52%

9o-II, 6%

A solution of methyl (6-(1H-1,2,4-triazol-1-yl)pyridin-3-yl)(hydroxy)carbamate (8o) (100 mg, 0.425 mmol) and Togni reagent I (168 mg, 0.510 mmol, 1.20 equiv) in CH$_2$Cl$_2$ (4.25 mL, 0.100 M) was stirred at 23° C. under N$_2$ atmosphere for 18 h. The reaction mixture was concentrated in vacuo. The residue was dissolved in MeNO$_2$ (4.25 mL, 0.100 M) and the reaction mixture was stirred at 80° C. for 4 h. The reaction mixture was placed in the freezer. The solid was filtered and washed with hexanes. Filtration afforded 2o (61.7 mg, 0.203 mmol, 48% yield) as a slightly brown solid. The filtrate was concentrated in vacuo and purified by preparative TLC (thickness: 1 mm) using hexanes:Et$_2$O (7:3 (v/v)) for development (prep TLC was developed six times). The purification afforded 9o (3.7 mg, 0.0122 mmol, 3%) and 9.3 mg (0.0307 mmol, 7% yield) of a 1:4.6 mixture of 9o and 9o-II. The combined reaction yield was 58%. The characterization data for 9o-II was obtained by further purification of the mixture by preparative TLC using hexanes:EtOAc (7:3 (v/v)) for development (prep TLC was developed six times). Data for 9o: white solid; R$_f$=0.41 (EtOAc:hexanes 1:1 (v/v)). NMR Spectroscopy: $^1$H NMR (500 MHz, CDCl$_3$, ° C., δ): 8.95 (s, 1H), 8.75 (d, J=7.93 Hz, 1H), 8.08 (s, 1H), 7.80 (d, J=8.54 Hz, 1H), 7.00 (br. s, 1H), 3.85 (s, 3H). $^{13}$C NMR (125 MHz, CDCl$_3$, 25° C., δ): 153.5, 153.2, 143.2, 141.4, 140.6, 131.4, 123.0, 120.1 (q, J=262.8 Hz), 110.9, 53.2. $^{19}$F NMR (376 MHz, CDCl$_3$, 25° C., δ): −56.7 (s). Mass Spectrometry: HRMS (ESI-TOF) (m/z): calcd for C$_{10}$H$_9$F$_3$N$_5$O$_3$ ([M+H]$^+$), 304.0652, found, 304.0658. Data for 9o-II: white solid; R$_f$=0.27 (EtOAc:hexanes 1:1 (v/v)). NMR Spectroscopy: $^1$H NMR (700 MHz, CDCl$_3$, 25° C., δ): 9.30 (br. s, 1H), 9.14 (s, 1H), 8.08 (s, 1H), 7.81 (s, 1H), 6.88 (br. s, 1H), 3.83 (s, 3H). $^{13}$C NMR (175 MHz, CDCl$_3$, 25° C., δ): 153.3, 153.0, 145.9, 145.3, 141.8, 141.2, 126.1, 120.3 (q, J=262.0 Hz), 102.7, 53.4. $^{19}$F NMR (376 MHz, CDCl$_3$, 25° C., δ): −57.3 (d). Mass Spectrometry: HRMS (ESI-TOF) (m/z): calcd for C$_{10}$H$_9$F$_3$N$_5$O$_3$ ([M+H]$^+$), 304.0652, found, 304.0657.

N-(6-(1H-Benzo[d] imidazol-1-yl)-2-(trifluoromethoxy)pyridin-3-yl)acetamide (9p)

A solution of N-(6-(1H-benzo[d]imidazol-1-yl)pyridin-3-yl)-N-hydroxyacetamide (8p) (100 mg, 0.373 mmol) and Togni reagent I (148 mg, 0.448 mmol, 1.20 equiv) in CH$_2$Cl$_2$ (3.73 mL, 0.100 M) was stirred at 23° C. under N$_2$ atmosphere for 19 h. The reaction mixture was concentrated in vacuo (to about 10% initial volume) and the residue was triturated with hexanes. The purification afforded the title compound as a beige solid (117 mg, 0.348 mmol, 93% yield). R$_f$=0.21 (EtOAc:hexanes 4:1 (v/v)). NMR Spectroscopy: $^1$H NMR (700 MHz, CDCl$_3$, 25° C., δ): 9.00 (d, J=8.60 Hz, 1H), 8.52 (s, 1H), 8.04 (d, J=8.17 Hz, 1H), 7.86 (d, J=7.74 Hz, 1H), 7.60 (br. s, 1H), 7.49 (d, J=8.60 Hz, 1H), 7.43-7.35 (m, 2H), 2.31 (s, 3H). $^{13}$C NMR (175 MHz, CDCl$_3$, 25° C., δ): 168.9, 144.3, 144.2, 141.8, 140.9, 133.1, 131.9, 124.8, 123.9, 121.5, 120.7, 120.2 (q, J=262.4 Hz), 112.8, 111.6, 24.9. $^{19}$F NMR (376 MHz, CDCl$_3$, 25° C., δ): −56.5 (s). Mass Spectrometry: HRMS (ESI-TOF) (m/z): calcd for C$_{15}$H$_{12}$F$_3$N$_4$O$_2$ ([M+H]$^+$), 337.0907, found, 337.0910.

N-(6-(1H-Benzo[d] [1,2,3] triazol-1-yl)-2-(trifluoromethoxy)pyridin-3-yl)acetamide (9q)

A solution of N-(6-(1H-benzo[d] [1,2,3]triazol-1-yl)pyridin-3-yl)-N-hydroxyacetamide (8q) (100 mg, 0.371 mmol) and Togni reagent I (147 mg, 0.445 mmol, 1.20 equiv) in CH$_2$Cl$_2$ (3.71 mL, 0.100 M) was stirred at 23° C. under N$_2$ atmosphere for 18 h. The reaction mixture was then stirred at 50° C. for 4 h. The reaction mixture was concentrated in vacuo and the residue was triturated with hexanes. The purification afforded the title compound as a slightly yellow solid (108 mg, 0.319 mmol, 86% yield). R$_f$=0.37 (EtOAc:hexanes 2:3 (v/v)). NMR Spectroscopy: $^1$H NMR (400 MHz, (CD$_3$)$_2$SO, 25° C., δ): 10.04 (s, 1H), 8.73 (d, J=8.53 Hz, 1H), 8.42-8.32 (m, 1H), 8.30-8.18 (m, 2H), 7.77 (t, J=7.65 Hz, 1H), 7.63-7.51 (m, 1H), 2.18 (s, 3H). $^{13}$C NMR (175 MHz, (CD$_3$)$_2$SO, 25° C., δ): 169.4, 146.0, 144.9, 142.7, 136.8, 130.5, 129.6, 125.5, 122.5, 119.9, 119.8 (q, J=260.0 Hz), 113.0, 112.6, 23.6. $^{19}$F NMR (376 MHz, (CD$_3$)$_2$SO, 25° C., δ): −57.0 (s). Mass Spectrometry: HRMS (ESI-TOF) (m/z): calcd for C$_{14}$H$_{11}$F$_3$N$_5$O$_2$ ([M+H]$^+$), 338.0859, found, 338.0860.

N-(6-(5-Fluoro-1H-indol-1-yl)-2-(trifluoromethoxy)pyridin-3-yl)acetamide (9r)

A solution of N-(6-(5-fluoro-1H-indol-1-yl)pyridin-3-yl)-N-hydroxyacetamide (8r) (50.0 mg, 0.175 mmol) and Togni reagent I (69.3 mg, 0.210 mmol, 1.20 equiv) in CH$_2$Cl$_2$ (1.75 mL, 0.100 M) was stirred at 23° C. under N$_2$ atmosphere for 15 h. The reaction mixture was concentrated in vacuo. The crude residue was triturated with hexanes. The crude residue was purified by flash chromatography eluting with EtOAc:hexanes (3:17 to 1:1 (v/v)). The purification afforded the title compound as a yellow solid (45.0 mg, 0.127 mmol, 73% yield). R$_f$=0.36 (EtOAc:hexanes 2:3 (v/v)). NMR Spectroscopy: $^1$H NMR (400 MHz, CDCl$_3$, 25° C., δ): 8.89 (d, J=8.78 Hz, 1H), 8.20 (dd, J=9.03, 4.52 Hz, 1H), 7.64 (d, J=3.51 Hz, 1H), 7.35 (br. s, 1H), 7.32 (d, J=8.78 Hz, 2H), 7.28 (dd, J=9.29, 2.51 Hz, 1H), 7.04 (td, J=9.10, 2.64 Hz, 1H), 6.67 (d, J=3.51 Hz, 1H), 2.29 (s, 3H). $^{13}$C NMR (175 MHz, CDCl$_3$, 25° C., δ): 168.7, 158.8 (d, J=236.1 Hz), 144.8, 143.9, 133.0, 131.6, 131.1 (d, J=10.0 Hz), 126.9, 120.2 (q, J=262.1 Hz), 119.6, 114.4 (d, J=9.1 Hz), 111.7 (d,

N-(6-(5-Bromo-1H-pyrrolo[2,3-b]pyridin-1-yl)-2-(trifluoromethoxy) pyridin-3-yl)acetamide (9s)

A solution of N-(6-(5-bromo-1H-pyrrolo[2,3-b]pyridin-1-yl)pyridin-3-yl)-N-hydroxyacetamide (8s) (50.0 mg, 0.144 mmol) and Togni reagent I (57.1 mg, 0.172 mmol, 1.20 equiv) in $CH_2Cl_2$ (1.44 mL, 0.100 M) was stirred at 23° C. under $N_2$ atmosphere for 20 h. The reaction mixture was concentrated in vacuo. The crude residue was purified by flash chromatography eluting with EtOAc:hexanes (1:19 to 2:3 (v/v)). The crude product was triturated with haxanes. The purification afforded the title compound as a white solid (38.2 mg, 0.0920 mmol, 64% yield). $R_f$=0.39 (EtOAc:hexanes 3:7 (v/v)). NMR Spectroscopy: $^1H$ NMR (700 MHz, $CDCl_3$, ° C., δ): 8.89 (d, J=9.03 Hz, 1H), 8.81 (d, J=8.60 Hz, 1H), 8.41 (d, J=2.15 Hz, 1H), 8.19 (d, J=3.87 Hz, 1H), 8.05 (d, J=2.15 Hz, 1H), 7.34 (br. s, 1H), 6.57 (d, J=3.87 Hz, 1H), 2.28 (s, 3H). $^{13}C$ NMR (175 MHz, $CDCl_3$, 25° C., δ): 168.5, 145.8, 144.0, 143.5, 142.6, 133.0, 131.4, 127.5, 125.0, 120.2 (q, J=261.8 Hz), 120.0, 113.6, 112.7, 102.6, 24.9. $^{19}F$ NMR (376 MHz, $CDCl_3$, 25° C., δ): −56.4 (s). Mass Spectrometry: HRMS (ESI-TOF) (m/z): calcd for $C_{15}H_{11}BrF_3N_4O_2$ ([M+H]$^+$), 415.0012, found, 415.0018.

N-(6-(2-(Thiazol-4-yl)-1H-benzo[d] imidazol-1-yl)-2-(trifluoromethoxy)pyridin-3-yl)acetamide (9t)

A solution of N-hydroxy-N-(6-(2-(thiazol-4-yl)-1H-benzo[d]imidazol-1-yl)pyridin-3-yl)acetamide (8t) (100 mg, 0.285 mmol) and Togni reagent I (113 mg, 0.188 mmol, 1.20 equiv) in $CH_2Cl_2$ (2.85 mL, 0.100 M) was stirred at 23° C. under $N_2$ atmosphere for 20 h. The reaction mixture was then stirred at 50° C. for 4 h. The reaction mixture was concentrated in vacuo and the residue was triturated with hexanes. The purification afforded the title compound as a beige solid (113 mg, 0.270 mmol, 95% yield). $R_f$=0.42 (EtOAc). $^1H$ NMR (700 MHz, $(CD_3)_2SO$, 25° C., δ): 10.00 (s, 1H), 9.05 (s, 1H), 8.64 (d, J=8.60 Hz, 1H), 8.48 (s, 1H), 7.82 (d, J=7.31 Hz, 1H), 7.55 (d, J=8.17 Hz, 1H), 7.47 (d, J=7.31 Hz, 1H), 7.40-7.30 (m, 2H), 2.18 (s, 3H). $^{13}C$ NMR (175 MHz, $(CD_3)_2SO$, 25° C., δ): 169.5, 154.8, 146.6, 145.8, 145.0, 142.3, 141.2, 135.2, 135.1, 124.1, 123.5, 123.4, 122.7, 119.8, 119.6, 119.5 (q, J=260.0 Hz), 110.8, 23.6. $^{19}F$ NMR (376 MHz, $(CD_3)_2SO$, 25° C., δ): −57.2 (s). Mass Spectrometry: HRMS (ESI-TOF) (m/z): calcd for $C_{18}H_{13}F_3N_5O_2S$ ([M+H]$^+$), 420.0737, found, 420.0738.

N-(6-(2,6-Dichloro-9H-purin-9-yl)-2-(trifluoromethoxy)pyridin-3-yl)acetamide (9u) and N-(6-(2,6-dichloro-9H-purin-9-yl)-4-(trifluoromethoxy)pyridin-3-yl)acetamide (9u-II)

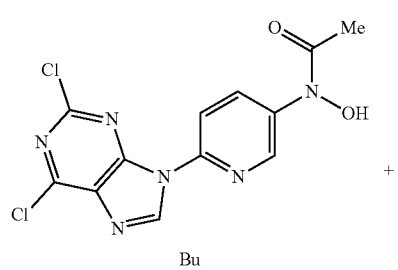

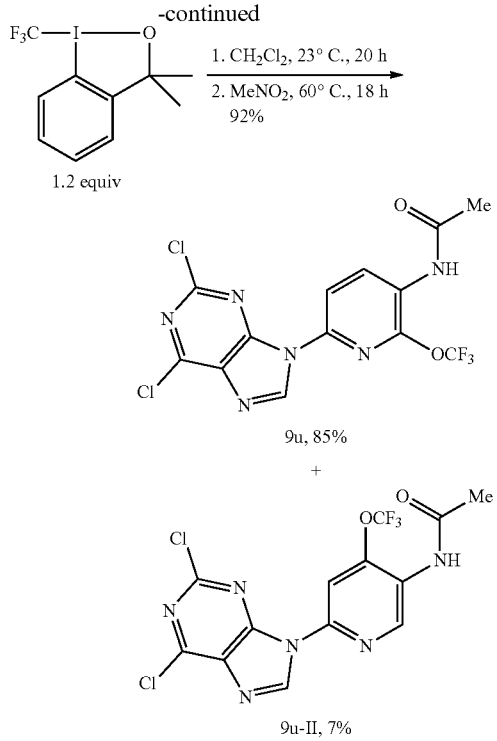

A solution of N-(6-(2,6-dichloro-9H-purin-9-yl)pyridin-3-yl)-N-hydroxyacetamide (8u) (38.4 mg, 0.113 mmol) and Togni reagent I (44.9 mg, 0.136 mmol, 1.20 equiv) in $CH_2Cl_2$ (1.13 mL, 0.100 M) was stirred at 23° C. under $N_2$ atmosphere for 20 h. The reaction mixture was concentrated in vacuo. The residue was dissolved in $MeNO_2$ (1.13 mL, 0.100 M) and the reaction mixture was stirred at 60° C. for 18 h. The reaction mixture was concentrated in vacuo. The residue was purified by preparative TLC (thickness: 1 mm) using hexanes:EtOAc (1:1 (v/v)) for development (prep TLC was developed three times). The purification afforded 9u (39.0 mg, 0.0968 mmol, 85% yield) and 9u-II (3.3 mg, 0.0081 mmol, 7% yield). Data for 9u: white solid; $R_f$=0.44 (EtOAc:hexanes 1:1 (v/v)). NMR Spectroscopy: $^1H$ NMR (700 MHz, $CDCl_3$, ° C., δ): 9.11 (d, J=8.60 Hz, 1H), 8.94 (s, 1H), 8.47 (d, J=8.60 Hz, 1H), 7.53 (s, 1H), 2.31 (s, 3H). $^{13}C$ NMR (175 MHz, $CDCl_3$, 25° C., δ): 168.8, 153.9, 152.6, 151.7, 143.6, 143.5, 138.4, 133.1, 132.3, 123.2, 120.1 (q, J=263.4 Hz), 113.1, 24.9. $^{19}F$ NMR (376 MHz, $CDCl_3$, 25° C., δ): −56.7 (s). Mass Spectrometry: HRMS (ESI-TOF) (m/z): calcd for $C_{13}H_8Cl_2F_3N_6O_2$ ([M+H]$^+$), 407.0032, found, 407.0037. Data for 9u-II: white solid; $R_f$=0.22 (EtOAc:hexanes 1:1 (v/v)). NMR Spectroscopy: $^1H$ NMR (700 MHz, $CDCl_3$, 25° C., δ): 9.60 (s, 1H), 9.20 (s, 1H), 8.67 (d, J=1.72 Hz, 1H), 7.39 (br. s, 1H), 2.33 (s, 3H). $^{13}C$ NMR (175 MHz, $CDCl_3$, 25° C., δ): 168.4, 153.9, 152.7, 151.6, 145.8, 143.9, 143.3, 142.9, 132.4, 126.2, 120.4 (q, J=262.3 Hz), 104.6, 24.7. $^{19}F$ NMR (376 MHz, $CDCl_3$, 25° C., δ): −57.9 (s). Mass Spectrometry: HRMS (ESI-TOF) (m/z): calcd for $C_{13}H_8Cl_2F_3N_6O_2$ ([M+H]$^+$), 407.0032, found, 407.0035.

Ethyl (E)-3-(4-fluoro-3-(2-methoxy-5-((methoxycarbonyl)amino)-6-(trifluoromethoxy) pyridin-3-yl)phenyl)acrylate (9v)

A solution of ethyl (E)-3-(4-fluoro-3-(5-(hydroxy(methoxycarbonyl) amino)-2-methoxypyridin-3-yl)phenyl)

acrylate (8v) (46.1 mg, 0.118 mmol) in CH$_2$Cl$_2$ (11.3 mL) was cooled to 4° C. A solution of Togni reagent I (46.9 mg, 0.142 mmol, 1.20 equiv) in CH$_2$Cl$_2$ (0.500 mL) was then added dropwise and the reaction mixture was stirred at 4° C. for 29 h. The reaction mixture was concentrated in vacuo. The residue was purified by preparative TLC (thickness: 1 mm) using hexanes:EtOAc (9:1 (v/v)) for development (prep TLC was developed four times). The purification afforded the title compound as a white solid (28.5 mg, 0.0622 mmol, 53% yield). R$_f$=0.62 (EtOAc:hexanes 3:7 (v/v)). NMR Spectroscopy: $^1$H NMR (700 MHz, CDCl$_3$, 25° C., δ): 8.44 (br. s, 1H), 7.66 (d, J=15.92 Hz, 1H), 7.57-7.50 (m, 2H), 7.15 (t, J=9.03 Hz, 1H), 6.68 (br. s, 1H), 6.38 (d, J=15.92 Hz, 1H), 4.26 (q, J=6.88 Hz, 2H), 3.89 (s, 3H), 3.80 (s, 3H), 1.33 (t, J=7.10 Hz, 3H). $^{13}$C NMR (175 MHz, CDCl$_3$, 25° C., δ): 166.9, 161.1 (d, J=252.7 Hz), 154.6, 154.0, 143.2, 134.2, 131.7 (d, J=2.6 Hz), 130.9 (d, J=3.3 Hz), 129.6 (d, J=8.7 Hz), 124.0 (J=15.6 Hz), 120.3 (q, J=261.5 Hz), 118.6 (d, J=1.8 Hz), 116.7, 116.6, 116.3, 115.7, 60.7, 54.5, 52.9, 14.4. $^{19}$F NMR (376 MHz, CDCl$_3$, 25° C., δ): −56.4 (s), −111.4 (s). Mass Spectrometry: HRMS (ESI-TOF) (m/z): calcd for C$_{20}$H$_{19}$F$_4$N$_2$O$_6$ ([M+H]$^+$), 459.1174, found, 459.1184.

Methyl 4-((4-(2-methoxy-5-((methoxycarbonyl)amino)-6-(trifluoro-methoxy)pyridin-3-yl)phenyl)ethynyl)benzoate (9w)

A solution of methyl 4-((4-(5-(hydroxy(methoxycarbo-nyl)amino)-2-methoxypyridin-3-yl)phenyl)ethynyl)benzoate (8w) (50.0 mg, 0.116 mmol) and Togni reagent I (45.9 mg, 0.139 mmol, 1.20 equiv) in CH$_2$Cl$_2$ (1.16 mL, 0.100 M) was stirred at 23° C. under N$_2$ atmosphere for 18 h. The reaction mixture was purified by preparative TLC (thickness: 1 mm) using CH$_2$Cl$_2$ for development (prep TLC was developed twice). The purification afforded the title compound as a white solid (39.6 mg, 0.0791 mmol, 68% yield). R$_f$=0.27 (CH$_2$Cl$_2$). NMR Spectroscopy: 1H NMR (700 MHz, CDCl$_3$, 25° C., δ): 8.51 (br. s, 1H), 8.03 (d, J=8.17 Hz, 2H), 7.68-7.50 (m, 6H), 6.68 (br. s, 1H), 3.93 (s, 3H), 3.92 (s, 3H), 3.81 (s, 3H). $^{13}$C NMR (175 MHz, CDCl$_3$, 25° C., δ): 166.7, 154.1, 142.3, 135.8, 133.1, 131.8, 131.7, 129.7, 129.6, 129.3, 128.1, 122.2, 121.8 (q, J=260.8 Hz), 121.3, 119.5, 116.7, 92.4, 89.5, 54.4, 52.9, 52.4. $^{19}$F NMR (376 MHz, CDCl$_3$, 25° C., δ): −56.4 (s). Mass Spectrometry: HRMS (ESI-TOF) (m/z): calcd for C$_{25}$H$_{20}$F$_3$N$_2$O$_6$ ([M+H]$^+$), 501.1268, found, 501.1273.

N-(6-(((8R,9S,13S,14S)-13-Methyl-17-oxo-7,8,9,11,12,13,14,15,16,17-decahydro-6H-cyclopenta[a]phenanthren-3-yl)oxy)-2-(trifluoro-methoxy)pyridin-3-yl)acetamide (9x)

A solution of N-hydroxy-N-(6-(((8R,9S,13S,14S)-13-methyl-17-oxo-7,8,9,11,12,13,14,15,16,17-decahydro-6H-cyclopenta[a]phenanthren-3-yl)oxy)pyridin-3-yl) acetamide (8x) (66.0 mg, 0.157 mmol) and Togni reagent I (62.1 mg, 0.188 mmol, 1.20 equiv) in CH$_2$Cl$_2$ (1.57 mL, 0.100 M) was stirred at 23° C. under N$_2$ atmosphere for 20 h. The reaction mixture was purified by preparative TLC (thickness: 1 mm) using hexanes:EtOAc (3:2 (v/v)) for development (prep TLC was developed three times). The purification afforded the title compound as a white foamy solid (54.0 mg, 0.111 mmol, 71% yield). R$_f$=0.49 (EtOAc:hexanes 1:1 (v/v)). NMR Spectroscopy: $^1$H NMR (700 MHz, CDCl$_3$, 25° C., δ): 8.62 (d, J=8.61 Hz, 1H), 7.37 (s, 1H), 7.27 (d, J=8.37 Hz, 1H), 6.91 (dd, J=8.39, 2.37 Hz, 1H), 6.88 (d, J=2.15 Hz, 1H), 6.68 (d, J=9.03 Hz, 1H), 2.92-2.86 (m, 2H), 2.51 (dd, J=18.93, 8.60 Hz, 1H), 2.44-2.37 (m, 1H), 2.30 (td, J=11.19, 3.44 Hz, 1H), 2.22 (s, 3H), 2.18-2.11 (m, 1H), 2.09-2.04 (m, 1H), 2.04-1.99 (m, 1H), 1.96 (dt, J=12.48, 3.01 Hz, 1H), 1.67-1.59 (m, 2H), 1.59-1.42 (m, 4H), 0.92 (s, 3H). $^{13}$C NMR (175 MHz, CDCl$_3$, 25° C., δ): 221.0, 168.6, 156.9, 151.7, 143.5, 138.2, 136.5, 134.7, 126.6, 120.8, 120.1 (q, J=261.5 Hz), 118.1, 118.0, 108.1, 50.6, 48.1, 44.2, 38.2, 36.0, 31.7, 29.5, 26.5, 25.9, 24.6, 21.7, 14.0. $^{19}$F NMR (376 MHz, CDCl$_3$, 25° C., δ): −56.4 (s). Mass Spectrometry: HRMS (ESI-TOF) (m/z): calcd for C$_{26}$H$_{28}$F$_3$N$_2$O$_4$ ([M+H]$^+$), 489.1996, found, 489.2004.

N-(6-((6R,12aR)-6-(Benzo[d][1,3]dioxol-5-yl)-2-methyl-1,4-dioxo-1,3,4,6,12,12a-hexahydropyrazino[1',2':1,6]pyrido[3,4-b]indol-7(2H)-yl)-2-(trifluoromethoxy)pyridin-3-yl)acetamide (9y)

A solution of N-(6-((6R,12aR)-6-(benzo[d] [1,3]dioxol-5-yl)-2-methyl-1,4-dioxo-1,3,4,6,12,12a-hexahydropyrazino[1',2':1,6]pyrido[3,4-b]indol-7(2H)-yl)-2-(trifluoromethoxy)pyridin-3-yl)acetamide (8y) (50.0 mg, 0.0927 mmol) in CH$_2$Cl$_2$ (8.77 mL) was cooled to 4° C. A solution of Togni reagent I (39.3 mg, 0.119 mmol, 1.20 equiv) in CH$_2$Cl$_2$ (0.500 mL) was then added dropwise and the reaction mixture was stirred at 4° C. for 16 h. The reaction mixture was concentrated in vacuo. The residue was purified by preparative TLC (thickness: 1 mm) using hexanes:EtOAc (1:4 (v/v)) for development (prep TLC was developed twice). The purification afforded the title compound as a white solid (37.3 mg, 0.0614 mmol, 66% yield). R$_f$=0.48 (EtOAc). NMR Spectroscopy: $^1$H NMR (700 MHz, (CD$_3$)$_2$SO, 25° C., δ): 9.99 (s, 1H), 8.53 (d, J=8.53 Hz, 1H), 7.80-7.72 (m, 1H), 7.42-7.36 (m, 1H), 7.34 (d, J=8.53 Hz, 1H), 7.25-7.19 (m, 2H), 6.59 (s, 1H), 6.51 (d, J=8.03 Hz, 1H), 6.32 (d, J=1.76 Hz, 1H), 6.23 (dd, J=8.03, 1.76 Hz, 1H), 5.83 (s, 2H), 4.55 (dd, J=11.54, 4.77 Hz, 1H), 4.24-4.15 (m, 1H), 3.92 (d, J=17.32 Hz, 1H), 3.65 (dd, J=16.19, 4.64 Hz, 1H), 3.12 (dd, J=15.81, 12.30 Hz, 1H), 2.90 (s, 3H), 2.18 (s, 3H). $^{13}$C NMR (175 MHz, (CD$_3$)$_2$SO, 25° C., δ): 169.4, 166.9, 166.3, 146.7, 146.0, 145.4, 141.7, 136.4, 136.0, 134.9, 134.2, 126.1, 123.4, 122.3, 121.3, 120.7, 119.7 (q, J=262.6 Hz), 119.1, 118.4, 110.4, 109.9, 107.5, 107.4, 100.9, 54.7, 53.9, 51.4, 32.8, 23.6, 23.2. $^{19}$F NMR (376 MHz, (CD$_3$)$_2$SO, 25° C., δ): −56.6 (s). Mass Spectrometry: HRMS (ESI-TOF) (m/z): calcd for C$_{30}$H$_{25}$F$_3$N$_5$O$_6$ ([M+H]$^+$), 608.1751, found, 608.1761.

Example 8. Trifluoromethoxylation of Pyrimidine Substrates

Figure 3:
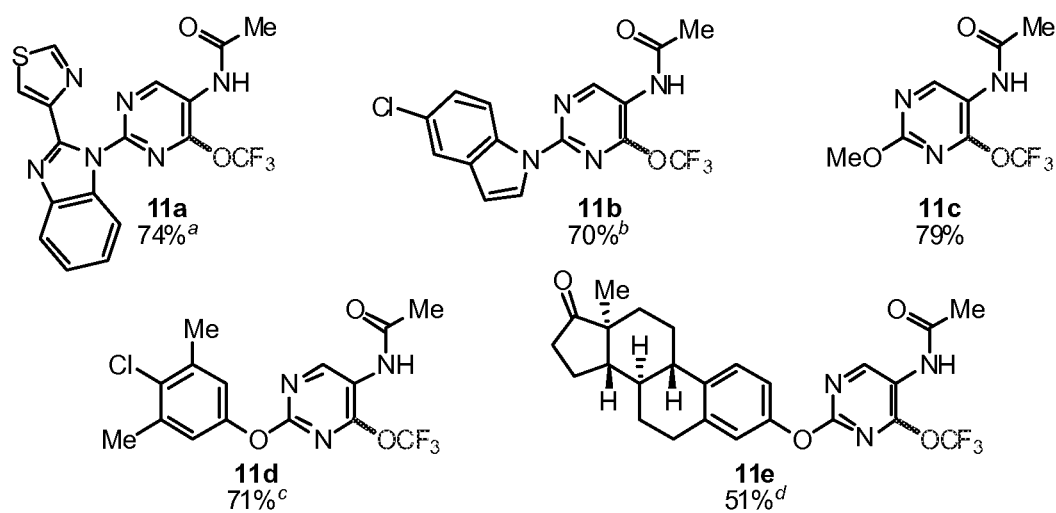
FIG. 3. Compounds 11a-11e. Cited yields are of isolated material by column chromatography. $^{a}$Following the O-trifluoromethylation reaction in CH₂Cl₂ at RT, the reaction mixture was concentrated, the residue was dissolved in MeNO₂, and the resulting mixture was heated at 80° C. $^{b}$CH₂Cl₂ (0.01 M). $^{c}$RT→50° C. in CH₂Cl₂ (0.03 M). $^{d}$RT→50° C. in CH₂Cl₂.

To probe the applicability of the trifluoromethoxylation reaction to other heteroarenes, pyrimidines substituted with benzimidazolyl (10a), indolyl (10b), methoxy (10c), phenoxy (10d), or estronyl (10e) groups were examined (Scheme 8). These substrates were trifluoromethoxylated to afford the corresponding desired products (11a-11e) in good yields. Products 11a-11e are shown in FIG. 3.

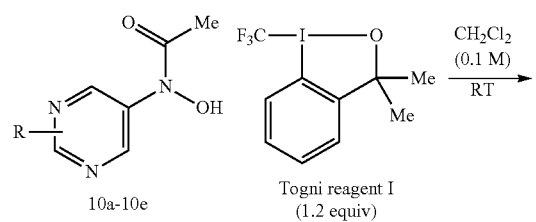

Scheme 8.

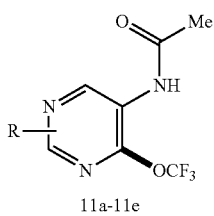

N-Hydroxy-N-(2-(2-(thiazol-4-yl)-1H-benzo[d]imidazol-1-yl)pyrimidin-5-yl)acetamide (10a)

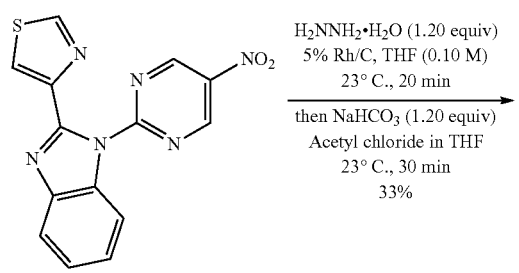

Under $N_2$ atmosphere, 4-(1H-benzo[d]imidazol-2-yl)thiazole (362 mg, 1.80 mmol, 1.20 equiv) was dissolved in THF (7.50 mL, 0.240 M) and stirred at 0° C. NaH (72.0 mg, 1.80 mmol, 1.20 equiv, 60% dispersion in mineral oil) was added in portionwise. After 30 min, a solution of 2-chloro-5-nitropyrimidine (239 mg, 1.50 mmol. 1.00 equiv) in THF (2.50 mL, 0.600 M) was added and then the reaction mixture was slowly warmed up to 50° C. for 12 h. The reaction mixture was poured to water (100 mL), extracted with EtOAc, washed with brine. The combined organic layers was dried ($MgSO_4$), filtered and concentrated in vacuo. The residue was purified by chromatography on silica gel, eluting with hexanes:EtOAc (5:1 to 1:1 (v/v)), to afford the title compound as a yellow solid (369 mg, 1.14 mmol, 76% yield). $R_f$=0.33 (hexanes:EtOAc 2:1 (v/v)). NMR Spectroscopy: $^1$H NMR (700 MHz, $CDCl_3$, 25° C., δ): 9.46 (s, 2H), 8.70 (d, J=2.15 Hz, 1H), 8.20 (s, 1H), 8.18-8.13 (m, 1H), 7.89 (dd, J=6.45, 2.58 Hz, 1H), 7.48-7.43 (m, 2H). $^{13}$C NMR (175 MHz, $CDCl_3$, 25° C., δ): 159.0, 154.5, 154.4, 152.7, 147.6, 147.3, 143.0, 139.7, 134.1, 125.7, 125.2, 121.1, 120.6, 113.6. Mass Spectrometry: HRMS (ESI-TOF) (m/z): calcd for $C_{14}H_9N_6O_2S$ ([M+H]$^+$), 325.0502, found, 325.0506. Under $N_2$ atmosphere, a suspension of 4-(1-(5-nitropyrimidin-2-yl)-1H-benzo[d]imidazol-2-yl)thiazole (200 mg, 0.620 mmol, 1.00 equiv) and 5% Rh/C (7.12 mg, 0.60 mol % Rh) in THF (6.20 mL, 0.100 M) was stirred at 23° C. Hydrazine monohydrate (37.0 mg, 0.740 mmol, 1.20 equiv) was added dropwise. The reaction mixture was stirred at 23° C. for 20 min. $NaHCO_3$ (62.2 mg, 0.740 mmol, 1.20 equiv) was added, followed by dropwise addition of a solution of acetyl chloride (58.1 mg, 0.740 mmol, 1.20 equiv) in THF (6.20 mL, 0.120 M). The reaction mixture was stirred at 23° C. for 30 min and then poured to water (100 mL), extracted with EtOAc. The combined organic layers was dried ($MgSO_4$), filtered and concentrated in vacuo. The residue was purified by chromatography on silica gel, eluting with hexanes:EtOAc (1:1 (v/v)), to afford the title compound as a yellow gum (72 mg, 0.204 mmol, 33% yield). $R_f$=0.13 (EtOAc). NMR Spectroscopy: $^1$H NMR (700 MHz, $(CD_3)_2SO$, 25° C., δ): 11.23 (s, 1H), 9.21 (s, 2H), 9.00 (br. s., 1H), 8.49 (d, J=1.72 Hz, 1H), 7.81 (dd, J=6.45, 1.72 Hz, 1H), 7.74-7.65 (m, 1H), 7.41-7.32 (m, 2H), 2.32 (s, 3H). $^{13}$C NMR (175 MHz, $(CD_3)_2SO$, 25° C., δ): 171.5, 154.5, 151.2, 148.0, 146.8, 146.3, 142.3, 135.4, 134.8, 124.3, 123.6, 122.0, 119.6, 111.9, 22.1. Mass Spectrometry: HRMS (ESI-TOF) (m/z): calcd for $C_{16}H_{13}N_6O_2S$ ([M+H]$^+$), 353.0815, found, 353.0817.

N-(2-(5-Chloro-1H-indol-1-yl)pyrimidin-5-yl)-N-hydroxyacetamide (10b)

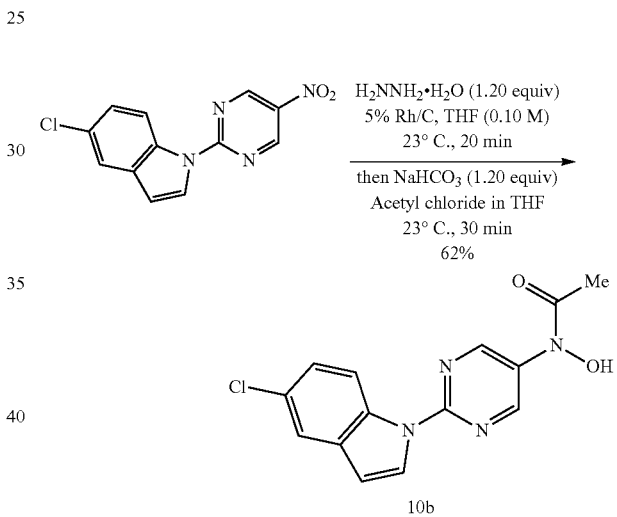

Under $N_2$ atmosphere, 5-chloro-1H-indole (0.570 g, 3.76 mmol, 1.20 equiv) was dissolved in DMF (10 mL, 0.376 M) and stirred at 0° C. NaH (0.15 g, 3.76 mmol, 1.20 equiv, 60% dispersion in mineral oil) was added in portionwise. After 30 min, a solution of 2-chloro-5-nitropyrimidine (0.500 g, 3.13 mmol. 1.00 equiv) in DMF (5.6 mL, 0.559 M) was added and then the reaction mixture was slowly warmed up to 50° C. for 12 h. The reaction mixture was poured to a solution of LiCl (100 mL), extracted with EtOAc. The combined organic layers washed with brine, dried ($MgSO_4$), filtered and concentrated in vacuo. The residue was purified by chromatography on silica gel, eluting with hexanes:EtOAc (10:1 to 5:1 (v/v)), to afford the title compound as a yellow solid (0.710 g, 2.58 mmol, 83% yield). $R_f$=0.76 (hexanes:EtOAc 4:1 (v/v)). NMR Spectroscopy: $^1$H NMR (700 MHz, $CDCl_3$, 25° C., δ): 9.43 (s, 2H), 8.69 (d, J=8.60 Hz, 1H), 8.27 (d, J=3.87 Hz, 1H), 7.58 (d, J=1.72 Hz, 1H), 7.33 (dd, J=8.82, 1.94 Hz, 1H), 6.73 (d, J=3.01 Hz, 1H). $^{13}$C NMR (175 MHz, $CDCl_3$, 25° C., δ): 158.7, 154.8, 138.2, 133.9, 133.3, 129.6, 127.5, 125.0, 121.0, 118.1, 109.7. Mass Spectrometry: HRMS (ESI-TOF) (m/z): calcd for $C_{12}H_{11}ClN_5O_2$ ([M+NH$_4$]$^+$), 292.0596, found, 292.0599. Under $N_2$ atmosphere, a suspension of 5-chloro-1-(5-nitropyrimidin-2-yl)-1H-indole (300 mg, 1.09 mmol, 1.00 equiv) and 5% Rh/C (12.6 mg, 0.60 mol % Rh) in THF (10.9 mL, 0.100 M) was stirred at 23° C. Hydrazine monohydrate (65.6 mg, 1.31 mmol, 1.20 equiv) was added dropwise. The reaction mixture was stirred at 23° C. for 20 min. NaHCO$_3$ (110 mg, 1.31 mmol, 1.20 equiv) was added, followed by dropwise addition of a solution of acetyl chloride (103 mg, 1.31 mmol, 1.20 equiv) in THF (10.9 mL, 0.120 M). The reaction mixture was stirred at 23° C. for 30 min and then poured to water (100 mL), extracted with EtOAc. The combined organic layers was dried (MgSO$_4$), filtered and concentrated in vacuo. The residue was recrystalized from hexanes/EtOAc, to afford the title compound as a yellow solid (205 mg, 0.677 mmol, 62% yield). R$_f$=0.14 (hexanes:EtOAc 2:1 (v/v)). $^1$H NMR (700 MHz, (CD$_3$)$_2$SO, 25° C., δ): 11.10 (s, 1H), 9.13 (s, 2H), 8.69 (d, J=9.03 Hz, 1H), 8.30 (d, J=3.87 Hz, 1H), 7.72 (d, J=2.15 Hz, 1H), 7.34 (dd, J=8.60, 2.15 Hz, 1H), 6.78 (d, J=3.87 Hz, 1H), 2.28 (s, 3H). $^{13}$C NMR (175 MHz, (CD$_3$)$_2$SO, 25° C., δ): 171.0, 152.5, 148.9, 133.1, 133.0, 132.0, 127.3, 126.4, 123.4, 120.2, 117.0, 106.1, 21.8. Mass Spectrometry: HRMS (ESI-TOF) (m/z): calcd for C$_{14}$H$_{12}$ClN$_4$O$_2$ ([M+H]$^+$), 303.0643, found, 303.0645.

N-Hydroxy-N-(2-methoxypyrimidin-5-yl)acetamide (10c)

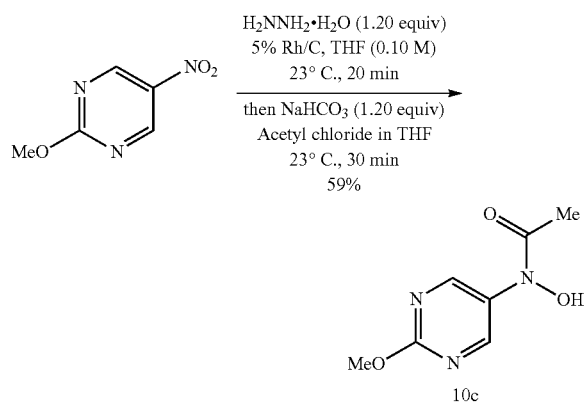

Under N$_2$ atmosphere, a suspension of 2-methoxy-5-nitropyrimidine (180 mg, 1.16 mmol, 1.00 equiv) and 5% Rh/C (13.8 mg, 0.60 mol % Rh) in THF (11.6 mL, 0.100 M) was stirred at 23° C. Hydrazine monohydrate (69.7 mg, 1.39 mmol, 1.20 equiv) was added dropwise. The reaction mixture was stirred at 23° C. for 20 min. NaHCO$_3$ (117 mg, 1.39 mmol, 1.20 equiv) was added, followed by dropwise addition of a solution of acetyl chloride (109 mg, 1.39 mmol, 1.20 equiv) in THF (11.6 mL, 0.120 M). The reaction mixture was stirred at 23° C. for 30 min and then filtered through a short pad of celite. The celite was washed with EtOAc. The combined organic solution was concentrated in vacuo. The residue was purified by chromatography on silica gel, eluting with hexanes:EtOAc (2:1 to 0:1 (v/v)), to afford the title compound as a gray gum (125 mg, 0.682 mmol, 59% yield). R$_f$=0.33 (EtOAc). NMR Spectroscopy: $^1$H NMR (700 MHz, (CD$_3$)$_2$SO, 25° C., δ): 10.93 (br. s, 1H), 8.81 (s, 2H), 3.91 (s, 3H), 2.22 (br. s., 3H). $^{13}$C NMR (175 MHz, (CD$_3$)$_2$SO, 25° C., δ): 170.7, 161.8, 151.0, 131.8, 54.9, 21.6. Mass Spectrometry: HRMS (ESI-TOF) (m/z): calcd for C$_7$H$_{10}$N$_3$O$_3$ ([M+H]$^+$), 184.0717, found, 184.0718.

N-(2-(4-Chloro-3,5-dimethylphenoxy)pyrimidin-5-yl)-N-hydroxyacetamide (10d)

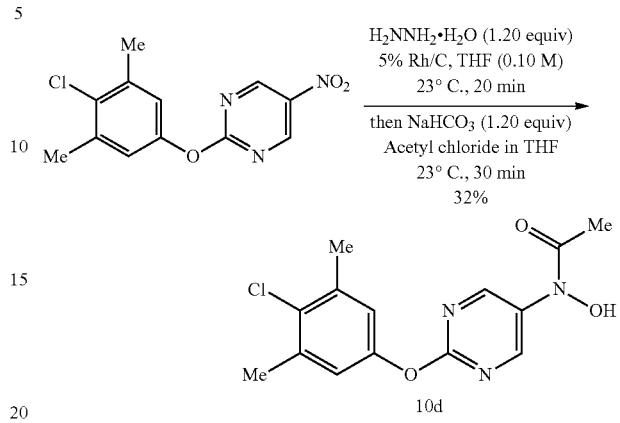

Under N$_2$ atmosphere, 4-chloro-3,5-dimethylphenol (240 mg, 1.52 mmol, 1.20 equiv) was dissolved in THF (8.40 mL, 0.181 M) and stirred at 0° C. NaH (60.8 mg, 1.52 mmol, 1.20 equiv, 60% dispersion in mineral oil) was added portionwise. After 30 min, a solution of 2-chloro-5-nitropyrimidine (200 mg, 1.24 mmol. 1.00 equiv) in THF (4.00 mL, 0.310 M) was added and then the reaction mixture was slowly warmed to 50° C. for 12 h. The reaction mixture was poured to water (100 mL), extracted with EtOAc, washed with brine. The combined organic layers was dried (MgSO$_4$), filtered and concentrated in vacuo. The residue was purified by chromatography on silica gel, eluting with hexanes:EtOAc (20:1 to 1:1 (v/v)), to afford the title compound as a yellow solid (288 mg, 1.03 mmol, 83% yield). R$_f$=0.61 (hexanes:EtOAc 10:1 (v/v)). NMR Spectroscopy: $^1$H NMR (500 MHz, CDCl$_3$, 25° C., δ): 9.32 (s, 2H), 6.94 (s, 2H), 2.41 (s, 6H). $^{13}$C NMR (125 MHz, CDCl$_3$, 25° C., δ): 167.1, 156.5, 149.9, 139.1, 138.4, 132.7, 121.1, 21.1. Mass Spectrometry: HRMS (ESI-TOF) (m/z): calcd for C$_{12}$H$_{11}$ClN$_3$O$_3$ ([M+H]$^+$), 280.0483, found, 280.0483. Under N$_2$ atmosphere, a suspension of 2-(4-chloro-3,5-dimethylphenoxy)-5-nitropyrimidine (140 mg, 0.500 mmol, 1.00 equiv) and 5% Rh/C (5.70 mg, 0.60 mol % Rh) in THF (5.00 mL, 0.100 M) was stirred at 23° C. Hydrazine monohydrate (30.0 mg, 0.60 mmol, 1.20 equiv) was added dropwise. The reaction mixture was stirred at 23° C. for 20 min. NaHCO$_3$ (50.4 mg, 0.600 mmol, 1.20 equiv) was added, followed by dropwise addition of a solution of acetyl chloride (47.1 mg, 0.600 mmol, 1.20 equiv) in THF (5.00 mL, 0.120 M). The reaction mixture was stirred at 23° C. for 30 min and then poured to water (100 mL), extracted with EtOAc. The combined organic layers was dried (MgSO$_4$), filtered and concentrated in vacuo. The residue was purified by chromatography on silica gel, eluting with hexanes:EtOAc (1:1 to 0:1 (v/v)), to afford the title compound as a yellow solid (49.1 mg, 0.160 mmol, 32% yield). R$_f$=0.53 (EtOAc). NMR Spectroscopy: $^1$H NMR (700 MHz, (CD$_3$)$_2$SO, 25° C., δ): 10.99 (br. s., H), 8.86 (s, 2H), 7.08 (s, 2H), 2.33 (s, 6H), 2.23 (br. s., 3H). $^{13}$C NMR (175 MHz, (CD$_3$)$_2$SO, 25° C., δ): 170.9, 161.0, 151.0, 137.1, 133.0, 129.9, 121.6, 21.6, 20.3. Mass Spectrometry: HRMS (ESI-TOF) (m/z): calcd for C$_{14}$H$_{15}$ClN$_3$O$_3$ ([M+H]$^+$), 308.0802, found, 308.0797.

N-Hydroxy-N-(2-(((8R,9S,13S,14S)-13-methyl-17-oxo-7,8,9,11,12,13,14,15,16,17-decahydro-6H-cyclopenta[a]phenanthren-3-yl)oxy)pyrimidin-5-yl)acetamide (10e)

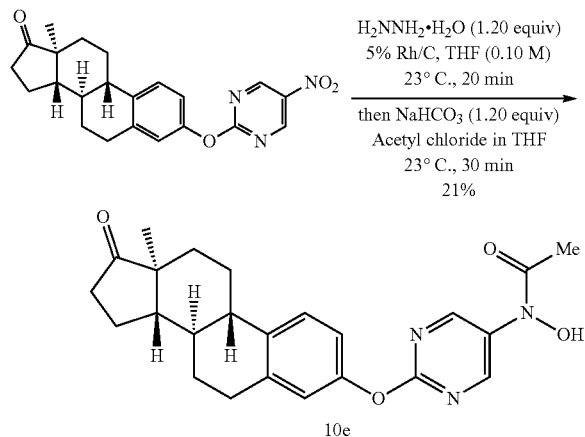

Under $N_2$ atmosphere, estrone (200 mg, 0.740 mmol, 1.00 equiv) was dissolved in THF (3.70 mL, 0.200 M) and stirred at 0° C. NaH (29.6 mg, 0.740 mmol, 1.00 equiv, 60% dispersion in mineral oil) was added in portionwise. After 30 min, a solution of 2-chloro-5-nitropyrimidine (130 mg, 0.81 mmol. 1.10 equiv) in THF (1.30 mL, 0.623 M) was added and then the reaction mixture was slowly warmed to 50° C. for 12 h. The reaction mixture was poured to water (100 mL), extracted with EtOAc, washed with brine. The combined organic layers was dried ($MgSO_4$), filtered and concentrated in vacuo. The residue was purified by chromatography on silica gel, eluting with hexanes:EtOAc (5:1 to 2:1 (v/v)), to afford the title compound as a yellow solid (235 mg, 0.597 mmol, 81% yield). $R_f$=0.33 (hexanes:EtOAc 4:1 (v/v)). NMR Spectroscopy: $^1$H NMR (700 MHz, $CDCl_3$, 25° C., δ): 9.32 (s, 2H), 7.38 (d, J=8.60 Hz, 1H), 6.97 (dd, J=8.60, 2.15 Hz, 1H), 6.92 (d, J=2.15 Hz, 1H), 2.97-2.91 (m, 2H), 2.51 (dd, J=19.36, 8.60 Hz, 1H), 2.46-2.40 (m, 1H), 2.34 (td, J=11.08, 4.09 Hz, 1H), 2.19-2.11 (m, 1H), 2.10-2.02 (m, 2H), 1.98 (dt, J=12.80, 2.85 Hz, 1H), 1.68-1.57 (m, 3H), 1.57-1.46 (m, 3H), 0.92 (s, 3H). $^{13}$C NMR (175 MHz, $CDCl_3$, 25° C., δ): 220.8, 167.3, 156.4, 150.2, 138.9, 138.3, 127.0, 121.2, 118.5, 50.5, 48.0, 44.3, 38.0, 35.9, 31.6, 29.6, 26.4, 25.8, 21.7, 13.9. Mass Spectrometry: HRMS (ESI-TOF) (m/z): calcd for $C_{22}H_{24}N_3O_4$ ([M+H]$^+$), 394.1761, found, 394.1758.

Under $N_2$ atmosphere, a suspension of (8R,9S,13S,14S)-13-methyl-3-((5-nitropyrimidin-2-yl)oxy)-6,7,8,9,11,12,13,14,15,16-decahydro-17H-cyclopenta[a]phenanthren-17-one (170 mg, 0.430 mmol, 1.00 equiv) and 5% Rh/C (4.90 mg, 0.60 mol % Rh) in THF (4.30 mL, 0.100 M) was stirred at 23° C. Hydrazine monohydrate (26.0 mg, 0.52 mmol, 1.20 equiv) was added dropwise. The reaction mixture was stirred at 23° C. for 20 min. $NaHCO_3$ (43.7 mg, 0.520 mmol, 1.20 equiv) was added, followed by dropwise addition of acetyl chloride (40.8 mg, 0.520 mmol, 1.20 equiv) in THF (4.30 mL, 0.120 M). The reaction mixture was stirred at 23° C. for 30 min and then poured to water (100 mL), extracted with EtOAc. The combined organic layers was dried ($MgSO_4$), filtered and concentrated in vacuo. The residue was purified by chromatography on silica gel, eluting with hexanes: EtOAc (2:1 (v/v)), to afford the title compound as a yellow solid (38 mg, 0.0902 mmol, 21% yield). $R_f$=0.50 (EtOAc). NMR Spectroscopy: $^1$H NMR (700 MHz, $(CD_3)_2SO$, 25° C., δ): 10.98 (br. s., 1H), 8.83 (s, 1H), 7.33 (d, J=8.17 Hz, 1H), 6.93 (dd, J=8.60, 2.58 Hz, 1H), 6.89 (d, J=2.58 Hz, 1H), 2.88-2.84 (m, 2H) 2.45 (dd, J=19.15, 8.39 Hz, 1H), 2.42-2.38 (m, 1H), 2.30-2.25 (m, 1H), 2.23 (br. s., 3H), 2.11-2.05 (m, 1H), 2.00-1.93 (m, 2H) 1.80-1.76 (m, 1H), 1.62-1.36 (m, 6H), 0.86 (s, 3H). $^{13}$C NMR (175 MHz, $(CD_3)_2SO$, δ): 219.7, 170.8, 161.3, 150.8, 138.0, 136.6, 132.8, 126.6, 121.2, 118.7, 49.6, 47.3, 43.6, 37.6, 35.4, 31.4, 29.0, 25.9, 25.4, 21.6, 21.2, 13.5. Mass Spectrometry: HRMS (ESI-TOF) (m/z): calcd for $C_{24}H_{28}N_3O_4$ ([M+H]$^+$), 422.2074, found, 422.2074.

N-(2-(2-(Thiazol-4-yl)-1H-benzo[d]imidazol-1-yl)-4-(trifluoromethoxy) pyrimidin-5-yl)acetamide (11a)

A solution of N-hydroxy-N-(2-(2-(thiazol-4-yl)-1H-benzo[d] imidazol-1-yl)pyrimidin-5-yl)acetamide (10a) (52.0 mg, 0.148 mmol) and Togni reagent I (58.8 mg, 0.178 mmol, 1.20 equiv) in $CH_2Cl_2$ (1.48 mL, 0.100 M) was stirred at 23° C. under $N_2$ atmosphere for 22 h. The reaction mixture was concentrated in vacuo. The residue was dissolved in $MeNO_2$ (1.48 mL, 0.100 M) and the reaction mixture was stirred at 80° C. for 18 h. The reaction mixture was concentrated in vacuo. The residue was purified by preparative TLC (thickness: 1 mm) using hexanes:EtOAc (1:4 (v/v)) for development (prep TLC was developed twice). The purification afforded the title compound as an off-white solid (45.9 mg, 0.109 mmol, 74% yield). $R_f$=0.59 (EtOAc). NMR Spectroscopy: 1H NMR (700 MHz, $CDCl_3$, 25° C., δ): 9.70 (s, 1H), 8.66 (d, J=2.15 Hz, 1H), 8.14 (d, J=2.15 Hz, 1H), 7.97 (dd, J=6.24, 3.23 Hz, 1H), 7.86-7.82 (m, 1H), 7.80 (s, 1H), 7.42-7.36 (m, 2H), 2.23 (s, 3H). $^{13}$C NMR (175 MHz, $CDCl_3$, 25° C., δ): 168.8, 152.7, 152.1, 151.5, 149.4, 147.3, 147.1, 142.7, 134.6, 125.1, 124.4, 120.8, 120.1, 119.6, 119.5 (q, J=265.7 Hz), 112.8, 24.4. $^{19}$F NMR (376 MHz, $CDCl_3$, 25° C., δ): −57.0 (s). Mass Spectrometry: HRMS (ESI-TOF) (m/z): calcd for $C_{17}H_{12}F_3N_6O_2S$ ([M+H]$^+$), 421.0689, found, 421.0693.

N-(2-(5-Chloro-1H-indol-1-yl)-4-(trifluoromethoxy) pyrimidin-5-yl)acetamide (11b)

A solution of N-(2-(5-chloro-1H-indol-1-yl)pyrimidin-5-yl)-N-hydroxyacetamide (10b) (50.0 mg, 0.165 mmol) and Togni reagent I (65.4 mg, 0.198 mmol, 1.20 equiv) in $CH_2Cl_2$ (16.5 mL, 0.010 M) was stirred at 23° C. under $N_2$ atmosphere for 24 h. The reaction mixture was concentrated in vacuo. The residue was purified by preparative TLC (thickness: 1 mm) using hexanes:EtOAc (3:2 (v/v)) for development (prep TLC was developed twice). The purification afforded the title compound as an off-white solid (42.8 mg, 0.115 mmol, 70% yield). $R_f$=0.61 (EtOAc: hexanes 1:1 (v/v)). NMR Spectroscopy: $^1$H NMR (700 MHz, $CDCl_3$, 25° C., δ): 9.55 (s, 1H), 8.54 (d, J=9.03 Hz, 1H), 8.13 (d, J=3.44 Hz, 1H), 7.56 (d, J=2.15 Hz, 1H), 7.28 (dd, J=8.60, 2.15 Hz, 1H), 7.18 (s, 1H), 6.62 (d, J=3.44 Hz, 1H), 2.29 (s, 3H). $^{13}$C NMR (175 MHz, $CDCl_3$, 25° C., δ): 168.5, 152.6, 152.4, 151.1, 133.5, 132.5, 128.2, 127.1, 124.2, 120.6, 120.0 (q, J=265.0 Hz), 116.8, 116.6, 107.0, 24.4. $^{19}$F NMR (376 MHz, $CDCl_3$, 25° C., δ): −56.6 (s). Mass Spectrometry: HRMS (ESI-TOF) (m/z): calcd for $C_{15}H_{11}ClF_3N_4O_2$ ([M+H]$^+$), 371.0517, found, 371.0523.

N-(2-Methoxy-4-(trifluoromethoxy)pyrimidin-5-yl) acetamide (11c)

A solution of N-hydroxy-N-(2-methoxypyrimidin-5-yl)acetamide (10c) (45.0 mg, 0.246 mmol) and Togni reagent I (97.4 mg, 0.295 mmol, 1.20 equiv) in CH$_2$Cl$_2$ (2.46 mL, 0.100 M) was stirred at 23° C. under N$_2$ atmosphere for 21 h. The reaction mixture was concentrated in vacuo. The residue was purified by preparative TLC (thickness: 1 mm) using hexanes:EtOAc (1:1 (v/v)) for development (prep TLC was developed twice). The purification afforded the title compound as a white solid (48.7 mg, 0.194 mmol, 79% yield). R$_f$=0.38 (EtOAc:hexanes 1:1 (v/v)). NMR Spectroscopy: $^1$H NMR (700 MHz, CDCl$_3$, 25° C., δ): 9.22 (s, 1H), 7.46 (br. s, 1H), 3.96 (s, 3H), 2.22 (s, 3H). $^{13}$C NMR (175 MHz, CDCl$_3$, 25° C., δ): 168.8, 160.4, 154.5, 154.3, 119.7 (q, J=264.3 Hz), 115.3, 55.6, 24.0. $^{19}$F NMR (376 MHz, CDCl$_3$, 25° C., δ): −56.6 (s). Mass Spectrometry: HRMS (ESI-TOF) (m/z): calcd for C$_8$H$_9$F$_3$N$_3$O$_3$ ([M+H]$^+$), 252.0591, found, 252.0593.

N-(2-(4-Chloro-3,5-dimethylphenoxy)-4-(trifluoromethoxy)pyrimidin-5-yl)acetamide (11d)

A solution of N-(2-(4-chloro-3,5-dimethylphenoxy)pyrimidin-5-yl)-N-hydroxyacetamide (10d) (30.5 mg, 0.0991 mmol) and Togni reagent I (39.3 mg, 0.119 mmol, 1.20 equiv) in CH$_2$Cl$_2$ (2.97 mL, 0.334 M) was stirred at 23° C. under N$_2$ atmosphere for 24 h. The reaction mixture was then stirred at 50° C. for 22 h. The reaction mixture was concentrated in vacuo. The residue was purified by preparative TLC (thickness: 1 mm) using hexanes:EtOAc (3:2 (v/v)) for development (prep TLC was developed once). The purification afforded the title compound as a white solid (26.5 mg, 0.0705 mmol, 71% yield). R$_f$=0.40 (EtOAc:hexanes 2:3 (v/v)). NMR Spectroscopy: $^1$H NMR (400 MHz, CDCl$_3$, 25° C., δ): 9.32 (s, 1H), 7.16 (br. s, 1H), 6.92 (s, 2H), 2.38 (s, 6H), 2.25 (s, 3H). $^{13}$C NMR (175 MHz, CDCl$_3$, 25° C., δ): 168.5, 159.3, 154.2, 153.5, 150.2, 137.8, 131.7, 121.3, 119.8 (q, J=265.1 Hz), 116.7, 24.3, 21.0. $^{19}$F NMR (376 MHz, CDCl$_3$, 25° C., δ): −56.7 (s). Mass Spectrometry: HRMS (ESI-TOF) (m/z): calcd for C$_{15}$H$_{14}$ClF$_3$N$_3$O$_3$ ([M+H]$^+$), 376.0670, found, 376.0677.

N-(2-(((8S,9R,13R,14R)-13-Methyl-17-oxo-7,8,9,11,12,13,14,15,16,17-decahydro-6H-cyclopenta[a]phenanthren-3-yl)oxy)-4-(trifluoromethoxy)pyrimidin-5-yl)acetamide (11e)

A solution of N-hydroxy-N-(2-(((8S,9R,13R,14R)-13-methyl-17-oxo-7,8,9,11,12,13,14,15,16,17-decahydro-6H-cyclopenta[a]phenanthren-3-yl)oxy)pyrimidin-5-yl)acetamide (10e) (25.0 mg, 0.0593 mmol) and Togni reagent I (23.5 mg, 0.0712 mmol, 1.20 equiv) in CH$_2$Cl$_2$ (0.593 mL, 0.100 M) was stirred at 23° C. under N$_2$ atmosphere for 16 h. The reaction mixture was then stirred at 50° C. for 24 h. The reaction mixture was concentrated in vacuo. The residue was purified by preparative TLC (thickness: 1 mm) using hexanes:EtOAc (3:2 (v/v)) for development (prep TLC was developed twice). The purification afforded the title compound as a white solid (14.9 mg, 0.0304 mmol, 51% yield). R$_f$=0.47 (EtOAc:hexanes 3:2 (v/v)). NMR Spectroscopy: $^1$H NMR (700 MHz, CDCl$_3$, 25° C., δ): 9.32 (s, 1H), 7.32 (d, J=8.60 Hz, 1H), 7.14 (s, 1H), 6.96 (dd, J=8.39, 2.37 Hz, 1H), 6.92 (d, J=2.58 Hz, 1H), 2.95-2.90 (m, 2H), 2.51 (dd, J=18.93, 8.60 Hz, 1H), 2.45-2.39 (m, 1H), 2.31 (td, J=11.19, 3.87 Hz, 1H), 2.25 (s, 3H), 2.19-2.11 (m, 1H), 2.09-2.05 (m, 1H), 2.04-2.00 (m, 1H), 1.97 (dt, J=12.58, 3.17 Hz, 1H), 1.67-1.60 (m, 2H), 1.58 (dd, J=12.48, 3.87 Hz, 1H), 1.56-1.43 (m, 3H), 0.92 (s, 3H). $^{13}$C NMR (175 MHz, CDCl$_3$, 25° C., δ): 221.0, 168.4, 159.6, 154.3, 153.5, 150.5, 138.3, 137.4, 126.7, 121.5, 119.8 (q, J=265.1 Hz), 118.7, 116.5, 50.6, 48.1, 44.3, 38.1, 36.0, 31.7, 29.6, 26.5, 25.8, 24.3, 21.7, 14.0. $^{19}$F NMR (376 MHz, CDCl$_3$, 25° C., δ): −56.6 (s). Mass Spectrometry: HRMS (ESI-TOF) (m/z): calcd for C$_{25}$H$_{27}$F$_3$N$_3$O$_4$ ([M+H]$^+$), 490.1948, found, 490.1957.

Example 9. Gram Scale Reaction of Pyridine Substrates and Further Functionalization To ensure that the products disclosed herein can serve as useful building blocks for molecular screening, the protocol must be scalable and further functionalization of the trifluoromethoxylated products must be possible. To evaluate the reaction efficacy on preparative scale, a gram-scale reaction of 8a (1.39 g, 5.00 mmol) was performed (Scheme 9a) and the efficiency of the small-scale reaction was retained upon scale-up. The trifluoromethoxylated products also proved to be versatile (Scheme 9). For examples, 9a could be further elaborated through palladium-catalyzed Suzuki and Sonogashira couplings to afford the desired products (13a, 15a) in good yields. In addition, deprotected amino-pyridine (9a') could be efficiently incorporated into other molecules through amidation and palladium-catalyzed Buchwald-Hartwig coupling (12a, 14a).

Scheme 9.

a. Gram-scale synthesis of 9a

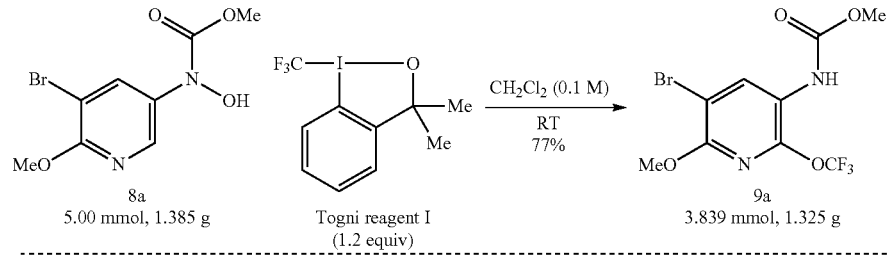

b. Post-functionalization of 2a and 2a′

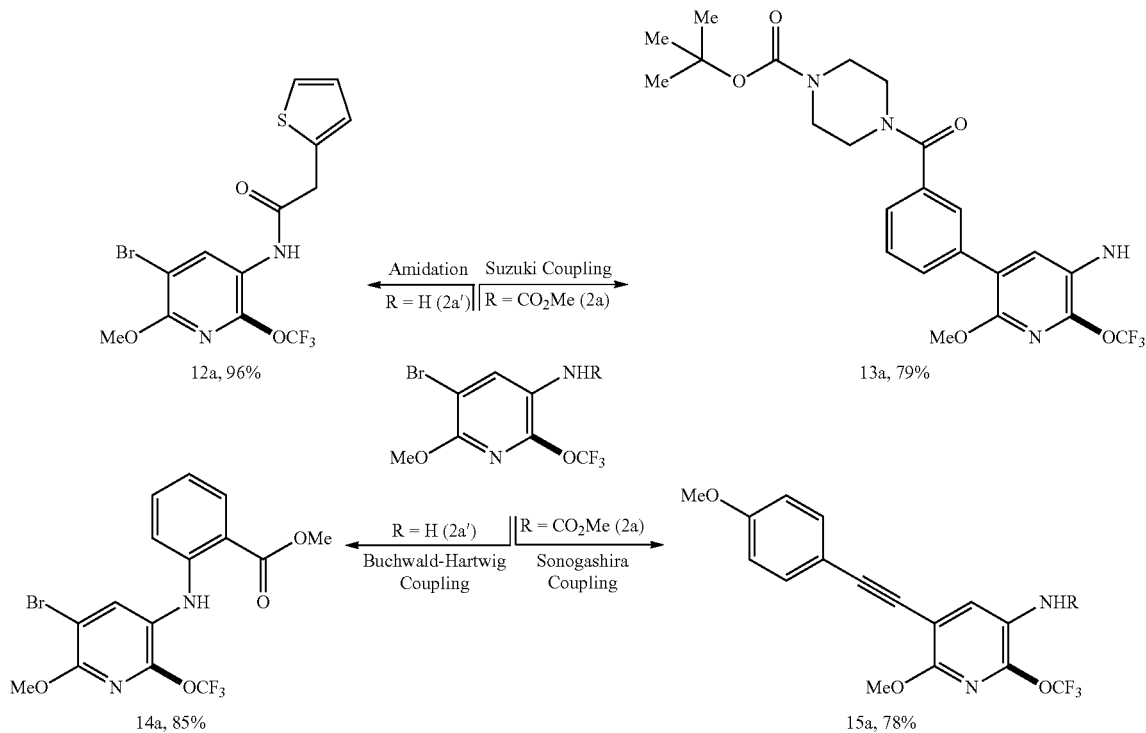

Methyl (5-bromo-6-methoxy-2-(trifluoromethoxy) pyridin-3-yl) carbamate (9a)

A solution of methyl (5-bromo-6-methoxypyridin-3-yl) (hydroxy)carbamate (8a) (1.39 g, 5.00 mmol) and Togni reagent I (1.98 g, 6.00 mmol, 1.20 equiv) in CH$_2$Cl$_2$ (50.0 mL, 0.100 M) was stirred at 23° C. under N$_2$ atmosphere for 18 h. The reaction mixture was concentrated in vacuo. The residue was purified by flash chromatography eluting with hexanes and then with EtOAc:hexanes (3:17 (v/v)). The purification afforded the title compound (2.51 g, 9.05 mmol, 95% yield), which was spectroscopically identical to the compound prepared according to the standard procedure (vide supra).

N-(5-Bromo-6-methoxy-2-(trifluoromethoxy)pyridin-3-yl)-2-(thiophen-2-yl)acetamide (12a)

To a solution of 2-(thiophen-2-yl)acetic acid (49.5 mg, 0.348 mmol, 2.0 equiv), DMF (1 drop) and DCM (3.50 mL, 0.100 M) at 0° C. under N$_2$ atmosphere was added dropwise oxalyl chloride (44.2 mg, 0.348 mmol, 2.0 equiv) via a syringe. The resulting mixture was stirred at 23° C. for 2 h, concentrated to afford crude acid chloride, which was used in the subsequent step without further purification. The above crude acid chloride was dissolved in CH$_3$CN (1.5 mL, 0.0232 M) and added to a solution of 5-bromo-6-methoxy-2-(trifluoromethoxy)pyridin-3-amine (9a′) (50 mg, 0.174 mmol, 1.0 equiv) in CH$_3$CN (3.5 mL, 0.0497 M) at 23° C. under N$_2$ atmosphere. The reaction mixture was stirred at 23° C. for another 2 h, concentrated in vacuo and purified by chromatography on silica gel, eluting with hexanes:EtOAc (5:1 (v/v)), to afford the title compound as a yellow solid (69.0 mg, 0.167 mmol, 96% yield). R$_f$=0.20 (EtOAc: hexanes 1:4 (v/v)). NMR Spectroscopy: $^1$H NMR (500 MHz, CDCl$_3$, 25° C., δ): 8.87 (s, 1H), 7.40 (br. s., 1H), 7.34 (dd, J=5.04, 1.07 Hz, 1H), 7.09-7.03 (m, 2H), 3.97 (s, 2H), 3.92 (s, 3H). $^{13}$C NMR (125 MHz, CDCl$_3$, 25° C., δ): 168.1, 154.2, 142.2, 136.5, 134.8, 128.3, 127.9, 126.6, 119.9 (q, J=261.8 Hz), 116.8, 102.6, 55.2, 38.4. $^{19}$F NMR (376 MHz, CDCl$_3$, 25° C., δ): −57.1 (s). Mass Spectrometry: HRMS (ESI-TOF) (m/z): calcd for C$_{13}$H$_{11}$BrF$_3$N$_2$O$_3$S ([M+H]$^+$), 412.9600, found, 412.9605.

tert-Butyl 4-(3-(2-methoxy-5-((methoxycarbonyl)amino)-6-(trifluoromethoxy)pyridin-3-yl)benzoyl) piperazine-1-carboxylate (13a)

Methyl (5-bromo-6-methoxy-2-(trifluoromethoxy)pyridin-3-yl)carbamate (9a) (0.0600 g, 0.170 mmol, 1.00 equiv), methyl tert-butyl 4-(3-(4,4,5,5-tetramethyl-1,3,2-dioxaborolan-2-yl)benzoyl) piperazine-1-carboxylate (0.103 g, 0.240 mmol, 1.40 equiv), Na$_2$CO$_3$ (0.287 g, 0.430 mmol, 2.5 equiv), THF:H$_2$O 4:3 (1.01 mL, 0.200 M), and palladium-tetrakis(triphenylphosphine) (0.002 g, 0.020 mmol, 0.0500 equiv) were degassed via three freeze-pump-thaw cycles. The resulting mixture was heated at 60° C. for 72 hours and then allowed to cool to room temperature after which water was added (twice the volume of THF:H$_2$O 4:3 used). The mixture was then extracted with ethyl acetate (twice the volume of THF:H$_2$O 4:3 used) and the organic extracts was dried with MgSO$_4$, filtered purified by preparative TLC (thickness: 1 mm) using EtOAc:hexanes (2:3 (v/v)) for development (prep TLC was developed three times) to afford the pure cross-coupled product as a white solid (0.077 g, 0.14 mmol, 79% yield). R$_f$=0.20 (EtOAc:hexanes 2:3 (v/v)). NMR Spectroscopy: $^1$H NMR (700 MHz, CDCl$_3$, 25° C., δ): 8.47 (br. s, 1H), 7.64-7.59 (m, 2H), 7.47 (t, J=8.17 Hz, 1H), 7.40 (d, J=7.31 Hz, 1H), 6.68 (br. s, 1H), 3.90 (s, 3H), 3.80 (s, 3H), 3.76 (br. s., 2H), 3.60-3.34 (m, 6H), 1.47 (s, 9H). $^{13}$C NMR (175 MHz, CDCl$_3$, °C., δ): 170.4, 154.7, 154.1, 142.5, 135.7, 135.5, 133.4, 130.7, 128.9, 127.9, 126.7, 121.0, 120.2 (q, J=261.2 Hz), 116.7, 80.5, 54.4, 52.9, 47.7, 43.8, 42.2, 28.5. $^{19}$F NMR (376 MHz, CDCl$_3$, 25° C., δ): −56.4 (s).

Methyl 2-((5-bromo-6-methoxy-2-(trifluoromethoxy)pyridin-3-yl)amino)benzoate (14a)

A mixture of 5-bromo-6-methoxy-2-(trifluoromethoxy)pyridin-3-amine (9a') (50.0 mg, 0.200 mmol, 1.20 equiv), methyl 2-iodobenzoate (44.5 mg, 0.170 mmol, 1.00 equiv), xantphos (10.0 mg, 0.0170 mmol, 0.100 equiv), NaO$^t$Bu (2.30 mg, 0.238 mmol, 1.40 equiv), and Pd$_2$(dba)$_3$ (7.80 mg, 0.00850 mmol, 0.05 equiv) in toluene (0.850 mL, 0.200 M) was stirred at 100° C. under N$_2$ for 40 hours and then allowed to cool to room temperature. The reaction was purified by preparative TLC (thickness: 1 mm) using EtOAc:hexanes (1:10 (v/v)) for development (prep TLC was developed two times) to afford title compound as a colorless liquid (61.0 mg, 0.145 mmol, 85% yield). R$_f$=0.71 (EtOAc:hexanes 1:10 (v/v)). NMR Spectroscopy: $^1$H NMR (700 MHz, CDCl$_3$, 25° C., δ): 9.23 (s, 1H), 8.01-7.97 (m, 1H), 7.95 (s, 1H), 7.36 (t, J=7.74 Hz, 1H), 6.87 (d, J=8.60 Hz, 1H), 6.82-6.79 (m, 1H), 3.99 (s, 3H), 3.92 (s, 3H). $^{13}$C NMR (125 MHz, CDCl$_3$, 25° C., δ): 168.9, 154.5, 147.2, 146.8, 139.7, 134.5, 131.9, 120.2 (q, J=260.9 Hz), 119.7, 118.3, 113.4, 112.8, 102.1, 52.3, 52.1. $^{19}$F NMR (376 MHz, CDCl$_3$, 25° C., δ): −56.5 (s). Mass Spectrometry: HRMS (ESI-TOF) (m/z): calcd for C$_{15}$H$_{13}$BrF$_3$N$_2$O$_4$ ([M+H]$^+$), 421.0005, found, 421.0010.

Methyl (6-methoxy-5-((4-methoxyphenyl) ethynyl)-2-(trifluoromethoxy)pyridin-3-yl)carbamate (15a)

Under N$_2$ atmosphere methyl (5-bromo-6-methoxy-2-(trifluoromethoxy)pyridin-3-yl)carbamate (15a) (0.0500 g, 0.140 mmol, 1.00 equiv), 1-ethynyl-4-methoxybenzene (0.0270 g, 0.200 mmol, 1.40 equiv), copper(I) iodide (0.550 mg, 2.90 μmol, 0.0200 equiv), and [1,1'-bis(diphenylphosphino) ferrocene]dichloropalladium(II), complex with dichloromethane (1.20 mg, 1.40 μmol, 0.0200 equiv in THF (0.72 mL, 0.200 M), was heated at 60° C. overnight and then allowed to cool to room temperature after which water was added (twice the volume of THF). The mixture was then extracted with ethyl acetate (twice the volume of THF:H$_2$O 4:3 used) and the organic extracts was dried with MgSO$_4$, filtered purified by preparative TLC (thickness: 1 mm) using EtOAc:hexanes (1:9 (v/v)) for development (prep TLC was developed three times) to afford the pure cross-coupled product as a white solid (0.045 g, 0.11 mmol, 78% yield). R$_f$=0.38 (EtOAc:hexanes 3:16 (v/v)). NMR Spectroscopy: $^1$H NMR (700 MHz, CDCl$_3$, 25° C., δ): 8.54 (br. s, 1H), 7.50-7.46 (m, 2H), 6.90-6.85 (m, 2H), 6.60 (br. s, 1H), 3.96 (s, 3H), 3.83 (s, 3H), 3.81 (s, 3H). $^{13}$C NMR (175 MHz, CDCl$_3$, 25° C., δ): 160.0, 157.3, 153.9, 142.1, 135.4, 133.4, 120.3 (q, J=261.6 Hz), 116.1, 115.0, 114.1, 105.3, 95.0, 81.7, 55.5, 54.8, 52.9. $^{19}$F NMR (376 MHz, CDCl$_3$, 25° C., δ): −56.4 (s).

Example 10. Mechanistic Studies and Proposed Reaction Mechanism

To gain some insight into the reaction mechanism, reactions in the presence of radical trap butylated hydroxytoluene (BHT) (Scheme 10a) were performed. We chose to use substrate 8d because we could isolate the O-trifluoromethylated intermediate 8d' and study each step (i.e. O-trifluoromethylation and OCF$_3$-migration) separately. Addition of BHT (1 equiv) to a reaction mixture of 8d and Togni reagent I had detrimental effect to the formation of O-trifluoromethylated N-hydroxylamine intermediate 8d'. This result suggests the involvement of radical species in the reaction pathway, which is in agreement with literature precedent.[4b,17] On the other hand, BHT did not affect the reaction yield for the OCF$_3$-migration process (step 2, Scheme 10a). These experiments argue against the presence of long-lived radical species in the OCF$_3$-migration process and are consistent with our previous finding.[28] Moreover, introduction of electron rich substituent para to the N—OCF$_3$ group facilitates the OCF$_3$-migration process. These observations support the formation of nitrenium ion and trifluoromethoxide.[24,28] On the basis of these results, a plausible mechanism for the trifluoromethoxylation reaction is illustrated in Scheme 10b. Deprotonation of 8d forms N-hydroxyl anion I, which undergoes single-electron transfer (SET) with Togni reagent I to generate N-hydroxyl radical II, trifluoromethyl radical, and alkoxide III. Recombination of N-hydroxyl radical and trifluoromethyl radical affords the O-trifluoromethylated hydroxylamine 1d', which could be isolated and characterized. This intermediate will then undergo thermally induced heterolytic cleavage of the N—O bond to form a tight ion pair of nitrenium ion IV and trifluoromethoxide. Recombination of this ion pair gives V, which upon tautomerization yields the desired product 9d.

Scheme 10.

a. Mechanistic studies using radical inhibitor

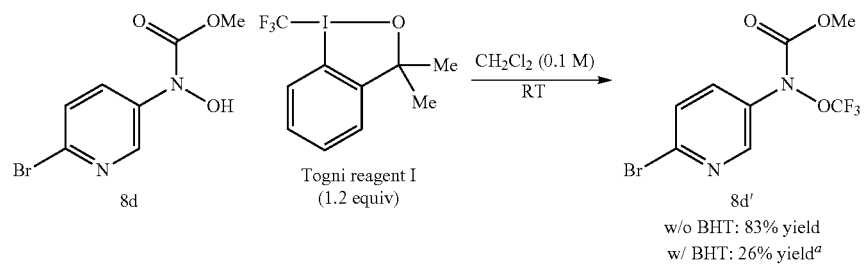

8d

Togni reagent I
(1.2 equiv)

8d'
w/o BHT: 83% yield
w/ BHT: 26% yield$^a$

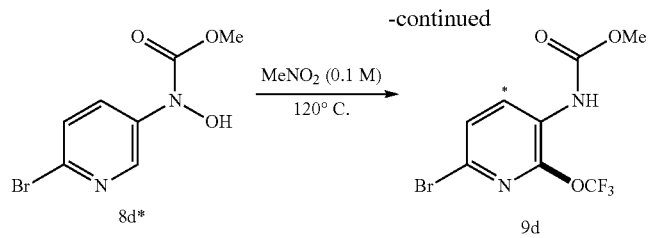

8d*

9d
w/o BHT: 94% yield (2.4:1)
w/ BHT: 90% yield (2.5:1)[a]

b. Proposed reaction mechanism

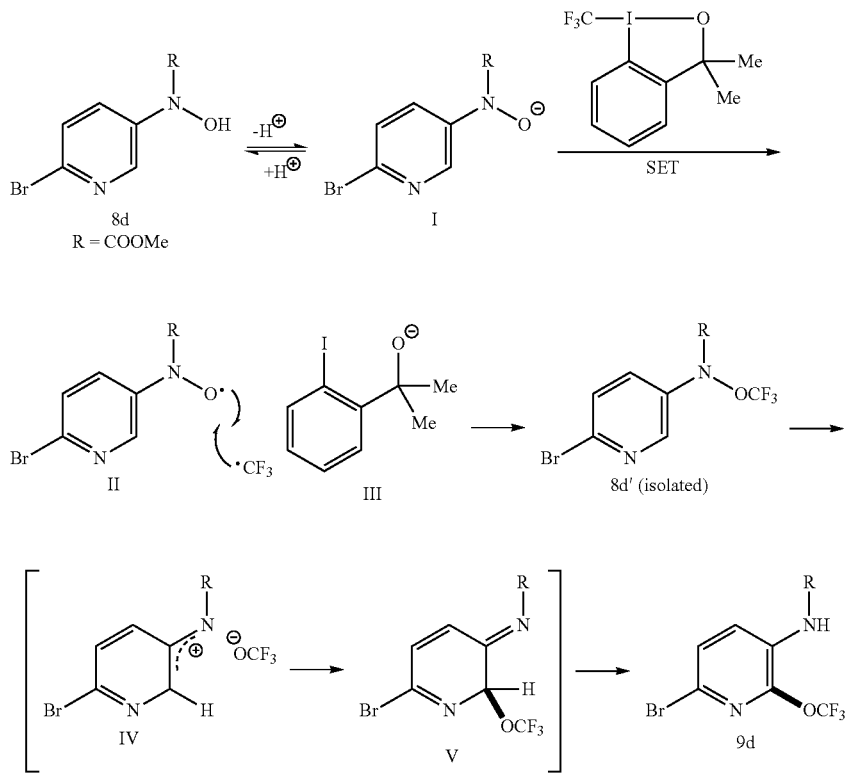

Methyl-(6-bromopyridin-3-yl)(trifluoromethoxy)carbamate (8d')

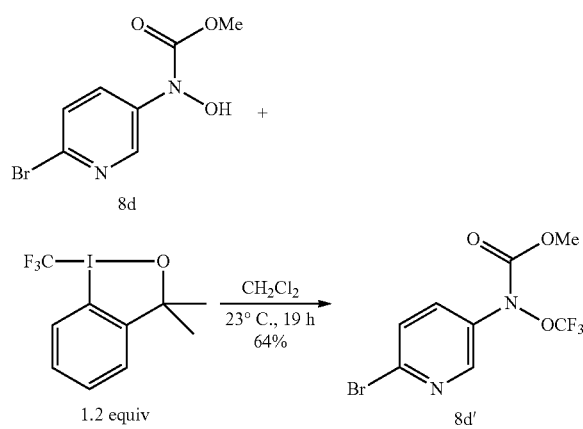

A solution of methyl (6-bromopyridin-3-yl)(hydroxy)carbamate (8d) (120.0 mg, 0.486 mmol) and Togni reagent I (192.4 mg, 0.583 mmol, 1.20 equiv) in $CH_2Cl_2$ (4.86 mL, 0.100 M) was stirred at 23° C. under $N_2$ atmosphere for 19 h. The reaction mixture was concentrated in vacuo. The residue was purified by preparative TLC (thickness: 1 mm) using hexanes:EtOAc (97:3 (v/v)) for development (prep TLC was developed four times). The band corresponding to 2-(2-iodophenyl)propan-2-ol was on the bottom of the band corresponding to the product, so only top of the band corresponding to the product was scraped of the PLC plate. The purification afforded the title compound as a white solid (97.4 mg, 0.309 mmol, 64% yield). $R_f$=0.49 (EtOAc:hexanes 1:9 (v/v)). NMR Spectroscopy: $^1$H NMR (700 MHz, $CDCl_3$, 25° C., δ): 8.45 (br. s, 1H), 7.60 (m, 1H), 7.56 (d, J=8.60 Hz, 1H), 3.90 (s, 3H). $^{13}$C NMR (175 MHz, $CDCl_3$, 60° C., δ): 155.2, 145.9, 141.2, 137.3, 133.9, 128.5, 122.7 (q, J=263.7 Hz), 55.3. $^{19}$F NMR (376 MHz, $CDCl_3$, 25° C., δ): −66.2 (s). Mass Spectrometry: HRMS (ESI-TOF) (m/z): calcd for $C_8H_7BrF_3N_2O_3$ ($[M+H]^+$), 314.9587, found, 314.9592.

5-Bromo-6-methoxy-2-(trifluoromethoxy)pyridin-3-amine (9a')

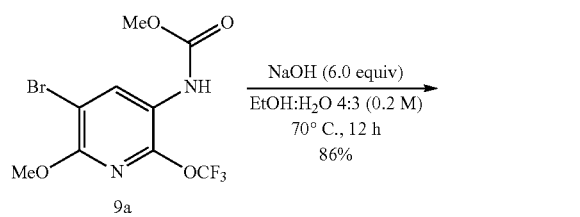

To a stirred suspension of (5-bromo-6-methoxypyridin-3-yl)(hydroxy)carbamate (0.370 g, 1.07 mmol, 1.00 equiv) and sodium hydroxide (0.257 g, 6.43 mmol, 6.00 equiv) in EtOH:H$_2$O 4:3 (6.32 mL, 0.200 M) was heated at 70° C. overnight, cool to −20° C., diluted with water and the crystals formed were filtered off to afford the deprotection of methyl carbamates as pure slightly light yellow solid (0.263 g, 0.92 mmol, 86% yield). R$_f$=0.69 (EtOAc:hexanes 3:7 (v/v)). NMR Spectroscopy: $^1$H NMR (500 MHz, (CD$_3$)$_2$SO, 25° C., δ): 7.55 (s, 1H), 5.17 (s, 2H), 3.77 (s, 3H). $^{13}$C NMR (175 MHz, (CD$_3$)$_2$SO, 25° C., δ): 147.73, 137.95, 131.06, 129.42, 120.01 (q, J=257.3 Hz), 102.74, 54.17. $^{19}$F NMR (376 MHz, CDCl$_3$, 25° C., δ): −56.9 (s). Mass Spectrometry: HRMS (ESI-TOF) (m/z): calcd for C$_7$H$_7$BrF$_3$N$_2$O$_2$ ([M+H]$^+$), 288.9618, found, 288.9629.

O-Trifluoromethylation in the Presence of a Radical Trap

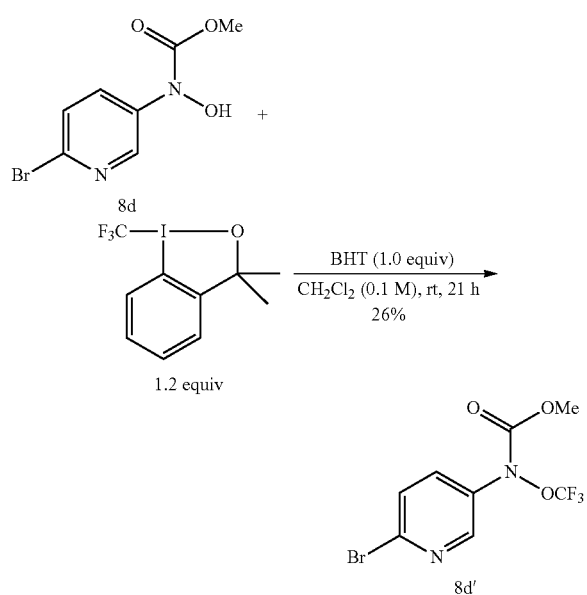

A solution of methyl (6-bromopyridin-3-yl)(hydroxy)carbamate (8d) (12.4 mg, 0.0502 mmol, 1.00 equiv), BHT (11.0 mg, 0.0500 mmol, 1.00 equiv) and Togni reagent I (19.8 mg, 0.0600 mmol, 1.2 equiv) in CH$_2$Cl$_2$ (0.500 mL) was stirred at 23° C. under N$_2$ atmosphere for 21 h. Trifluorotoluene (6.14 μL) and CDCl$_3$ (0.250 mL) were added and the reaction mixture was analyzed by $^{19}$F NMR. The $^{19}$F NMR analysis indicated that the yield of O-trifluoromethylation of 8d in the presence of BHT (26%) was much lower than in the absence of the radical trap (83%).

O—CF$_3$ Migration in the Presence of a Radical Trap w/o BHT

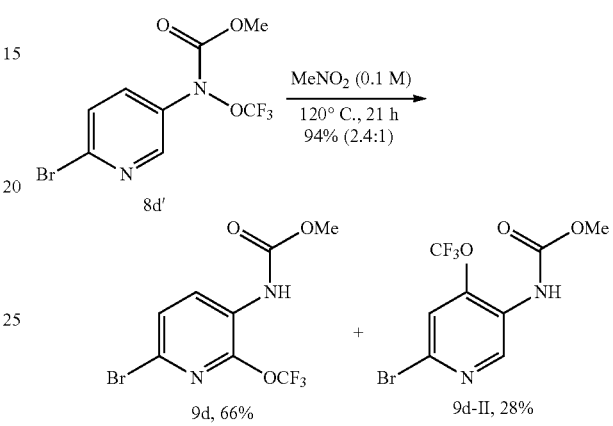

with BHT:

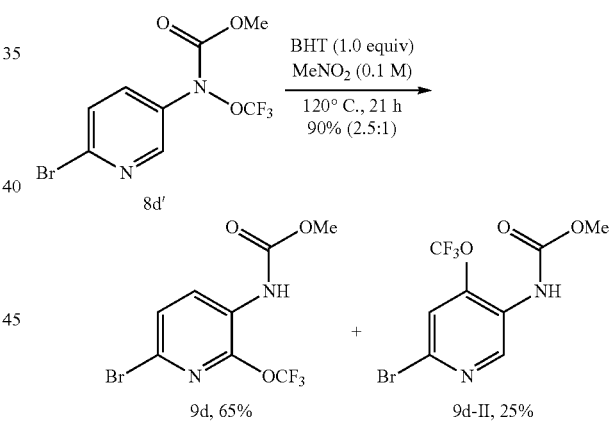

Reaction without BHT:

Under N$_2$ atmosphere, a solution of methyl (6-bromopyridin-3-yl) (trifluoromethoxy)carbamate (9.45 mg, 30.0 μmol) (8d') in MeNO$_2$ (0.300 mL, 0.100 M) was heated at 120° C. for 21 h. Trifluorotoluene (3.68 μL) and CDCl$_3$ (0.400 mL) were added and the reaction mixture was analyzed by $^{19}$F NMR. The $^{19}$F NMR analysis indicated that the yield of OCF$_3$-migration reaction was 94% (2.4:1).

Reaction with BHT:

Under N$_2$ atmosphere, a solution of methyl (6-bromopyridin-3-yl) (trifluoromethoxy)carbamate (8d') (9.45 mg, 30.0 μmol, 1.00 equiv) and BHT (11.0 mg, 50.0 μmol, 1.00 equiv) in MeNO$_2$ (0.300 mL, 0.100 M) was heated at 120° C. for 21 h. Trifluorotoluene (3.68 μL) and CDCl$_3$ (0.400 mL) were added and the reaction mixture was analyzed by $^{19}$F NMR. The $^{19}$F NMR analysis indicated that the yield of OCF$_3$-migration reaction was 90% (2.5:1).

Example 11. Additional Substrates

An additional aspect of the invention provides substituted or unsubstituted aryl and heteroaryl analogs of the compounds of Scheme 2 and Schemes 7-8 that readily undergo the two-step trifluoromethylation-migration sequence or the one-pot trifluoromethylation-migration reaction.

DISCUSSION

Clearly, direct trifluoromethoxylation reactions that avoid use of highly toxic and thermally labile reagents are greatly desired. Therefore, we initiated a program to develop easily-handled and bench stable trifluoromethoxylation reagents for direct introduction of the $OCF_3$ group into various organic molecules to facilitate studies of this functional group in the context of material, agricultural, and pharmaceutical regimes. In the course of the trifluoromethoxylation reagent development, we observed a thermally induced $OCF_3$-migration to generate synthetically useful ortho-trifluoromethoxylated aniline derivatives (Scheme 1).[13] Herein, we report the first synthesis, isolation, and characterization of protected N-aryl-N-(trifluoro-methoxy) amines[14] and their application in the synthesis of ortho-$OCF_3$ aniline derivatives.

A proposed mechanistic pathway for $OCF_3$-migration is depicted in Scheme 6A. The thermally induced heterolytic cleavage of the N—O bond of 2 liberates an ion pair of a nitrenium ion and trifluoromethoxide (I). Recombination of this ion pair affords intermediate II, which then tautomerizes to restore the aromaticity and generate the desired product 3. The proposed mechanism is supported by the following observations. First of all, comparable yields were obtained regardless of the presence or absence of the radical trap (BHT) in the reaction mixture (Scheme 11B). This indicates that formation of long-lived radical species under the reaction conditions is unlikely. Secondly, we isolated benzoxazole 4r from the rearrangement reaction of 2r (Scheme 11C). Presumably, this side product can result from the competing reaction pathway a once the nitrenium ion III is generated. Finally, Kikugawa and coworkers reported an $AlCl_3$-mediated regioselective $OCH_3$-migration of N-methoxy-N-phenylamides to produce ortho-$OCH_3$ aniline derivatives.[3] A reaction mechanism involving a heterolytic cleavage of the N—O bond to furnish an ion pair was proposed (Scheme 11D).

Scheme 11. Evidence for the proposed reaction mechanism.

A: Proposed Reaction Mechanism: $OCF_3$-Migration via an Ion Pair Formation

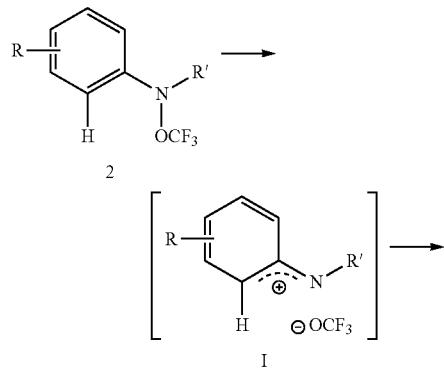

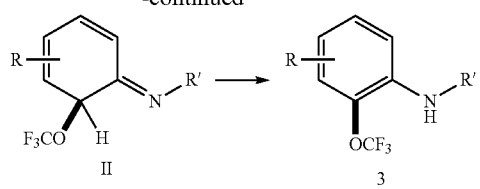

B: $OCF_3$-Migration in the Presence of Radical Trap

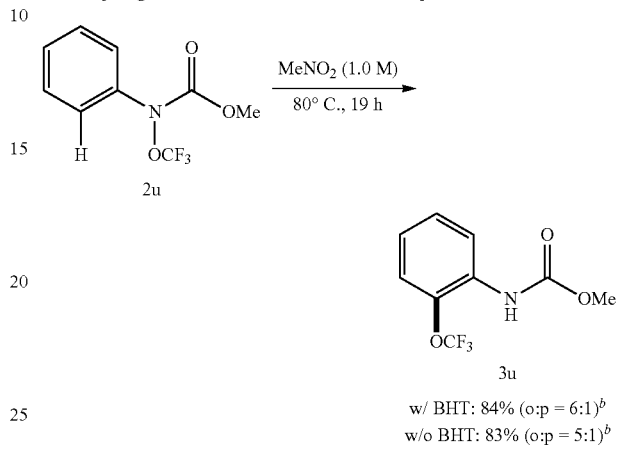

w/ BHT: 84% (o:p = 6:1)[b]
w/o BHT: 83% (o:p = 5:1)[b]

C: Benzoxazole Formation via Trapping of Carbocation Intermediate

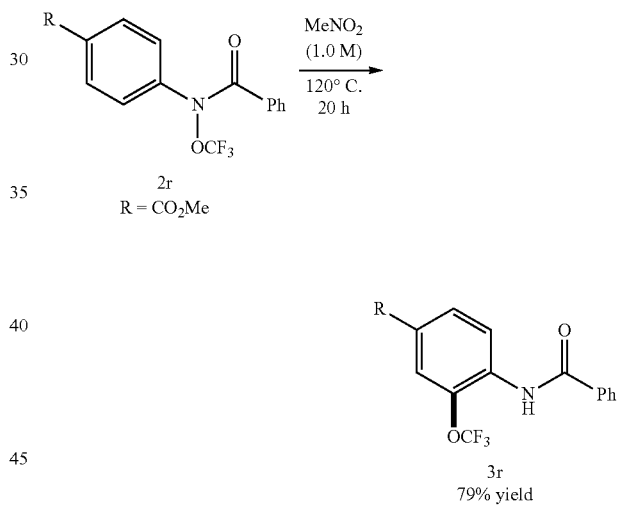

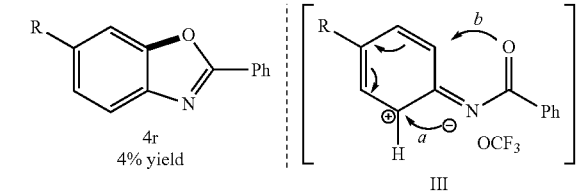

D: Kikugawa's Report: Al-Mediated $OCH_3$-Migration via an Ion Pair Mechanism4[1]

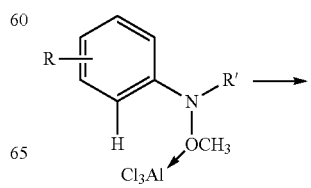

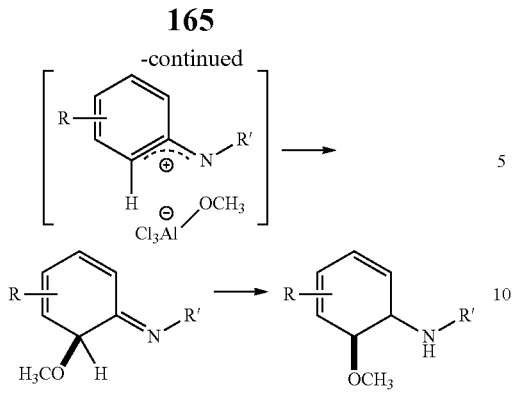

[a] 1 equiv of BHT was used.

The first O-trifluoromethylation of a wide range of protected N-aryl-N-hydroxylamines and the first $OCF_3$-migration reaction to afford various ortho-$OCF_3$ aniline derivatives, which can be useful synthons for agrochemical and pharmaceutical development, as been developed.[2a,b,5g,22] The $OCF_3$-migration reaction proceeds through the heterolytic cleavage of the N—O bond followed by recombination of the resulting ion pair. The arene trifluoromethoxylation protocol utilizes bench stable reagents, is amenable to gram-scale and one-pot synthesis, and displays high levels of ortho-selectivity as well as functional group tolerance.

Also, the first mild, general, and scalable protocol for the regioselective synthesis of trifluoromethoxylated pyridines and pyrimidines was been established. Several unique features distinguish our strategy from the existing approaches: (i) many substrates with complex skeleton could be trifluoromethoxylated at or below room temperature; (ii) a wide range of functional groups and substitution patterns are tolerated; (iii) this transformation could be amenable to gram-scale synthesis; (iv) the halogen or amino group could be used as synthetic handles for further elaborations, and (v) the operational simplicity of our protocol would render trifluoromethoxylation available to broader synthetic community. Since heteroarenes are ubiquitous in biologically active natural products, pharmaceuticals, and agrochemicals, $OCF_3$-containing heteroarenes will be invaluable for the discovery and development of new drugs, agrochemicals, and functional materials. Our current efforts are directed toward development of intermolecular trifluoromethoxylation of hydrocarbons.

REFERENCES

[1] a) F. M. D. Ismail, J. Fluorine Chem. 2002, 118, 27-33; b) H. J. Bohm, D. Banner, S. Bendels, M. Kansy, B. Kuhn, K. Muller, U. Obst-Sander, M. Stahl, Chem Bio Chem 2004, 5, 637-643; c) J. P. Begue, D. Bonnet-Delpon, J. Fluorine Chem. 2006, 127, 992-1012; d) C. Isanbor, D. O'Hagan, J. Fluorine Chem. 2006, 127, 303-319; e) K. L. Kirk, J. Fluorine Chem. 2006, 127, 1013-1029; f) K. L. Kirk, Curr. Top. Med. Chem. 2006, 6, 1447-1456; g) K. L. Kirk, Curr. Top. Med. Chem. 2006, 6, 1445-1445; h) W. K. Hagmann, J. Med. Chem. 2008, 51, 4359-4369; i) D. O'Hagan, Chem. Soc. Rev. 2008, 37, 308-319; j) S. Purser, P. R. Moore, S. Swallow, V. Gouverneur, Chem. Soc. Rev. 2008, 37, 320-330; k) I. Ojima, Fluorine in Medicinal Chemistry and Chemical Biology, Wiley-Blackwell, Chichester, U.K., 2009; l) T. Liang, C. N. Neumann, T. Ritter, Angew. Chem., Int. Ed. 2013, 52, 8214-8264; Angew. Chem. 2013, 125, 8372-8423; m) D. Barnes-Seeman, J. Beck, C. Springer, Curr. Top. Med. Chem. 2014, 14, 855-864.

[2] a) F. Leroux, P. Jeschke, M. Schlosser, Chem. Rev. 2005, 105, 827-856; b) P. Jeschke, E. Baston, F. R. Leroux, Mini-Rev. Med. Chem. 2007, 7, 1027-1034; c) F. R. Leroux, B. Manteau, J. P. Vors, S. Pazenok, Beilstein J. Org. Chem. 2008, 4; d) S. Fantasia, J. M. Welch, A. Togni, J. Org. Chem. 2010, 75, 1779-1782; e) B. Manteau, S. Pazenok, J. P. Vors, F. R. Leroux, J. Fluorine Chem. 2010, 131, 140-158.

[3] a) D. Federsel, A. Herrmann, D. Christen, S. Sander, H. Willner, H. Oberhammer, J. Mol. Struct. 2001, 567, 127-136; b) I. F. Shishkov, H. J. Geise, C. Van Alsenoy, L. V. Khristenko, L. V. Vilkov, V. M. Senyavian, B. Van der Veken, W. Herrebout, B. V. Lokshin, O. G. Garkusha, J. Mol. Struct. 2001, 567, 339-360; c) E. G. Kapustin, V. M. Bzhezovsky, L. M. Yagupolskii, J. Fluorine Chem. 2002, 113, 227-237; d) J. Klocker, A. Karpfen, P. Wolschann, Chem. Phys. Lett. 2003, 367, 566-575.

[4] C. Hansch, A. Leo, Substituent Constants for Correlation Analysis in Chemistry and Biology, Wiley, New York, 1979.

[5] a) P. O'Reilly, S. Kobayashi, S. Yamane, W. Phillips, P. Raymond, B. Castanho, Brighton Crop Prot. Conf.-Pest Dis. 1992, 427-434; b) G. Bensimon, L. Lacomblez, V. Meininger, P. Bouche, C. Delwaide, P. Couratier, O. Blin, F. Viader, H. Peyrostpaul, J. David, J. M. Maloteaux, J. Hugon, E. C. Laterre, A. Rascol, M. Clanet, J. M. Vallat, A. Dumas, G. Serratrice, B. Lechevallier, A. J. Peuch, T. Nguyen, C. Shu, P. Bastien, C. Papillon, S. Durrleman, E. Louvel, P. Guillet, L. Ledoux, E. Orvoenfrija, M. Dib, N. Engl. J. Med. 1994, 330, 585-591; c) F. G. Delorenzi, Pulm Pharmacol 1994, 7, 129-135; d) H. J. Santel, B. A. Bowden, V. M. Sorensen, K. H. Muller, Brighton Crop Prot. Conf.-Pest Dis. 1999, 23-28; e) I. Beria, B. Valsasina, M. G. Brasca, W. Ceccarelli, M. Colombo, S. Cribioli, G. Fachin, R. D. Ferguson, F. Fiorentini, L. M. Gianellini, M. L. Giorgini, J. K. Moll, H. Posteri, D. Pezzetta, F. Roletto, F. Sola, D. Tesei, M. Caruso, Bioorg. Med. Chem. Lett. 2010, 20, 6489-6494; f) I. Beria, R. T. Bossi, M. G. Brasca, M. Caruso, W. Ceccarelli, G. Fachin, M. Fasolini, B. Forte, F. Fiorentini, E. Pesenti, D. Pezzetta, H. Posteri, A. Scolaro, S. R. Depaolini, B. Valsasina, Bioorg. Med. Chem. Lett. 2011, 21, 2969-2974; g) G. Landelle, A. Panossian, F. R. Leroux, Curr. Top. Med. Chem. 2014, 14, 941-951.

[6] a) L. M. Yagupolskii, Dokl. Akad. Nauk SSSR 1955, 105, 100-102; b) N. N. Yarovenko, A. S. Vasileva, Zh. Obshch. Khim. 1958, 28, 2502-2504; c) Yagupols. L, V. I. Troitskaya, Zh. Obshch. Khim. 1961, 31, 915-924; d) L. M. Yagupolskii, V. V. Orda, Zh. Obshch. Khim. 1964, 34, 1979-1984; e) R. Louw, P. W. Franken, Chem Ind-London 1977, 127-128; f) A. E. Feiring, J. Org. Chem. 1979, 44, 2907-2910; g) J. Salome, C. Mauger, S. Brunet, V. Schanen, J. Fluorine Chem. 2004, 125, 1947-1950.

[7] W. A. Sheppard, J. Org. Chem. 1964, 29, 1-11.

[8] a) M. Kuroboshi, K. Suzuki, T. Hiyama, Tetrahedron Lett. 1992, 33, 4173-4176; b) K. Kanie, Y. Tanaka, K. Suzuki, M. Kuroboshi, T. Hiyama, Bull. Chem. Soc. Jpn. 2000, 73, 471-484; c) M. Kuroboshi, K. Kanie, T. Hiyama, Adv. Synth. Catal. 2001, 343, 235-250.

[9] a) T. Umemoto, Chem. Rev. 1996, 96, 1757-1777; b) T. Umemoto, K. Adachi, S. Ishihara, J. Org. Chem. 2007, 72, 6905-6917; c) K. Stanek, R. Koller, A. Togni, J. Org. Chem. 2008, 73, 7678-7685; d) R. Koller, K. Stanek, D.

Stolz, R. Aardoom, K. Niedermann, A. Togni, *Angew. Chem., Int. Ed.* 2009, 48, 4332-4336; *Angew. Chem.* 2009, 121, 4396-4400.

[10] a) G. L. Trainor, *J. Carbohydr. Chem.* 1985, 4, 545-563; b) M. Nishida, A. Vij, R. L. Kirchmeier, J. M. Shreeve, *Inorg. Chem.* 1995, 34, 6085-6092; c) A. A. Kolomeitsev, M. Vorobyev, H. Gillandt, *Tetrahedron Lett.* 2008, 49, 449-454; d) O. Marrec, T. Billard, J. P. Vors, S. Pazenok, B. R. Langlois, *J. Fluorine Chem.* 2010, 131, 200-207; e) O. Marrec, T. Billard, J. P. Vors, S. Pazenok, B. R. Langlois, *Adv. Synth. Catal.* 2010, 352, 2831-2837.

[11] C. H. Huang, T. Liang, S. Harada, E. Lee, T. Ritter, *J. Am. Chem. Soc.* 2011, 133, 13308-13310.

[12] a) S. Rozen, *Chem. Rev.* 1996, 96, 1717-1736; b) F. Venturini, W. Navarrini, A. Famulari, M. Sansotera, P. Dardani, V. Tortelli, *J. Fluorine Chem.* 2012, 140, 43-48. C) Huang, C. H.; Liang, T.; Harada, S.; Lee, E.; Ritter, T. J. Am. Chem. Soc. 2011, 133, 13308.

[13] Analogous OCH$_3$-migration mediated by AlCl3 was developed, see: Y. Kikugawa, M. Shimada, *J. Chem. Soc., Chem. Commun.* 1989, 1450-1451.

[14] O-Trifluoromethylated N-Phenylhydroxamic acid was reported as a side product in copper-catalyzed three-component oxytrifluoromethylation of alkenes, see: a) X. Y. Jiang, F. L. Qing, *Angew. Chem., Int. Ed.* 2013, 52, 14177-14180; O-trifluoromethylation of N,N-dialkylhydroxylamines was reported by Togni, see: b) V. Matousek, E. Pietrasiak, L. Sigrist, B. Czarniecki, A. Togni, *Eur. J. Org. Chem.* 2014, 2014, 3087-3092.

[15] a) A. Ferry, T. Billard, B. R. Langlois, E. Bacque, *J. Org. Chem.* 2008, 73, 9362-9365; *Angew. Chem.* 2009, 121, 8703-8707; b) A. Ferry, T. Billard, B. R. Langlois, E. Bacque, *Angew. Chem., Int. Ed.* 2009, 48, 8551-8555; c) F. Toulgoat, S. Alazet, T. Billard, *Eur. J. Org. Chem.* 2014, 2014, 2415-2428.

[16] a) P. Eisenberger, S. Gischig, A. Togni, *Chem. Eur. J.* 2006, 12, 2579-2586; b) V. Matousek, E. Pietrasiak, R. Schwenk, A. Togni, *J. Org. Chem.* 2013, 78, 6763-6768.

[17] Y. Li, A. Studer, *Angew. Chem., Int. Ed.* 2012, 51, 8221-8224; *Angew. Chem.* 2012, 124, 8445-8348.

[18] a) Z. Q. Lao, W. H. Zhong, Q. H. Lou, Z. J. Li, X. B. Meng, *Org. Biomol. Chem.* 2012, 10, 7869-7871; b) Q. Q. Xia, W. Z. Chen, *J. Org. Chem.* 2012, 77, 9366-9373; c) Y. Z. Yan, Y. H. Zhang, C. T. Feng, Z. G. Zha, Z. Y. Wang, *Angew. Chem., Int. Ed.* 2012, 51, 8077-8081; *Angew. Chem.* 2012, 124, 8201-8205; d) M. Salamone, M. Milan, G. A. DiLabio, M. Bietti, *J. Org. Chem.* 2013, 78, 5909-5917.

[19] X. Wang, Y. X. Ye, S. N. Zhang, J. J. Feng, Y. Xu, Y. Zhang, J. B. Wang, *J. Am. Chem. Soc.* 2011, 133, 16410-16413.

[20] B. R. Langlois, N. Roques, *J. Fluorine Chem.* 2007, 128, 1318-1325.

[21] I. Ben-David, D. Rechavi, E. Mishani, S. Rozen, *J. Fluorine Chem.* 1999, 97, 75-78.

[22] a) P. Jimonet, F. Audiau, M. Barreau, J. C. Blanchard, A. Boireau, Y. Bour, M. A. Coleno, A. Doble, G. Doerflinger, C. D. Hu, M. H. Donat, J. M. Duchesne, P. Ganil, C. Gueremy, E. Honore, B. Just, R. Kerphirique, S. Gontier, P. Hubert, P. M. Laduron, J. Le Blevec, R. Meunier, J. M. Miquet, C. Nemecek, M. Pasquet, O. Piot, J. Pratt, J. Rataud, N. Reibaud, J. M. Stutzmann, S. Mignani, *J. Med. Chem.* 1999, 42, 2828-2843; b) J. P. Parrish, D. B. Kastrinsky, F. Stauffer, M. P. Hedrick, I. Hwang, D. L. Boger, *Bioorg. Med. Chem.* 2003, 11, 3815-3838; c) A. J. Roecker, P. J. Coleman, *Curr. Top. Med. Chem.* 2008, 8, 977-987; d) A. Sankaranarayanan, G. Raman, C. Busch, T. Schultz, P. I. Zimin, J. Hoyer, R. Kohler, H. Wulff, *Mol. Pharmacol.* 2009, 75, 281-295.

[23] Noritake, S.; Shibata, N.; Nakamura, S.; Toru, T.; Shiro, M. Eur. J. Org. Chem. 2008, 3465.

[24] Tabolin, A. A.; Ioffe, S. L. Chem. Rev. 2014, 114, 5426.

[25] (a) Novikov, V. N.; Pozharskii, A. F.; Doronkin, V. N. Khim. Geterotsikl. Soedin. 1976, 244; (b) Hirota, M.; Masuda, H.; Hamada, Y.; Takeuchi, I. Bull. Chem. Soc. Jpn. 1979, 52, 1498; (c) Mcgill, C. K.; Rappa, A. Adv. Heterocycl. Chem. 1988, 44, 1.

[26] (a) Ishida, H.; Isami, S.; Matsumura, T.; Umehara, H.; Yamashita, Y.; Kajita, J.; Fuse, E.; Kiyoi, H.; Naoe, T.; Akinaga, S.; Shiotsu, Y.; Arai, H. Bioorg. Med. Chem. Lett. 2008, 18, 5472; (b) St Jean, D. J.; Fotsch, C. J. Med. Chem. 2012, 55, 6002.

[27] Sullivan, M. B.; Cramer, C. J. *J. Am. Chem. Soc.* 2000, 122, 5588.

[28] Hojczyk, K. N.; Feng, P.; Zhan, C.; Ngai, M.-Y. Angew. Chem. Int. Ed. 2014, 53, 14559.

What is claimed is:

1. A process of producing a trifluoromethoxylated aryl or trifluoromethoxylated heteroaryl having the structure:

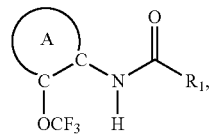

wherein

A is an aryl or heteroaryl, each with or without substitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl),—S-(alkyl), —S-(alkenyl), —S-(alkynyl), —S-(aryl), or —S-(heteroaryl), comprising:

maintaining the compound having the structure:

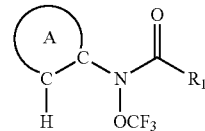

in a suitable solvent under conditions sufficient to produce the trifluoromethoxylated aryl or trifluoromethoxylated heteroaryl having the structure:

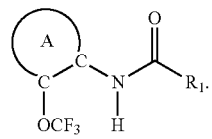

2. The process of claim 1, wherein the suitable solvent is chloroform, dichloromethane, nitromethane, dimethylformamide, diethyl ether, tetrahydrofuran, dioxane, dichloroethane, or hexane.

3. The process of claim 1, wherein the maintaining is carried out at room temperature.

4. The process of claim 1, wherein the maintaining is carried out at a temperature of 50-140° C.

5. The process of claim 1, wherein the compound is maintained in the suitable solvent for 10-50 hours.

6. The process of claim 1, wherein A is a phenyl or pyridine.

7. The process of claim 1, wherein A is a furanyl, thiophenyl, pyrrolyl, thiazolyl, imidazolyl, pyrazolyl, isooxazolyl, isothiazolyl, naphtalenyl, anthracenyl, pyrimidinyl, pyrazinyl, pyridazinyl, indolyl, indolinyl, benzofuranyl, benzothiophenyl, or quinolonyl furan.

8. The process of claim 1, wherein the compound produced has the structure:

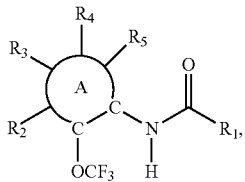

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl),—S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl),—S-(alkyl), —S-(alkenyl), —S-(alkynyl), —S-(aryl), —S-(heteroaryl), pyridinyl, furanyl, thiophenyl, pyrrolyl, thiazolyl, imidazolyl, pyrazolyl, isooxazolyl, isothiazolyl, naphtalenyl, anthracenyl, pyrimidinyl, pyrazinyl, pyridazinyl, indolyl, indolinyl, benzofuranyl, benzothiophenyl, or quinolonyl.

9. The process of claim 1, wherein the compound produced has the structure:

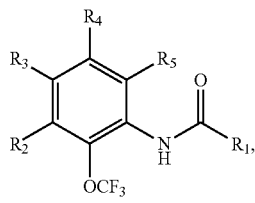

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl),—S-(alkyl), —S-(alkenyl), —S-(alkynyl), —S-(aryl), or —S-(heteroaryl); and $R_2$, $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl),—S-(alkyl), —S-(alkenyl), —S-(alkynyl), —S-(aryl), —S-(heteroaryl), pyridinyl, furanyl, thiophenyl, pyrrolyl, thiazolyl, imidazolyl, pyrazolyl, isooxazolyl, isothiazolyl, naphtalenyl, anthracenyl, pyrimidinyl, pyrazinyl, pyridazinyl, indolyl, indolinyl, benzofuranyl, benzothiophenyl, or quinolonyl.

10. The process of claim 1, wherein the compound produced has the structure:

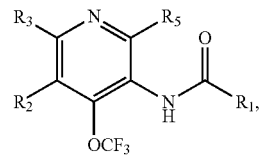

wherein $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), —O-(heteroaryl),—S-(alkyl), —S-(alkenyl), —S-(alkynyl), —S-(aryl), or —S-(heteroaryl); and $R_2$, $R_3$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl),—S-(alkyl), —S-(alkenyl), —S-(alkynyl), —S-(aryl), —S-(heteroaryl), pyridinyl, furanyl, thiophenyl, pyrrolyl, thiazolyl, imidazolyl, pyrazolyl, isooxazolyl, isothiazolyl, naphtalenyl, anthracenyl, pyrimidinyl, pyrazinyl, pyridazinyl, indolyl, indolinyl, benzofuranyl, benzothiophenyl, or quinolonyl;

or the structure:

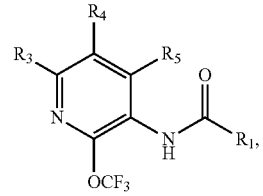

wherein $R_1$ is —H, -(alkyl), -(alkenyl), -(alkynyl), -(aryl), -(heteroaryl), -(alkylaryl), -(alkylheteroaryl), —NH-(alkyl)-N(alkyl)$_2$, —NH-(alkenyl), —NH-(alkynyl) —NH-(aryl), —NH-(heteroaryl), —O-(alkyl), O-(alkenyl), —O-(alkynyl), —O-(aryl), —O-(heteroaryl),—S-(alkyl), —S-(alkenyl), —S-(alkynyl), —S-(aryl), or —S-(heteroaryl); and $R_3$, $R_4$ and $R_5$ is each independently —H, halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl) —NH-(aryl), —NH-(heteroaryl), —CO$_2$-(alkyl), —CO$_2$-(alkenyl), —CO$_2$-(alkynyl) —CO$_2$-(aryl), —C(—CO$_2$-(heteroaryl), —C(O)NH-(alkyl), —C(O)NH-(alkenyl), —C(O)NH-(alkynyl) —C(O)NH-(aryl), —C(O)NH-(heteroaryl), —C(O)N(alkyl)$_2$, —OH, —OAc, —O-(alkyl), —O-(alkenyl), —O-(alkynyl), —O-(aryl), —O-(heteroaryl),—S-(alkyl), —S-(alkenyl), —S-(alkynyl), —S-(aryl), —S-(heteroaryl), pyridinyl, furanyl, thiophenyl, pyrrolyl, thiazolyl, imidazolyl, pyrazolyl, isooxazolyl, isothiazolyl, naphtalenyl, anthracenyl, pyrimidinyl, pyrazinyl, pyridazinyl, indolyl, indolinyl, benzofuranyl, benzothiophenyl, quinolonyl, pyrazolinyl, triazolyl, benzimidazolyl, benzotriazolyl, azaindolyl, or purinyl.

11. The process of claim 1 comprising producing a trifluoromethoxylated aryl or trifluoromethoxylated heteroaryl having the structure:

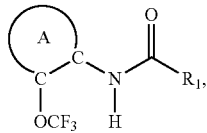

wherein

A is an aryl or heteroaryl, each with or without substitution; and $R_1$ is —H, -(alkyl), -(alkenyl), -(alkynyl), -(aryl), -(heteroaryl), -(alkylaryl), -(alkylheteroaryl), —NH-(alkyl), —N(alkyl)$_2$, —NH-(alkenyl), —NH-(alkynyl) —NH-(aryl), —NH-(heteroaryl), —O-(alkyl), —O-(alkenyl), —O-(alkynyl), —O-(aryl), or —O-(heteroaryl), comprising:

maintaining the compound having the structure:

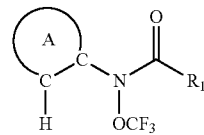

in a suitable solvent under conditions sufficient to produce the trifluoromethoxylated aryl or trifluoromethoxylated heteroaryl having the structure:

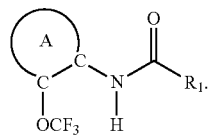

\* \* \* \* \*